United States Patent [19]

Mills

[11] Patent Number: 5,750,754
[45] Date of Patent: May 12, 1998

[54] HETEROCYCLIC COMPOUNDS

[75] Inventor: Stuart D. Mills, Cheshire, England

[73] Assignee: Zeneca Limited, London, United Kingdom

[21] Appl. No.: 658,097

[22] Filed: Jun. 4, 1996

[30] Foreign Application Priority Data

| Mar. 29, 1993 | [GB] | United Kingdom | 9306451 |
| Mar. 29, 1993 | [GB] | United Kingdom | 9306453 |
| Dec. 15, 1993 | [GB] | United Kingdom | 9325605 |
| Dec. 15, 1993 | [GB] | United Kingdom | 9325610 |
| Sep. 7, 1995 | [GB] | United Kingdom | 9518188 |

[51] Int. Cl.$^6$ ............................................. C07C 309/07
[52] U.S. Cl. ...................................... 558/52; 560/179
[58] Field of Search ............................. 560/179; 558/52

[56] References Cited

U.S. PATENT DOCUMENTS

| 3,875,165 | 4/1975 | Archibald et al. |
| 4,933,482 | 6/1990 | Sayo et al. ........................... 560/179 |
| 5,039,805 | 8/1991 | Alig et al. |
| 5,084,466 | 1/1992 | Alig et al. |
| 5,107,016 | 4/1992 | Pennetreau ......................... 560/179 |
| 5,227,490 | 7/1993 | Hartman et al. |
| 5,252,735 | 10/1993 | Morris |
| 5,254,573 | 10/1993 | Bovy et al. |
| 5,264,420 | 11/1993 | Duggan et al. |
| 5,276,049 | 1/1994 | Himmelsbach et al. |
| 5,281,585 | 1/1994 | Duggan et al. |
| 5,434,289 | 7/1995 | Mikami et al. ..................... 560/179 |

FOREIGN PATENT DOCUMENTS

| 74101 | 10/1991 | Australia |
| 10403 | 7/1992 | Australia |
| 20569 | 1/1993 | Australia |
| 21119 | 2/1993 | Australia |
| 20892 | 3/1993 | Australia |
| 27062 | 4/1993 | Australia |
| 41201 | 12/1993 | Australia |
| 2008116 | 9/1990 | Canada |
| 2037153 | 9/1991 | Canada |
| 2061661 | 9/1992 | Canada |
| 2093770 | 10/1993 | Canada |
| 2094773 | 10/1993 | Canada |
| 0074768 | 3/1983 | European Pat. Off. |
| 0100158 | 2/1984 | European Pat. Off. |
| 0154969 | 9/1985 | European Pat. Off. |
| 0201988 | 11/1986 | European Pat. Off. |
| 0233051 | 8/1987 | European Pat. Off. |
| 0244115 | 11/1987 | European Pat. Off. |
| 0264883 | 4/1988 | European Pat. Off. |
| 0320032 | 6/1989 | European Pat. Off. |
| 0359389 | 3/1990 | European Pat. Off. |
| 0478328 | 4/1992 | European Pat. Off. |
| 0478362 | 4/1992 | European Pat. Off. |
| 0478363 | 4/1992 | European Pat. Off. |
| 0479481 | 4/1992 | European Pat. Off. |
| 0512829 | 11/1992 | European Pat. Off. |
| 0512831 | 11/1992 | European Pat. Off. |
| 0513675 | 11/1992 | European Pat. Off. |
| 0529858 | 3/1993 | European Pat. Off. |
| 0539343 | 4/1993 | European Pat. Off. |
| 0540334 | 5/1993 | European Pat. Off. |
| 0560730 | 9/1993 | European Pat. Off. |
| 0614664 | 9/1994 | European Pat. Off. |
| 2298330 | 8/1976 | France |
| 94 2178 | 1/1995 | South Africa |
| 94 2179 | 1/1995 | South Africa |
| 1474296 | 5/1977 | United Kingdom |
| 9015620 | 12/1990 | WIPO |
| 01299 | 2/1991 | WIPO |
| 05562 | 5/1991 | WIPO |
| 13552 | 8/1992 | WIPO |
| 17196 | 10/1992 | WIPO |
| 18117 | 10/1992 | WIPO |
| 22533 | 12/1992 | WIPO |
| 07867 | 4/1993 | WIPO |

(List continued on next page.)

OTHER PUBLICATIONS

Vogel et al, Chem. Abst. vol. 97, #92,034Z (1982).

Alig, et al., "Low Molecular Weight, Non-peptide Fibrinogen Receptor Antagonists", J. Med. Chem., 1992, 32, 4393–4407.

Harman, et al., "Non-peptide Fibrinogen Receptor Antagonists 1. Discovery and Design of Exosite Inhibitors", J. Med. Chem., 1992, 35, 4640–4642.

Catto, et al., 1-(2-Pyrindinyl)piperazine Derivatives with Antianaphylactic, Antibronchospastic, and Mast Cell Stabilizing Activities, J. Med. Chem. 1987, 30, 13–19.

Chemical Abstract, 98, 125889b; Derwent Abstract 82-1-248J; Registery No.= 85000-31-3; all abstracts of JP57,183,738 (82,183,738). Nov. 1992.

Sammes, et al., "Synthetic Applications of N–N Linked Heterocycles. Part 15.[1] A Facile Synthesis of 4–Pyridyl-(aryl)amines via the Reaction Between 4–Chloro-1-pyridiniopyridinium Salts and Aryl Amines", J. Chem. Soc., Perkin I, 1983-973–978.

*Primary Examiner*—James H. Reamer
*Attorney, Agent, or Firm*—Cushman Darby & Cushman Intellectual Property Group of Pillsbury Madison & Sutro LLP

[57] ABSTRACT

A compound of the general formula

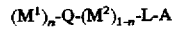

$$(M^1)_n\text{-}Q\text{-}(M^2)_{1-n}\text{-}L\text{-}A \qquad \text{I}$$

wherein: n is 0 or 1;
$M^1$ is an amino group;
Q is an aromatic heterocyclic group containing a basic nitrogen atom;
$M^2$ is an imino group;
L is a template group; and
A is an acidic group, or an ester or amide derivative thereof, or a sulphonamide group;
and pharmaceutically acceptable salts and pro-drugs thereof, for use in the treatment of a disease in which platelet aggregation mediated by the binding of adhesion molecules to GPIIb-IIIa is involved and the optically active compound (−)-(3R)-3-methyl-4-{4-[4-(4-pyridyl)-piperazin-1-yl] phenoxy}butyric acid is also disclosed.

2 Claims, No Drawings

U.S. PATENT DOCUMENTS

| | | |
|---|---|---|
| 08174 | 4/1993 | WIPO . |
| 08181 | 4/1993 | WIPO . |
| 10091 | 5/1993 | WIPO . |
| 12074 | 6/1993 | WIPO . |
| 14077 | 7/1993 | WIPO . |
| 16038 | 8/1993 | WIPO . |
| 19046 | 9/1993 | WIPO . |
| 22303 | 11/1993 | WIPO . |
| 14775 | 7/1994 | WIPO . |
| WO 94 22834 | 10/1994 | WIPO . |
| WO 94 22835 | 10/1994 | WIPO . |
| 4194 | 3/1995 | Zimbabwe . |
| 4294 | 3/1995 | Zimbabwe . |

HETEROCYCLIC COMPOUNDS

The present invention relates to a group of heterocyclic compounds which inhibit cell adhsion (for example, platelet aggregation), to processes for their preparation and to pharmaceutical compositions containing them.

A variety of diseases involve cell adhesion during their development. For example, platelet aggregation is involved in the formation of blood thrombi, which can lead to diseases such as thrombosis, (e.g. stroke and thrombotic events accompanying unstable angina and transient ischaemic attack), myocardial infarction, atherosclerosis, thromboembolism and reocclusion during and after thrombolytic therapy.

It is widely believed that the platelet membrane glycoprotein IIb/IIIa (GPIIb/IIIa) mediates platelet aggregation. Adhesion molecules such as fibrinogen and von Willebrand Factor are believed to bind to GPIIb/IIIa sites on adjacent platelets and thereby cause them to aggregate. Other adhesion molecules which are known to bind to the GPIIb/IIIa are fibronectin, vitronectin and thrombospondin.

Compounds which inhibit platelet aggregation and the binding of adhesion molecules to GPIIb/IIIa are known. Commonly these compounds are based upon the binding sites of the adhesion molecules, which are peptides. For example, the portion of fibrinogen which is believed to bind to GPIIb/IIIa is the amino acid sequence RGD. This sequence may be viewed as comprising an arginine group separated from an acidic group by a template group.

Surprisingly, as a result of random screening, the ability to inhibit platelet aggregation and to inhibit the binding of fibrinogen to GPIIb/IIIa has now been found to be possessed by certain heterocyclic compounds containing a 4-(4-pyridyl)piperazin-1-yl or related group.

According to one aspect, therefore, the present invention provides a compound of the general formula

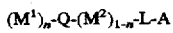   (I)

wherein n is 0 or 1;
$M^1$ is an amino group;
Q is an aromatic heterocyclic group containing a basic nitrogen atom;
$M^2$ is an imino group;
L is a template group; and
A is an acidic group, or an ester or amide derivative thereof, or a sulphonamide group;
and pharmaceutically acceptable salts and pro-drugs thereof, for use in the treatment of a disease in which platelet aggregation mediated by the binding of adhesion molecules to GPIIb-IIIa is involved.

Without wishing to be bound by theory, it is believed that the basic nitrogen atom in the aromatic heterocyclic group represented by Q functions as a replacement for the strongly basic guanidine group in arginine. The function of the nitrogen atom which is attached to Q in the amino group represented by $M^1$ or the imino group represented by $M^2$ is believed to be to contribute to the ability of the nitrogen atom in Q to function as a base. For example, when $(M^1)_n$-Q-$(M^2)_{1-n}$ represents a 4-(4-pyridyl)piperazin-1-yl group, the nitrogen atom in the piperazin-1-yl group is believed to contribute to the ability of the nitrogen atom in the pyridyl group to function as a base as shown below:

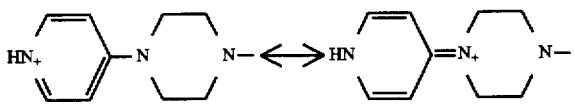

As will be described in more detail hereinafter, the group $(M^1)_n$-Q-$(M^2)_{1-n}$ has been found to be associated with ability to antagonise the binding of fibrinogen to GPIIb/IIIa when combined with an acidic or sulphonamide group and a wide variety of template groups. Ester and amide derivatives of the acids have also been found to be active, but generally with lower potency than the acids. This activity may be due to the intrinsic activity of the compounds or to their hydrolysis to the corresponding acids in the test systems used. The group $(M^1)_n$-Q-$(M^2)_{1-n}$ has also been found to be associated with a favourable effect on bioavailability. Certain of the compounds of formula I have been found to possess particularly good activity on oral administration. Commonly, esters and amides have been found to possess superior oral activity to their parent acids.

In the compounds of formula I, $M^1$ is an amino group, including —$NR^1R^2$ in which $R^1$ and $R^2$ are each independently hydrogen or (1–4C)alkyl or together form (4–5C) alkylene. Examples of values for $R^1$ and $R^2$ are hydrogen and methyl. Examples of values for —$NR^1R^2$ are dimethylamino and pyrrolidin-1-yl.

Q is an aromatic heterocyclic group containing a basic nitrogen atom, including imidazoly, pyridyl, pyrimidyl, pyrazinyl, quinolyl and purinyl, optionally substituted by one or more substituents, including (1–4C)alkyl, (1–4C) alkoxy, halogeno, and (3–4C)alkylene which, together with the two atoms to which it is attached forms a ring. Examples of values for the aromatic heterocyclic group are 2-imidazolyl, 4-imidazolyl, 2-pyridyl, 3-pyridyl, 4-pyridyl, 4-pyrimidyl, 2-pyrazinyl, 2-quinolinyl, 4-quinolinyl and 6-purinyl. Examples of values for optional substituents are: for (1–4C)alkyl, methyl; for (1–4C)alkoxy, methoxy; for halogeno, chloro and bromo; and for (3–4C)alkylene, butylene. Examples of values for Q are 3-pyridyl; 4-pyridyl; 2-methyl-4-pyridyl; 2,6-dimethyl-4-pyridyl; 4-pyrimidyl; 4-(5,6,7,8-tetrahydro)quinolinyl; 4-quinolinyl and 2-methyl-4-quinolinyl. Preferably, when Q is pyridyl, pyrimidyl, pyrazinyl, quinolyl or purinyl, the basic nitrogen atom contained by Q is located at the 4-position relative to $M^1$, when n is 1, or $M^2$, when n is 0. Q is preferably 4-pyridyl, optionally substituted as defined hereinabove.

$M^2$ is an imino group; including —$NR^3$— in which $R^3$ is hydrogen, (1–4C)alkyl or a (2–3C)alkylene bridge attached to Q; and —$NR^4$-D-$TR^5$— in which (i) T is N; D is $CH_2CO$; $CH_2SO_2$; (2–3C)alkylene optionally substituted by carboxy, (1–4C)alkoxycarbonyl, (1–4C)alkoxymethyl or a (2–3C)alkylene bridge attached to Q; and $R^4$ and $R^5$ together represent (2–3C)alkylene or $CH_2CO$, or each independently represents hydrogen or (1–4C)alkyl or $R^5$ represents hydrogen or (1–4C)alkyl and $R^4$ represents (2–3C)alkylene attached to Q; or (ii) T is CH; D is $CH_2CO$, $CH_2CH_2NH$, (1–3C)alkylene optionally substituted by carboxy or (1–4C)alkoxycarbonyl, or (2–3C)alkyleneoxy; and $R^4$ and $R^5$ together represent (1–3C)alkylene; or (iii) $R^4$ and —D-$TR^5$— together form a (5–6C)alkenylene group.

Examples of values for —NR³— when R³ is hydrogen or (1-4C)alkyl are NH and methylimino.

Examples of values for the group Q-M² when M² is a group of formula —NR³— in which R³ is a (2-3C)alkylene bridge attached to Q are 1,2,3,4-tetrahydro-1,6-naphthyridin-1-yl and pyrrolo[3,2-c]pyridin-1-yl.

Examples of values for —NR⁴-D-TR⁵— when T is N are 5-oxoimidazolidin-1,3-diyl; 2-oxopiperazin-1,4-diyl, 2,6-dioxopiperazin-1,4-diyl, 1,1-dioxo-1,2,5-thiadiazin-2,5-diyl, piperazin-1,4-diyl, 2-carboxypiperazin-1,4-diyl, 3-carboxypiperazin-1,4-diyl, 2-methoxycarbonylpiperazin1,4-diyl, 3-methoxycarbonylpiperazin-1,4-diyl, 2-methoxymethylpiperazin-1,4-diyl, 3-methoxymethylpiperazin-1,4-diyl and N-2-(N'-methyl) aminoethyl(N-methyl)amino.

Examples of values for Q-M² when T is N and D is (2-3C)alkylene optionally substituted by a (2-3C)alkylene bridge attached to Q include 1,2,3,4-tetrahydro-1,6-naphthyridin-2-yl and pyrrolo[3,2-c]pyridin-2-ylethylamino.

Examples of values for —NR⁴-D-TR⁵— when T is CH are pyrrolidin-3,1-diyl, 3-oxo-pyrrolidin-4,1-diyl 2-carboxypyrriolidin-4,1-diyl, 2-methoxycarbonylpyrrolidin-4,1-diyl, 2-ethoxycarbonylpyrrolidin-4,1-diyl, piperidin-3,1-diyl, piperidin-4,1-diyl, piperazin-2,4-diyl and morpholin-2,4-diyl.

An example of a group of formula —NR⁴-D-TR⁵— in which R⁴ and —D-TR⁵— together form a (5-6C)alkenylene group is 1,2,3,6-tetrahydropyridin-4,1-diyl.

Particularly preferred values for M² are piperazin-1,4-diyl, piperidin-4,1-diyl and 2-oxo-piperazin-1,4-diyl.

Preferably n is 0.

Accordingly, particularly preferred values for the group (M¹)ₙ-Q-(M²)₁₋ₙ are 4-(4-pyridyl)piperazin-1-yl, 4-(4-pyridyl)-2-oxopiperazin-1-yl and 1-(4-pyridyl)piperidin-4-yl.

L is a template group, including (4-7C)alkylene and a group of formula X¹-Y-X² in which X¹ is a bond or a linking group, including (1-4C)alkylene, (2-4C)alkenylene, (2-4C) alkynylene, (1-2C)alkylenephenylene, phenyleneoxy, phenyleneoxymethylene, phenylenecarbonyl, phenyleneCONH, (1-3C)alkylenecarbonyl, (1-2C) alkylenecarbonyl substituted by benzyl or p-hydroxybenzyl, methylidenepylrrolidin-1-ylacetyl, (1-2C)-alkylenecarbonyloxy, (1-2C)alkyleneCONH, (1-2C) alkyleneCONH(1-2C)alkyleneCO, (1-2C)alkyleneCONH (1-2C)alkyleneCONH, benzyl(1-2C)alkyleneCONH, (1-4C)alkyleneoxy, (1-2C)alkyleneoxy(1-2C)alkylene, (1-2C)alkyleneoxy(1-2C)alkylenecarbonyl, (1-3C) alkyleneCH(OH), and, when M² is —NR⁴-D-TR⁵—, carbonyl, carbonyl(1-3C)alkylene, CONH, (1-2C) alkyleneNHCO and CONH(1-3C)alkylene, and when T is CH, oxy, oxy(1-3C)alkylene, oxy(1-2C)alkylenecarbonyl or oxy(1-2C)alkylenephenylene; or, when n is 0, X¹ together with M² may form a group of formula

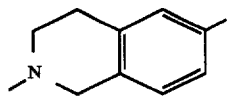

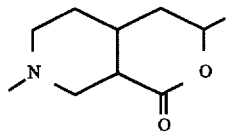

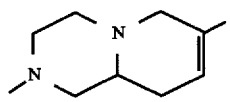

Examples of values for X¹ are a bond, methylene, ethylene, propylene, 1-methylethylene, ethenylene, ethynylene, methylenephenylene, phenyleneoxy, phenyleneoxymethylene, phenylenecarbonyl, phenyleneCONH, methylenecarbonyl, ethylenecarbonyl,1-methylethylenecarbonyl, ethylidinecarbonyl, 2-propylidinecarbonyl, benzylmethylenecarbonyl, p-hydroxybenzylmethylenecarbonyl, methylidenepyrrolidin-1-ylacetyl, methylenecarbonyloxy, methyleneCONH, methyleneCONHmethyleneCONH, benzylmethyleneCONH, methyleneoxy, ethyleneoxy, propyleneoxy, butylencoxy, methyleneoxymethylene, methyleneoxymethylenecarbonyl, methyleneCH(OH), and, when M² is —NR⁴-D-TR⁵—, carbonyl, carbonylmethylene, carbonylethylene, CONH, methyleneNHCO, CONHmethylene, and when T is CH; oxy, oxymethylene, methyleneNHCO, oxymethylenecarbonyl and oxymethylenephenylene. Particularly preferred values for X¹ include methylenecarbonyl, ethylenecarbonyl ethylidinecarbonyl, carbonyl, carbonylethylene, methyleneoxy, ethyleneoxy and, when M² is —NR⁴-D-TR⁵— and T is CH; oxy.

Y is a cyclic group, including groups of formulae:

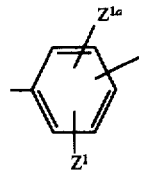 (a)

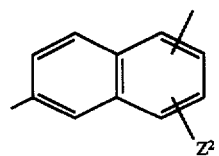 (b)

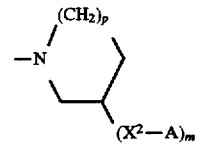 (c)

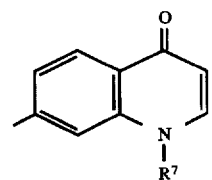 (d)

in which m is 0 or 1, p is 1 or 2, q is 0,1,2 or 3, $Z^1$, $Z^{1a}$ and $Z^2$ represent hydrogen or optional substituents, including hydroxy, halogeno, (1–4C)alkyl, (2–4C)alkenyl, (2–4C)alkynyl, (1–4C)alkoxy, (1–4C)alkylthio, (2–4C)alkenyloxy, nitro, amino, (1–4C)alkylamino, (2–4C)alkanoylamino, cyano and (1–4C)alkoxycarbonyl, or have one of the meanings given for $X^2$-A, $Z^3$ represents hydrogen or hydroxy, $R^7$ is hydrogen, (1–4C)alkyl or phenyl(1–4C)alkyl, $R^8$ is as defined for $R^7$, and E is O, S or NH; and $R^{11}$ is hydrogen, (1–4C)alkyl, phenyl(1–4C)alkyl or a group of formula $X^2$-A; or Y is an amide-containing group, including $CONR^{22}$, $NR^{22}CO$ and a group of formula in which $R^{22}$ represents hydrogen, (1–4C)alkyl or phenyl (1–2C)alkyl.

Preferred groups of formula (a) are groups in which $X^1$ and $X^2$ are attached respectively at the 1 and 3 or 1 and 4 positions. $Z^1$ is preferably located ortho to $X^2$; that is to say at the 2 or 6 position. Examples of such groups include 1,3-phenylene, 5-methoxycarbonylmethoxy-1,3-phenylene, 5-carboxymethoxy-1,3-phenylene, 1,4-phenylene, 2-methoxy-1,4-phenylene, 3-methoxy-1,4-phenylene, 2,6-dichloro-1,4-phenylene, 2,6-di-tert-butyl-1,4-phenylene, 2-carboxymethoxy-1,4-phenylene, 2-methoxycarbonylmethoxy-1,4-phenylene and 2-ethoxycarbonylmethoxy-1,4-phenylene, 3-methyl-1,4-phenylene, 2-allyl-1,4-phenylene, 2-propyl-1,4-phenylene, 2-nitro-1,4-phenylene, 2-methyl-1,4-phenylene, 3-methoxycarbonylmethoxy-1,4-phenylene, 3-ethoxycarbonylmethoxy-1,4-phenylene, 3-carboxymethoxy-1,4-phenylene, and 2-tert-butyloxycarbonylmnethyloxy-1,4-phenylenie.

Examples of values for $Z^1$, $Z^{1a}$ and $Z^2$ are hydrogen, hydroxy, chloro, fluoro and bromo, methyl, ethyl, propyl, t-butyl, allyl, methoxy, methylthio, allyloxy, nitro, cyano, methoxycarbonyl, carboxymethoxy, methoxycarbonylmethoxy, ethoxycarbonylmethoxy and tert-butyloxycarbonylmethoxy.

Examples of values for $R^7$, $R^8$ and $R^{11}$ are hydrogen, methyl and benzyl.

When Y is a group of formula (c), preferably m is 0 and p is 2.

Y is preferably a 1,2-, 1,3- or 1,4-phenylene group of formula (a); a napth-1,6-diyl group of formula (b); a piperidin-4,1-diyl group of formula (c) a 4-quinolon-3,7-diyl group of formula (d); a tetralon-6,2-diyl group of formula (e); a benzofuran-2,5-diyl group of formula (f); a 4-quinolon-7,3-diyl group of formula (i); a cyclohexa-4,1-diyl group of formula (k); a piperidin-3,1-diyl group of formula (l); a pyridin-2,5-diyl or pyridin-2,6-diyl group of formula (m); a quinolin-6,2-diyl or quinolin-6,4-diyl group of formula (n); a naphth-1,4-diyl group of formula (o); a 2-pyridon-4,1-diyl group of formula (p); a 4-pyridon-2,5-diyl group of formula (q), a piperidin-1,4-diyl group of formula (r); a cyclohexa-3,1-diyl group of formula (s); a piperidin-1,3-diyl group of formula (t), CONH, NHCO or a 2-carboxyethylidinecarboxamido group.

Examples of values for Y are 1,2-phenylene; 1,3-phenylene; 5-methoxycarbonyl-1,3-phenylene; 1,4-phenylene; 2,6-dichloro-1,4-phenylene; 2-methyl-1,4-phenylene; 2-propyl-1,4-phenylene; 2-allyl-1,4-phenylene; 2,6-di-tert-butyl-1,4-phenylene; 2-methoxy-1,4-phenylene; 3-methoxy-1,4-phenylene; 2-carboxymethoxy-1,4-phenylene; 2-methoxycarbonylmethoxy-1,4-phenylene; 2-ethoxycarbonylmethoxy-1,4-phenylene; 2-tert-butyloxycarbonylmethoxy-1,4-phenylene; 3-carboxymethoxy-1,4-phenylene; 3-methoxycarbonylmethoxy-1,4-phenylene; 2-nitro-1,4-phenylene; naphth-1,6-diyl; piperidin-4,1-diyl; 3-carboxymethoxypiperidin-4,1-diyl; 1-ethyl-4-quinolon-3, 7-diyl; 1-propyl-4-quinolon-3,7-diyl; tetralon-6,2-diyl; benzofuran-2,5-diyl; 1-benzyl-4-quinolon-7,3-diyl; 1-hydroxycyclohexa-1,4-diyl; piperidin-3,1-diyl; pyridin-2, 5-diyl; pyridin-2,6-diyl; quinolin-6,2-diyl; quinolin-6,4-diyl; naphth-1,4-diyl; 2-pyridon-4,1-diyl; 1-benzyl-4-pyridon-2,5-diyl; piperidin-1,4-diyl; cyclohexa-3,1-diyl; piperidin-1,3-diyl; CONH and 2-carboxyethylidenecarboxamido.

$X^2$ is a bond or a linking group, including, (1–4C) alkylene, (2–4C)alkenylene, oxy(1–4C)alkylene, oxy(5–6C) alkylene, oxy(2–4C)alkenylene, thio(1–3C)alkylene, $SO_2$ (1–3C)alkylene, amino(1–3C)alkylene, $SO_2NH$(1–3C) alkylene, $NR^{21}$ CO(1–2C)alkylene, $CONR^{21}$ (1–2C) alkylene (where $R^{21}$ represents hydrogen, (1–4C)alkyl or benzyl), in any of which the alkylene group may optionally be substituted by (2–4C)alkenyl; (2–4C)alkynyl; (1–4C) alkoxy; carboxy; (1–4C)alkoxycarbonyl; phenyl(1–4C) alkoxycarbonyl; phenyl(1–2C)alkylNHCO; carboxy(1–2C) alkyl; phenyl(1–2C)alkyl; phenylsulphonyl(1–2C)alkyl; pyridyl, phenyl; amino or a group of formula $NR^{12}XR^6$ in which X is $SO_2$, CO or $CO_2$; $R^{12}$ is hydrogen or (1–4C)alkyl and $R^6$ is (1–6C)alkyl, (6–10C)aryl, (6–10C)aryl(1–4C) alkyl, di(1–4C)alkylamino(1–4C)alkyl, morpholino(1–4C) alkyl, piperidino(1–4C)alkyl or N-(1–4C)alkylpipenidino (1–4C)alkyl.

Examples of values for $X^2$ are a bond, methylene, ethylene, ethenylene, oxymethylene, 2-oxyethylene, 3-oxypropylene, 2-oxyprop-2-ylene, 4-oxybutylene, 5-oxypentylene, thiomethylene, aminomethylene, carboxamidomethylene, 2-carboxamidoethylene, 2-phenylethylidene, oxy(imethoxycarbonyl )methylene, 1-(2-carboxyethyl)ethylene,1-(benzyloxycarbonyl)ethylene, and groups of formula $CH_2CH(NR^{12}XR^6)$ such as 1-(butylsulphonylamino)ethylene [$CH_2CH$ $(NHSO_2CH_2CH_2CH_2CH_3)$ ], 1-(methylsulphonylamino) ethylene, 1-(benzylsulphonylamino)ethylene, 1-(p-toluenesulphonylamino)ethylene, 2-(butylsulphonylamino) ethylene, 2-(p-toluenesulphonylamino)ethylene, 3-oxy(1-(butylsulphonylamino)propylene), 2-carboxamido(2-phenyl)ethylene and 2-carboxamidopropylene.

Examples of values for L when it represents (4–7C) alkylene include butylene, pentylene and hexylene.

A is an acidic group, including carboxy or an ester or amide thereof, an acyl sulphonamide group of formula $CONHSO_2R^9$, including groups in which $R^9$ is (1–4C)alkyl or optionally substituted phenyl; a 1H-tetrazol-5-yl group or a sulphonamide group of formula $NHSO_2R^{10}$ in which $R^{10}$ is (1–6C)alkyl such as methyl or butyl; fluoro(1–6C)alkyl such as trifluoromethyl; or phenyl unsubstituted or substituted by one or two optional substituents selected from (1–4C)alkyl, (1–4C)alkoxy and halogen; for example p-tolyl.

A is preferably a carboxy group, a (1–4C)alkoxycarbonyl group such as methoxycarbonyl, ethoxycarbonyl, propoxycarbonyl, isopropoxycarbonyl, or tert-butoxycarbonyl, a (1–6C)alkylsulphonamide group such as methanesulphonylamino, butylsulphonylaamino, or p-tolylsulphonylaimno.

Accordingly, particularly preferred groups of formula Y-$X^2$-A are 2-(4-phenoxy)acetic acid and 2,2'-(4-phenylene-1,2-dioxy)diacetic acid.

One group of compounds of particular interest is that of general formula Ia

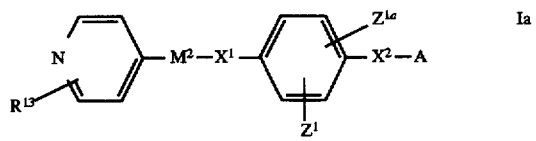

in which $M^2$, $X^1$, $Z^1$, $Z^{1a}$ and $X^2$ are as defined hereinabove; A is a carboxyl group or an ester thereof as defined hereinabove, and $R^{13}$ is hydrogen, (1–4C)alkyl, (1–4C) alkoxy or halogen.

Another group of compounds of particular interest is that of general formula Ib

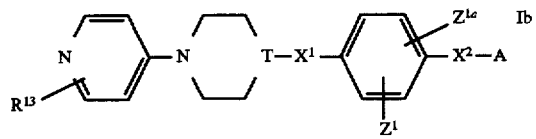

in which T, $X^1$, $Z^1$, $Z^{1a}$, $X^2$, $R^{13}$ and A are as defined hereinabove.

Another group of compounds of particular interest is that of general formula Ic

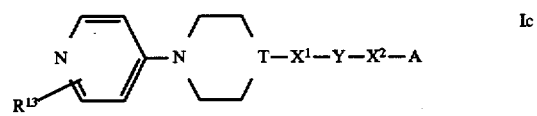

in which T, $X^1$, Y, $X^2$, $R^{13}$ and A are as defined hereinabove.

Another group of compounds of particular interest is that of general formula Id

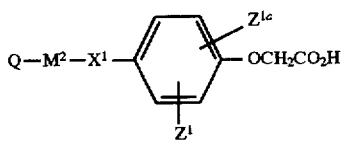

in which Q, $M^2$, $X^1$, $Z^1$ and $Z^{1a}$, are as defined hereinabove, and the ester or amide derivative thereof and pharmaceutically acceptable salts and pro-drugs thereof.

Another group of compounds of particular interest is that of general formula Ie

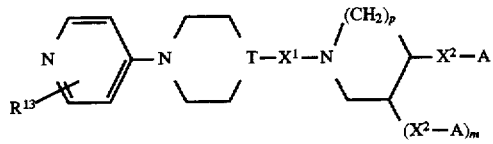

in which $X^1$, $X^2$, $R^{13}$, m, p and A are as defined hereinabove.

Another group of compounds of particular interest is that of general formula If

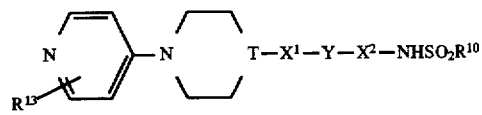

in which T, $X^1$, Y, $X^2$, $R^{13}$ and $R^{10}$ are as defined hereinabove.

Examples of values for $R^{13}$ are methyl, methoxy and chloro.

A particularly preferred group of compounds is that of formula Ia in which $M^2$ is piperazin-1,4-diyl, piperidin-4,1-diyl or 2-oxopiperazin-1,4-diyl.

Two preferred sub-groups of compounds of formula Ia may be identified. One consists of those compounds of formula Ia in which $X^1$ represents a bond. In this sub-group, $X^2$ preferably represents an oxy(2–4C)alkylene group, especially an oxypropylene group, optionally substituted on the alkylene group as defined hereinabove. The other consists of those compounds of formula Ia in which $X^2$ represents oxymethylene. In this sub-group $X^1$ preferably represents methylenecarbonyl.

Examples of specifically preferred compounds are those of Examples 1, 2, 50, 51, 61, 62, 240, 241, 242 and 243 herein.

Examples of ester derivatives of a carboxy group are esters formed with alcohols such as (1–6C)alkanols, for example methanol, ethanol, propanol, isopropanol and ter-t.butanol; indanol; adamantol; (1–6C)alkanoyloxy(1–4C) alkanols such as pivaloyloxymethanol; glycolamides; (S-methyl-2-oxo-1,3-dioxol-4-yl)methyl alcohol; and (1–4C)alkoxycarbonyl(1–4C)alkanols. It will be appreciated that compounds of formula I in which Y is a group of formula (a) or (b) in which $Z^1$ or $Z^2$ is hydroxy may form internal esters. An example of such an internal ester is a compound in which $X^1.Y.X^2.$A represents:

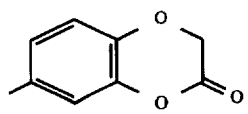

Examples of amide derivatives of a carboxy group include amides derived from ammonia or amines such as (1–4C) alkylamines, for example methylamine; di(1–4C) alkylamines); C(1–4C)alkoxy(1–4C)alkylamines such as methoxyethylaminie; phenyl(1–2C)alkylamines such as benzylamine; and amino acids such as glycine or an ester thereof.

Examples of pro-drugs of compounds of formula I include compounds possessing metabolically labile groups, in other words groups that are cleaved in vivo to afford a compound of formula I. Such groups include metabolically labile ester and amide derivatives. It will be appreciated that certain of the compounds of general formula I are in the form of enantiomers. It will be understood that the invention includes any enantiomer which has the property of inhibiting platelet aggregation and the binding of adhesion molecules to GPIIb-IIIa, whether present in a mixture with the other enantiomer (for example in a racemic mixture), or substantially free of the other enantiomer.

As used in this specification, the terms alkyl, alkylene, alkenylene or alkynylene include branched and unbranched groups. However, where specific terms are used, for example propyl, isopropyl or propylene, these indicate whether the group is branched or not. Diradicals, for example 2-oxo-piperazin-1,4-diyl, are numbered assuming that formula I is read from right to left with the group A being at the right hand side, as depicted in formula I hereinabove. Hence, for example, 2-oxo-piperazin-1,4-diyl signifies the group:

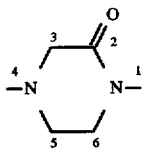

It will be appreciated that in this specification, the order of the two numbers immediately preceding the term "diyl" in the name of a diradical signifies the orientation of the diradical in a compound of formula I. Thus the first number signifies the position in the diradical closest to the group A. For example, the diradical represented by formula (d) hereinbefore is named herein as a 4-oxoquinolon-3,7-diyl group whereas the diradical represented by formula (i) is named herein as a 4-oxoquinolon-7,3-diyl group. Particular pharmaceutically acceptable salts include, for example, salts with acids affording physiologically acceptable anions, such as salts with mineral acids, for example a hydrogen halide (such as hydrogen chloride and hydrogen bromide), sulphulic acid or phosphoric acid, and salts with organic acids, for example trifluoroacetic acid. Other pharimaceutically acceptable salts include, for example salts with inorganic bases such as alkali metal and alkaline earth metal salts (for example sodium salts), ammonium salts, and salts with organic amines and quaternary bases forming physiologically acceptable cations such as salts with methylamine, dimethylamine, trimethylamine, ethylenediamine, piperiidine, morpholine, pyrrolidine, piperazine, ethanolamine, triethanolamine, N-methylglucanmne, tetramethylammonium hydroxide and benzyltiimethylammonium hydroxide. Many of the compounds of formula I, and the pharmaceutically acceptable salt and pro-drugs thereof, are novel, and accordingly are provided as one aspect of the invention.

According to another aspect, the invention provides a process for preparing a compound of general formula I, or a metabolically labile ester or amide thereof, or a pharmaceutically acceptable salt thereof, which comprises (A) For a compound of formula I in which n is 0 and $M^2$ is $NR^3$ or —$NR^4$-D-$NR^5$—, reacting a compound of formula $Q-M^2H$ or an acid addition salt thereof with a compound of formula $$U^1.L.A \qquad \qquad III$$

in which $U^1$ is a leaving atom or group.

Examples of values for $U^1$ include halogen, such as chlorine or bromine, and hydrocarbylsulphonyloxy, such as methanesulphonyloxy and p-toluenesulphonyloxy. When the group in L to which $U^1$ is attached is a carbonyl group, $U^1$ may also represent a hydroxy group or a reactive derivative thereof. Examples of reactive derivatives of a hydroxyl group include acyloxy groups such as acetyloxy, and groups formed in situ by reacting a compound of formula III in which $U^1$ is hydroxy with a peptide coupling reagent. Examples of peptide coupling reagents include carbodiimides such as 1,3-dicyclohexylcarbodiiminde (DCC) preferably in combination with 1-hydroxybenzotriazole hydrate (HOBT). Examples of acid addition salts include, for example the hydrochlorides. The reaction may conveniently be effected at a temperature in the range of from −10° to 120° C., preferably from 10° to 100° C. Suitable solvents include, for example, ethers such as tetrahydrofuran, amides such as dimethylformamide, nitriles such as acetonitrile, halogenated hydrocarbons such as dichloromethane and alcohols such as ethanol or isopropanol. In some circumstances, for example when an acid addition salt of a compound of formula II is used as starting material, or when the compound of formula II is relatively unreactive, the reaction may advantageously be performed in the presence of a base. Examples of suitable bases include tertiary amines, such as triethylamine, and alkali metal hydroxides, carbonates and bicarbonates, such as sodium or potassium hydroxide, carbonate or bicarbonate. When the compound of formula II is relatively unreactive a strong base such as an alkali metal hydride, for example potassium hydride, may conveniently be used.

(B) For a compound of formula I in which A is carboxy, decomposing an ester of formula $$(M^1)_n\text{-}Q\text{-}(M^2)_{1-n}\text{-}L\text{-}COOR^{20} \qquad \qquad IV$$

in which $R^{20}$ is a carboxyl protecting group. $R^{20}$ may be any conventional carboxyl protecting group that may be removed without interfering with other parts of the molecule. Examples of carboxyl protecting groups include (1–6C)alkyl groups (such as methyl, ethyl, propyl or t-butyl), phenyl and benzyl, the phenyl moiety in any of which may optionally bear 1 or 2 of halogeno, (1–4C)alkyl, (1–4C)alkoxy or nitro.

The decomposition may be carried out using any one or more of the conventional reagents and conditions known in the art for converting carboxylic esters into carboxylic acids. Thus, for example, the decomposition may conveniently be performed by base catalysed hydrolysis, for example by using an alkali metal hydroxide such as lithium, potassium or sodium hydroxide or an amine such as triethylamine, in the presence of water. The base catalysed hydrolysis may conveniently be performed in the presence of a solvent such as an alcohol, for example methanol or ethanol, or an ether such as tetrahydrofuran or dioxan. Alternatively the decomposition may be carried out by acid catalysed hydrolysis, for example using aqueous acetic acid or trifluoroacetic acid. The temperature is conveniently in the range of from −10° to 100° C., for example from 10° to 50° C. When the alcohol residue is t-butyl, this may also conveniently be removed by heating, for example at a temperature in the range of from 80° to 150° C., alone or in the presence of a suitable diluent such as diphenylether or diphenylsulphone. A benzyl group may conveniently be removed by catalytic hydrogenation, for example by hydrogenation in the presence of palladium on carbon at a temperature in the range of from −10° to 100° C. in the presence of a solvent such as an alcohol, for example methanol or ethanol.

(C) For a compound of formula I in which L represents $X^1.Y.X^2$ and Y is a group of formula (c), reacting a compound of formula $$(M^1)_n\text{-}Q\text{-}(M^2)_{1-n}\text{-}X^1.U^2 \qquad \qquad V$$

in which $U^2$ is a leaving atom or group, or an acid addition salt thereof, with a compound of formula $$H.Y.X^2.A \qquad \qquad VI$$

or an acid addition salt thereof, in which $X^2$ and A are as defined hereinabove and Y is a group of formula (c) as defined hereinabove.

Examples of values for $U^2$ include halogen, such as chlorine or bromine, and hydrocarbylsulphonyloxy, such as methanesulphonyloxy and p-toluenesulphonyloxy. When the group in $X^1$ to which $U^2$ is attached is a carbonyl group, $U^2$ may also represent a hydroxy group or a reactive derivative thereof. Examples of reactive derivatives of a hydroxyl group include acyloxy groups such as acetyloxy, and groups formed in situ by reacting a compound of formula V in which $U^2$ is hydroxy with a peptide coupling reagent. Examples of peptide coupling reagents include carbodiimides such as 1,3-dicyclohexylcarbodiimide (DCC), preferably in combination with 1-hydroxybenzotriazole hydrate (HOBT). Examples of acid addition salts include, for example the hydrochlorides. The reaction may conveniently be effected at a temperature in the range of from −10° to 120° C., preferably from 10° to 100° C. Suitable solvents include, for example, ethers such as tetrahydrofuran, amides such as dimethylformamide, nitriles such as acetonitrile, halogenated hydrocarbons such as dichloromethane and alcohols such as ethanol. In some circumstances, for example when an acid addition salt of a compound of formula VI is used as starting material, the reaction may advantageously be performed in the presence of a base. Examples of suitable bases include tertiary amines, such as triethylamine, and alkali metal hydroxides, carbonates and bicarbonates, such as sodium or potassium hydroxide, carbonate or bicarbonate.

(D) For a compound of formula I in which n is 0, reacting a compound of formula $$Q\text{-}U^3 \qquad \qquad VII$$

in which $U^3$ is a leaving atom or group, with a compound of formula $$H.M^2.L.A \qquad \qquad VIII$$

or an acid addition salt thereof, in which L and A are as defined hereinabove. Examples of values for $U^3$ include halogen, such as chlorine or bromine, and cyano. Examples of acid addition salts include, for example the hydrochlorides. The reaction may conveniently be effected at a temperature in the range of −10° to 120° C., preferably from 10° to 100° C. Suitable solvents include, for example, ethers such as tetrahydrofuran and dioxan, amides such as dimethylformamide, nitriles such as acetonitrile, halogenated hydrocarbons such as dichloromethane, alcohols such as ethanol and water.

In some circumstances, for example when an acid addition salt of a compound of formula VIII is used as starting material, the reaction may advantageously be performed in the presence of a base. Examples of suitable bases include tertiary amines, such as triethylamine, and alkali metal hydroxides, carbonates and bicarbonates, such as sodium or potassium hydroxide, carbonate or bicarbonate.

(E) For a compound of formula I in which L is $X^1.Y.X^2$ and $X^1$ comprises a CONH group, reacting the appropriate carboxylic acid of formula

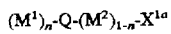
$(M^1)_n\text{-}Q\text{-}(M^2)_{1-n}\text{-}X^{1a}$  IX in which $X^{1a}$ is a residue of a carboxylic acid group, or a reactive derivative thereof, with the appropriate amine of formula

$X^{1b}.Y.X^2.A$  X in which $X^{1b}$ is a residue of an amine group.

Examples of values for $X^{1a}$ are (1–2C)alkyleneCOOH, benzyl(1–2C)alkyleneCOOH and COOH. Examples of values for $X^{1b}$ are $H_2N$ and $H_2N(1\text{-}3C)$alkylene.

Examples of reactive derivatives of the compounds of formula IX include acyl halides such as the chlorides and bromides, and groups formed in situ by reacting a residue of a carboxylic acid with a peptide coupling reagent, such as carbodimide, for example 1,3-dicyclohexylcarbodimide, preferably in combination with 1-hydroxybenzotriazole hydrate (HOBT).

The reaction is conveniently performed at a temperature in the range of from 0° to 100° C. Suitable solvents include halogenated hydrocarbon such as methylene chloride, amide, such as dimethylformamide and tertiary amines such as triethylamine.

(F) For a compound of formula I in which L is $X^1.Y.X^2$ and $X^1$ is (2–4C)alkenylene, reactinog a compound of formula

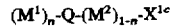
$(M^1)_n\text{-}Q\text{-}(M^2)_{1-n}\text{-}X^{1c}$  XI in which $X^{1c}$ is an appropriate aldehyde-containing group with the appropriate Wittig reagent of formula

$X^{1d}.Y.X^2.A$  XII in which $X^{1d}$ is a triarylphosphonylalkylene group such as triphenylphosphinylmethylene.

The reaction is conveniently performed at a temperature in the range of from –20° to 50° C., preferably from 0° to 25° C. Convenient solvents include ethers such as tetrahydrofuran, sulphoxides such as dimethylsulphoxide and aromatic hydrocarbons such as toluene.

(G) For a compound of formula I in which L is $X^1.Y.X^2$ and $X^1$ comprises an oxy (ether) link, reacting the appropriate compound of formula

$(M^1)_n\text{-}Q\text{-}(M^2)_{1-n}\text{-}X^{1e}$  XIII with the appropriate compound of formula

$X^{1f}.Y.X^2A$  XIV in which one of $X^{1e}$ and $X^{1f}$ is a residue of an alcohol group, and the other is a residue of an alcohol group or a group containing a leaving atom or group.

When $X^{1e}$ and $X^{1f}$ both represent residues of alcohol groups, the reaction may conveniently be effected in the presence of a dehydrating agent such as diethyl azodicarboxylate-triphenylphosphinc. Suitable solvents for the reaction include ethers such as tetrahydrofuran, and amides such as dimethylformamide. The reaction is conveniently effected at a temperature in the range of from 0° to 50° C.

(H) For a compound of formula I in which $X^2$ is $CH_2CH(NHXR^6)$ reacting a compound of formula

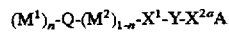
$(M^1)_n\text{-}Q\text{-}(M^2)_{1-n}\text{-}X^1\text{-}Y\text{-}X^{2a}A$  XV in which $X^{2a}$ is $CH_2CH(NH_2)$, or an acid addition salt thereof, with a compound of formula

$R^6.X.U^4$  XVI in which $U^4$ is a leaving atom or group.

Examples of values for $U^4$ include halogen, such as chlorine or bromine. Examples of acid addition salt include for example, the hydrochloride. The reaction may conveniently be effected at a temperature in the range of from –10° to 120° C. preferably from 10° to 100° C. Suitable solvents include for example ethers such as tetrahydrofuran, amides such as dimethylformamide, nitriles such as acetonitrile, halogenated hydrocarbon such as dichloromethane and alcohols such as ethanol. The reaction is conveniently performed in the presence of a base, for example a tertiary amine such as triethylamine.

(I) For a compound of formula I in which L is $X^1.Y.X^2$ and $X^2$ represents oxyalkylene or oxyalkenylene, reacting a compound of formula

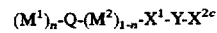
$(M^1)_n\text{-}Q\text{-}(M^2)_{1-n}\text{-}X^1\text{-}Y\text{-}X^{2c}$  XVIII with the appropriate compound of formula

$X^{2d}\text{-}A$  XIX in which $X^{2c}$ is a hydroxy group, or a reactive derivative thereof (such as a halide), and $X^{2d}$ is a hydroxyalkylene or hydroxyalkenylene group, or a reactive derivative thereof (such as a halide, for example a bromide).

The reaction is conveniently performed in the presence of a strong base, such as an alkali metal hydride, for example, sodium hydride. Suitable solvents include amides, such as dimethylformamide. The reaction is conveniently performed at a temperature in the range of from 0° to 1 00C.

(J) For a compound of formula I in which L is $X^1.Y.X^2$ and $X^2$ represents CONHalkylene, reacting a compound of formula

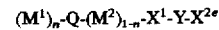
$(M^1)_n\text{-}Q\text{-}(M^2)_{1-n}\text{-}X^1\text{-}Y\text{-}X^{2e}$  XX with the appropriate compound of formula

$X^{2f}\text{-}A$  XXI in which $X^{2e}$ represents a carboxyl group or a reactive derivative thereof (such as an acyl halide, for example an acyl chloride, or anhydride) and $X^{2f}$ represents an aminoalkylene group, or an acid addition salt thereof (such as a hydrochloride).

Suitable solvents include tertiary amines such as triethylamine halogenated hydrocarbons such as methylene chloride and amides such as dimethylformamide. The reaction is conveniently performed at a temperature in the range of from 0° to 100° C.

(K) For a compound of formula I in which L is $X^1.Y.X^2$ and $X^1$ represents CONH or CONHalkylene, reacting a compound of formula II with a compound of formula

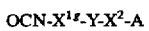    XXII in which $X^{1g}$ is a bond or an alkylene group.

The reaction is conveniently performed at a temperature in the range of from 0° to 100° C. Suitable solvents include halogenated hydrocarbons, such as dichloromethane.

(L) For a compound of formula I in which L is $X^1$-Y-$X^2$ and A is $NHSO_2R^{10}$, reacting a compound of formula

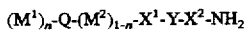    XXIV with a compound of formula

    XXV in which $U^5$ is a leaving atom or group, such as a halogen atom, for example a chlorine atom.

The reaction is conveniently performed in the presence of a base such as a tertiary amine, for example triethylamine, and at a temperature in the range of from −10° to 40° C. Suitable solvents include amides such as dimethylformamide and halogenated hydrocarbons such as dichloromethane.

(M) For a compound of formula I in which L is $X^1.Y.X^2$ and $X^1$ is (1–2C)alkylenecarbonyloxy, reacting a compound of formula

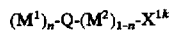    XXVI in which $X^{1k}$ represents (1–2C)alkylenecarboxy or a reactive derivative thereof, with a compound of formula

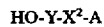    XXVII

The reaction is conveniently performed at a temperature in the range of from 0° to 100° C. Suitable solvents include halogenated hydrocarbons such as dichloromethane.

(N) For a compound of formula I in which L represents $X^1.Y.X^2$, $X^1$ represents (1–3C)alkylenecarbonyl and Y represents a phenylene group of formula (a), reacting a compound of formula

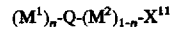    XXVIII in which $X^{11}$ represents a (1–3C)alkylenecarboxyl group, or a reactive derivative thereof, with a compound of formula VI in the presence of a Lewis acid.

Example of suitable Lewis acids include aluminium trichloride. Examples of reactive derivatives of compounds of formula XXVIII include the halides, such as the chlorides.

The reaction is conveniently performed at a temperature in the range of from −10° to 50° C. Suitable solvents include halogenated hydrocarbons, such as dichloromethane.

(O) For a compound of formula I in which L represents $X^1.Y.X^2$ and $X^2$ represents $NR^{21}CO(1-2C)$alkylene, reacting a compound of formula

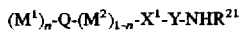    XXX with a compound of formula

-A    XXX in which $X^{2h}$ represents a carboxy(1–2C)alkyl group, or a reactive derivative thereof.

Examples of reactive derivatives of compounds of formula XXX include halides, such as chlorides, and anhydrides.

The reaction is conveniently performed at a temperature in the range of from 0° to 100° C. Suitable solvents include amides such as dimethylformamide.

Certain compounds of formula I may be converted into other compounds of formula I using conventional methods. For example, a compound of formula I in which L represents $X^1.Y.X^2.A$ in which $X^1$ is a (2–4C)alkylene group may be prepared by hydrogenating a corresponding compound of formula I in which $X^1$ represents a (2–4C)alkenylene group. The hydrogenation may be effected, for example, in the presence of palladium on charcoal and in a suitable solvent such as an alcohol, for example ethanol. A compound of formula I in which L represents $X^1.Y.X^2.A$ in which $X^1$ is (1–3C)alkyleneCH(OH) may be prepared by reducing a corresponding compound of formula I in which $X^1$ is (1–3C)alkylenecarbonyl. The reduction may be effected, for example, using an alkali metal borohydride such as sodium borohydride.

The intermediates used in the aforementioned processes are known or may be prepared by methods analogous to those known for the preparation of known compounds.

Thus, the compounds of formula IV may be prepared by methods analogous to processes (A) and (C) to (H) herein, but starting from the appropriately protected starting materials. It will be appreciated that some compounds of formula IV are compounds according to the invention.

The compounds of formula II in which n is 0 and $M^2$ is a 2-oxopiperazin-1,4-diyl group may be prepared by reacting piperazinone with a compound of formula VII. The compounds of formula XV may be prepared by deprotecting a corresponding compound of formula:

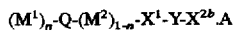    XVII wherein $X^{2b}$ is $CH_2CH(NHR^{11})$ and $R^{11}$ is an amine protecting group.

Examples of amine protecting groups include oxycarbonyl groups such as benzyloxycarbonyl. A benzyloxycarbonyl group may conveniently be removed, for example, by hydrogenation in the presence of a catalyst such as palladium on charcoal.

The compounds of formula XVII may be prepared by a method analogous to the preparation of a compound of formula I, but starting from the appropriate starting material. For example, if a compound of formula XVII in which $X^1$ is methyleneoxy and Y is phenylene, is desired this may be prepared by a method analogous to process (G) herein, starting with a compound of formula XIII and the appropriate N-protected derivative of tyrosine.

The compounds of formula XVIII may be prepared by reacting a compound of formula VII with a compound of formula

 XXIII in which $X^{2g}$ is a hydroxy group or a protected derivative thereof (for example a methoxy group), followed if necessary by the removal of any protecting group, (for example by treatment with hydrobromic acid) and, if desired, conversion of the hydroxy group into a reactive derivative thereof by a known method.

Many of the intermediates, for example compounds of formulae XV and XVII, and the compounds of formula II and VIII in which $M^2$ is 2-oxopiperazin-1,4-diyl are novel and form further aspects of this invention.

The compounds of formula I may be converted into pharmaceutically acceptable salts and/or metabolically labile esters or amides thereof by methods well known in the art. For example, a pharmaceutically acceptable salt may be formed by reacting a compound of formula I with an acid capable of affording a physiologically acceptable anion, or a base capable of affording a physiologically acceptable cation. A pharmaceutically acceptable metabolically labile ester or amide may be formed respectively by esterifying a compound of formula I using a conventional technique, or reacting an acid, or a reactive derivative thereof with the appropriate amine.

The ability of the compounds of formula I to inhibit platelet aggregation may be demonstrated using a standard test (a) based on that described by Born (*Nature*, 1962, 194, 927–929) and involving:

(i) aggregating human, citrated, platelet-rich plasma by addition of adenosine diphosphate so as to generate a dose-response curve;

(ii) generating a dose-response curve for ADP stimulated platelet aggregation in the presence of increasing amounts of a test compound (generally in the range $10^{-5}$M to $10^{-10}$M); and (iii) calculating a $pA_2$ value indicating potency of platelet aggregation inhibition for the test compound, averaged over several concentrations, from the calculated 50% response value for ADP aggregation in the presence and absence of the test compound.

Test (a) may be modified so as to assess the effects of a test compound ex vivo on the aggregation of human blood platelets after administration of the test compound to a laboratory animal, such as a rat, rabbit, guinea pig, mouse or dog. For example, groups of four male, fasted Alderley Park Wistar rats are orally dosed with a test compound or appropriate vehicle, and at suitable time intervals (1,3,5 and 8 hours after dosing) animals are anaesthetised with fluothane and bled by heart puncture. Blood is collected into 3.2% citrate (1 part to 9 parts whole blood) and platelet poor plasma (ppp) prepared by centrifugation (4500×g for 10 min).

Human blood is collected into 3.2% trisodium citrate (1 part to 9 parts whole blood) and centrifugated (200×g for 15 min) to produce platelet rich plasma (prp).

Equal volumes (125 µl) of rat ppp and human prp are mixed together, ADP added, and the whole incubated (37° C.) and stirred (900 rpm) in a BioData platelet aggregometer. Aggregation is induced with ADP and agonist $EC_{50}$ values calculated for human prp/rat ppp mixtures from animals dosed with test compound or vehicle. A mean concentration ratio (concentration of ADP required to cause a 50% aggregation response in human prp/rat ppp mixtures from animals dosed with antagonist, divided by the concentration of ADP to cause 50% aggregation in human prp/rat ppp mixtures from animals dosed with vehicle) is calculated at each time point.

The ability of the compounds of formula I to inhibit binding of fibrinogen to GPIIb-IIIa may be demonstrated using the following standard test (b) involving:

(i) Preparation of human platelet lysates.

Platelet rich plasma (PRP) is harvested by centrifugation (1000 rpm, 15 mins) of whole blood anticoaoulated with acid citrate dextrose (trisodium citrate 85 mM, citric acid 70 mM, d-glucose 110 mM) 1 part to 6 parts blood. Prostacyclin ($PGI_2$, 1 µM) is added to the PRP before centrifugation (2400 pm, 15 mins) and the resulting pellet is resuspended in modified Tyrodes' solution (NaCl 130 mM, KCl 26 mM, $NaHCO_3$ 12 mM, $NaH_2PO_4$ 0.5 mM, $MgCl_2$ 1 mM, $CaCl_2$ 20 mM, Glucose 12 mM, HEPES 5 mM) containing bovine serum albumin 3.5 g/L, $PGI2$ 1 µM and hirudin 0.5 U/ml. The platelet suspension is centrifuged (2400 rpm, 15 mins) and the resultant pellet resuspended in 500 µl of lysis buffer (octyl glucoside 50 mM, HEPES 10 mM, NaCl 150 mM, $CaCl_2$ 1 mM, $MgCl_2$ 1 mM, PMSF 1 mM, NEM 10 mM, leupeptin 0.1 mM), agitated at 4° C. for 15 minutes then centrifuged at 24000 rpm, 15 mins. The supernatant is stored at 4° C. and the pellet re-suspended in 500 µl of lysis buffer. The centrifugation process is repeated a further 3 tlimes, the pooled supernatants being stored at −70° C.

(ii) Receptor purification.

GP IIb/IIa is isolated from human platelet lysates using a 2 ml peptide (KYGRGDS) coupled CNBr activated Sepharose affinity column. A 1.5 ml volume of platelet lysate is placed on the column and allowed to stand overnight at 4° C. Buffer (30 mls, octyl gluicoside 25 mM, HEPES 10 mM, NaCl 150 mM, CaCl2 1 mM, MgCl2 1 mM, PMSF 1 mM, NEM 10 mM, leupeptin 0.1 mM) is passed through the column and 2 ml fractions are collected throughout. GPIIb/IIIa is eluted with 12 mls of buffer containing HHLG-GAKQAGDV (2 mg/ml, pH 7.5), the column is washed using 4 mls buffer and the remaining GPIIb/IIIa eluted using 12 mls buffer containing GRGDSPG (1 mg/ml pH 7.5). The column is finally washed using 20 mls of buffer and can be used for up to three such preparations. Fractions containing FGPIIb/IIIa are identified using gel electrophoresis and immunoblotting, pooled and stored at −70° C.

(iii) GPIIb/IIIa ELISA 96 well microtitre plates are coated with 100 µl purified human platelet fibrinogen receptor (GPIIb/IIIa) diluted in coating buffer (Tris-HCl 20 mM, NaCl 150 mM, $CaCl_2$ 1 mM, pH 7.4) and left overnight at 4° C. The plates are washed using washing buffer (Tris-HCl 50 mM, NaCl 100 mM, $CaCl_2$ 2 mM, pH 7.4) and non-specific binding, blocked by the addition of 200 µl 2% BSA (2 hours, 30° C.). The plates are washed prior to incubation (2 hours, 30° C.) with 100 µl biotinylated fibrinogen (10 nm) containing either vehicle or test compound. The plates are washed, incubated with streptavidin (5 µg/ml, 1 hour, ambient temperature), then washed again before the addition of 100 µl biotinylated horse radish peroxidase (0.1 µg/ml, 1 hour, ambient temperature). The plates are then washed and equal volumes of peroxidase substrate (3, 5, tetramethyl benzidine 0.4 g/l) and $H_2O_2$ (0.02%) are mixed together immediately before addition of 150 µl to each well. Colour is allowed to develop for 10–15 mins before optical densities are read at 650 nM.

| Abbreviations | |
|---|---|
| PMSF | Phenylmethylsulphonylfluoride |
| HEPES | (N-[2-Hydroxyethyl]piperazine-N-[2-ethanesulphonic acid] |
| NEM | N-ethyl maleimide |

The concentration of compound required to cause 50% inhibition of biotinylated fibrinogen binding, is calculated and expressed as a $pIC_{50}$ ($-\log(IC_{50})$).

In general, test compounds shiowing activity in this test show a $pIC_{50}$ of greater than about 4.0.

The effects of each of the compounds of formula I exemplified herein in the above tests are gyiven in the table below. Where a range of values is given, the compound has been tested more than once. A dash (—) signifies that a compound has not been tested.

TABLE OF BIOLOGICAL TEST RESULTS

| Example | Test (a) | Test (b) |
|---|---|---|
| 1 | 6.5–6.8 | 5.8–6.4 |
| 2 | 7.1–7.3 | 7.6 |
| 3 | 6.3 | 6.6 |
| 4 | 8.9 | 9.1 |
| 5 | 6.0 | 6.0 |
| 6 | 7.2 | 7.6 |
| 7 | 6.3 | 5.2–5.4 |
| 8 | 6.5 | 7.1 |
| 9 | 4.9 | 4.3 |
| 10 | 5.7 | 6.0 |
| 11 | 5.7 | 4.4 |
| 12 | 6.3 | 7.2 |
| 13 | 5.3 | 4.4–4.8 |
| 14 | 5.1 | <4 |
| 15 | 5.6 | 5.9 |
| 16 | 6.8 | 6.7 |
| 17 | 7.4 | 7.7 |
| 18 | 6.3 | 6.5 |
| 19 | 5.6 | 5.7 |
| 20 | 5.3 | 4.8 |
| 21 | 6.8–7.2 | 6.3–6.8 |
| 22 | 6.7–6.9 | 5.4 |
| 23 | 6.0 | 4.5–5.2 |
| 24 | 5.7 | 4.5 |
| 25 | 5.1 | 4.8 |
| 26 | 5.8 | 6.2 |
| 27 | 5.1 | 5.6 |
| 28 | 4.7 | 5.7 |
| 29 | — | — |
| 30 | 5.3 | 5.9 |
| 31 | — | — |
| 32 | 6.7 | 7.3 |
| 33 | 6.4 | 6.9 |
| 34 | 8.7 | 8.7 |
| 35 | 6.4 | 7.2 |
| 36 | 8.7 | 9.0 |
| 37 | 5.6 | 6.7 |
| 38 | 7.5 | 8.7 |
| 39 | 4.6 | 6.6 |
| 40 | 7.1 | 7.7 |
| 41 | <4 | <4 |
| 42 | 4.3 | 5.2 |
| 43 | 4.4 | 5.5 |
| 44 | 5 | 7 |
| 45 | 5.4 | 6.1 |
| 46 | 6 | 7.6 |
| 47 | 5.2 | 4.4 |
| 48 | 5.0 | 6.6 |
| 49 | 7.1 | 8.2 |
| 50 | 6.0–6.1 | <4 |
| 51 | 7–7.9 | 7.6–8.4 |
| 52 | 5 | <4 |
| 53 | 5.8 | 5.9 |
| 54 | 4.8 | <4 |
| 55 | 4.5 | 4.8 |
| 56 | 5.5 | 4.8 |
| 57 | 7.6 | 7.6 |
| 58 | 5.5 | 4.4 |
| 59 | 7.2 | 7.5 |
| 60 | 5 | 4.8 |
| 61 | 7.5 | 6.7 |
| 62 | 7.9–8.6 | 8.1 |
| 63 | 6.9 | 6.5 |
| 64 | 7.5 | 7.7 |
| 65 | 5.2 | 5.6 |
| 66 | 5.7 | 6.6 |
| 67 | 8.6 | 8.5 |
| 68 | 6.5 | 7.9 |
| 69 | 4.9 | 5.4 |
| 70 | 7.1 | 7.8 |
| 71 | 4.9 | 4.4 |
| 72 | 6.3 | 4.4 |
| 73 | 6.3 | 7.2 |
| 74 | 5 | 5.7 |
| 75 | 4.5 | 5.4 |
| 76 | 4.5 | 5.9 |
| 77 | 5.1 | 6.3 |
| 78 | 6.8 | 6.6 |
| 79 | 7.9 | 8.5 |
| 80 | 6.6 | 6.4 |
| 81 | 4.8 | 6.7 |
| 82 | 6.3 | 7.9 |
| 83 | 4.4 | 5.7 |
| 84 | 7.2 | 7.7 |
| 85 | 5.8 | 6.6 |
| 86 | 5.4 | 6.7 |
| 87 | 5.6 | 7.2 |
| 88 | 9 | 8.6 |
| 89 | 7.4 | 8.7 |
| 90 | 8 | 8.5 |
| 91 | 6.8 | 6.7 |
| 92 | 5.7 | 7.1 |
| 93 | 7.9 | 8.5 |
| 94 | 6.5 | 8.6 |
| 95 | 5 | 5.1 |
| 96 | 7.1 | 8.4 |
| 97 | 5.4 | 5.5 |
| 98 | 7.6 | 8.5 |
| 99 | 5.4 | 6.6 |
| 100 | 4.4 | 5.4 |
| 101 | 6.3 | 7.5 |
| 102 | 5.7 | 5.8 |
| 103 | 4.5 | 5.1 |
| 104 | <4 | 4.7 |
| 105 | 6.6 | 6.6 |
| 106 | 4.8 | 4.4 |
| 107 | 4.5 | <4 |
| 108 | 6.3 | 5.9 |
| 109 | 6.5 | 6.2 |
| 110 | 5.2 | <4 |
| 111 | 5.3 | 5.2 |
| 112 | 5.2 | 5.5 |
| 113 | <4 | 4.6 |
| 114 | <4 | 5.6 |
| 115 | 5.4 | <4 |
| 116 | 5.7 | 5.6 |
| 117 | 4.9 | 5.4 |
| 118 | 6.7 | 6.4 |
| 119 | 4.5 | <4 |
| 120 | 5.4 | 4.3 |
| 121 | 5.9 | 5.4 |
| 122 | 6.2 | 5.4 |
| 123 | 6.0 | 7.0 |
| 124 | 6.1 | 6.6 |
| 125 | 6.8 | 7.8 |
| 126 | 4.8 | 5.5 |
| 127 | 5.8 | 6.7 |
| 128 | 6.8 | 6.3 |
| 129 | 7.9 | 6.5 |
| 130 | <4 | 5.4 |

TABLE OF BIOLOGICAL TEST RESULTS -continued

| Example | Test (a) | Test (b) |
|---|---|---|
| 131 | 4.6 | 4.5 |
| 132 | 4.2 | 4.5 |
| 133 | 5.7 | 4.5 |
| 134 | 4.8 | 4.6 |
| 135 | 4.5 | <4 |
| 136 | 6.9 | 5.6 |
| 137 | 7.2 | 5.5 |
| 138 | 5 | 4.9 |
| 139 | 6.6 | 5.4 |
| 140 | 5.8 | 6.3 |
| 141 | 4.5 | 4.5 |
| 142 | 5.3 | 5.3 |
| 143 | 5.0 | 4.5 |
| 144 | 5.3 | 5.3 |
| 145 | 5.5 | 5.3 |
| 146 | 5.1 | 5.2 |
| 147 | 6.4 | 6.2 |
| 148 | 7.3 | 7.5 |
| 149 | 4.7 | 4.7 |
| 150 | 6.5 | 6.5 |
| 151 | 6.2 | 5.4 |
| 152 | 7.0 | 7.0 |
| 153 | 4.8 | 4.3 |
| 154 | 5.0 | 5.6 |
| 155 | 5.5 | <4 |
| 156 | 4.7 | 5.8 |
| 157 | 6.5 | 7.1 |
| 158 | 6.2 | 7.0 |
| 159 | 6.3 | 5.7 |
| 160 | 6.1 | 7.8 |
| 161 | 4.9 | 4.3 |
| 162 | 4.7 | 6.2 |
| 163 | 6.4 | 6.6 |
| 164 | 8.1 | 7.2–7.4 |
| 165 | 5.9 | 4.7 |
| 166 | 5.8 | 6.5 |
| 167 | 6.6 | 6.7 |
| 168 | 6.1 | 6.4 |
| 169 | 4.4 | 5.0 |
| 170 | 4.8 | <4 |
| 171 | 5.2 | <4 |
| 172 | 5.2 | 4.3 |
| 173 | 5.9 | 6.7 |
| 174 | 6.4–6.8 | 8.0–8.3 |
| 175 | 5.9 | 6.2 |
| 176 | 6.7 | 8.0 |
| 177 | 5.8 | 4.1 |
| 178 | 5.5 | 6.0 |
| 179 | 4.8 | 5.4 |
| 180 | 5.5 | — |
| 181 | 6.5 | — |
| 182 | 5.1 | 4.7 |
| 183 | 4.5 | <4 |
| 184 | 5.3 | <4 |
| 185 | 5.4 | 4.8 |
| 186 | 5.3 | 5.9 |
| 187 | 4.8 | — |
| 188 | 6.0 | — |
| 189 | 5.9 | 6.5 |
| 190 | 4.2 | 4.7 |
| 191 | <4 | 5.4 |
| 192 | <4 | 6.6 |
| 193 | 4.4 | 6.6 |
| 194 | 5.4 | 6.9 |
| 195 | 5.6 | 6.8 |
| 196 | 4.0 | 5.2 |
| 197 | 4.2 | 4.8 |
| 198 | 6.1 | 7.7 |
| 199 | 6.3 | — |
| 200 | 7.9 | 8.4 |
| 201 | 4.3 | <4 |
| 202 | — | — |
| 203 | 7.2 | 8 |
| 204 | 7.1 | 8.9 |
| 205 | 6.6 | — |
| 206 | 6.6 | 8.0 |
| 207 | 6.5 | 6 |
| 208 | 6.5 | — |
| 209 | 6.7 | — |
| 210 | 6.5 | — |
| 211 | 5.8 | 6.8 |
| 212 | 7.1 | — |
| 213 | 6.7 | 6.3 |
| 214 | — | — |
| 215 | 6.9 | — |
| 216 | 5.7 | — |
| 217 | 6.5 | — |
| 218 | 6.0 | — |
| 219 | 7.5 | — |
| 220 | 5.5 | — |
| 221 | 6.8 | — |
| 222 | 6.5 | 5.6 |
| 223 | 6.0 | 5.8 |
| 224 | 4.5 | 6.3 |
| 225 | 6.8 | — |
| 226 | 4.7 | 5.5 |
| 227 | 5.6 | 7.0 |
| 228 | 5.0 | <4 |
| 229 | 5.4 | 7.1 |
| 230 | 5.0 | 5.3 |
| 231 | 6.7 | 7.5 |
| 232 | 4.5 | — |
| 233 | 5.2 | 6.3 |
| 234 | 6.2 | 6.7 |
| 235 | 5.2 | 6.7 |
| 236 | 6.1 | — |
| 237 | 6.1 | 7.5 |
| 238 | 5.9 | — |
| 239 | 5.6 | — |
| 240 | 7.6 | — |
| 241 | 8.2 | — |
| 242 | 6.5 | — |
| 243 | 8.0 | — |

In general, it has been found that compounds of formula I in which A is carboxy show a higher level of activity in test (a), and test (b) than those in which A is an ester group. However, the compounds in which A is an ester group have often been found to show a higher level of activity than those where A is carboxy in test (a) when the test is modified to assess the activity of test compounds on oral administration. For example, the compound described in Example 1 hereinafter has been found to give a $pA_2$ of 6.5–6.8 in test (a) and a $pIC_{50}$ of 5.8–6.4 in test (b), whereas the compound of Example 2 has been found to give a $pA_2$ of 7.1–7.3 in test (a) and a $pIC_{50}$ of 7.6 in test (b). However, the compound of Example 1 has been found to be active for up to 12 hours when dosed orally to dogs at 5 mg/kg. Without wishing to be bound by theory it is accordingly believed that the compounds of formula I in which A represents an ester group function as pro-drugs for compounds of formula I in which A is a carboxyl group.

As stated previously, the compounds of formula I may be used in the therapy or prevention of diseases in which cell adhesion (especially platelet aggregation) is involved, for example thrombosis (e.g. stroke and thrombotic events accompanying unstable angina and transient ischaenic attack), myocardial infarction, atherosclerosis, thromboembolism and reoceilusion during and after thrombolytic therapy. The compounds may also be useful for the prevention of reocciusion and restenosis following percutanieous transluminal coronary angioplasty (PTCA) and coronary artery bypass graft. It will also be appreciated that the compounds may be useful in the treatment of other diseases mediated by binding of adhesion molecules to GPIIb/IIIa, for example cancer.

According to another aspect, therefore, the invention provides a method of inhibiting platelet aggregation in a warm-blooded mammal requiring such treatment, which comprises administering an effective amount of a compound of formula I, or a pharmaceutically acceptable salt or pro-drug thereof.

According to yet another aspect, the invention provides a method of inhibiting binding of fibrinogen to GPIIb/IIIa in a warm-blooded animal requiring such treatment, which comprises administering an effective amount of a compound of formula I, or a phamaceutically acceptable salt or pro-drug thereof.

According to a further aspect, the invention provides the use of a compound of formula I or a pharmaceutically acceptable salt or pro-drug thereof for the manufacture of a medicament for the prevention or treatment of a disease involving platelet aggregation.

According to yet another aspect, the invention provides the use of a compound of formula I or a pharmaceutically acceptable salt or pro-drug thereof, for the manufacture of a medicament for the prevention or treatment of a disease involving binding of fibrinogen to GPIIb/IIIa.

In general, a compound of formula I will be administered for this purpose by an oral, rectal, topical, intravenous, subcutaneous, intramuscular or inhalation route, so that a dose in the range of from 0.01 to 50 mg/kg body weight will be given, depending upon the route of administration, the age and sex of the patient, and the severity of the condition to be treated.

The compounds of formula I will generally be used in the form of a pharmaceutical composition comprising a compounid of formula I or a pharmaceutically acceptable salt thereof as defined hereinabove, together with a pharmaceutically acceptable diluent or carrier. Such a composition is provided as a further feature of the invention and may be in a variety of dosage forms. For example, it may be in the form of tablets, capsules, solutions or suspensions for oral administration; in the form of cream or ointments or a transdermal (skin) patch for topical administration; in the form of a suppository for rectal administration; in the form of a sterile solution or suspension for administration by intravenous or intramuscular injection; in the form of an aerosol or a nebuliser solution or suspension, for administration by inhalation; and in the form of a powder, together with pharmaceutically acceptable inert solid diltients such as lactose, for administration by insufflation. Depending upon the route of administration, the composition may comprise, for example, from 0.1 to 99.9% by weight of a compound of formula I.

The pharmaceutical compositions may be obtained by conventional procedures using pharmaceutically acceptable diluents and carriers well known in the art. Tablets and capsules for oral administration may conveniently be formed with an enteric coating, for example comprising cellulose acetate phthalate, to minimise contact of the active ingredient of formula I with stomach acids.

The compounds according to the invention may be co-adminstrated or co-formulated with one or more agents known to be of value in diseases or conditions intended to be treated; for example a known platelet aggregation inhibitor (e.g. aspirin, a thromboxane antagonist or a thromboxane synthase inhibitor), hypolipidemic agent, anti-hypertensive agent, thrombolytic agent (such as streptokinase, urokinase, prourokinase, tissue plasminogen activator and derivatives thereof), beta-adrenergic blocker or a vasodilator may usefully also be present in a pharmaceutical composition of the invention for use in treating a heart or vasecular disease or condition.

In addition to their use in therapeutic medicine, the compounds of formula I are also useful as pharmacological tools in the development and standardisation of test systems for the evaluation of the effects of adhesion molecules in laboratory animals such as cats, dogs, rabbits, monkeys, rats and mice, as part of the search for new therapeutic agents. The compounds of formula I may also be used because of their platelet aggregation inhibitory properties in helping to store blood and to maintain the viability of blood and blood vessels in warm-blooded animals (or parts thereof) undergoing artificial extracorporeal circulation, for example during limb or organ transplants. When used for this purpose a compound of formula I, or a physiologically acceptable salt thereof, will generally be administered so that a steady state concentration in the range, for example, 0.1 to 10 mg. per litre is achieved in the blood.

As a further aspect of the present invention we provide the novel optically active compound (−)-(3R)-3-methyl-4-{4-[4-(4-pyridyl)piperazin-1-yl]phenoxy}butyric acid, [hereinafter (−)-(3R)] and pharmaceutically-acceptable salts, esters, amides or solvates thereof. The optically active (−)-(3R) compound of Example 246 is an optical isomer of the racemic mixture (3RS)-3-methyl-4-{4-[4-(4-pyridyl)piperazin-1-yl]phenoxy}butyric acid of Example 203).

Organic compounds can exist in optically active forms. Such compounds possess the property of being able to rotate the plane of plane-polarised ligYht in either a dextrorotary [prefix (+)] or laevorotary [prefix (−)] manner. Typically an optically active compound possesses an asymmetric or chiral atom such as a tetrahedral carbon atom which is bonded to four different atoms or groups. The four different atoms or groups can be arranged around the asymmetric carbon atom in two ways to give two chiral compounds which are structurally related as mirror images of one another. Such compounds are termed stereoisomers or enantiomers. Enantiomers have identical physical and chemical properties except that they rotate the plane of plane-polarised light by an equal amount but in opposite directions. A racemic mixture is a mixture of equal amounts of a pair of enantiomers. Such a mixture does not cause rotation of the plane of plane-polarised light.

The stereochemical purity of an organic compound can be of importance in the fields of pharmaceutical chemistry and pharmacology. Many macromolecules such as the enzymes and receptors within warm-blooded animals which are involved in the maintenance of life are built up from chiral building blocks such as the chiral amino acids. The individual enantiomers which together make up a racemic mixture of a pharmacologically active compound may interact to differing extents with a chiral macromolecule such as an enzyme or receptor. The individual enantiomers may therefore possess different potencies as enzyme inhibitors or receptor antagonists. In addition the rate and extent of the absorption, distribution, metabolism and excretion observed when one enantiomer is dosed to a warm-blooded animal may differ from that observed when the mirror image form is so dosed, i.e. the enantiomers may possess different pharmacokinetic properties.

Furthermore the stereochemical purity of an organic compound may also be of importance to the nature and extent of the side effects which may be obtained when a pharmacologically-active compound is dosed. Thus one enantiomer may be a useful compound whereas the other enantiomer may give rise to deleterious side effects or toxicity. It has, for example, been suggested that one of the enantiomers of thalidomide was a safe and effective sedative whereas the other enantiomer controlled the racemnic mixture's teratogenic side effect.

As a possible aid in the search for compounds with an improved therapeutic ratio, it would be desirable to find a compound with increased potency over the compounds such as that of Example 203.

It is also known that there are several classes of adhesion molecules such as the integrins, selectins and cadherins. Integrins are found on leucocytes and platelets and selectins are found on leucocytes and endothelial cells. Within each class of adhesion molecules there are many members. The integrin family includes, for example, GPIIb/IIIa which binds fibrinogen, the integrin $\alpha_v\beta_3$ which binds vitronectin and the integrin $\alpha_5\beta_1$ which binds fibronectin. It is believed that the more useful therapeutic platelet aggregation inhibitors will possess selectivity of inhibitory effect between classes of adhesion molecules and between family members of each class of adhesion molecules. Thus it would also be desirable to find a compound which possesses this selectivity or which possesses greater selectivity than known platelet aggregation inhibitors.

Furthermore it is known that there are several classes of GPIIb/IIIa antagonists. For example, monoclonal antibody antagoniists to GPIIb/IIIa have been raised. In addition, small molecules which inhibit the binding of adhesion molecules to GPIIb/IIIa are also known, for example from U.S. Pat. Nos. 5,039,805 and 5,084,446, from Canadian Patent Application Nos. 2,008,161, 2,037,153 and 2,061,661, and from Alig et ali, *J. Med. Chem.*, 1992, 35, 4393. Commonly the structures of these compounds are based upon the binding regions of the adhesion molecules, for example the amino acid sequence RGD (arginyl glycyl aspartate) within the structure of fibrinogen. It is believed that such compounds can be used to inhibit platelet aggregation and, for example, thrombus formation for sufficient time to allow healing of damaged tissue without the deleterious sequelae of over-robust platelet aggregation processes. It is a theoretical concern relating to the various classes of GPIIb/IIIa antagonists that the inhibition of platelet aggregation may lead to a decrease in the rate of blood clotting and hence an increase in bleeding events and times. Although a small increase in bleeding times may be acceptable, certain clinically relevant bleeding events such as intracranial haemorrhage could be life-threatening.

Thus it would be desirable to find a compound with the advantage of the potent GPIIb/IIIa antagonist activity disclosed for the compound of Example 203 which did not possess, or which possessed to a lesser decree, the disadvantages of increased bleeding, times and/or deleterious clinically relevant bleeding, events associated with the known GPIIb/IIIa antagonists.

According, to the present invention there is provided the optically active compound (−)-(3R)-3-methyl-4- {4-[4-(4-pyridyl)piperazin-1-yl]phenoxy}butyric acid, or a pharmaceutically-acceptable salt, ester, amide or solvate thereof, substantially free of the (+)-(3S) stereoisomer.

The (−)-(3R) compound possesses substantially better potency as a GPIIb/IIIa antagonist than the corresponding (+)-(3S) isomer (greater than 10-fold more potent). The (−)-(3R) compound also possesses selectivity of inhibitory effect between classes of adhesion molecules and between family members of those classes. For example, the compound possesses activity against the binding of GPIIb/IIIa to fibrinogen (pIC$_{50}$ =7.65) but not the binding of $\alpha_v\beta_3$ to vitronectin (pIC$_{50}$ less than 4) or the binding of $\alpha_v\beta_1$ to fibronectin (pIC$_{50}$ less than 4).

Accordingly the (−)-(3R) compound is a novel, potent and selective fibrinogen receptors antagonist that substantially reduces the liability or possibility of obtaining adverse effects such as excessive bleeding associated with the administration of other fibrinogen receptor antagonists such as the (3RS)-racemic mixture. Use of the (−)-(3R) compound also eliminates the liability or possibility of obtaining adverse effects associated with the administration of the therapeutically less effective (+)-(3S) compound which is a constituent of the (3RS)-racemic mixture. Use of the (−)-(3R) compound allows a clearer stuctuire-activity-toxicity analysis and provides an improved therapeutic ratio. It is therefore desirable to use the (−)-(3R) compound of the present invention rather that the (3RS)-racemic mixture of Example 203.

Particular pharmaceutically-acceptable salts of the (−)-(3R) compound of the invention include, for example, salts with acids affording physiologically-acceptable anions, such as salts with mineral acids, for example a hydrogen halide such as hydrogen chloride or hydrogen bromide, suilphuric acid or phosphoric acid, and salts with organic acids, for example trifluoroacetic acid. Other pharmaceutically-acceptable salts include, for example salts with inorganic bases such as alkali metal and alkaline earth metal salts e.g. sodium salts, ammonium salts, and salts with organic amines and quaternary bases forming physiologically-acceptable cations such as salts with methylamine, dimethylamine, trimethylamine, ethylenediamine, piperidine, morpholine, pyrriolidine, piperazine, ethanolamine, triethanolaminie, N-methylglucamine, tectramethylammonium hydroxide and benzyltrimethylammonium hydroxide.

Particular pharmaceutically-acceptable esters of the (−)-(3R) compound of the invention include, for example, ester derivatives of the carboxylic acid group in the compound of the invention, for example esters formed with alcohols such as (1–6C)alcohols (e.g. methanol, ethanol, propanol and tert-butanol), indanol, adamantol, (1–6C)alkanoyloxy-(1–4C)alcohols (e.g. pivaloyloxymethanol) and (1–4C) alkoxycarbonyl-(1–4C)alcohols (e.g. methoxycarbonylmethanol).

Particular pharmnaceutically-acceptable amides of the (−)-(3R) compound of the invention include, for example, amide derivatives of the carboxylic acid group in the compound of the invention, for example amides formed with amines such as ammonia, (1–4C)alkylamines (e.g. methylamine), di-(1–4C)alkylamines (e.g. dimethylamine, N-ethyl-N-methylamine and diethylamine), (1–4C)alkoxy-(2–4C)alkylamines (e.g. 2-methoxyethylamine), phenyl-(1–4C)alkylamines (e.g. benzylamine) and amino acids (e.g. glycine or an ester thereof). Thus particular amides of the (−)-(3R) compound of the invention include the N-methyl-N,N-dimethyl-, N-ethyl-N-methyl- and N,N-diethyl-butyramides.

Particular pharmaceutically-acceptable solvates of the (−)-(3R) compound of the invention include, for example, hydrates e.g. a hemi-hydrate, mono-hydrate, di-hydrate or tri-hydrate or an alternative quantity thereof.

The phrase "substantially free of the (+)-(3S) stereoisomer" as used hereinbefore means that there is at least 90% by weight of the (−)-(3R) isomer and 10% by weight or less of the corriesponding (+)-(3S) isomer. Preferably there is at least 95% by weight of the (−)-(3R) isomer and 5% by weight or less of the (+)-(3S) isomer. More preferably there is at least 99% by weight of the (−)-(3R) isomer and 1% by weight or less of the (+)-(3S) isomer.

The (−)-(3R) compound of the invention, or a pharmacelutically-acceptable salt, ester, amide solvate thereof may be prepared by any process known in the art for the preparation of such a compound. Suitable procedures include asymmetric synthesis involving an appropriate chiral intermediate and resolution of the (3RS)-racemic mixture. Such procedures represent a further feature of the invention and include the following:

a) Reaction of 4-[4-(4-pyridyl)piperazin-1-yl]phenol, or a reactive derivative thereof, with the chiral intermediate (3R)-4-hydroxy-3-methylbutyric acid or an ester thereof, or a reactive derivative thereof.

The reaction is conveniently performed in the presence of a strong base such as an alkali metal hydride, for example, sodium hydride. Suitable solvents include amides, such as dimethylformamide. The reaction is conveniently performed at a temperature in the range of from 0° to 100° C.

Suitable esters of the chiral intermediate (3R)-4-hydroxy-3-methylbutyric acid include, for example, the methyl, ethyl, propyl and tert-butyl esters. Suitable reactive derivatives thereof include, for example, (3R)-4-halogeno-3-methylbutyric acid or an ester thereof (e.g. a methyl or ethyl ester) such as the 4-chloro and 4-bromo derivatives, (3R)-4-alkanesulphonyloxy-3-methylbutyric acid or an ester thereof (e.g. a methyl or ethyl ester) such as the 4-methanesulphonyloxy derivative or (3R)-4-arylsulphonyloxy-3-methylbutyric acid or an ester thereof (e.g. a methyl or ethyl ester) such as the 4-(p-toluenesulphonyloxy) derivative.

b) Reaction of a compound of formula I

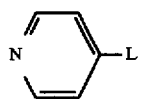

in which L is a leaving atom or group, with the chiral intermediate (3R)-3-methyl-4-[4-(piperazin-1-yl)phenoxy]butyric acid, or an acid addition salt thereof.

Examples of values for L include halogen, such as chlorine or bromine, and cyanlo.

Examples of acid addition salts of (3R)-3-methyl-4-[4-(piperazin-1yl)-phenoxy]butyric acid include, for example the hydrochlorides.

The reaction may conveniently be effected at a temperature in the range of from −10° to 120° C., preferably from 10° to 100° C. Suitable solvents include, e.g. others such as tetrahydrofuran and dioxan, amides such as dimethylformamide, nitriles such as acetonitrile, halogenated hydrocarbons such as dichloromethane, alcohols such as ethanol and water.

In some circumstances, for example when an acid addition salt of (3R)-3-methyl-4-[4-(piperazin-1-yl)phenoxy] butyric acid is used as startling material, the reaction may advanitageously be performed in the presence of a base. Examples of suitable bases include tertiary amines, such as triethylamine, and alkali metal hydroxides, carbonates and bicarbonates, such as sodium or potassium hydroxide, carbonate or bicarbonate.

c) Decomposition of an ester of formula II

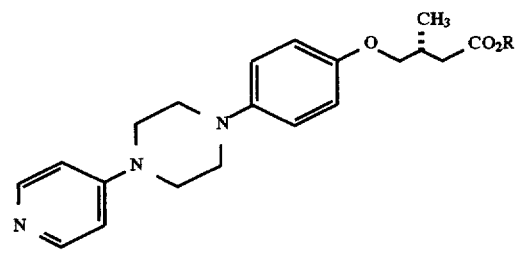

in which R is a carboxyl protecting group.

R may be any conventional carboxyl protecting group that may be removed without interfering with other parts of the molecule. Examples of carboxyl protecting groups include (1–6C)alkyl groups (such as methyl, ethyl, propyl or t-butyl), phenyl and benzyl, the phenyl moiety in any of which may optionally bear 1 or 2 of halogeno, (1–4C)alkyl, (1–4C)alkoxy or nitro.

The decomposition may be carried out usinig any one of the conventional reagents and conditions known in the art for converting carboxylic esters into carboxylic acids. Thus, for example, the decomposition may be performed by base catalysed hydrolysis, e.g. using an alkali metal hydroxide such as lithium, potassium or sodium hydroxide, or a tertiary amine such as triethylamine in the presence of water. The base catalysed hydrolysis may be performed in the presence of a solvent such as an alcohol, e.g. methanol or ethanol, or an ether such as tetrahydrofuLran or dioxan. Alternatively the decomposition may be carried out by acid catalysed hydrolysis, e.g. using aqueous acetic acid or trifluoroacetic acid. The temperature is conveniently in the range of from −10° to 100° C., for example from 10° to 50° C. When the alcohol residue is t-butyl, this may be removed by heating, e.g. at a temperature in the range of from 80° to 150° C., alone or in the presence of a suitable diluent such as diphenylether or diphenylsulphone. A benzyl group may be removed by catalytic hydrogenation , e.g. by hydrogenation in the presence of palladium on carbon at a temperature in the range of from −10° to 100° C. in the presence of a solvent such as an alcohol, for example methanol or ethanol.

d) Resolution of the (3RS)-racemic mixture, (3RS)-3-methyl-4-{4-[4-(4-pyridyl)piperazin-1-yl]phenoxy}butyric acid.

The resolution of the butyric acid derivative of the (3RS)-racemic mixture may be carried out by conventional means, for example by salt formation usinig an optically active base followed by separation, for example by fractional crystallisation of the two salts so produced and regeneration of the separated (−)-(3R) and (+)-(3S) compounds by acidification of the separated salts.

The resolution of the butyric acid derivative of the (3RS)-racemic mixture may also be carried out by the conventional means of forming a diastereoisomeric pair of esters by reaction with an optically active alcohol, separation of the esters, for example by chromatography, and regeneration of the separate (−)-(3R) and (+)-(3S) compounds by hydrolysis of the separated esters. An analogous route involving the preparation of a diastereoisomeric pair of amides may also be employed.

Certain of the chiral intermediates defined hereinbefore are novel, thus according to a further aspect of the invention there is provided the compound tert-butyl (3R)-3-methyl-4-hydroxybutyrate, or a reactive derivative thereof, substantially free of the (3S) stereoisomer. A particular reactive derivative which may be mentioned is tert-butyl (3 R)-3-methyl-4-(p-toluenesulphonyloxy)butyrate.

The phrase "substantially free of the (3S) stereoisomer" as used hereinbefore has the same meaning as given in relation to the (−)-(3R) compound of the invention.

When a pharmaccutically-acceptable salt of the (−)-(3R) compound of the invention is required, it may be obtained, for example, by reaction of said compound with a suitable acid or base using a conventional procedure. When a pharmaceutically-acceptable ester or amide of the (−)-(3R) compound of the invention is required, it may be obtained, for example, by reaction of said compound with a suitable alcohol or amine as appropriate using a conventional procedure.

The ability of the (−)-(3R) compound of the invention to inhibit platelet aggregation and to inhibit the binding of fibrinogen to GPIIb/IIIa may be demonstrated using the standard test procedures (a) and (b) described above.

The (−)-(3R) compound of the invention possesses activity against the adenosine diphosphate (ADP) induced aggregation of human platelets with a pA$_2$=7.3, and against the binding of fibrinogen to GPIIb/IIIa with a pIC$_{50}$=7.65.

As stated previously, the (−)-(3R) compound of the invention may be used in the therapy or prevention of diseases in which cell adhesion (especially platelet aggregation) is involved, for example venous or arterial thrombosis (e.g. pulmonary embolism, stroke and thrombotic events accompanying unstable angina and transient ischaemic attack), myocardial infarction, atherosclerosis, thromboembolism and reocclusion during and after thrombolytic therapy. The compounds may also be useful for the prevention of reocclusion and restenosis following percutaneous transluminal coronary angioplasty (PTCA) and coronary artery bypass graft. It will also be appreciated that the compounds may be useful in the treatment of other diseases mediated by binding of adhesion molecules to GPIIb/IIIa, for example cancer.

According to a further aspect of the invention there is provided the use of the (−)-(3R) compound, or a pharmaceutically-acceptable salt, ester, amide or solvate thereof, substantially free of the (+)-(3S) stereoisomer as a pharmaceutical.

According to a further aspect of the invention there is provided a method of inhibiting platelet aggregation in a warm-blooded animal requiring such treatment which comprises administering an effective amount of the (−)-(3R) compound, or a pharmaccutically-acceptable salt, ester, amide or solvate thereof, substantially free of the (+)-(3S) stereoisomer.

According to a further aspect of the invention there is provided a method of inhibiting binding of fibrinogen to GPIIb/IIIa in a warm-blooded animal requiring such treatment which comprises administering an effective amount of the (−)-(3R) compound, or a pharmaceutically-acceptable salt, ester, amide or solvate thereof, substantially free of the (+)-(3S) stereoisomer.

According to a further aspect of the invention there is provided a method of inhibiting thrombotic events accompanying unstable angina in a warm-blooded animal requiring such treatment which comprises administering an effective amount of the (−)-(3R) compound, or a pharmaceutically-acceptable salt, ester, amide or solvate thereof, substantially free of the (+)-(3S) stereoisomer.

According to a further aspect of the invention there is provided a method of inhibiting platelet aggregation in a warm-blooded animal requiring such treatment while substantially reducing adverse effects associated with the administration of the (3-RS)-racemic mixture, which comprises administering an effective amount of the (−)-(3R) compound, or a pharmaceutically-acceptable salt, ester, amide or solvate thereof, substantially free of the (+)-(3S) stereoisomer.

Pharmaceutical compositions of the (−)-(3R) compound may be formulated and administered as described previously.

The invention will now be illustrated by the following non-limiting Examples in which unless otherwise stated:

(i) concentrations and evaporations were carried out by rotary evaporation in vacuo;
(ii) operations were carried out at ambient temperature, that is in the range 18°–26° C;
(iii) column chromatography was carried out on silica (Merck Art. 9385) available from E Merck and Co., Darmstadt, Germany; and on neutral alumina (ICN Alumina N, Akt. I, III or IV) available from ICN Biomedicals GmbH, D-3440 Eschwege, Germany;
(iv) yields are given for illustration only and are not necessarily the maximum attainable by diligent process development;
(v) proton NMR spectra were normally determined at 200 MHz or 250 MHz in dimethylsulphoxide-d$_6$ using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d, doublet; and
(vi) ether refers to diethyl ether, THF to tetrahydrofuran, DMF to N,N-dimethylformamide, DMSO to dimethylsulphoxide, TFA to trifluoroacetic acid; HOBT to 1-hydroxybenzotriazole; and NBA to m-nitrobenzylalcohol.
(vii) drying with PS paper refers to the use of Whatmans PS phase separating paper.

EXAMPLE 1

Methyl 4-[2-[4-(4-pyridyl)piperazin-1-yl]acetyl] phenoxyacetate

A solution of methyl 4-bromoacetylphenoxyacetate (4.3 g) in acetonitrile (50 ml) was added dropwise over 40 minutes to a stirred solution of 1- (4-pyridyl)piperazine (4.9 g) in acetonitrile (100 ml). Stirring was continued for a further 1.5 hours, then the solution was filtered and the filtrate evaporated in vacuo. The solid residue was triturated with water (50 ml), then dried and suspended in methylene chloride (50 ml). The suspension was then filtered and the filtrate concentrated to a small volume. Purification by flash chromatography on neutral alumina eluting first with dichloromethane, then 0.5% v/v methanol/dichloromethane and finally 1% v/v methanol/dichloromethane gave the title compound, 1.93 g, as a solid: m.p. 150°–152° C.; NMR (d$_6$DMSO) γ 8.14(2H,d), 7.98(2H,d), 7.03(2H,d), 6.78(2H, d), 4.90(2H,s), 3.83(2H,s), 3.72(3H,s), 3.34(4H,bt), 2.65 (4H,bt); m/e 370 (M+H)$^+$; calculated for C$_{20}$H$_{23}$N$_3$O$_4$: C, 65.0; H, 6.3; N, 11.4. found: C, 65.2; H, 6.4; N, 11.3%.

EXAMPLE 2

4-[2-[4- (4-Pyridyl)piperazin-1-yl]phenoxyacetic acid

A stirred solution of the product of Example 1 (550 mg) in methanol (10 ml) was treated with a M sodium hydroxide solution (1.65 ml) and stirring continued for a further 2 hours. The mixture was diluted with water (10 ml) and the resulting solution concentrated in vacuo. Water (20 ml) was added and then a M hydrochloric acid solution (1.65 ml). On cooling to 4° C., a solid precipitated. This mixture was concentrated in vacuo, the solid collected and washed with ice-water, then dried to give the title compound, 320 mg, as a solid: m.p. 294°–296° C.; NMR (d$_6$DMSO+TFA) δ 8.34 (2H,d), 7.95(2H,d), 7.26(2H,d), 7.10(2H,d), 5.06(2H,s), 4.82(2H,s), 4.06(4H,bs), 3.52(4H,bs); m/e 356(M+H)$^+$; calculated for C$_{19}$H$_{21}$N$_3$O$_4$: C, 64.2; H, 6.0; N, 11.8. found: C, 64.1; H, 6.1; N, 11.6%.

EXAMPLE 3

Dimethyl 2,2'-[4-[2-[4-pyridyl)piperazin-1-yl)] acetyl]phenylene-1,2-dioxy]diacetate A solution of dimethyl 2,2'-[(4-bromoacetyl)phenylene1, 2-dioxy]diacetate (3.0 g) in acetonitrile (15 ml) was added dropwise over 30 minutes to a stirred solution of 1-(4- pyridyl)piperazine (2.6 g) in acetonitrile (75 ml) and the mixture stirred overnight. The mixture was then filtered and the filtrate evaporated to give an oil. Purification by flash chromatography on silica eluting first with 2.5% v/v methanol/dichloromethane then 5% v/v methanol/ dichloromethane gave a solid. Trituration with ether gave the title compound, 0.95 g, as a solid: m.p. 81°–83° C.; NMR (d$_6$DMSO) δ 8.14(2H,d), 7.67(1H,dd), 7.52(1H,d), 7.03(1H, d), 6.80(2H,d), 4.94(2H,s), 4.88(2H,s), 3.81(2H,s), 3.69(6H, s), 3.29(4H,t), 2.60(4H,t); m/c 458 (M+H)$^+$; calculated for $C_{23}H_{27}O_7N_3$. 0.25$H_2O$: C, 59.8; H, 6.0; N, 9.1. found C, 59.7; H, 6.2; N, 8.8%.

The starting material was prepared as follows:

i) Methyl bromoacetate (19.1 ml) was added dropwise to a stirred mixture of 3,4-dihydroxyacetophenone (12.6 g) and anhydrous potassium carbonate (27.5 g) in acetone (250 ml). Stirring was continued for 16 hours when the mixture was filtered and the solvent removed in vacuo. The residue after trituration with ether gave dimethyl 2,2'-[(4-acetyl)phenylene-1,2-dioxy)]diacetate, 13.1 g, as an off-white solid: m.p. 101°–102° C.; NMR (d$_6$DMSO) δ 7.60(1H,dd), 7.41(1H,d), 7.02(1H,d), 4.94(2H,s), 4.89 (2H,s), 3.71(6H,s), 2.50(3H,s); m/e 297(M+H)$^+$; calculated for $C_{14}H_{16}O_7$: C, 56.8; H, 5.4. found: C, 56.4; H, 5.5%.

ii) A solution of bromine (2.27 ml) in chloroform (10 ml) was added dropwise over 15 minutes to a stirred solution of the product of step i) (12.9 g) in chloroform (40 ml) at 30° C.. The mixture was then stirred for 2 hours at ambient temperature when the solvent was removed in vacuo. The resulting waxy solid, on trituration with ethanol, gave dimethyl 2,2'-([4-bromoacetyl]phenylene-1,2-dioxy)diacetate, 11.5 g, as a cream solid: m.p. 76°–78° C.; NMR (d$_6$DMSO) δ 7.66(1H,dd), 7.47(1H,d), 7.06(1H,d), 4.96(2H,s), 4.90(2H,s), 4.62(2H,s), 3.71(6H, s); m/e 375/377 (M+H)$^+$, 1 Br pattern.

EXAMPLE 4

2,2'-[4-[2-[4-(4-Pyridyl)piperazin-1-yl]acetyl] phenylene-1,2-dioxy]diacetic acid A stirred solution of the product of Example 3 (300 mg) in methanol (4 ml) was treated with a M sodium hydroxide solution (1.31 ml) and the mixture stirred for 1 hour. The mixture was diluted with water (10 ) and the resulting solution concentrated to about 7 ml when a M hydrochloric acid solution (1.31 ml) was added. On cooling to 4° C. the solid formed was collected, then washed with ice-water and dried to give the title compound, 120 mg, as a white solid: m.p. 180–184° C. (dec); NMR (d$_6$DMSO) δ 8.16(2H,d), 7.61(2H,t), 6.93(1H,d), 6.87(2H,d), 4.73(2H,s), 4.68(2H,s), 3.77(2H,s), 3.44(4H,bt), 2.58(4H,bt); m/e 430 (M+H)$^+$; calculated for $C_{21}H_{23}O_7N_3$. 0.75$H_2O$: C, 56.9; H, 5.5; N, 9.5. found C, 57.0; H, 5.6; N, 9.3%.

EXAMPLE 5

Methyl 4-[2-[4-(4-pyridyl)piperazin-1-yl]acetyl]-2-methoxyphenoxyacetate

A solution of methyl 4-bromoacetyl 2-methoxyphenoxyacetate (1.27 g) in acetonitrile (10 ml) was added dropwise over 15 minutes to a stirred solution of 1-(4-pyridyl)piperazine (1.30 g) in acetonitrile (30 ml). After stirring overnight the liquors were decanted from the solid residue, then concentrated in vacuo. Purification by flash chromatography on silica, eluting with dichloromethane then 5% v/v methanol/dichloromethane gave a solid. Trituration with ether gave the title compound, 420 mg: m.p. 110–112° C.; NMR (d$_6$DMSO) δ 8.14(2H,d), 7.65(1H,dd), 7.55(1H,d), 6.97(1H,d), 6.80(2H,d), 4.90(2H,s), 3.87(5H,s), 3.72(3H,s), 3.33(4H,t), 2.62(4H,t); m/e 400(M+H)$^+$; calculated for $C_{21}H_{25}N_3O_5$: C, 63.1; H, 6.3; N, 10.5. found: C, 62.9; H, 6.3; N, 10.4%.

EXAMPLE 6

4-[2-[4-(4-Pyridyl)piperazin-1-yl]acetyl]-2-methoxyphenoxyacetic acid

In a similar manner to Example 2, but starting from the product of Example 5, the title compound was prepared in 47% yield: m.p. 218°–224° C.; NMR (d$_6$DMSO) δ 8.16(2H, d), 7.65(1H,dd), 7.53(1H,d), 6.92(1H,d), 6.85(2H,d), 4.73 (2H,s), 3.86(2H,s), 3.82(3H,s), 3.36(4H,t), 2.63(4H,t); m/e 386(M+H)$^+$; calculated for $C_{20}H_{23}N_3O_5$. $H_2O$: C, 59.5; H, 6.2; N, 10.4. found: C, 59.5; H, 5.9; N, 10.1%.

EXAMPLE 7

Methyl 4-[3-[4-(4-pyridyl)piperazin-1-yl]propanoyl] phenoxyacetate

In a similar manner to Example 3, but starting from methyl 4-[3-chloropropanoyl]phenoxyacetate was prepared the title compound in 65% yield: m.p. 93°–95° C.; NMR (d$_6$DMSO) δ 8.14(2H,d), 7.96(2H,d), 7.04(2H,d), 6.81(2H, d), 4.92(2H, s), 3.71(3H,s), 3.29(4H,t), 3.17(2H,t), 2.72(2H, t), 2.51(4H,t); m/c 384 (M+H)$^+$; calculated for $C_{21}H_{25}N_3O_4$ C, 65.8; H, 6.6; N, 11.0. found C, 65.6; H, 6.8; N, 10.8%.

The starting material was prepared as follows:

i) Aluminium chloride (33.35 g) was added portionwise to a stirred cooled (<0° C.) solution of methyl phenoxyacetate (14.46 ml) and 3-chloropropanyl chloride (9.55 ml) in dichloromethane (500 ml). After the addition the ice-bath was removed and the mixture stirred for 1 hour when it was poured into ice-water (500 ml). The organic phase was separated and the aqueous portion extracted two times with dichloromethane. The combined dichloromethane extracts were washed with water, then brine and dried (MgSO$_4$). The residue, after removal of the solvent in vacuo and trituration with ether gave methyl 4-[3-chloropropanoyl]phenoxyacetate, 22.3 g, as a solid: m.p. 89°–90° C.; NMR (d$_6$DMSO) δ 7.95(2H,d), 7.05 (2H,d), 4.92(2H,s), 3.91(2H,t), 3.71(3H,s), 3.49(2H,t); m/e 257(M+H)$^+$; calculated for $C_{12}H_{13}ClO_4$: C, 56.1; H, 5.0. found: C, 55.8; H, 5.1%.

EXAMPLE 8

4-[3-[4-(4-Pyridyl)piperazin-1-yl]propanoyl] phenoxyacetic acid

In a similar manner to Example 2, but starting from the product of Example 7, the title compound was prepared in 60% yield: m.p. 238°–239° C.; NMR (d$_6$DMSO+d$^4$ acetic acid) δ 8.21(2H,d), 7.97(2H,d), 7.15(2H,d), 7.02(2H,d), 4.77(2H,s), 3.64(4H,t), 3.21(2H,t), 2.82(2H,t), 2.62(4H,t); m/e 370(M+H)$^+$; calculated for $C_{20}H_{23}N_3O_4$: C, 65.0; H, 6.3; N, 11.4. found C, 64.6; H, 6.4; N, 11.1%.

EXAMPLE 9

Methyl 4-[2-[4-(4-pyridyl)piperazin-1-yl]acetyl] phenylthioacetate

In a similar manner to Example 3, but starting fiom methyl 4-bromoacetylphenylthioacctate, the title compound was prepared in 27% yield: m.p. 109°–110° C.; NMR (d$_6$DMSO) δ 8.15(2H,d), 7.93(2H, d), 7.40(2H,d), 6.80(2H, d), 4.07(2H,s), 3.86(2H,s), 3.66(3H,s), 3.30(4H,t), 2.61(4H, t); m/e 386 (M+H)$^+$; calculated for C$_{20}$H$_{23}$N$_3$O$_3$S. 0.25 H$_2$O: C, 61.4; H, 6.0; H, 10.7. found C, 61.8; H, 6.0; H, 10.6%.

The starting material was prepared as follows:

i) Aluminium chloride (18.03 g) was added portionwise to a stirred cooled (<5° C.) solution of methyl phenylthioacetate (9.84 g) and bromoacetyl chloride (4.46 ml) in dichloromethane (250 ml) keeping the temperature below 5° C. The mixture was then stirred for one hour at ambient temperature then poured onto ice. After a filtration, the organic phase was separated and the aqueous portion extracted two times with dichloromethane. The combined dichloromethane extracts were washed with brine, dried (MgSO$_4$), filtered and evaporated to give 4-bromoacetylphenylthioacetate; 11.52 g, as a solid: m.p. 48°–50° C.; NMR (CDCl$_3$) δ 7.91(2H,d), 7.40(2H,d), 4.39(2H,s), 3.76(5H,s); m/e 302/304 (M+H)$^+$, 1 Br pattern.

EXAMPLE 10

4-[2-[4-(4-Pyridyl)piperazin-1-yl]acetate] phenylthioacetic acid

In a similar manner to Example 2, but starting from the product of Example 9, the title compound was prepared in 83% yield: m.p. 240°–244° C.; NMR (d$_6$DMSO) δ 8.16(2H, d), 7.93(2H,d), 7.39(2H,d), 6.66(2H,d), 3.92(2H,s), 3.86 (2H,s), 3.38(4H,t), 2.64(4H,t); m/e 372(M+H)$^+$; calculated for C$_{19}$H$_{21}$N$_3$O$_3$S. 0.25H$_2$O: C, 60.6; H, 5.7; N, 11.2. found C, 60.5; H, 5.6; N, 10.8%.

EXAMPLE 11

Methyl 3-[4-[2-[4-(4-pyridyl)piperazin-1-yl]acetyl] phenyl]propionate

A solution of methyl 3-(4-bromoacetylphenyl)propionate (380 mg) in acetonitrile (4 ml) was added dropwise over 15 minutes to a stirred solution of 1-(4-pyridyl)piperazine (450 mg) in acetonitrile (10 ml) and the mixture stirred overnight. The mixture was then filtered and the filtrate concentrated in vacuo to give an oil. Purification by flash chromatography on silica eluting first with dichloromethane then 5% v/v methanol/dichloromethane gave a solid. Trituration with ether gave the title compound, 172 mg, as a solid: m.p. 141°–143° C.; NMR (d$_6$DMSO) δ 8.15(2H,d), 7.92(2H,d), 7.37(2H,d), 6.83(2H,d), 3.89(2H,s), 3.59(3H,s), 3.37(4H,t), 2.93(2H,t), 2.69(2H,t), 2.65(4H,t); m/e 368(M+H)$^+$; calculated for C$_{21}$H$_{25}$N$_3$O$_3$.0.25H$_2$O: C, 67.8; H, 6.9; N, 11.3. found: C, 67.8; H, 6.9; N, 11.1%.

EXAMPLE 12

3-[4-[2-[4-(4-Pyridyl)piperazin-1-yl]acetyl]phenyl] propionic acid

A stirred solution of the product of Example 11 (70 mg) in methanol (0.5 ml) was treated with a M sodium hydroxide solution (0.19 ml) and stirring continued for 3 hours. The methanol was removed in vacuo and the residue diluted with water (1 ml), then a M hydrochloric acid solution (0.19 ml) added. On cooling to 4° C. a solid precipitated which was collected, washed with ice-water, then dried to give the title compound, 36.5 mg: m.p. 245°–247° C.; NMR (d$_6$DMSO) δ 8.05(2H,d), 7.91(2H,d), 7.36(2H,d), 6.86(2Hd), 3.89(2H, s), 3.34(4H,t), 2.87(2H,t), 2.62(4H,t), 2.58(2H,t); m/e 354 (M+H)$^+$: calculated for C$_{20}$H$_{23}$N$_3$O$_3$.0.2H$_2$O: C, 67.2; H, 6.6; N, 11.8. found: C, 67.6; H, 6.6; N, 11.4%.

EXAMPLE 13

Methyl 4-[2-[4-(4-pyridyl)piperazin-1-yl]acetyl] phenylacetate

A solution of methyl 4-chloroacetylphenylacetate (260 mg) in acetonitrile (4 ml) was added dropwise over 15 minutes to a stirred solution of 1-(4-pyridyl)piperazine (375 mg) in acetonitrile (10 ml) and the mixture stirred overnight. The supernatent was decanted from the solid formed, concentrated in vacuo and purified by flash chromatography on neutral alumina, eluting with dichloromethane then 0.25% v/v methanol/dichloromethane and finally 0.5% v/v methanol dichloromethane. Concentration of the fractions in vacuo gave the title compound, 96 mg, as a white crystalline solid: m.p. 127°–129° C.; NMR (d$_6$DMSO) δ 8.15(2H,d), 7.98(2H,d), 7.41(2H,d), 6.81(2H,d), 3.91(2H,s), 3.78(2H,s), 3.53(3H,s), 3.33(4H,t), 2.64(4H,t); m/e 354(M+H)$^+$; calculated for C$_{20}$H$_{23}$N$_3$O$_3$: C, 68.0; H, 6.6; N, 11.9. found: C, 68.2; H, 6.6; N, 11.9%.

EXAMPLE 14

Ethyl 4-[2-[4-(4-pyridyl)piperazin-1-yl]acetyl] phenylacetate

Using a method similar to that of Example 13, but starting from ethyl 4-chloroacetylphenylacetate and purification by flash chromatography on silica, eluting with dichloromethane then 5% v/v methanol/dichloromethane, the title compound was prepared in 13% yield as solid: m.p. 122°–124° C.; NMR (d$_6$DMSO) δ 8.01(2H,d), 7.29(2H,d), 7.25(2H,d), 6.67(2H,d), 3.93(2H,q), 3.75(2H,s), 3.60(2H,s), 3.18(4H,t), 2.47(4H,t), 1.03(3H,t); m/e 368 (M+H)$^+$; calculated for C$_{21}$H$_{25}$N$_3$O$_3$: C, 68.6; H, 6.9: N, 11.4. found: C, 68.2; H, 6.8; N, 11.3%.

EXAMPLE 15

4-[2-[4-(4-Pyridyl)piperazin-1-yl]acetyl] phenylacetic acid, trifluoroacetate salt A stirred solution of the product of Example 13 (142 mg) in methanol (1 ml) was treated with M sodium hydroxide solution (0.46 ml) and stirring continued for 2 hours. The methanol was removed invacuo, the residue diluted with water (1 ml), then a Mhydrochloric acid solution (0.46 ml) was added. This solution was transferred to a 1 inch preparative reverse phase hplc column (VYDAC$^R$ 218TP1022) and eluted with water, acetonitrile/trifluoroacetic acid in a gradient from 98:2:0.1 v/v/v to 75:25:0.1 v/v/v. The pure fractions, on freeze-drying gave, the title compound 96 mg, as a foam: NMR (d$_6$DMSO) δ 8.34(2H,d), 7.95(2H,d), 7.48(2H,d), 7.25(2H,d), 4.67(2H,b), 3.93(4H,b), 3.72(2H,s), 3.20(4H,b); m/e 340 (M+H)$^+$; calculated for C$_{19}$H$_{21}$N$_3$O$_3$. 2.25 CF$_3$COOH: C, 47.4; H, 3.9; N, 7.1. found: C, 47.8; H, 3.8; N, 7.0%.

EXAMPLE 16

(RS) Methyl 4-[2-[4-(4-pyridyl)piperazin-1-yl]-2-methylacetyl]phenoxyacetate A solution of RS methyl 4-(2-methylbromoacetyl) phenoxyacetate (1.2 g) in acetonitrile (10 ml) was added dropwise over 30 minutes to a stirred solution of 1-(4- pyridyl)piperazine (1.3 g) in acetonitrile (30 ml) and the mixture stirred overnight. The mixture was then filtered and the filtrate evaporated to give an oil. Purification by flash chromatography, eluting first with dichloromethane then successively 2.5%, 3%, 4%, 5% and 10% v/v methanol/dichloromethane gave the title compound, 220 mg as a solid: m.p. 81°–83° C.; NMR (d$_6$DMSO) δ 8.13(2H,d), 8.06(2H,d), 7.02(2H,d), 6.77(2H,d), 4.92(2H,s), 4.33(1H,q), 3.72 (3H,s), 3.26(4H,t), 2.63(4H,t), 1.16(3H,d); m/e 384(M+H)$^+$; calculated for C$_{21}$H$_{25}$N$_3$O$_4$: C, 65.8; H, 6.6; N, 11.0. found C, 65.7; H, 6.8; N, 10.9%.

EXAMPLE 17

RS 4-[2-[4-(4-Pyridyl)piperazin-1-yl]2-methylacetyl]phenoxyacetic acid sodium chloride adduct dihydrate A stirred solution of the product of Example 16, (110 mg) in methanol (1 ml) was treated with a M sodium hydroxide solution (0.32 ml) and stirTing continued overnight. The methanol was removed in vacuo and the residue diluted with water and a M hydrochloric acid solution (0.32 ml) added. The solvent was removed in vacuo to give a yellow foam which, on trituration with ether gave the title compound, 116 mg: NMR (d$_6$DMSO) δ 8.17 (2H,d), 8.06(2H,d), 7.01(2H,d), 6.98(2H,d), 4.76(2H,s), 4.37(1H,q), 3.47(4H,t), 1.16(3H,d), m/e 370 (M+H)$^+$; calculated for C$_{20}$H$_{23}$N$_3$O$_4$.NaCl.2H$_2$O: C, 51.8; H,5.8;N, 9.1. found: C,52.0; H, 5.6; N, 8.9%.

EXAMPLE 18

2.2'-[4-[3-[4-(4-Pyridyl)piperazin-1-yl]propanoyl]phenylene-1,2-dioxy]diacetate, trifluoroacetate salt ·

Di-tertiary butyl 2,2'-[4-[3-[4-(4-pyridyl)piperazin-1 -yl] propanoyllphenylene-1,2-dioxy]diacetate (555 mg) was dissolved in 90% v/v trifluoroacetate acidjwater (15 ml) and the mixture stirred for one hour. The solvent was removed by evaporation in vacuo and the residual oil on trituration with ether gave the title compound, 608 mg, as a solid: m.p. 42°–44° C.; NMR (d$_6$DMSO) δ 8.26(2H,d), 7.15(2H,d), 6.80(3H,m), 4.67(2H,s), 4.63(2H,s), 3.65(8H,b), 3.39(1H,q), 2.75(2H,m), 2.66(2H,m), 1.09(1.5H,t); m/e 444 (M+H)$^+$; calculated for C$_{22}$H$_{25}$N$_3$O$_7$. 1.3 CF$_3$COOH. 1H$_2$O. 0.25 C$_4$H$_{10}$O: C, 48.9; H, 4.9; N, 6.7. found C, 49.1; H, 5.0; N, 6.3%; calculated CF$_3$COOH; 23.6. found 23.2%.

The starting material was prepared as follows:

i) Solid sodium hydride (1.6 g of a 60% w/w dispersion in mineral oil) was added to a stirred, cooled (4° C.) solution of 3,4-dihydroxybenizaldehyde (2.76 g) in THF (50 ml). The mixture was then stirred for a further 15 minutes at ambient temperature, cooled to 4° C. when tertiary butyl bromoacetate (6.5 ml) was added followed by DMF (5 ml). After one hour the mixture was diluted with ether (100 ml), washed with water and brine, then dried (MgSO$_4$) and evaporated to give a solid. Recrystallisation from cyclohexane gave di-tertiary butyl 2,2'-([4-formyl) )phenylene-1,2-dioxy)diacetate, 4.1 g, as pale yellow crystals: m.p. 96° C.; NMR (d$_6$DMSO) δ 9.82(1H,s), 7.54(1H,dd), 7.33(1 H,d), 7.08(1H,d), 4.82(2H,s), 4.75 (2H.s), 1.43(18H,s), rnle 366 (M+); calculated for C$_{19}$H$_{26}$O$_7$; C, 62.4; H, 7.3. found C, 62.3; H, 7.2%.

ii) To a solution of the product of step i) (10.0 g) and malonic acid (42 g) in pyridine (150 ml) was added a few drops of piperidine and the mixture heated on a steam-bath for 4 hours. The pyridine was removed in vacuo, water 300 ml added and the mixture extracted with ether (3×100 ml). The combined extracts were washed with water, brine, dried (MgSO$_4$) then evaporated to give a gum. Recrystallisation from cyclohexane gave di-tertiary butyl 2.2'-( [4-(3-propenoic acid)]phenylene-1,2-dioxy)diacetate. 0.5 cyclohexane adduct, 6.6 g, m.p. 104°–106° C.; NMR (d$_6$DMSO) δ 12.20(1 H,b), 7.48(1 H,d), 7.26(1 H,s), 7.20(1H,d), 6.89(1H,d), 6.40(1H,d), 4.74(2H,s), 4.72(2H,s), 1.43(18H,s), 1.40(6H,s); m/e 408 (M+).

iii) 10% w/w palladium on charcoal (250 mg) was added to a solution of the product of step ii) (2.05 g) in ethyl acetate (100 ml) and the mixture hydrogenated at room temperature and pressure until the theoretical amount of hydrogen had been taken up. Charcoal was added, the mixture stirred for 5 minutes then filtered through diatomaneous earth and the filtrate evaporated to dryness giving di-tertiary butyl 2,2'-(4-[1-(2-carboxyethyl)lphenylene-1, 2-dioxy)diacetate, 1.9 g, as a colourless gum: NMR (CDCl$_3$) δ 6.76(3H,m), 4.58(2H,s), 4.56(2H,s), 2.86(2H,t), 2.60(2H,t), 1.47(18H,s); m/e 410(M+). This gum slowly crystallised to give a white solid of m.p. 68°–70° C.; calculated for C$_{21}$H$_{30}$O$_8$: C, 61.5; H, 7.4. found: C,61.7; H, 7.7%.

iv) To a stirred solution of the product of step iii) (615 mg) in dry DMF was added N,N'-diiosopropylethylamine (0.78 ml), HOBT (230 mg), 2-(1H-benzotriazole-1-yl)-1, 1,3,3-tetramethyluronium hexafluorophosphate (596 mg). After 15 minutes 1-(4-pyridyl)piperazine (245 mg) was added and stirring continued overnight. The DMF was removed in vacuo, the resulting oil partitioned between ethyl acetate (60 ml), and water (20 ml). The organic phase was separated, washed successively with water (20 ml), M sodium hydroxide solution (20 ml), brine (3×20 ml) then dried and the solvent evaporated to give an oil. Purification of this oil by flash chromatography on silica, eluting with 6.5% v/v methanol in dichloromethane gave di-tertiary butyl 2,2'-[4-[3-[4-(4-pyridyl)piperazin-1-ylpropanoyl]phenylene-1,2-dioxy]diacetate, 728 mg, as a froth: m.p. 57°–61° C., NMR (d$_6$DMSO) δ 8.16(2H,d), 6.80(5H,m), 4.63(2H,s), 4.59(2H,s), 3.58(4H,b), 3.32(4H,b), 2.73(2H,m), 2.61(2H,m), 1.45(18H,s); m/e 556(M+H)$^+$; calculated for C$_{30}$H$_{41}$N$_3$O$_7$. 0.5H$_2$O: C, 63.8; H, 7.5; N, 7.4. found: C, 63.5; H, 7.4; N, 7.1%.

EXAMPLE 19

N-[4-[2-[4-(4-Pyridyl)piperazin-1-yl]acetyl]phenyl-4-methylphenyl]-sulphonamide A mixture of 1-(4-pyridyl)piperazine (1.79 g), N-(4-bromoacetylphenyl)-4-methylphenylsulphonamide (3.68 g) and triethylamine (1.39 ml) in isopropanol (50 ml) was stirred for 18 hours. The precipitated solid was collected, triturated with dichloromethane, filtered and dried. This solid was further purified by flash chromatography on neutral alumina eluting successively with dichloromethane, 2.5% v/v methanol/dichloromethane then 5% v/v methanol/dichloromethane. Evaporation of the desired fractions to a small volume followed by addition of dichloromethane gave a crystalline solid. This solid was collected, washed with dichloromethane to give the title compound, 440 mg, as crystals: m.p. 168°–170° C.; NMR (d$_6$DMSO) δ 8.14(2H,d), 7.86(2H,d), 7.71(2H,d), 7.35(2H,d), 7.18(2H,d), 6.80(2H,d), 3.79(2H,s), 3.31(4H,t), 2.59(4H,t), 2.33(3H,s); m/e 451 (M+H)$^+$; calculated for C$_{24}$H$_{26}$N$_4$O$_3$S: C, 64.0; H, 5.8; N, 12.4. found C, 63.4; H, 5.7; N, 12.2%.

EXAMPLE 20

N-4-[2-[4-(4-Pyridyl)piperazin-1-yl]acetyl]phenyl-1-butanesulphonamide

A solution of N-(4-bromoacetylphenyl)-1-butanesulphonamide (410 mg) in acetonitnile (10 ml) was added to a stirred solution of 1-(4-pyridyl)piperazine (400 mg) in acetonitrile (10 ml) and the mixture stirred for 18 hours. The solvent was removed in vacuo and the residue purified by flash chromatography on silica eluting with 20% v/v methanol/dichloromethane then on neutral alumina eluting with 2% v/v methanol/dichloromethane. The residue, after evaporation of the eluant fraction was triturated with ether to give N-(4-[(4-pyridylpiperazin-1-yl)acetyl]phenyl)-1-butanesulphonamide, 166 mg, as a white solid: m.p. 185°–189° C. dec; NMR ($d_6$DMSO) δ 8.13(2H,d), 7.98(2H, d), 7.28(2H,d), 6.79(2H,d), 3.82(2H,d), 3.32(4H,t), 3.15(2H, m), 2.63(4H,t), 1.65(2H,m), 1.36(2H,m), 0.83(3H,t); m/e 417 $(M+H)^+$; calculated for $C_{21}H_{28}N_4O_3S$: C, 60.6; H, 6.8; N, 13.5. found C,60.5; H, 6.8; N, 13.1%.

EXAMPLE 21

N-[4-[2-[4-(4-Pyridyl)piperazin-1-yl]acetyl]phenyl]methyl-4-methylphenylsulphonamide A solution of N-([4-bromoacetylphenyl]methyl)-4-methylphenylsulphonamide (470 mg) in acetonitrile (10 ml) was added to a stirred solution of 1-(4-pyridyl)piperazine (400 mg) in acetonitrile (10 ml) and the mixture stirred for 18 hours. The solvent was evaporated in vacuo and the residue purified by flash chromatography on silica, eluting with 10% v/v methanol/dichloromethane. On evaporation of the eluant fraction to a small volume crystallisation occurred. These crystals, on filtration and washing with dichloromethane gave the title compound, 130 mg, as a solid: m.p. 215°–219° C. dec; NMR ($d_6$DMSO) δ 8.14(3H, m), 7.91(2H,d), 7.69(2H,d), 7.38(4H,d), 6.82(2H,d), 4.03 (2H,d), 3.89(2H,s), 3.32(4H,t), 2.62(4H,t), 2.39(3H,s); m/e 465$(M+H)^+$; calculated for $C_{25}H_{28}N_4O_3S$: C, 64.6; N, 6.1; N, 12.1. found C, 64.7; H, 6.2; N, 12.0%.

The starting material was prepared as follows:

i) To a stirred suspension under argon of 4-acetylbenzylamine hydrochloride (700 mg) in dichloromethane (20 ml) was added triethylamine (1.15 ml) and stirring continued for 15 minutes. The mixture was cooled to 4° C., then 4-methylphenylsulphonyl chloride (790 mg) in dichloromethanie (5 ml) added dropwise over 30 minutes. The reaction mixture was stirred for 18 hours at ambient temperature, then diluted with further dichloromethane (50 ml), washed with water, dried ($MgSO_4$) and evaporated. Trituration of the residue gave N-([4-acetylphenyl]methyl)-4-methylphenysulphonamide (A), 1.02 g., as an off-white solid: m.p. 125°–128° C.; NMR ($d_6$DMSO) δ 8.13(1H,t), 7.86(2H,d), 7.68(2H,d), 7.37 (4H,dd), 4.03(2H,d), 2.55(3H,s), 2.39(3H,s); m/e 304$(M+H)^+$.

ii) A mixture of the product of step i) (1.0 g) and cupric bromide (1.47 g) in ethyl acetate (3.0 ml) was heated at reflux temperature for 16 hours. Additional cupric bromide (1.0 g) was added and heating continued for a further 8 hours. The mixture was filtered and the filtrate concentrated to dryness in vacuo. This residue was purified by flash chromatography on silica, eluting with hexane/ethyl acetate (2:1 v/v). Evaporation of the fractions gave N-(14-bromoacetylphenyl]methyl)-4-methylphenylsulphonamide, 1.13 g, as a white solid: m.p. 116°–117° C., NMR ($CDl_3$) δ 7.9(2H,d), 7.75(2H,d), 7.34(4H,m), 4.77(1H,t), 4.40(2H,s), 4.22(2H,d), 2.44(3H, s): m/e 382/384 $(M+H)^+$, 1 Br pattern.

EXAMPLE 22

N-[4-[2-[4-(4-Pyridyl)piperazin-1-yl]acetyl]phenyl]methyl-1-butanesulphonamide

In a similar manner to Example 21 but starting from N-[4-bromoacetylphenyl]methyl- 1-butanesulphonamide the title compound was obtained as a solid in 25% yield: m.p. 158°–160° C.; NMR ($d_6$DMSO) δ 8.14(2H,d), 7.98 (2H,d), 7.68(1H,t), 7.48(2H,d), 6.83(2H, d) 4.22(2H,d), 3.90 (2H,s), 3.32(4H,t), 2.94(2H,m), 2.63(4H,t), 1.60(2H,m), 1.32(2H,m), 0.84(3H,t); m/e 431 $(M+H)^+$; calculated for $C_{22}H_{30}N_4O_3S$. 0.5 $H_2O$: C, 60. 1; H, 7.1; N, 12.8. found: C,60.5; H, 7.2; N, 12.8%.

The starting material was prepared as follows:

i) In a similar manner to Example 21i) but starting from 1-butanesulphonyl chloride there was obtained, after flash chromatography on silica eluting with ethyl acetate/hexane (1:1 v/v), N-([4-acetylphenyl|methyl)l-butanesulphonamide in 89% yield as a white crystalline solid: m.p. 87°–89° C.; NMR ($d_6$DMSO) δ 7.93(2H,d), 7.67(1H,t), 7.49(2H,d), 4.22(2H,d), 2.95(2H,m), 2.56(3H, s), 1.61(2H,m), 1.32(2H,m), 0.86(3H,s); m/e 270 $(M+H)^+$.

ii) In a similar manner to Example 21ii) but starting from the product of step i) above, there was obtained, after chromatography on silica eluting with hexane/ethyl acetate (2:1 Iv/v), N-([4-bromoacetylphenyl]methyl)-1-butanesulphonamide as off-white crystals in 70% yield: m.p. 101°–103° C.; NMR ($d_6$DMSO) δ 7.99(2H,d), 7.69 (1H,t), 7.52(2H,d), 4.49(4.23(2H,d), 2.96(2H,m), 1.60 (2H,m), 1.33(2H,m), 0.86(3H,s); m/e 365/367 $(M+NH_4)^+$, 1 Br pattern.

EXAMPLE 23

N-[2-[4-[2-[4-(4-Pyridyl)piperazin-1-yl]acetyl]phenyl]ethyl]-4-methylphenylsulphonamide A solution of N-(2-[4-bromoacetylphenyl]ethyl)-4-methylphenylsulphonamide (485 mg) in acetonitrile (10 ml) was added to a stirred solution of 1-(4-pyridyl)piperazine (400 mg) in acetonitrile (10 ml) and the mixture was stirred for 18 hours. The solvent was evaporated in vacuo and the residue purified by flash chromatography on silica, eluting with 10% v/v methanol/dichloromethane. On evaporation of the eluant fraction crystallisation occured. These crystals on filtration and washing with dichloromethane gave the title compound, 230 mg, as an off-white solid: m.p. 133°–135° C.; NMR ($d_6$DMSO) δ 8.14(2H,bd), 7.90(2H,d), 7.65(2H, d), 7.59(1H,t), 7.35(2H,d), 7.29(2H,d), 6.81(2H,d), 3.37(2H, s), 3.33(4H,t), 2.98(2H,q), 2.76(2H,t), 2.63(4H,t), 2.38(3H, s); m/e 479$(M+H)^+$; calculated for $C_{26}H_{30}N_4O_3S$: C, 65.2; H, 6.3; N, 11.7; found. C 65.0; H, 6.3; N, 11.4%.

The starting material was prepared as follows:

i) To a stirred suspension under argon of 4-acetylphenethylamine hydrochloride (1 g) in dichloromethane (20 ml) was added triethylamine (0.94 ml) and stirring continued for 15 minutes. The mixture was cooled to 4° C., then 4-methylphenylsulphonyl chloride (1.29 g) in dichloromethane (5 ml) added dropwise over 30 minutes. The reaction mixture was stirred for 18 hours at ambient temperatuLe, then diluted with further dichloromethanie (50 ml), washed with water, dried ($MgSO_4$) and evaporated. Trituration of the residue gave N-(2-[4-acetylphenyl]ethyl)-4-methylphenylsulphonamide, 1.58 g, as a yellow crystalline solid: m.p. 124°–126° C.; NMR ($d_6$DMSO) δ 7.84(2H,d), 7.63(3H,m), 7.37(2H,d), 7.29 (2H,d), 2.98(2H,q), 2.75(2H,t), 2.55(3H,s), 2.39(3H,s); m/e 318$(M+H)^+$.

ii) A mixture of the product of step i) (1.5 g) and cupric bromide (2.1 g) in ethyl acetate (50 ml) was heated at reflux temperature for 16 hours. The mixture was filtered, and the filtrate concentrated to dryness in vacuo. This residue was purified by flash chromatography on silica, eluting with hexane/ethyl acetate (2:1 v/v). Evaporation of the fractions gave N-(2-[4-bromoacetylphenyl]ethyl)-4-methylphenylsulphonamide, 860 mg, as a white crystalline solid: m.p. 133°–136° C.; NMR (CDCl₃) δ 7.90 (2H,d), 7.70(2H,d), 7.29(2H,d), 7.22(2H,d), 4.41(2H,s), 4.29(1H,t), 3.26(2H,q), 2.86(2H,t), 2.43(3H,s), m/e 396/398(M+H)⁺, 1 Br pattern.

EXAMPLE 24

N-[2-[4-[2-[4-(4-Pyridyl)piperazin-1-yl]acetyl]phenyl]ethyl]-1-butanesulphonamide In a similar manner to Example 23 but starting from N-(2-[4-bromoacetylphenyl]-ethyl)-1-butanesulphonamide the title compound was obtained, after trituration of the residual gum from flash chromatography with ether, in 22% yield: m.p. 74–80° C. (dec); NMR (d₆DMSO) δ 8.15(2H,d), 7.94(2H,d), 7.39(2H,d), 7.10(1H,t), 6.64(2H,d), 3.70(2H,s), 3.37(4H,t), 3.21(2H,q), 2.85(4H,m), 2.64(4H,t), 1.52(2H, m), 1.31(2H,m), 0.84(3H,t); m/e 445 (M+H)⁺; calculated for C₂₃H₃₂N₄O₃S. 0.5 H₂O: C, 60.9; H, 7.3; N, 12.4. found: C, 60.5; H, 7.3; N, 12.1%.

The starting material was prepared as follows:

i) In a similar manner to Example 23i) but starting from 1-butanesulphonyl chloride there was obtained, after purification by flash chromatography on silica eluting with ethyl acetate hexane (1:1 v/v), N-(2-[4-acetylphenyl]ethyl) 1-butanesulphonamide in 65% yield as a white crystalline solid: m.p. 75°–76° C.; NMR (d₆DMSO) δ 7.90(2H,d), 7.40(2H,d), 7.09(1H,t), 3.20(2H,q), 2.88 (4H1,m), 2.57(3H,s), 1.53(2H,m), 1.31(2H,m), 0.84(3H, s); m/e 284 (M+H)⁺.

ii) In a similar manner to Example 23ii) but starting from the product of step i) above, there was obtained, after chromatography on silica eluting with hexane/ethyl acetate (2:1 v/v), N-(2-[4-bromoacetylphenyl]ethyl) 1-butanesulphonamide in 54% yield as pale yellow crystals: m.p. 84°–86° C.; NMR (CDCl₃) δ 7.96(2H,d), 7.36 (2H,d), 4.42(2H,s), 4.12(1H,t), 3.43(2H,q), 2.96(4H,m), 1.72(2H,m), 1.41 (2H,m), 0.92(3H,t); m/e 379/381 (M+NH₄)⁺, 1 Br pattern.

EXAMPLE 25

Methyl 5-[2-[4-(4-pyridyl)piperazin-1-yl]acetyl]benzofuran-2-carboxylate

To a solution of 1-(4-pyridyl)piperazine (262 mg) and triethylamine (0.1 ml) in acetonitrile (10 ml) was added dropwise over 40 minutes a solution of methyl 5-(2-bromoacetyl)benzofuran-2-carboxylate in acetonitrile (5 ml). The resulting mixture was stirred for 2 hours, concentrated and purified by flash column chromatography on grade III alumina, eluting with methanol/dichloromethane (1:99 to 4:96 v/v) to give the title compound as a solid (138 mg); m.p. 173°–177° C., NMR 2.66(4H,m), 3.8(4H,m), 3.91(3H,s), 4.00(2H,s), 6.82(2H,m), 7.8°–8.5(6H,m); m/e 380 (M+H⁺); calculated for C₂₁H₂₁N₃O₄. 0.5H₂O: C, 64.9; H, 5.7; N, 10.8. Found: C, 65.2; H, 5.7; N, 10.9%.

The starting ester was prepared as follows:

i) Methyl 5-acetylbenzofuran-2-carboxylate

To a solution of 2-benzofuranoic acid methyl ester in carbon disulphide (240 ml) cooled to 5° C. was added acetyl chloride (70 ml) followed portionwise over 1 hour by aluminium trichloride (40 g). The mixture was heated under reflux for 42 hours before cooling and decanting the carbon disulphide. The residual complex was destroyed by the addition of iced water (50 ml) and 2N HCl (50 ml). The resulting mixture was extracted with ethyl acetate (3×200 ml). The organic layers were combined, washed with water (100 ml), dried (MgSO₄) and concentrated. The residue was purified by flash column chromatography, eluting with ethyl acetate/hexane (10:90 to 40:60, v/v), to give methyl 5-acetylbenzofuran-2-carboxylate as a solid (3.099 g); NMR 2.68(3H,s), 4.00(3H,s), 7.6–8.35(4H,m).

ii) Methyl 5-(2-bromoacetyl)benzofuran-2-carboxylate

To a suspension of cupric bromide (489 mg) in ethyl acetate (5 ml) at reflux was added dropwise a solution of the product of step i) (272 mg) in chloroform (5 ml) and the resulting mixture was refluxed for a further 3 hr. The resulting mixture was filtered, washed well with ethyl acetate and then concentrated. The residue was purified by flash column chromatography, eluting with ethyl acetate/hexane (20:80 v/v), to give methyl 5-(2-bromoacetyl) benzofuran-2-carboxylate as a solid (247 mg); NMR 4.00 (3H,s), 4.49(2H,s), 7.6–8.4(4H,m).

EXAMPLE 26

5-[2-[4-(4-Pyridyl)piperazin-1-yl]acetyl]benzofuran-2-carboxylic acid

To a solution of the product of Example 25 (93 mg) in methanol (5 ml) was added 1N sodium hydroxide (0.54 ml) and the resulting mixture was stirred for 2 hours. The mixture was filtered and washed with methanol to give the title compound as a solid (42 mg); NMR 2.66(4H,m), 3.29(4H,m), 3.97(2H,s), 6.78–7.01(3H,m), 7.58–8.33(5H, m); mn/e 366(M+H)⁺; calculated for C₂₀H₁₉N₃O₄. 0.5H₂O C, 60.6; H, 4.8; N, 10.6; Found: C, 60.4; H, 4.5; N, 10.2%.

EXAMPLE 27

Ethyl 1-[2-[4-(4-pyridyl)piperazin-1-yl]acetyl]piperidin-4-carboxylate

A solution of ethyl-1-(bromoacetyl)piperidin-4-carboxylate (0.84 g, 3 mMoles) in acetonitrile (10 ml) was added dropwise to a stirred solution of 1-(4-pyridyl) piperazine (0.5 g, 3 mMoles) in acetonitrile (20 ml) and the resulting mixture was allowed to stand for 3 hours. The white precipitate was removed by filtration and the mother liquors were concentrated under reduced pressure to give a yellow foam. The foam was purified by chromatography (flash column made with grade III neutral alumina and eluted with a gradient of 0–1% ethanol in dichloromethane) to give the title compound (350 mg) as a colourless oil which was crystallised from cyclohexane to give colourless prisms; mp 102°–104° C.; Microanalysis, found: C,63.5; H,8.1, N, 15.5%; C₁₉H₂₈N₄O₃ requires C,63.3; H,7.8; N,15.5%; NMR (d₆DMSO + CD₃COOD): 1.2(t,3H), 1.3–1.7(m,2H), 1.8(m, 2H), 2.5–2.8(m,6H), 3.0–3.4(m,3H), 3.6(brs,4H), 3.9(d, 1 H), 4.0(q,2H), 4.2(d, 1 H), 7. 1 (d,2H), 8.2(d,2H); m/e 361 (M+H)⁺.

The starting material was prepared as follows:

i) A solution of ethyl isonipecotate (5.1 ml, 33 mMoles) in triethylaminie (4.7 ml, 33 mMoles) was added dropwise to a stirred ice-cooled solution of bromoacetyl bromide (2.9 ml, 33 mMoles) in ether (75 ml) and stirring was continued for 1 hour. The resulting suspension was washed sequentially with water (2×20 ml), dilute sodium bicarbonate solution (20 ml), dilute citric acid solution (20 ml), water (20 ml) and saturated brine (30 ml), and then the organic fraction was dried (MgSO₄) and concentrated under reduced pressure to give ethyl 1-(bromoacetyl)piperidin-4-carboxylate (4.6 g) as a yellow oil which was used without further purification; NMR (CDCl$_3$) 1.2(t,3H), 1.6–2.1(m,4H), 2.5(m,1H), 2.9(m, 1H), 3.2(m,1H), 3.8(s, 2H +m,1H), 4.15(q,2H), 4.3(m, 1H); n/Ce 278/280 (M+H)$^+$.

EXAMPLE 28

1-[2-[4-(4-Pyridyl)piperazin-1-yl]acetyl]piperidin-4-carboxylic acid

A solution of the product of Example 27 (200 mg, 0.56 mMoles) in dioxan (10 ml) and concentrated hydrochloric acid (5 ml) was heated on a steam bath for 30 minutes. The solvent was evaporated under reduced pressure and the residue was triturated with ether to give a foam. The foam was dissolved in warm ethanol (10ml), filtered and allowed to cool. The title compound crystallised as colourless prisms (70 mg); mp 280°–282° C. (dec); Microanalysis, found: C,50.0; H, 7.1; N,12.7; Cl,16.4; H$_2$O. 2.5%; C$_{17}$H$_{24}$N$_4$O$_3$.2HCl.0.5H$_2$O. 0.33C$_2$H$_6$O requires: C,49.4; H,6.8; N,13.0; Cl,16.5; H$_2$O, 2.1%; NMR (d$_6$DMSO+ CD$_3$COOD) 1.4–1.7(m,2H), 2.0(m,2H), 2.9(t,iH), 3.2(t,1H), 3.4–3.7(m,5H), 3.9–4.2(brs,4H), 4.3(d,1), 4.4(q,2H), 7.25(d, 2H), 8.3(d,2H), + signals due to ethanol (0.33 Mole eq) m/e 333 (M+H)$^+$.

EXAMPLE 29

Ethyl 2-[1-[2-[4-(4-pyridyl)piperazin-1-yl]acetyl] piperidin-4-yl]acetate

A solution containing 1-(4-pyridyl)-4-carboxymethylpiperazine dihydrochloride ¼H$_2$O(400 mg, 1.33 mMoles), triethylamine (0.4 ml, 2.66 mMoles) and HOBT (0.2 g, 1.46 mMoles) in dry dimethylformamide (20 ml) was treated with diisopropylcarbodiimide (0.23 ml 1.46 mMoles) and the mixture was stirred for 5 minutes. Ethyl 4-carboxymethylpiperidine was added and the mixture was stirred for a further 4 hours. The mixture was concentrated to half volume under reduced pressure and then poured into water (50 ml) and extracted with ethyl acetate (3×20 ml) and dichloromethane (3×20 ml). The combined organic extracts were concentrated under reduced pressure and the residue was purified by chromatography (flash column made with grade III alumina and eluted with a gradient of 0–1% methanol in dichloromethane) to give the title compound (130 mg) as a colourless oil; NMR (d$_6$DMSO) 0.9–1.1 (m,2H), 1.2(t,3H), 1.65(d,2H), 1.8–2.0(m,1H), 2.2(d,2H), 2.5(m,2H), 2.9–3.4(m,10H), 4.0(q,2H +m,1H), 4.3(d,1H), 6.8(d,2H ), 8.15(d,2H); m/e 375 (M+H)$^+$.

The starting materials were prepared as follows:
i) 1-(4-Pyridyl)-4-carboxymethylpiperazine, hydrochloride A solution of tert-butyl bromoacetate (1.0 ml, 6.1 mMoles) in acetonitrile (20 ml) was added to a stirred solution of 1-(4-pyridyl)-piperazine (2.0 g, 12.3 mMoles) in acetonitrile (30 ml) and the mixture was stirred for 4 hours. The white precipitate was removed by filtration and the filtrate was concentrated under reduced pressure to give a yellow foam. The foam was purified by chromatography (flash column made with grade III alumina and eluted with a gradient of 0–1% methanol in dichloromethane) to give a colourless crystalline solid (900 mg). Recrystallisation from cyclohexane gave tert-butyl 1-(4-pyiidyl)piperazine-4-acetic ester (500 mg) as coloulless prisms; mp 83°–85° C.; Microanalysis, found: C,65.2; H,8.6; N,15.0; C$_{15}$H$_{23}$N$_3$O$_2$ requires: C,65.0; H,8.4; N,15.1%; NMR (d$_6$DMSO) 1.4(s, 9H), 2.6(t,4H), 3.2(s,2H), 3.5(t,4H), 6.8(d,2H), 8.15(d,2H); m/e 278 (M+H)$^+$.

A solution of tert-butyl 1-(4-pyridyl)piperazine-4-acetic ester (400 mg, 1.4 mMoles) in concentrated hydrochloric acid (10 ml) was allowed to stand for 1.5 hours and was then concentrated under reduced pressure. The residue was triturated with hot acetone, filtered and washed with acetone to give 1-(4-pyridyl)-4-carboxymethylpiperazine, hydrochloride (350 mg) as a pale cream solid; Microanalysis, found: C,44.2; H,5.9; N,13.8; Cl,23.8; H$_2$O,1.4%; C$_{11}$H$_{15}$N$_3$O$_2$.2HCl.0.25H$_2$O requires: C,44.2; H,5.9; N,14.1; Cl,23.7; H$_2$O,1.3%; NMR (d$_6$DMSO) 3.4–3.6(brs, 4H), 4.0–4.2(brs,4H), 4.2(s,2H), 7.3(d,2H), 8.4(d,2H); m/e 222 (M+H)$^+$.

ii) Ethyl-4-carboxymethylpiperidine

A stirred suspension of sodium hydride (50% dispersion in mineral oil, 4.8 g, 0.1 Moles) in dimethoxyethane (300 ml) was ice-cooled and treated under an atmosphere of argon with triethyl phosphonoacetate (19.82 ml, 0.1 Moles), added dropwise. Stirring was continued for 1 hour during which time the temperature of the mixture was maintained <5° C. The cooling bath was removed and N-benzylpiperidone (17.85 ml, 0.1 Moles) was added dropwise. The mixture was stirred overnight at room temperature, then diluted with water (500 ml) and extracted with ether (3×200 ml). The combined organic extracts were washed with water (200 ml) and saturated brine (100 ml), dried (MgSO4) and concentrated under reduced pressure. The residue was purified by chromatography (flash column, eluted with hexane/ethyl acetate; 3:2) to give ethyl 4-carboxymethylene-N-benzylpiperidine ester (5.52 g) as a yellow oil; NMR (CDCl$_3$) 1.1 (t,3H), 2.2(t,2H), 2.4(m,4H), 3.4(s,2H), 4.0(q, 2H), 5.6(s,1H), 7.2(m,5H); m/e 260 (M+H)$^+$.

A solution of ethyl 4-carboxymethylene-N-benzylpiperidine ester (5.5 g, 21 mMoles) in ethanol (250 ml was stirred with 10% palladium on carbon under an atmosphere of hydrogen until a total of 950 ml of hydrogen had been consumed. An additional quantity of 10% palladium on carbon (500 mg) was added and stirring was continued for 4 hours to remove residual starting material. The mixture was filtered and concentrated under reduced pressure to give ethyl 4-carboxymethylpiperidine ester (3.31 g) as a slightly green oil which was used without further purification; NMR (CDCl$_3$) 1.0–1.2(m,2H), 1.25(t,3H), 1.7(s,2H), 1.9(m,1H), 2.2(d,2H), 2.6(td,2H), 3.05(dt,2H), 4.0(q,2H); m/e 172 (M+H)$^+$.

EXAMPLE 30

2-[1-[2-[4-(4-Pyridyl)piperazin-1-yl]acetyl] piperidin-4-yl]acetic acid

In a similar manner to Example 28, but starting from the product of Example 29, the title compound was prepared as colourless prisms from isopropanol; mp 248°–250° C. (decomposition); Microanalysis, found: C,50.2; H,6.8; N,12.6; H$_2$O,3.4%; C$_{18}$H$_{26}$N$_4$O$_3$.2HCl.0.8H$_2$O requires: C,49.8; H,6.9; N12.9; H$_2$O, 3.3%; NMR (d$_6$DMSO+ CD$_3$COOD) 0.9–1.3(m,2H), 1.7(m,2H), 1.9(m,1IH), 2.2(d, 2H), 2.7(t,1 H), 3.15(t,1H), 3.4–3.7(m,5H), 3.8–4.2(m,4H), 4.3–4.5(m,3H), 7.2(d,2H), 8.3(d,2H); m/e 347 (M+H)$^+$.

EXAMPLE 31

Tert-butyl 2-[1-[2-[4-(4-pyridyl)piperazin-1-yl] acetyl]piperidin-4-yloxy]acetate A solution of 1-(4-pyridyl)-carboxymethylpiperidine (400 mg, 1.33 mMoles) triethylamine (0.4 ml, 2.66 mMoles) and HOBT (0.2 g, 1.46 mMoles) in dry dimethylformamide (20 ml) was treated with diisopropylcarbodiimide (0.23 ml, 1.46 mMoles) and the mixture was stirred for 5 minutes. Tert-butyl piperidine-4-oxyacetic ester (614 mg, 2.8 mMoles) was added and the mixture was stirred for a further 6 hours. The mixture was concentrated to half volume under reduced pressure and then poured into water (50 ml) and extracted with dichloromethane (4×30 ml). The combined organic extracts were washed with saturated brine and concentrated under reduced pressure. The residue was purified by chromatography (flash column made with grade III alumina and eluted with a gradient of 0–1% methanol in dichloromethane) to give the title compound (240 mg) as a colourless oil; NMR ($d_6$DMSO) 1.3–1.7(m,2H +s,9H), 1.7–1.9(m,2H), 3.0–3.5(m,12H), 3.55(m, 1H), 3.8(m,2H), 4.0(s,2H), 6.8(d,2H), 8.15(d,2H); m/e 419 (M+H)$^+$.

The starting material was prepared as follows:

i) An ice-cooled solution containing 4-piperidinol (5 g, 50 mMoles) and triethylamine (7 ml, 50 mMoles) in dichloromethane (50 ml) was cautiously treated with benzylchloroformate (7.5 ml, 50 mMoles) and allowed to stir for 2 hours. Dichloromethane (25 ml) was added and the solution was washed sequentially with water (2×40 ml) and saturated brine (50 ml), then dried (MgSO4) and concentrated under reduced pressure. The residue was purified by vacuum flash chromatography, eluting with a gradient of 50–100% ether in hexane to give N-benzyloxycarbonyl piperidin-4-ol (7.5 g) as a colourless oil; NMR ($d_6$DMSO) 1.2–1.4(m,2H), 1.6–1.8(m,2H), 3.0–3.2(m,2H), 3.6–3.8(m,3H), 4.7(d,2H), 5.1(2,2H), 7.3 (m,5H); m/e 236 (M+H)$^+$.

A solution of N-benzyloxycarbonyl piperidin-4-ol (7 g, 30 mMoles) in dry THF (100 ml) was treated with sodium hydride (60% suspension in mineral oil, 1.3 g, 32 mMoles) and the resulting mixture was stirred until effervescence ceased (about 1 hour). Tert-butylbromoacetate (5.1 ml, 32 mMoles) was added and stirring was continued for a further 2 hours. The mixture was diluted with ether (200 ml), washed with water (3×75 ml) and saturated brine (75 ml), dried (MgSO4) and concentrated under reduced pressure. The residual oil was purified by chromatography (flash column eluted first with hexane/ether 1:1 and then with ether alone) to give tert-butyl N-benzyloxycarbonyl-piperidine-4-oxyacetic ester (3.0 g) as a colourless oil; NMR ($d_6$DMSO) 1.3–1.5(m,2H +s,9H), 1.7–1.9(m,2H), 3.0–3.2(m,2H), 3.5–3.8(m,3H), 4.0(s,2H), 5.1(s,2H), 7.35(m,5H); m/e 350 (M+H)$^+$.

A solution of tert-butyl N-benzyloxycarbonylpiperidine-4-oxyacetic ester (1.0 g, 2.9 mMoles) in iso-propanol (40 ml) was stirred with charcoal, filtered and stirred with 10% palladium on carbon (200 mg) under an atmosphere of hydrogen. When 50 ml of hydrogen had been consumed the mixture was filtered and the filtrate was concentrated under reduced pressure to give tert-butyl piperidine-4-oxyacetic ester (614 mg) as a colourless oil which was used without further purification.

EXAMPLE 32

2-[1-[2-[4-(4-Pyridyl)piperazin-1-yl]acetyl]piperidin-4-yloxy]acetic acid

A solution of the product of Example 31 (220 mg, 0.53 mMoles) in a mixture of dichloromethane (5 ml) and trifluoroacetic acid (5 ml) was allowed to stand for 1.5 hours and was then concentrated under reduced pressure. The residue was triturated with ether and crystallised from isopropanol (12 ml) to give the title compound (200 mg) as colourless prisms; mp 198°–200° C.; Microanalysis, found: C,45.0; H,4.8; N,9.4%; $C_{18}H_{26}N_4O_4.2CF_3COOH$ requires: C,44.8; H,4.8; N,9.5%; NMR ($d_6$DMSO) 1.3–1.7(m,2H), 1.8–2.0(m,2H), 3.0–4.2(m, 16H), 4.15(s,2H), 7.25(d,2H), 8.3(d,2H); m/e 363 (M+H)$^+$.

EXAMPLE 33

Methyl 2-S-(n-butylsulphonylamino)-3-[4-[1-(4-pyridyl)piperidin-4-yl]methoxyphenyl]propionate n-Butylsulphonyl chloride (0.32 ml) was added dropwise to a solution of methyl 2-Samino-3-[4-(1-(4-pyridyl)piperidin-4-yl)methoxyphenyl]-propionate (750 mg) and triethylamine (0.5 ml) in dichloromethane (15 ml) cooled in an ice bath. The mixture was allowed to reach ambient temperature and stirred for 5 hours and then refluxed for 2 hours. The reaction mixture was washed with water (20 ml) and saturated sodium chloride solution (15 ml) and dried (MgSO$_4$). The solvent was evaporated and the residue purified by flash chromatography eluting with methanol/dichloromethane (1.9 v/v) to give the title compound (650 mg) as a gum; NMR(CDCl$_3$) 0.87(t,3H), 1.26–1.7(m,6H), 1.95(d,2H), 2.1(m, 1H), 2.72–3.18(m,6H), 3.77(s,3H), 3.79 (d,2H), 3.96(d,2H), 4.32(m,1H), 4.82(brd,1H), 6.69(d,2H), 6.83(d,2H), 7.1(d,2H), 8.25(brd,2H); mass spectrum (+ve FAB MeOH/NBA): 490 (M+H)$^+$ [α]$_D^{22}$=14° C. (c=1, MeOH).

The starting material was prepared as follows:

i) Diethylazodicarboxylate (0.58 ml) was added dropwise to a stirred mixture of 4-(4-hydroxymethylpiperidin-1-yl) pyridine (700 mg), N-benzyloxycarbonyl-S-tyrosine methyl ester (1.2 g), triphenylphosphine (955 mg) and THF (40 ml) in an atmosphere of argon and cooled to 10° C. The mixture was allowed to reach ambient temperature and stirred for 48 hours. The solvent was removed by evaporation and the residue purified by flash chromatography eluting with methanol/dichloromethane (1:9 v/v) to give methyl 2S-(benzyloxycarbonylamino)-3-[4-(1-(4-pyridyl)piperidin-4-yl)methoxyphenyl]propionate (1.2 g) as a solid m.p. 68°–75° C.; NMR($d_6$DMSO) 1.2–1.4(m, 2H), 1.84(d,d,2H), 1.92–2.1(m, 1H), 2.7–3.02(m,4H), 3.6 (s,3H), 3.8(d,2H), 3.98(d,2H), 4.14–4.28(m, 1H), 4.98(s, 2H), 6.78–6.88(m,4H), 7.13(d,2H), 7.20–7.4(m,5H), 7.75 (d,1H), 8.13(d,2H); mass spectrum (+ve FAB, MeOH/NBA): 504(M+H)$^+$.

ii) A solution of the product of step i) (1 g) in ethanol (40 ml) and 10% palladium/carbon (200 mg) was stirred in a stream of hydrogen for 4 hours at ambient temperature. The mixture was filtered through a pad of diatomaceous earth and the solvent removed by evaporation to give methyl 2-S-amino-3-[4-(1-(4'-pyridyl)piperidin-4-yl)methoxyphenyl]propionate as an oil; NMR($d_6$DMSO) 1.13–1.44(m,2H), 1.75–2.13(m,3H), 2.64–2.94(m,4H), 3.51(m,1H), 3.57(s,3H), 3.81(d,2H), 3.96(d,2H), 6.8(dd, 2H), 6.83(d,2H), 7.08(d,2H), 8.12(dd,2H); mass spectrum (+ve FAB, MeOH/NBA): 370 (M+H)$^+$.

EXAMPLE 34

2-S-(n-Butylsulphonylamino)-3-[4-[1-(4-pyridyl)piperidin-4-yl]methoxyphenyl]propionic acid Lithium hydroxide (285 mg) was added to a solution of the product of Example 33 (520 mg) in a mixture of methanol (9 ml), THF (9 ml) and water (9 ml) and stirred at ambient temperature for 3.75 hours. The solvent was evaporated and water (5 ml) added to the residue. A 10% aqueous solution of potassium hydrogen sulphate (8 ml) was added and an oil separated. The oil was dissolved in methanol and filtered through diatomaceous earth. The solvent was evaporated, and the residue triturated with ethyl acetate gave the title compound (500 mg) as an amorphous solid. NMR (d$_6$DMSO) 0.81(t,3H), 1.1–1.6(m,6H), 1.85(d,2H), 2.0(brs, 1H), 2.58–3.0(m,6H), 3.68(t,2H), 3.8(d,2H), 3.98(d,2H), 6.8(brs,4H), 7.13(d,2H), 8.12(brs,2H); mass spectrum(+ve FAB, MeOH/NBA): 476(M+H)$^+$.

EXAMPLE 35

Methyl 2-S-(n-butylsulphonylamino)-3-[4-[2-[1-(4-pyridyl)piperidin-4-yl]ethoxy]phenyl]propionate n-Butylsulphonyl chloride (0.28 ml) was added dropwise to a solution of methyl 2-S-amino-3-[4-[2-[1-(4-pyridyl) piperidin-4-yl]ethoxy]phenyl]propionate (630 mg) and triethylamine (0.5 ml) in dichloromethane (15 ml) cooled in an ice-bath. The mixture was allowed to reach ambient temperature and stirred for 5 hours. The reaction mixture was diluted with dichloromethane (10 ml) and washed with water (20 ml), saturated sodium chloride solution (10 ml) and dried (MgSO$_4$). The solvent was evaporated and the residue purified by flash chromatography eluting with methanol/dichloromethane(1:9 v/v) to give the title compound (680 mg) as a gum; NMR (CDCl$_3$) 0.9(t,3H), 1.25–1.45(m,4H), 1.55–1.95(m,7H), 2.72–3.15(m,6H), 3.78 (s,3H),. 3.9(brd,2H), 4.0(t,2H), 4.32(brs,1H), 4.84(brs, 1 H), 6.68(d,2H), 6.83(d,2H), 7.09(d,2H), 8.23(brs,2H): mass spectrum(+ve FAB, MeOH/NBA): 504 (M+H)$^+$.

The starting material was prepared as follows:

i) Following the method of Example 33i) but using 4-(4-hydroxyethylpiperidin-1-yl)pyridine, methyl 2-S-(benzyloxycarbonylamino)-3-[4-[2-[1-(4-pyridyl) piperidin-4-yl]ethoxy]phenyl]propionate (900 mg) was prepared as an oil; NMR (d$_6$DMSO) 1.05–1.35(m,2H), 1.6–1.9(m,5H), 2.7–3.05(m,4H), 3.63(s,3H), 3.92(d,2H), 4.0(t,2H), 4.21(m,1H), 4.98(s,2H), 6.8(d,2H), 6.84(d,2H), 7.14(d,2H), 7.3(m,4H), 7.75(d, 1H), 8.12(d,2H); mass spectrum(+ve FAB, NBA/CH$_2$Cl$_2$): 518 (M+H)$^+$.

ii) Following the method of Example 33ii), but using the product of step i) above, methyl 2-S-amino-3-[4-[2-[1-(4-pyridyl)piperidin-4-yl]ethoxy]phenyl]propionate was prepared as a gum; NMR (d$_6$DMSO) 1.08–1.32(m,2H), 1.58–1.86(m,5H), 2.61–2.9(m,4H), 3.52(m,1H), 3.58(s, 3H), 3.82–4.02(m,4H), 6.79(dd,2H), 6.81(d,2H), 7.07(d, 2H), 8.1(dd,2H); mass spectrum(+ve FAB, MeOH/NBA): 384 (M+H)$^+$.

EXAMPLE 36

2-S-(n-Butylsulphonylamino)-3-[4-[2-[1-(4-pyridyl) piperidin-4-yl]ethoxy]phenyl]propionic acid Following the method of Example 34, but using the product of Example 35 the title compound (380 mg) was prepared; NMR (d$_6$DMSO) 0.78(t,3H), 1.05–1.5(m,6H), 1.6–1.9(m,5H), 2.5–3.05(m,6H), 3.8–4.05(m,6H), 4.6(brs, 1H), 6.85(m,4H), 7.19(d,2H), 8.13(brs,2H); mass spectrum (+ve FAB, MeOH/NBA): 490 (M+H)$^+$; microanalysis found: C, 57.7; H, 7.5; N, 8.0; H$_2$O, 7.1%; C$_{25}$H$_{35}$N$_3$O$_5$S.2H$_2$O requires: C, 57.1; H, 7.4; N, 8.0; H$_2$O, 6.9%.

EXAMPLE 37

Methyl 2-S-(n-butylsulphonylamino)-3-[4-[1-(4-pyridyl)piperidin-4-yl]oxyphenyl]propionate Using a procedure similar to that described in Example 35, but starting from the appropriate amino acid ester, the title compound was prepared NMR (CDCl$_3$) 0.9(t,3H), 1.25–1.45(m,2H), 1.55–1.8(m,2H), 1.8–2.15(m,4H), 2.6–2.88(m,2H), 2.9–3.2(m,2H), 3.3–3.45(m,2H), 3.55–3.74(m,2H), 3.78(s,3H), 4.27–4.4(m, 1H), 4.45–4.6 (m,1 H), 4.8(brd,2H), 6.7(d,2H), 6.86(d,2H), 7.1(d,2H), 8.26(brd,2H); mass spectrum (+ve FAB, MeOH/NBA): 476 (M+H)$^+$.

The starting material was prepared using similar procedures to those described in Example 35. There were thus prepared the following intermediates starting from 4-(4-hydroxypiperidin-1-yl)pyridine:

Methyl 2-S-(benzyloxycarbonylamino)-3-4-(1-(4'-pyridyl)piperidin-4-yl)oxyphenyl]propionate; NMR (d$_6$DMSO) 1.5–1.72(m,2H), 1.9–2.1 (m,2H), 2.7–3.02(m, 2H), 3.18(d,2H), 3.2–3.35(m,1H), 3.48–3.77(m, 1H), 3.62 (s,3H), 4.13–4.28(m, 1H), 4.5–4.65(m,1H), 4.97(s,2H), 6.8–6.94(m,4H), 7.14(d,2H), 7.77(d,1H), 8.15(d,2H); mass spectrum(+ve FAB, CH$_2$Cl$_2$/NBA): 518 (M+H)$^+$.

Methyl 2-S-amino-3-[4-(1-(4'-pyridyl)piperidin-4-yl)oxyphenyl]propionate; NMR (d$_6$DMSO): 1.54–1.72(m, 2H), 1.9–2.06(m,2H), 2.65–2.88(m,2H), 3.15–3.4(m,2H), 3.52(t,1H), 3.59(s,3H), 3.6–3.75(m,2H), 4.52–4.65(m,1H), 6.8–6.92(m,4H), 7.09(d,2H), 8.15(dd,2H); mass spectrum (+ve FAB, MeOH/NBA): 356 (M+H)$^+$.

EXAMPLE 38

2-S-(n-Butylsulphonylamino)-3-[4-[1-(4-pyridyl) piperidin-4-yl]oxyphenyl]propionic acid Using a similar procedure to that described in Example 34 but startinig from the product of Example 37, the title compound was obtaincd as a solid m.p.255°–258° C. dec.; NMR (d$_6$DMSO) 0.66(t,3H), 0.98–1.04(m,2H), 1.05–1.4(m, 2H), 1.44–1.62(m,2H), 1.8–1.96(m,2H), 2.49(t,2H), 2.61 (dd,1H), 2.87(dd,1H), 3.12–3.28(m,2H), 3.4–4.0(m,5H), 4.43–4.55(m, 1H), 6.79(m,4H), 7.09(d,2H), 8.04(brd,2H); mass spectrum(+ve FAB, MeOH/NBA): 462 (M+H)$^+$; microanalysis found: C, 59.6; H 6.9; N, 9.0%; C$_{23}$H$_{31}$N$_3$O$_5$S requires: C, 59.8; H, 6.8; N, 9.1%.

EXAMPLE 39

N-[N-[2-[4-(4-Pyridyl)piperazin-1-yl]acetal]-L-aspartyl]-L-phenylalanine

To a solution of O-benzyl-N-[O-benzyl-N-[2-[4-(4-pyridyl)piperazin-1-yl]acetyl]-L-aspartyl]-L-phenylalanine (0.92 g) in methanol (125 ml) under argon was added 10% Pd on C (0.45 g). The mixture was covered with a blanket of hydrogen and stirred at room temperature until deprotection was complete. The catalyst was filtered off through a pad of kieselguhr and the filtrate was evaporated to dryness. The resultant white solid was dissolved in water and lyophilised overnight to yield the title compound (274 mg) as a white solid: m.p. 153° C. (dec); NMR (d$_6$DMSO +CD$_3$CO$_2$D) δ 2.65(6H,m), 3.02(4H,m), 3.63(4H,m), 4.44 (1H,m), 4.67(1H,m), 7.13(2H,d), 7.23(5H,m), 8.22(2H,d); m/Z484 (M+H)$^+$; calculated for C$_{24}$H$_{29}$N$_5$O$_6$.m/Z 484 (M+H)$^+$; amino acid analysis: found; Asp, 1.00; Phe 0.99; requires; Asp, 1.00; Phe, 1.00.

The starting material was prepared as follows:

i) Boc-L-Asp(OBzl)-L-Phe-OBzl (9.91 g) was dissolved in a mixture of trifluoroacetic acid (50 ml) and dichloromethanie (50 ml). The resultant solution was stored at room temperature for 2 hr. The reaction mixture was evaporated to dryness to yield a residue which was triturated with ether, collected, washed thoroughly with ether and dried under high vacuum to yield L-Asp(OBzl)-L-Phe-OBzl, trifluoroacetate salt (8.36 g) as a white solid: NMR (CDCl$_3$) δ 2.88(2H,m), 3.07(2H,m), 4.33(1H, m), 4.78(1H,m), 5.02(2H,s), 5.06(2H,q), 6.20(3H,vbr), 7.04(2H,m), 7.26(13H,m), 7.65(1H,d); m/Z 461 (M+H)$^+$.

ii) To an ice-cold solution of 1-(4-pyridyl)-4-carboxymethylpiperazine dihydrochloride (307 mg), HOBt.H$_2$O (176 mg) and HBTU (436 mg) in DMF (8 ml) under argon was added diisopropylethylamine (1.07 ml), followed, after 5 minutes, by a solution of the product of step (i) (600 mg) in DMF (5 ml). The reaction mixture was allowed to warm to room temperature with stirring overnight under argon. The reaction mixture was diluted with ethyl acetate (100 ml) and washed with water, dilute KHSO$_4$ (aq.), dilute NaHCO$_3$ (aq.), water, dried (MgSO$_4$) and evaporated to yield O-benzyl-N-[O-benzyl-N-[2-[4-(4-pyridyl)piperazin-1-yl]acetyl]-L-aspartyl]-L-phenylalanine (690 mg) as an off-white amorphous solid: NMR (d$_6$DMSO+CD$_3$CO$_2$D) δ 2.50(4H,m), 2.69(2H,m), 2.96(4H,m), 3.54(4H,m), 4.52(1H,m), 4.72(1H,m), 5.00 (4H,s), 7.03(2H,d), 7.23(15H,m), 8.10(2H,m); m/Z 664 (M+H)$^+$.

EXAMPLE 40

N-[N-[N-2-[4-(4-Pyridyl)piperazin-1-yl]acetyl] glycyl]-L-aspartyl]-L-phenylalanine In a similar manner to Example 39, O-benzyl-N-[O-benzyl-N-[N-2-[4-(4-pyridyl)piperazin-1-yl]acetyl]glycyl]-L-aspartyl]-L-phenyl-alanine (0.42 g), 10% Pd on C (200 mg) and methanol (125 ml) under a blanket of hydrogen gave, after lyophilisation from water, the title compound (91 mg) as a white solid: m.p. 180° C. (dec); NMR (d$_6$DMSO+ CD$_3$CO$_2$D) δ 2.50(11H,m), 2.67(5H,m), 2.96(1H,m), 3.10 (3H,m), 3.72(4H,m), 3.82(2H,s), 4.44(1H,m), 4.64(1H,m), 7.13(2H,d), 7.23(5H,m), 8.18(2H,d); m/Z 541 (M+H)$^+$; amino acid analysis: found; Asp, 1.00; Phe 1.04; Gly, 0.98; requires; Asp, 1.00; Phe, 1.00; Gly, 0.98.

The starting material was prepared as follows:

i) In a similar manner to Example 39ii), Boc-Gly-OH (1.28 g), HOBt.H$_2$O (1.23 g), HBTU (3.04 g), diisopropylethylamine (5 ml), L-Asp(OBzl)-L-Phe-OBzl, trifluoroacetate salt (4.18 g) and DMF (40 ml) gave Boc-Gly-L-Asp (OBzl)-L-Phe-OBzl (4.4 g) as a white solid: NMR (CDCl$_3$) δ 1.47(9H,s), 2.63(1H,m), 3.08(3H,m), 3.69(2H, m), 4.80(2H,m), 5.10(2H,s), 5.13(2H,q), 6.97(1H,d), 7.05 (2H,m), 7.28(13H,m); m/Z 618 (M+H)$^+$.

ii) In a similar manner to Example 39i), the product of step i) (5.6 g), trifluoroacetic acid (30 ml) and dichloromethane (30 ml) gave Gly-L-Asp(OBzl)-L-Phe-OBzl, trifluoroacetate salt (5.6 g) as a colourless oil: NMR (CDCl$_3$+CD$_3$CO$_2$D) δ 2.80(2H,m), 3.09(2H,m), 3.85(2H, s), 4.83(1H,m), 4.93(1H,m), 5.07(2H,s), 5.10(2H,q), 7.05 (2H,m), 7.25 (13H,m); m/Z 5 18 (M+H)$^+$.

iii) In a similar manner to Example 39ii), 1-(4-pyridyl)-4-carboxymethylpiperaziine dihydrochloride (280 mg), HOBt.H$_2$O (160 mg), HBTU (400 mg), diisopropylethylamine (0.98 ml), the product of step (ii) (600 mg) and DMF (10 ml) gave O-benzyl-N-[O-benzyl-N- [N-2- [4-(4-pyridyl)piperazin-1-yl]acetyl]glycyl]-L-aspartyl]-L-phenylalanine (0.42 g) as an off-white solid: NMR (CDCl$_3$) δ 2.68(5H,m), 3.10(5H,m), 3.49 (4H,m), 3.93 (2H,d), 4.81(2H,m), 5.09(2H,s), 5.10(2H,q), 6.74(2H,d), 7.07(2H,m), 7.25(15H,m), 7.64(1H,t), 8.18(2H,d); m/Z 721 (M+H)$^+$.

EXAMPLE 41

Methyl 4-[2-[4-(2-methyl-4-quinolinyl)piperazin-1-yl]acetyl]phenoxyacetate

In a similar manner to Example 1, methyl 4-bromoacetylphenoxyacetate (1.62 g), 2-methyl-4-(1-piperazinyl)quinoline (preparation described in Sharma, M. et al (1981), Pol. J. Pharmacol. Pharm. 33(5), 539–44) (2.59 g) and acetonitrile (80 ml) yielded, after stirring at room temperature overnight, filtration and evaporation of the filtrate, an orange/brown oily residue which was purified by flash chromatography, first on neutral alumina by elution with 3% v/v methanol/dichloromethane, then on silica by elution with methanol/dichloromethane (0.5% v/v to 3% v/v), and finally by crystallisation from methanol/water, to yield the title compound (671 mg) as an off-white solid: NMR (CDCl$_3$) δ 2.68(3H,s), 2.92(4H,m), 3.32(4H,m), 3.83 (3H,s), 3.90(2H,s), 4.73(2H,s), 6.74(1H,s), 6.97(2H,d), 7.42 (1H,m), 7.63(1H,m), 7.98(2H,m), 8.06(2H,d); m/Z 434 (M+H)$^+$; calculated for C$_{25}$H$_{27}$N$_3$O$_4$: C, 69.3%; H, 6.28%; N, 9.69%; found: C, 69.2%; H,6.4%; N, 9.6%.

EXAMPLE 42

4-[2-[4-(2-Methyl-4-quinolinyl)piperazin-1-yl] acetyl]phenoxyacetic acid

A mixture of the product of Example 41 (100 mg) and 0.5% v/v triethylamine/water (20 ml) was stirred at room temperature overnight, by which time all of the solids had dissolved. The pale yellow solution was washed with ether, filtered and lyophilised overnight to yield the title compound (107 mg) as an off-white solid: NMR (d$_6$DMSO) δ 1.13 (2.7H,t), 2.58(3H,s), 2.83(4H,m), 2.97(1.8H,q), 3.18(4H,m), 3.88(2H,s), 4.70(2H,s), 6.87(1H,s), 6.99(2H,d), 7.45(1H,m), 7.63(1H,m), 7.83(1H,m), 7.94(1H,m), 8.01(2H,d); m/Z 420 (M+H)$^+$; calculated for C$_{24}$H$_{25}$N$_3$O$_4$.0.3 Et$_3$N. 1H$_2$O: C, 66.2%; H, 6.79%; N, 9.88%; found: C, 65.9%; H, 6.7%; N, 9.6%.

EXAMPLE 43

Methyl 4-[2-[4-(4-quinolinyl)piperazin-1-yl]acetyl] phenoxyacetate

In a similar manner to Example 1, methyl 4-bromoacetylphenoxyacetate (1.60 g), 4-(1-piperazinyl) quinoline (Preparation described in EP 281309 A1) (2.39 g) and acetonitrile (75 ml) yielded, after stirring at room temperature overnight, filtration and evaporation of the filtrate, an orange/brown oily residue which was purified by flash chromatography, first on neutral alumina by elution with 3% v/v methanol/dichloromethane, then on silica by elution with methanol/dichloromethane (0.5% v/v to 5% v/v), and finally by crystallisation from methanol/water, to yield the title compound (373 mg) as a yellow solid: NMR (CDCl$_3$) δ 2.91(4H,m), 3.33(4H,m), 3.82(3H,s), 3.89(2H,s), 4.72(2H,s), 6.86(1H,d), 6.96(2H,d), 7.48(1H,m), 7.65(1H, m), 8.02(2H,m), 8.06(2H,d), 8.73(1 H,d); m/Z 420 (M+H)$^+$; calculated for C$_{24}$H$_{25}$N$_3$O$_4$.0.25 H$_2$O: C, 68.0%; H, 6.06%; N, 9.91%; found: C, 67.9%; H, 6.0%; N, 9.7%.

EXAMPLE 44

4-[2-[4-(4-Quinolinyl)piperazin-1-yl]acetyl] phenoxyacetic acid trifluoroacetate salt In a similar manner to Example 42, the product of Example 43 (313 mg), and 1% v/v triethylamine/water (65 ml) gave, after 2 days stirring at room temperature, washing with ether, filtration and lyophilisation, an off-white solid which was purified by preparative rp-hplc on a DYNAMAX C-18, 60A [83-201-C] column using an acetonitrile/water mobile phase system containing 0.1% trifluoroacetic acid, to give, after lyophilisation, the title compound (200 mg) as a white solid: NMR (d$_6$DMSO) δ 3.45(4H,m), 3.99(4H,m), 4.85(4H,s), 7.13(2H,d), 7.32(1H,d), 7.74(1 H,m), 8.01(4H, m), 8.19(1H,m), 8.83(1H,d); m/Z 406 (M+H)$^+$; calculated for C$_{23}$H$_{23}$N$_3$O$_4$.2.0 CF$_3$CO$_2$H: C, 51.2%; H, 3.98%; N, 6.63%; found: C, 50.9%; H, 3.9%; N, 6.5%.

EXAMPLE 45

Methyl 4-[2-[4-(5,6,7,8-tetrahydro-4-quinolinyl) piperazin-1-yl]-acetyl]phenoxyacetate In a similar manner to Example 1, methyl 4-bromoacetylphenoxyacetate (1.23 g), a 1:1 mixture containing 4-(1-piperazinyl)quinoline and 4-(1-piperazinyl)-5, 6,7,8-tetrahydroquinoline (1.84 g) and acetonitrile (56 ml) yielded, after stirring at room temperature overnight, filtration and evaporation of the filtrate, an orange/brown oily residue which was purified by flash chromatography, first on neutral alumina by elution with 5% v/v methanol/ dichloromethane, then on silica by elution with methanol/ dichloromethane (0.5% v/v to 5% v/v), and finally by crystallisation of the lower Rf material from methanol/water, to yield the title compound (298 mg) as a cream solid: NMR (CDCl$_3$) δ 1.76(2H,m), 1.89(2H,m), 2.64(2H,m), 2.76(4H, m), 2.95(2H,m), 3.07(4H,m), 3.80(2H,s), 3.81(3H,s), 4.71 (2H,s), 6.68(1H,d), 6.95(2H,d), 8.03(2H,d), 8.28(1H,d); m/Z 424 (M+H)$^+$; calculated for C$_{24}$H$_{29}$N$_3$O$_4$.1.0 H$_2$O: C, 65.3%; H, 7.08%; N, 9.52%; found: C, 65.6%; H, 6.7%; N, 9.3%.

The starting material was prepared as follows:
i) To a solution of 4-chloroquinoline (3 g) in mixed xylenes (b.p. 137°–144° C.) (25 ml) was added 1-benzylpiperazine (6.46 g). The mixture was heated to reflux with stirring for 20 hours then cooled to room temperature. The precipitate that formed was filtered and washed with xylene. To the combined filtrate and washings was added decolourising charcoal and the mixture was heated to reflux for 20 minutes, cooled and filtered through kieselguhr. The filtrate was evaporated to dryness to yield 1-benzyl-4-(4-quinolinyl)piperazine (4.55 g) as a yellow solid: m.p. 105°–106° C.; NMR (CDCl$_3$) δ 2.75 (4H,m), 3.26(4H,m), 3.66(2H,s) 6.84(1H,d), 7.35(5H,m), 7.45(1H,m), 7.65(1H,m), 8.03(2H,m), 8.73(1H,m); m/Z 304 (M+H)$^+$.
ii) To a solution of the product of step i) (3 g) and p-toluene sulphonic acid monohydrate (3.79 g) in methanol (300 ml) under argon was added 10% Pd on C (1.5 g). The mixture was covered with a blanket of hydrogen and stirred vigorously at room temperature for 24 hours. The catalyst was filtered off through a pad of kieselguhr and the filtrate was evaporated to dryness. The oily residue was partitioned between water, ethyl acetate and a small volume of methanol, basified to pH9–10 by addition of 1N NaOH (aq.) and the organic layer was separated. The aqueous layer was saturated with salt and re-extracted a number of times with dichloromethane. The organic extracts were dried (MgSO$_4$) and evaporated to yield a 1:1 mixture of 1-(4-quinolinyl)piperazine and 1-(5,6,7,8-tetrahydroquinolin-4-yl)piperazine (1.84 g) as a yellow solid which was used without further purification: m/Z 214 and 218 (M+H)$^+$ for two products.

EXAMPLE 46

4-[2-[4-(5,6,7,8-Tetrahydro-4-quinolinyl)piperazin-1-yl]acetyl]phenoxyacetic acid In a similar manner to Example 42, the product of Example 45 (180 mg), and 0.5% v/v triethylamine/water (40 ml) gave, after stirring overnight at room temperature, washing with ether, filtration and lyophilisation, the title compound (121 mg) as an off-white fluffy solid: NMR (CDCl$_3$) δ 1.75(2H,m), 1.90(2H,m), 2.61(2H,m), 2.75(4H, m), 3.08(2H,m), 3.23(4H,m), 3.78(2H,s), 4.66(2H,s), 6.79 (1H,d), 6.99(2H,d), 7.98(2H,d), 8.41(1H,d); m/Z 410 (M+H)$^+$; calculated for C$_{23}$H$_{27}$N$_3$O$_4$, 0.03 Et$_3$N, 1.0 H$_2$O: C, 64.7%; H, 6.89%; N, 9.86%; found: C, 64.4%; H, 6.6%; N, 9.5%.

EXAMPLE 47

Methyl 4-[2-[4-(4-pyrimidinyl)piperazin-1-yl]acetyl] phenoxyacetate

To a mixture of 4-(1-piperazinyl)pyrimidine (preparation described in DE 2316920) (1.57 g) and triethylamine (3.87 g) in acetonitrile (40 ml) at room temperature was added dropwise over about 0.5 hour a solution of methyl 4-bromoacetylphenoxyacetate (2.73 g) in acetonitrile (25 ml). On completion of the addition the reaction mixture was stirred at room temperature for 2 days. The precipitated solid was filtered off, washed with acetonitrile and the combined filtrate and washings evaporated to dryness. The resultant red oil was purified by flash chromatography, first on silica by elution with 1–5% v/v methanol/dichloromethane, then on neutral alumina by elutioni with 3% v/v methanol/ dichloromethane, to yield the title compound (0.92 g) as an off-white solid: NMR (CDCl$_3$) δ 2.69(4H,m), 3.72(4H,m), 3.80(2H,s), 3.82(3H,s), 4.71(2H,s), 6.49(1H,m), 6.94(2H,d), 8.01(2H,d), 8.20(1H,d), 8.60(1H,s); m/Z 371 (M+H)$^+$; calculated for C$_{19}$H$_{22}$N$_4$O$_4$.0.4 H$_2$O: C 60.4%; H, 6.09%; N, 14.8%; found: C, 60.7%; H, 6.2%; N, 14.7%.

EXAMPLE 48

4-[2-[4-(4-Pyrimidinyl)piperazin-1-yl]acetyl] phenoxyacetic acid

In a similar manner to Example 42, the product of Example 47 (200 mg) and 1% v/v triethylamine/water (40 ml) gave, after stifling overnight at room temperature, washing with ether, filtration and lyophilisation, the title compound (152 mg) as an off-white solid: NMR (d$_6$DMSO) δ 3.14(4H,m), 3.93(4H,m), 4.61(2H,brni), 4.83(2H,s), 7.03 (1H,d), 7.09(2H,d), 7.96(2H,d), 8.3 1 (1H,d), 8.65(1H,s); m/Z 357 (M+H)$^+$; calculated for C$_{18}$H$_{20}$N$_4$O$_4$.0.34 H$_2$O: C, 59.6%; H, 5.75%; N, 15.5%; found: C, 59.2%; H, 6.0%; N, 15.0%.

EXAMPLE 49

[1-Benzyl-3-[4-(4-pyridyl)piperazin-1-yl]-4-quinolon-7-yl]oxyacetic acid trifluoroacetate salt To a stirred suspension of sodium hydride (80 mg) in dry DMF (5 ml) under argon at room temperature was added 1-benzyl-3-[4-(4-pyridyl)piperazin-1-yl]-4-quinolon-7-ol (377 mg), followed, after 1 hour, by tert.butyl bromoacetate (0.13 ml). After stirriing for a further 2 hours at room temperature under argon an extra aliquot of sodium hydride (40 mg) was added, followed, dropwise, by a further quantity of tert.butyl bromoacetate (0.13 ml). The reaction mixture was stirred at room temperature overnight then evaporated to dryness. The residue was purified by preparative rp-hplc on a DYNAMAX C-18, 60A [83-201-C] column using an acetonitrile/water mobile phase system containing 0.1% trifluoroacetic acid, to give, after lyophilisation, the de-esterified product as a gum, which, on trituration with water gave the title compound (22 mg) as an off-white solid: NMR (d₆DMSO) δ 3.30(4H,m), 4.00(4H,m), 4.83(2H,s), 5.61(2H,s), 7.00(2H,m), 7.38(7H,m), 7.96(1H,s), 8.25(1H, d), 8.38 2H,d); m/Z 471 (M+H)⁺; calculated for C₂₇H₂₆N₄O₄.1.0 CF₃CO2H. 2.0 H₂O: C, 56.1 %; H, 5.04%; N, 9.0%; found: C, 56.4%; H, 4.9%; N, 8.9%.

The starting material was prepared as follows:

i) To a solution of 1-ethoxycarbonylpiperazine (20 g) and triethylamine (14.1 g) in dichloromethane (200 ml) at 0° C. was added gradually with stirring over 10–15 minutes, methyl bromoacetate (20.3 g). On completion of the addition the reaction mixture was stirred at room emperature for 2 hours, washed with water and brine, dried (MgSO₄) and evaporated to yield 1-ethoxycarbonyl-4-methoxycarbonylmethylpiperazinie (29.1 g) as a colourless oil: NMR (CDCl₃) δ 1.28(3H,t), 2.56(4H,m), 3.25 (2H,s), 3.52(4H,m), 3.72(3H,s), 4.14(2H,q); m/Z 231 (M+H)⁺.

ii) To a solution of the product of step i) (10 g) in dry DMF (80 ml) was added dimethylformamide dimethyl acetal (DMFDMA) (30 ml) and the reaction mixture was heated to reflux. After 2 days a further quantity of DMFDMA (30 ml) was added and refluxing was continued for a further 2 days. The reaction mixture was evaporated and the residue partitioned between aqueous ammonium chloride solution and ethyl acetate. The organic layer was separated, washed with brine, dried (MgSO₄) and evaporated. The residue was purified by flash chromatography on silica by elution with ethyl acetate to yield 1-ethoxycarbonyl-4-(1-dimethylaimno-2-methoxycarbonylethen-2-yl)piperazine (7 g) as an orange oil: NMR (CDCl₃) δ 1.28(3H,t), 2.90(4H,m), 3.14(6H,s), 3.50(4H,m), 3.64(3H,s), 4.12(2H,q), 7.01(1H,s); m/Z 286 (M+H)⁺.

iii) A mixture of the product of step ii) (6.3 g), m-anisidine (2.5 ml), ethanol (65 ml) and concentrated hydrochloric acid (2.2 ml) was stirred at room temperature for 2 hours then evaporated. The residue was basified by careful addition of aqueous sodium carbonate solution. The mixture was extracted with ethyl acetate and the organic extracts were washed with brine, dried (MgSO₄) and evaporated to dryness. The residue was purified by flash chromatography on silica by elution with 70% v/v ether/hexane to yield 1-ethoxycarbonyl-4-(1-(3-methoxyphenyl)amino-2-methoxycarbonylethen-2-yl) piperazine (5.15 g) as an off-white solid: m.p. 120°–122° C.; NMR (CDCl₃) δ 1.28(3H,t), 2.90(4H,m), 3.50(4H,m), 3.71(3H,s), 3.81(3H,s), 4.18(2H,q), 6.52(3H,m), 7.21 (1H,t), 7.39(1H,d), 7.80(1 H,d); m/Z 364 (M+H)⁺.

iv) A mixture of the product of step iii) (8.5 g) and DOWTHERM (55 ml) was heated to 230°–270° C. for 1 hour. The dark coloured mixture was cooled to room temperature before excess hexane was added. Removal of the supernatant by decantation followed by washing gave a crude residue (4.66 g) which was used without further purification.

The residue (4.66 g) was added to a stirred mixture of 55% sodium hydride in mineral oil (0.67 g) and dry DMF under argon at room temperature. After stirring for 75 minutes benzyl bromide (1.86 ml) was added and the reaction mixture was stirred at room temperature overnight then evaporated and the residue partitioned between water and ethyl acetate. The organic layer was separated, washed with brine, dried (MgSO₄) and evaporated to yield an oily residue which was purified by flash chromatography on silica by elution with ethyl acetate to give the higher Rf product, 1-benzyl-3-(1-ethoxycarbonylpiperazin-4-yl)-7-methoxy-4-quinolone (1.8 g) as an off-white solid: m.p. 173°–4° C.; NMR (CDCl₃) δ 1.28(3H,t), 3.05(4H,m), 3.70 (4H,m), 3.75(3H,s), 4.18(2H,q), 5.27(2H,s), 6.59(1H,d), 6.89(1H,dd), 7.10(3H,m), 7.30(3H,m), 8.41 (1H,d); m/Z 422 (M+H)⁺.

v) A mixture of the product of step iv) (1.8 g), ethanol (40 ml) and 20% w/v aqueous potassium hydroxide solution (40 ml) was heated to reflux overnight, cooled and evaporated to dryness. The residue was partitioned between water and dichloromethane and the organic layer was separated, washed with brine, dried (MgSO₄) and evaporated to yield 1-benzyl-3-(piperazin-1-yl)-7-methoxy-4-quinoline (1.5 g) as a yellow foam: NMR (CDCl₃) δ 2.80(1H,m), 3.20(8H,m), 3.73(3H,s), 5.28(2H,s), 6.59 (1H,d), 6.88(1H,dd), 7.15(3H,m), 7.30(3H,m), 8.41(1H, d); m/Z 350 (M+H)⁺.

vi) A mixture of the product of step v) (1.1 g), xylene (110 ml), isoamyl alcohol (11 ml), 4-chloropyridine hydrochloride (1.1 g) and triethylamine (11 ml) was heated to reflux and stirred for 30 hours. During this period extra aliquots of 4-chloropyridine hydrochloride (6×1.1 g) and triethylamine (3×11 ml) were added at intervals. The reaction mixture was evaporated to dryness and the residue was purified by flash chromatography on silica by elution with methanol/dichloromethanie/concentrated ammonia (20:200:1) to give 1-benzyl-3-(4-(4-pyridyl)piperazin-1-yl)-7-methoxy-4-quinolonc (780 mg) as an orange-red solid: NMR (d₆DMSO) δ 3.2(4H,m), 3.75(3H,s), 3.80 (4H,m), 5.55(2H,s), 6.90(2H,m), 7.30(7H,m), 7.88(1H,s), 8.13(1H,d), 8.24(2H,d); m/Z 427 (M+H)⁺.

vii) To a solution of the product of step vi) (815 mg) in dry dichloromethane (10 ml) under argon was added a 1M solution of boron tribromide in dichloromethane (10 ml). The reaction was stirred at room temperature for 14 days, extra aliquots of BBr₃ solution being added after 3 and 7 days. After 2 weeks, excess 1M aqueous sodium hydroxide solution was added, dropwise at first, and the mixture stirred at room temperature for 3 hours. The precipitated material was filtered off and the aqueous layer of the filtrate separated. The pH of the aqueous layer was adjusted to 8 by addition of 2N HCl (aq.) and 1M NaHCO₃ (aq.) before being extracted with ethyl acetate. The organic extracts were washed with brine, dried (MgSO₄) and evaporated to dryness to yield 1-benzyl-3-(4-(4-pyridyl)piperazil]-1-yl)-4-quinolon-7-ol (75 mg) as an off-white solid: m.p. 141°–6° C.; NMR (d₆DMSO) δ 3.10(4H1,m), 3.50(4H,m), 5.40(2H,s), 6.67(1H,d), 6.72 (1H,dd), 6.90(2H,m), 7.30(5H,m), 7.76(1H,s), 8.07(1H, d), 8.15(2H,s), 10.15(1 H,brs); m/Z 413 (M+H)⁺.

EXAMPLE 50

Ethyl 4-[4-[4-(4-pyridyl)piperazin-1-yl]phenoxy]butyrate

A stirred suspension of 4-(4-(4-pyridyl)piperazin-1 -yl)-phenol (1.34 g) in dry DMF (20 ml) was treated with sodium hydride (60% dispersion in mineral oil, 0.21 g) and the mixture stirred for 1 hour. To the resulting solution was added ethyl 4-bromobutyrate and the mixture was stirred for 16 hours. Solvent was evaporated under reduced pressure and the residue was partitioned between ethyl acetate and water. The organic layer was washed with water, filtered through phase separating paper (Whatman 1PS) and evaporated. The residue was purified by flash chromatography on silica, eluting with 1.5/92.5/6 v/v/v methanol/ethyl acetate/aqueous ammonia (SG 0.89) and recrystallised from ethyl acetate/hexane to give the title compound (0.7 g) as a solid:

m.p. 84°–85° C.; NMR (CDCl₃) δ 8.3(2H,d); 6.86(4H,c) 6.72(2H,d); 4.12(2H,q); 4.0(2H,t); 3.47(4H,m); 3.20(4H,m); 2.5(2H,t); 2.1(2H,m); 1.26(3H,t); m/e 370(M+H)⁺; calculated for $C_{21}H_{27}N_3O_3$ C, 68.3; H, 7.4; N, 11.4. Found: C, 68.1; H, 7.4; N, 11.1%.

The starting material was prepared as follows:

i) 4-(Piperazin-1-yl)anisole (4.24 g) and 4-chloropyridine hydrochloride (3.35 g) were intimately mixed and heated at 160°–170° C. (bath temperature) for 7 minutes. The solid obtained on cooling was dissolved in water (75 ml) and the solution basified with aqueous ammonia. The solid precipitate was extracted into ethyl acetate and the organic extract washed with water, filtered through phase separating paper (Whatman 1PS) and evaporated. The residue was recrystallised from ethanol to give 4-[4-(4-pyridyl)piperazin-1-yl]anisole (1.84 g) as a solid: m.p. 165°–167° C.; NMR (CDCl₃) δ 8.3(2H,d); 6.86(4H,m); 6.71(2H,d); 3.78(3H,s); 3.46(4H,m); 3.2(4H,m).

ii) The product from step i) (1.5 g) in concentrated hydrobromic acid (30 ml) was heated under argon at 130°–135° C. for 2 ½ hours. The solution was cooled, poured into water (150 ml) and basified with aqueous ammonia. The precipitate was filtered, washed with water and dried to give 4-[4-(4-pyridyl)piperazin-1-yl]phenol (1.36 g) as a solid: m.p. 310°–312° C.; NMR (d₆DMSO) δ 8.2(2H,d); 6.8(4H,m); 6.66(2H,d); 3.45(4H,m); 3.08(4H,m).

EXAMPLE 51

4-[4-[4-(4-Pyridyl)piperazin-1-yl]phenoxy]butyric acid

A solution of the product of Example 50 (0.1 g) in aqueous sodium hydroxide (1N, 0.8 ml) and ethanol (2 ml) was kept for 2 hours. The solution was evaporated and the residue dissolved in water (5 ml). Hydrochloric acid (1N, 0.8 ml) was added and the precipitate was filtered and washed with water and ether to give the title compound as a solid: m.p. 305°–306° C.; m/e 342 (M+H)⁺; NMR (d₆DMSO) δ 8.0(2H,d), 6.72(6H1,m); 3.74(2H,t); 3.3(4H,m); 2.94(4H,m); 2.19(2H,t); 1.72(2H,m); calculated for $C_{19}H_{23}N_3O_3$: C, 66.8; H, 6.8; N, 12.3. Found: C, 67.0; H, 6.8; N, 12.2%.

EXAMPLE 52

Ethyl 5-[4-[4-4-pyridyl)piperazin-1-yl]phenoxy] pentanoate

In a similar manner to Example 50, but starting from ethyl 5-bromopentanoate, was prepared the title compound in 41% yield (from ethyl acetate/hexane): m.p. 79°–82° C.; NMR (CDCl₃) δ 8.2(2H,d), 6.88(4H,m), 6.7(2H,d), 4.13 (2H,q), 3.47(4H,m), 3.17(4H,m), 2.36(2H,m), 1.8(4H,m), 1.33(3H,t); m/e 384(M+H)⁺, calculated for $C_{22}H_{29}N_3O_3.0.25H_2O$: C, 68.1; H, 7.6; N, 10.8. Found: C, 68.2; H, 7.8; N, 10.5%.

EXAMPLE 53

5-[4-[4-(4-Pyridyl)piperazin-1-yl]phenoxy]pentanoic acid

In a similar manner to Example 51, but starting from the product of Example 52, the title compound was made in 50% yield: m.p. 237°–241° C.; NMR (d₆DMSO) δ 8.2(2H, d); 6.97(4H,m), 6.83(2H,d); 3.69(2H,t), 3.57(4H,m), 3.13 (4H,m); 2.27(2H,t), 1.67(4H1,m); m/e 356(M+H)⁺; calculated for $C_{20}H_{25}N_3O_3$ 0.75H₂O: C, 65.0; H, 7.2; N, 11.3. Found: C, 65.0; H, 6.9; N, 11.1%.

EXAMPLE 54

Ethyl 4-[4-(4-pyridyl)piperazin-1-yl] phenoxycrotonate

In a similar manner to Example 50, but starting from ethyl 4-bromocrotoniate, was prepared the title compound in 3% yield (from ethyl acetate/hexanie): m.p. 127°–128° C.; NMR (CDCl₃) δ 8.3(2H,d), 7.1(1H,m), 6.9(4H,m), 6.7(2H,m), 6.18(2H,m), 4.66(2H,m), 4.25(2H,q), 3.49(4H,m), 3.2(4H, m), 1.3(3H,t); m/e 368(M+H)⁺; calculated for $C_{21}H_{25}N_3O_3$: C, 68.6; H, 6.9; N, 11.4. Found C, 68.4; H. 6.9; N. 10.7%.

EXAMPLE 55

3-[3-[4-(4-Pyridyl)piperazin-1-ylmethyl]] benzamido-3-phenylpropionic acid

Sodium hydroxide solution (1N, 0.5 ml) was added to a solution of methyl 3-[3-[4-(4-pyridyl)piperazin-1-ylmethyl] ]benzamido-3-phenylpropionate (0.116 g) in methanol (5 ml) at room temperature. After 16 hours, hydrochloric acid (1N, 0.5 ml) was added and the solution evaporated to dryness. The residue was warmed with dichloromethane (5 ml) and the insoluble solid was isolated by decantation and heated in water (5 ml) to give, after cooling a solid (0.062 g); NMR (d₆DMSO/CD₃COOD) δ 8.13(2H,d), 7.77(2H,m), 7.14–7.5(7H, complex), 7.06(2H,d), 5.42(1H,m), 3.56(6H, d), 2.8(2H,m); inme 445(M+H)⁺: calculated for $C_{26}H_{28}N_4O_3 \cdot 0.5H_2O$: C,68.9; H, 6.44; N, 12.35. Found: C, 68.7; H. 6.5; N, 12.2%.

The starting material was prepared as follows:

i) A solution of 3-chloromethyl benzoyl chloride (0.189 g) in DMF (2 ml) was added to a mixture of methyl 3-amino-3-phenylpropionate hydrochloride (0.215 g) and triethylamine (0.35 ml) in DMF (15 ml) with stirring at room temperature. After 3 hours, water (50 ml) was added and the mixture was extracted with dichloromethane. The organic layer was dried (MgSO₄) and evaporated to give an oil which solidified under high vacuum to give methyl 3-(3-chloromethyl)benzamido-3-phenylpropionate in 100% yield; NMR (CDCl₃) δ 7.72–8.7(10H, complex), 5.62(1H,m), 4.6(2H,s), 3.66(3H,s), 3.0(2H,m).

ii) A solution of 1-(4-pyridyl)piperazine (0.33 g) in acetonitrile (7.5 ml) was added to a stirred solution of the product of step i) in acetonitrile (5 ml). After sixteen hours at room temperature, the mixture was filtered and the filtrate evaporated. The residue was dissolved in dichloromethane (75 ml) and the solution washed with water (2×25ml), dried (MgSO₄) and evaporated. The residue was purified by flash column chromatography, the product being eluted with 5% v:v methanol in dichloromethane to give methyl 3-[3-[4-(4-pyridyl)piperazin-1-ylmethyl]] benzamido-3-phenylpropionate as a solid (0.18 g); NMR (CDCl₃) δ 8.35(2H,d); 7.85(1H,s), 7.72(1H,m), 7.39(7H, m), 6.68(2H,d), 5.62(1H,m), 3.65(3H,s), 3.6(2H,s), 3.0 (2H,m); m/e 459 (M+H)⁺; calculated for $C_{27}H_{30}N_4O_3 \cdot 0.5H_2O$: C, 69.3; H,6.6; N,12. Found: C, 69.1; H, 6.6; N, 11.8%.

EXAMPLE 56

Methyl 3-[4-[4-(4-pyridyl)piperazin-1-yl]] benzaminopropionate

Methyl 3-aminopropionate hydrochloride (0.195 g) and triethylamine (0.59 ml) were added to a stirred suspension of 4-[(4-pynidyl)piperazini-1-yl]benzoyl chloride hydrochloride (0.473 g) at room temperature. The mixture was stirred for two days and solvent removed under reduced pressure. The residue was purified by flash column chromatography. The product was obtained by elution with 1/9/0.1 v:v:v methanol/dichloromethane/0.88 S.G. aqueous ammonia as a solid which was recrystallised from ethyl acetate to give the title compound (0.2 g): m.p. 197°–199° C.; NMR ($d_6$DMSO) δ 8.19(2H,d); 7.72(2H,d); 7.13(2H,d); 6.90(2H, d); 3.82(4H,m); 3.56(3H,s); 3.48(6H,m), 2.50(2H,t); m/e 369(M+H)$^+$; calculated for $C_{20}H_{24}N_4O_3 \cdot 0.25H_2O$: C,64.4; H, 6.6; N, 15.0. Found: C,64.3; H, 6.6; N, 14.9%.

The starting material was prepared as follows:

i) An intimate mixture of 1-(4-pyridyl)piperazine (1.63 g) and 4-bromobenzoic acid (1.05 g) was heated at 220° C. for 6 hours. The resulting glass was cooled and triturated with methanol (50 ml) to give, as an off-white solid, 4-((4-pyridyl)piperazin-1-yl)benzoic acid; m.p>350° C.; IR(cm$^{-1}$) 1682, 1600, 1514, 1236, 1013.

(ii) Oxalyl chloride (0.5 ml) was added to a stirred suspension of 4-((4-pyridyl)piperazin-1-yl)benzoic acid in dichloromethane (15 ml), followed by DMF (1 drop). The mixture was stirred for 2 hours and evaporated to dryness to give 4-[(4-pyridyl)piperazin-1-yl]benzoyl chloride which was used immediately.

EXAMPLE 57

3-[4-[4-(4-Pyridyl)piperazin-1-yl]] benzamidopropionic acid

To a solution of the product of Example 56 (0.062 g) in methanol (1 ml) was added sodium hydroxide solution (1N, 0.1 7 ml) and the solution kept for 4 days at room temperature. Hydrochloric acid (1N, 0.17 ml) was added to give the title compound as a solid (0.052 g); m.p. >330° C.; NMR ($d_6$DMSO) 6.96(2H,d); 3.76(4H,m); 3.46(6H, complex); 2.5(2H,m); m/e 355 (M+H)$^+$; calculated for $C_{19}H_{22}N_4O_3 \cdot 0.7 H_2O$: C, 62.2; H, 6.4; N, 15.3. Found: C, 62.3; H, 6.4; N, 15.3%.

EXAMPLE 58

Methyl 3-[4-[4-(4-pyridyl)piperazin-1-yl] benzamido]-3-phenylpropionate

In a similar manner to Example 56, but starting from methyl 3-amino-3-phenylpropionate, was prepared the title compound in 26% yield as a solid (after trituration with hot ethyl acetate); NMR ($d_6$DMSO) δ 8.6(1H,d); 8.2(1H,brs); 7.75(2H,d); 7.3(5H,m); 7.0(2H,d); 6.85(2H, brs); 5.45(1H, m); 3.55(3H,s); 3.45(8H,m), 292(2H,m); m/e 355 445(M+H)$^+$; calculated for $C_{26}H_{28}N_4O_3 \cdot 0.5H_2O$: C, 68.9; H, 6.4; N, 12.4. Found. C, 68.7; H, 6.3; N, 12.3%.

EXAMPLE 59

3-[4-[4-(4-Pyridy)piperazin-1-yl]benzamido]-3-phenylpropionic acid

In a similar manner to Example 51, but starting from the product of Example 58, was prepared the title compound in 73% yield as a solid; NMR ($d_6$DMSO) δ 8.61(1H,d); 8.2(2H,brs); 7.78(2H,d); 7.3(5H,m); 7.0(2H,d); 6.9(2H,d); 5.43(1H,m); 3.45(8H,m); 2.82(1 H,m); m/e 431 (M+H)$^+$; calculated for $C_{25}H_{26}N_4O_3$ 0.5H$_2$O: C, 68.3; H, 5.9; N, 12.8 Found: C, 68.3; H, 6.0; N, 12.9%.

EXAMPLE 60

Methyl 3-[4-[4-(4-pyridyl)piperazin-1-yl] benzamido]butyrate

In a similar manner to Example 56, but starting from methyl 3-aminobutyrate, was prepared the title compound in 11% yield (recrystallised from ethyl acetate/hexane) as a solid; m.p. 130°–132° C.; NMR ($d_6$DMSO) δ 8.28(2H,d); 8.07(1H,d); 7.77(2H,d); 7.13(2H, 7.0(2H,d); 4.36(1H,m); 3.74(4H,m); 3.6(3H,s); 3.48(4H,m); 2.55(2H,m); 1.2(3H,d); m/e 383(M+H)$^+$; calculated for $C_{21}H_{26}N_4O_3 \cdot 0.25H_2O$: C, 65.2; H, 6.9; N, 14.5. Found: C, 65.3; H, 6.8; N, 14.4%.

EXAMPLE 61

Methyl 4-[2-[4-(4-pyridyl)piperazin-2-one-1-yl] acetyl]phenoxyacetate

A dispersion of potassium hydride in mineral oil (35% w/w, 0.63 g) was added to a stirred suspension of 4-(4-pyridyl)piperazin-2-one (0.885 g) in DMF (10 ml) and the mixture was stirr-ed at room temperature for 2 hours. To the anion thus formed, was added methyl 4-bromoacetylphenoxyacetate (1.44 g) and the mixture was stirred at room temperature for 20 hours. Solvent was evaporated and the residue partitioned between dichloromethane (20 ml) and water (20 ml). The organic layer was dried (MgSO$_4$) and evaporated. The residue was purified by flash column chromatography, the product being eluted with 1/9/0.1 v:v:v methanol/dichloromethane/0.88 S.G aqueous ammonia. Recrystallisation from ethyl acetate gave the title compound. m.p. 164°–165° C.; NMR ($d_6$DMSO) δ 8.2(2H, d), 7.97(2H,d), 7.08(2H,d), 6.83(2H,d), 4.93(4H,d), 4.02 (2H,s), 3.71(3H,s), 3.7(2H,m), 3.52(2H,m); m/e 384 (M+H)$^+$; calculated for $C_{20}H_{21}N_3O_5$: C, 62.7; H, 5.52; N, 11.0. Found: C, 62.6; H, 5.6; N, 10.9%.

The starting material was prepared as follows:

i) An intimate mixture of piperazinone (4.2 g) and 4-chloropyridine hydrochloride (7.33 g) was stirred and heated at 200° C. for 10 minutes and allowed to cool. The product was purified by flash column chromatography and eluted with 1/9/0.1 v:v:v methanol/methylene chloride/ 0.88 S.G. aqueous ammonia. The solid thus obtained was recrystallised from ethanol to give 4-(4-pyridyl)piperazin-2-one (1.75 g); m.p. 268°–270° C.; NMR ($d_6$DMSO) δ 8.2(3H,m); 6.8(12H,m); 3.85(2H,s); 3.52(2H,m); 3.31 (2H,m); m/e 178(M+H)$^+$.

EXAMPLE 62

4-[2-[4-(4-Pyridyl)piperazin-2-one-1-yl]acetyl] phenoxyacetic acid

In a similar manner to Example 51, but starting from the product of Example 61, was prepared the title compound in 20% yield as a solid NMR ($d_6$DMSO) δ 8.22(2H,d), 7.97 (2H,d), 7.04(2H,d), 6.89(2H,d); 4.93(2H,s), 4.77(2H,s), 4.07 (2H,s), 3.72(2H,m), 3.49(2H,m); m/e 370(M+H)$^+$; calculated for $C_{19}H_{19}N_3O_5 \cdot 2.5H_2O$: C, 55.1; H, 5.8; N, 10.1. Found: C, 55.1; H, 5.3; N, 10.6%.

EXAMPLE 63

Methyl 4-[[4-(4-pyridyl)piperazin-1-yl] carboxamido]phenoxy acetate

To a solution of 1-(4-pyridyl)piperazine (0.4 g) in dichloromethane (10 ml) was added a solution of methyl 4-isocyanatophenoxyacetate (0.5 g) in dichloromethane (5 ml). The resulting solution was stirred for 3 hours at room temperature. Solvent was evaporated and the residue triturated with ethanol to give the title compound as a solid (0.155 g); NMR ($d_6$DMSO) δ 8.55(1H,s), 8.22(2H,d), 7.28 (2H,d), 7.02(2H,d), 6.82(2H,d), 4.72(2H,s), 3.7(3H,s), 3.58 (8H,m); n/e 371(M+H)$^+$; calculated for $C_{19}H_{22}N_4O_4 \cdot H_2O$: C, 58.8; H, 6.2; N, 14.4 Found: C, 58.7; H, 5.8; N, 14.8%.

The starting material was prepared as follows:

Methyl 4-aminophenoxyacetate (2.2 g) in ethyl acetate (dried with calcium chloride) (50 ml) was added dropwise to a stirred solution of phosgene in toluene (115 ml, ~2M) at 75° C. After addition the mixture was stirred at 75° C. for 1.5 hours and at 95°–105° C. for 16 hours. Solvent was evaporated to give an oil (2.5 g); IR shows a strong band at 2273 $cm^{-1}$.

EXAMPLE 64

4-[[4-(4-Pyridyl)piperazin-1-yl]carboxamido] phenoxyacetic acid

In a similar manner to Example 51, but starting from the product of Example 63, was prepared the title compound in 86% yield as a solid; NMR ($d_6$DMSO) δ 8.45(11H,s); 8.2(2H,d), 7.35(2H,d), 6.35(4H,m), 4.55(2H,s), 3.49(8H,m), m/e 357(M+H)$^+$; calculated for $C_{18}H_{20}N_4O_4$.0.75 $H_2O$: C, 58.5; H, 5.8; N, 15.2. Found: C, 58.5; H, 5.9; N, 15.1%.

EXAMPLE 65

Ethyl-4-[4-(4-pyridyl)piperazin-1-yl]-4-quinolon-3-ylcarboxylic acid

A mixture of 1-ethyl-7-chloro-4-quinolon-3-ylcarboxylic acid (182 mg) and 1-(4-pyridyl) piperazine (125 mg ) was heated to 200° C. for 20 minutes. The mixture was cooled and methanol (5 ml) was added. The resulting solid was filtered and washed with methanol (10 ml) to give the title compound (68 mg), as a solid: NMR ($d_6$DMSO) δ 1.4(t,3H), 3.75–3.85(m,4H), 3.9–4.0(m,4H), 4.55(q,2H), 6.9(d, 1 H), 7.2(d,2H), 7.3(dd, 1H), 8.2(d, 1H), 8.3(d,2H), 8.9(s, 1H); m/e 379(M+H)$^+$

EXAMPLE 66

Methyl 2-RS-(n-butylsulphonylamino)-3-[4-[2-[4-(4-pyridyl)piperazin-1-yl]acetyl]phenyl]propionate To a solution of 1-(4-pyridyl) piperazine (296 mg) and triethylamine (0.25 ml) in acetonitrile (10 ml) was added, dropwise, over 30 minutes a solution of methyl-2-RS-(n-butylsulphonylamino)-3-(4-bromoacetylphenyl) propionate (382 mg) in acetonitrile (8 ml). The mixture was stirred for an additional 4 hours. The solvent was removed by evaporation to give an oil which was purified by flash column chromatography on silica, eluting with methanol/ dichloromethane (5:95 to 10:90 v/v) to give the title compound as a solid (202 mg): NMR ($d_6$DMSO) 0.7(t,3H), 1.05–1.4(m,4H), 2.55–2.7(m,4H), 2.8–3.2(m,4H), 3.25–3.4 (m,4H), 3.65(s,3H), 3.9(s,2H), 4.1–4.25(m, 1H), 6.85(d, 2H), 7.45(d,2H), 7.95(d, 1H), 7.95(d,2H), 8.15(d,2H); m/e 503(M+H)$^+$; calculated for $C_{25}H_{34}N_4O_5S$.0.5$H_2O$: C, 58.7; H, 6.85; N, 10.9. Found: C, 58.8; H, 6.9; N, 10.6.

The starting material was prepared as follows:
i) Methyl 2-amino-3-(4-acetylphenyl)propionate was prepared by the method described by M.P. Doyle JOC (1977), 42, 2431 and G.H.Cleland JOC (1969), 34, 744.
ii) n-Butylsulphonyl chloride(0.6ml) was added dropwise over 15 minutes to a solution of the product of step i) (926 mg) and triethylamine (0.7 ml) in dichloromethane (20 ml). The resulting mixture was stirred for a further 3 hours before it was poured into water (10 ml) and extracted with dichloromethane (3×20 ml). The organic extracts were combined, dried (MgSO$_4$) and then evaporated to give a gum. Purification by flash column chromatography on silica, eluting with ethyl acetate/hexane (40:60 v/v) gave methyl 2-RS-(n-butylsulphonylamino)-3-(4-acetylphenyl)propionate (794 mg) as a solid: NMR ($d_6$DMSO) 6 0.75(t,3H), 1.0–1.4(m,4H), 2.55(s,3H), 2.65 (s,3H), 2.8–2.95(m,2H), 3.05–3.2(m,2H), 3.65(s,3H), 4.1–4.25(m,1H), 7.45(d,2H), 7.85(d,1H), 7.9(d,2H); m/e 342(M+H)$^+$.
iii) To a suspension of CuBr$_2$ (822 mg) in ethyl acetate (8 ml) at reflux was added, dropwise over 10 minutes, a solution of the product from step ii) in chloroform (8 ml). The resulting mixture was refluxed for 3 hours. The imxture was cooled, filtered and the solvent was removed by evaporation to give an oil. Purification by flash column chromatography on silica, eluting with ethyl acetate/ hexane (10:90 to 50:50 in 10% increments v/v) gave methyl 2-RS-(n-butylsulphonylano)-3-(4-bromoacetylphenyl) propionate (387 mg) as an oil: NMR (CDCl$_3$) δ 0.9(t,3H), 1.25–1.4(m,2H), 1.6–1 75(m,2H), 2.75–2.85(m,2H), 3.05–3.3(m,2H), 3.8(s,3H), 4.35–4.45 (m, 1H), 4.4(s,2H), 4.8(d,1H), 7.35(d,2H), 7.95(d,2H); nme 420/422 (M+H)$^+$, Br pattern.

EXAMPLE 67

2-RS-(n-Butylsulphonylamino)-3-[4-[2-[4-(4-pyridyl)piperazine-1-yl]acetyl]phenyl]propionic acid To a solution of the product of Example 66 (105 mg) in methanol (4mi) was added 2N sodium hydroxide (0.25 ml) and the resulting solution was stirred for 3 hour. The mixture was concentrated, dissolved in water (2 ml) and acidified with acetic acid. The resulting solution was transferred to a reverse phase hplc column (Dynamax C18 83-201-C 60A) and eluted with 0.1% TFA in water/acetonitrile. The pure fractions, on freeze drying, gave the title compound (89 mg) as a solid: NMR ($d_6$DMSO) δ 0.8(t,3H), 1.15–1.6(m,4H), 2.75(t,2H), 2.9–3.05(m, 1H), 3.2–3.3(m, 1H), 3.4–3.5(m, 4H), 3.95–4.2(m,5H), 4.95(s,2H), 7.25(d,2H), 7.55(d,2H), 8.0(d,2H), 8.35(d,2H); m/e 489(M+H)$^+$; calculated for $C_{24}H_{32}N_4O_5S$.3 CF$_3$COOH: C, 43.4 ; H, 4.2 ; N, 6.7 ; TFA, 41.2. Found C, 43.7 ; H, 4.3; N, 6.8; TFA, 42.7.

EXAMPLE 68

2-RS-(n-Butylsulphonylamino)-3-[4-(4-pyridyl) piperazin-1-yl methylene]phenylpropionic acid To a solution of ethyl 2-RS-(n-butylsulphonylamino)-3-[4-(4-pyl-idyl)piperazin-1-yl methylene]phenylpropionate in methanol (3 ml) was added 2N sodium hydroxide (0.3 ml). The mixture was stirred for 3 hours and then concentrated. The resulting slurry was dissolved in water (2 ml) and acidified with acetic acid. The resulting solution was transfered to a reverse phase hplc column (Dynamax C18 83-201-C 60 A) and eluted with 0.1% TFA in water/ acetonitric. The pure product fractions, on freeze drying, gave the title compound (165 mg) as a solid: NMR ($d_6$DMSO) 6 0.8(t,3H), 1.1–1.6(m,4H), 2.65–2.95(m,4H), 3.2–3.3(m,4H), 3.85–4.0(mn,4H), 4.05–4.15(m,1H), 4.3(s, 2H), 7.2(d,2H), 7.4s,5H),8.3(d,62H); m/e 461(M+H)$^+$; calculated for $C_{23}H_{32}N_4O_4S.H_2O$. 2CF$_3$COOH: C, 45.9; H, 5.1; N, 7.9. Found C, 45.5 ; H, 4.8 ; N, 7.5.

The starting material was prepared as follows:
i) To a solution of α,α'-dibromo-p-xylene (6.59 g), N-(diphenylmethylene) glycine ethyl ester (4.76 g) and potassium iodide in 1,4-dioxane (120 ml), cooled to 10° C., was added 40% aq. benzyltrimethylammonium hydroxide(7.45 ml) over 1 hour. The mixture was allowed to warm to room temperature and then to stir for 2.5 hours. The mixture was partitioned between water (50 ml) and ethyl acetate (100 ml). The organic layer was separated, dried (MgSO$_4$) and evaporated to give an oil. Purification by flash column chromatography on silica, eluting with etheilhexane (10:90 v/v) gave ethyl RS-N-(diphenylmethylene)-4- (bromomethyl)phenylalanine ethyl ester (3.58 g) as an oil: NMR (d$_6$DMSO) δ 1.5(t, 3H), 3.0–3.2(m,2H), 4.05–4.15(m,3H), 4.65(s,2H), 6.55–6.65(m,2H), 7.0(d,2H),7.25(d,2H), 7.3–7.5(m,8H); n/e 450/452(M+H)$^+$Br pattern.

ii) To a warm solution of 1-(4-pyridyl)piperazine (296 mg) and triethylamine (0.14 ml) in acetonitrile (1 ml) was added slowly over 40 minutes a solution of the product from step i) (409 mg) in acetonitrile (5 ml). The resulting mixture was stirred at room temperature for 18 hours. The mixture was concentrated and purified by flash column chromatography on silica, eluting with methanol/dichloromethane (3:97 to 10:90 v/v) to give RS-N-(diphenylmethylene)-4-[4-(4-pyridyl)piperazin-1-ylmethylene]phenyl-alanine ethyl ester (305 mg) as a solid: NMR (d$_6$DMSO) δ 1.15(t,3H), 2.4–2.5(m,4H), 3.0–3.2(m,2H), 3.25–3.35(m,4H), 3.45(s,2H), 4.05–4.15 (m,3H), 6.65(d,2H), 6.75(d,2H), 7.0(d,2H), 7.15(d,2H), 7.35–7.5(m,8H), 8.1(d,2H); m/e 533(M+H)$^+$.

iii) To a suspension of the product from step ii) in ether (5 ml) was added 1N hydrochloric acid (2.2 ml) and the resulting mixture was stirred for 1 hour. The mixture was partitioned between ether (20 ml) and 1N hydrochloric acid (10 ml). The acid layer was separated, basified with aqueous sodium bicarbonate and extracted with dichloromethane (3×20 ml). The organic extracts were combined, dried (MgSO$_4$) and evaporated to give RS-4-[4-(4-pyridyl)-piperazin-1-ylmethylene]phenytalanine ethyl ester as an oil: NMR (d$_6$DMSO) δ 1.1 (t,3H), 2.4–2.5(m,4H), 2.7–2.9(m,2H), 3.2–3.35(m,4H), 3.5–3.6 (m,1H), 4.0(q,2H), 6.8(m,2H), 7.2(dd,4H), 8. I(bm,2H); m/e 369(M+H)$^+$.

iv) To a solution of the product of step iii) (1 37 mg) and triethylamine (0.11 ml) in tetrahydrofuran (5 ml) was added 0.75 ml of a stock solution of n-butylsulphonyl chloride 0.2 ml in 3 ml of tetrahydrofuran) and the resulting mixture was stirred for 3 hours. The solvent was removed by evaporation to give a gum. Purification by flash column chromatography on silica, eluting with methanol/dichloromethane (5:95 to 10:90 v/v) gave ethyl 2-(RS)-(n-butylsulphonylamino)-3-[4-(4-pyridyl) piperazin-1-ylmethylenelphenylpropionate as a solid which was used without further purification.

EXAMPLE 69

Methyl 3-[6-[4-(4-pyridyl)piperazin-1-yl]pyrid-3-ylcarboxamido]propionate

To 6-[4-(4-pyridyl)piperazin-1-yl]nicotiniic acid was added dimethylformamide (0.1 ml) and thionyl chloride (5 ml)and the resulting mixture was refluxed for 2 hour. The excess thionyl chloride was removed by evaporation and the resulting solid was suspended in dichloromethane (10 ml) to which was added methyl-3-aminopropionate hydrochloride (546 mg). The resulting mixture was cooled to 5° C. and triethylamine(3 ml) was added dropwise over 15 minutes. The mixture was stirred at room temperature for 18 hours. The mixture was partitioned between dichloromethane(50 ml) and aqueous sodium bicarbonate(25 ml). The organic layer was separated, dried (MgSO$_4$), and evaporated to give a gum. Purification by flash column chromatography on silica, eluting with methanol/dichloromethane (6:94 to 15:85 v/v), gave the title compound (339 mg) as a gum: NMR (d$_6$DMSO) δ 2.6(t,2H), 3.4–3.5(m,2H), 3.5–3.6(m,4H), 3.6 (s,3H), 3.7–3.8(m,4H), 6.9–7.0(m,3H), 8.0(dd,1H), 8.2(d, 2H), 8.35(t,1H), 8.6(d,1H); m/e 370(M+H)$^+$; calculated for C$_{19}$H$_{23}$N$_5$O$_3$.1.5H$_2$O: C, 57.6; H, 6.5; N, 17.6. Found: C, 57.3; H,5.9; N,17.5.

The starting material was prepared as follows:

i) A mixture of 6-chloronicotinic acid (3.21 g) and 1-(4-pyridyl) piperazine (3.32 g) was heated to 220° C. for 3 minutes. The mixture was cooled and methanol (10 ml)was added. The resulting suspension was boiled for 10 minutes, cooled and filtered to give 6-[4-(4-pyridyl) piperazin-1-yl]nicotinic acid (2.51 g) which was used without further purification.

EXAMPLE 70

3-[6-[4-(4-Pyridyl)piperazin-1-yl]pyrid-3-ylcarboxamido]propionic acid

To a solution of the product of Example 69 (136 mg) in methanol (8 ml) was added 2N sodium hydroxide (0.9 ml). The mixture was stirred for 3h and then concentrated. The resulting gum was dissolved in water (4 ml) and acidified with acetic acid. The precipitate was filtered and washed with water to give the title compound (83 mg) as a solid: NMR (d$_6$DMSO+TFA) δ 2.5–2.6(m,2H), 3.45–3.55(m,2H), 3.95–4.1 1(m,8H), 7.2(d,2H), 7.4(d,1H), 8.3–8.4(m,3H), 8.55(d,1H); m/e 356(M+H)$^+$; calculated for C$_{18}$H$_{21}$N$_5$O$_3$.H$_2$O: C, 57.9;H, 6.1; N, 18.75. Found: C, 57.7; H, 5.8; N, 18.5.

EXAMPLE 71

4-[[4-(4-Pyridyl)piperazin-1-yl]quinolin-6-yl] oxyacetic acid

To a solution of methyl 4-[4-(4-pyridyl)piperazin-1-yl]quinolin-6-yloxyacetate (146 mg) in methanol (5 ml) was added 2N sodium hydroxide (0.7 ml). The mixture was stirred for 3 hours before evaporation to dryness. The resulting gum was dissolved in water (3 ml) and acidified with acetic acid. This was transfered to a reverse phase hplc column (Dynamax C18 83-201-C 60A) and eluted with 0.1% TFA in water/acetonitrile. The pure fractions, on freeze drying, gave the title compound (261 mg) as a solid: NMR (d$_6$DMSO) δ 3.9–4.1(m,8H), 4.9(s,2H), 7.15(d,1H), 7.2(d, 2H), 7.45(d,1H), 7.7(dd,1H), 8.0(d,1H), 8.35(d,2H), 8.65(d, 1H); m/e 365(M+H)$^+$; calculated for C$_{20}$H$_{20}$N$_4$O$_3$.2TFA.0.5H$_2$O: C,47.9; H, 3.8; N, 9.3. Found: C, 48.1; H, 3.6; N, 9.2.

The starting material was prepared as follows:

i) To a solution of methyl 4-bromoquinolin-6-yloxyacetate (169 mg) in isopropanol (10 ml) was added 1-(4-pyridyl) piperazine (93 mg) followed by 2 drops of saturated ethereal HCl. The resulting mixture was refluxed for 18 hours. The mixture was filtered and concentrated. Purification by flash column chromatography on silica, eluting with methanol/dichloromethane (10% to 15% v/v in 1% increments) gave methyl 4-[4-(4-pyridyl)piperazin-1-yl]quinolin-6-yloxyacetate (74 mg) as a solid: NMR (d$_6$DMSO) δ 3.2–3.4(m,4H), 3.6–3.7(m,4H), 3.75(s, 3H), 5.0(s,2H), 6.95(d,2H), 7.05(d, 1H), 7.25(d, 1H), 7.45(dd, 1H), 7.9(d,1H), 8.25(d,2H), 8.6(d,1H); m/e 379(M+H)$^+$.

EXAMPLE 72

0:6 Mixture of isopropyl 2-[4-(4-pyridyl)piperazin-1-yl]-quinolin-6-yloxyacetate and methyl 2-[4-(4-pyridyl)piperazin-1-yl]oxyacetate In a similar manner to Example 71i) the title mixture of compounds was obtained. NMR (d$_6$DMSO) δ 1.2(d,4H, 0.6 isopropyl ester), 3.5–3.6(m,4H), 3.7(s,1,2H, 0.4 methyl ester), 3.73–3.85(m,4H), 4.8 and 4.85(s, 2H), 5.0(m,0.6 isopropyl ester), 6.9–7.0(m,2H),7.15–7.35(m,3H), 7.55(d, 1 H), 8.0(dd, 1 H), 8.1 5–8.25(m,2H); m/e 427/429(M+H)⁺.

EXAMPLE 73

2-[4-(4-Pyridyl)piperazin-1-yl]quinolin-6-yloxyacetic acid

To a solution of the product of Example 72 (145 mg) in methanol (5 ml) was added 2N sodium hydroxide (0.7 ml). The mixture was stirred for 3 hours before evaporating to (dryness. The resulting gum was dissolved in water (3ml) and acidified with acetic acid. The resulting precipitate was filtered and washed with water to give the title compound (47 mg): NMR (d₆DMSO) δ 3.6–3.7(m,4H), 3.8–3.9(m,4H), 4.75(s,2H), 7.0(d,2H), 7.15(d,1 H), 7.2–7.3(m,2H), 7.55(d, 1H), 8.0(d,1H), 8.25(d,2H); m/e 365(M+H)⁺; calculated for C₂₀H₂₀N₄O₃.0.25H₂O : C,65.1; H. 5.6; N, 15.2. Found: C, 65.1; H, 5.4; N, 15.0.

EXAMPLE 74

3-[6-[4-(4-Pyridyl)piperazin-1-yl]pyrid-2-yl]carboxamidopropionic acid

To a solution of isoamyl 3-[6-[4-(4-pyridyl]pipazin-1-yl]-pyrid-2-yl]carboxamidopropionate (140 mg) in methanol (10 ml) was added 1N sodium hydroxide and the resulting solution was stirred for 18 hours. The mixture was filtered and the solvent was removed by evaporation to give the title compound as a white solid: NMR (d₆DMSO+ CD₃COOD) δ 2.5–2.6(m,2H), 3.55(t,2H), 3.8(s,8H), 6.9(d, 1H), 7.05(d,2H), 7.35(d, IH), 7.6–7.7(m,1H), 8.15(d,2H); m/e 356(M+H)⁺.

The starting material was prepared as follows:

i) A suspension of 2,6-dibromopyridine (19 g) in diethylether (200 ml) was added to a mixture of n-butyl lithium (130 ml of a 1.6M solution in hexane) and diethylether (200 ml) cooled to −50° C. The resulting solution was stirred at −50° C. for 10 minutes before pouring onto a slurry of diethyl ether (100 ml) and dry-ice. The mixture was allowed to warm to room temperature and filtered. The resulting solid was dissolved in 2N sodium hydroxide (350 ml) and extracted with diethyl ether (2×300 ml). The aqueous layer was separated and acidified with 2N hydrochloric acid. The resulting precipitate was filtered and washed with water to give 6-bromo-2-pyridine carboxylic acid (7.25 g): NMR (d₆DMSO) δ 7.69(d,1H), 7.95(d, 1H), 8.05(dd, 1H); m/e 202(M+H)⁺.

ii) In a similar manner to Example 69 but starting from 6-bromo-2-pyridine carboxylic acid was prepared methyl 3-(6-bromopyridin-2-carboxamido)propionate; NMR (d₆DMSO) δ 2.65(t,2H), 3.5–3.6(m,2H), 3.6(s,3H), 7.7–8.05(m,3H), 8.7(1H); m/e 287/289(M+H)⁺Br pattern.

iii) To a solution of the product of step ii) (770 mg) in isoamyl alcohol (2.5 ml) was added 1-(4-pyridyl) piperazine (540 mg) and 2 drops of saturated ethereal HCl. The resulting mixture was refluxed for 18 hours. The mixture was concentrated and purified by flash column chromatography on silica, eluting with methanol/dichloromethane (3:97 v/v), to give isoamyl 3-[6-[4-(4-pyridyl)piperazin-1-yl]pyrid-2-yl]carboxamidopropionate as a gum: NMR (d₆DMSO) δ 1.25–1.35(m,6H), 1.4–1.7(m,3H), 2.6(t,2H), 3.35–3.6(m, 8H), 3.7–3.75(m,2H), 4.05(t,2H), 6.85(d,2H), 7.05(d,1H), 7.3(d,1H), 7.7(dd, 1H), 8.2(d,2H), 8.6(t,1H), m/e 426(M+H)⁺.

EXAMPLE 75

4-[4'-[N-Methyl-N-(4-pyridyl)]aminomethyl] biphenyloxyacetic acid

To a solution of Methyl 4-[4'-[N-methyl-N-(4-pyridyl)] aminiomethyl]-biphenyloxyacetate (50 mg) in methanol (5 ml) was added 1N sodium hydroxide (0.45 ml) and the resulting mixture was stirred for 18 hours. The resulting precipitate was filtered to give the title compound (29 mg): NMR (d₆DMSO) δ 2.9(s,3H), 4.05(s,2H), 5.35(s,2H), 6.8–6.95(m,4H), 7.35–7.55(dd,4H), 7.6(d,2H), 8.2(d,1H), 8.45(d,1H); m/e 349(M+H)⁺; calculated for C₂₁H₂₀N₂O₃.2.25H₂O : C,64.9; H. 6.05; N, 7.2. Found: C, 65.2; H. 6.4; N, 7.2.

The starting material was prepared as follows:

i) To a solution of 4-hydroxy-4-biphenylcarboxylic acid (2.14 g) in tetrahydroftiran (25 ml) under an argon atmosphere was added slowly 1M borane-THF complex (50 ml). The resulting mixture was stirred for 18 hours before the addition of ethyl acetate (10 ml) and water (100 ml). The resulting mixture was acidified with 2N hydrochloric acid and stirred for 30 minutes. The aqueous layer was extracted with ethyl acetate (2×100 ml). The organic extracts were combined, dried (MgSO₄) and evaporated . Recrystallisation from a small volume of ethyl acetate gave 4-hydroxy-4-biphenylmethanol (580 mg): NMR (d₆DMSO) δ 4.5(s,2H), 6.85(d,2H), 7.35(d,2H), 7.45–7.55(dd,4H), 9.45(s,1H); m/e 201(M+H)⁺.

ii) To a solution of 4-hydroxy-4-biphenylmethanol (580 mg) in acetone (15 ml) was added anhydrous potassium carbonate (1.2 g) followed by methyl bromoacetate (0.3 ml). The resulting mixture was stirred for 72 hours and filtered. The solvent was removed by evaporation to give a solid which was recrystallised from ethyl acetate to give methyl 4-(4'-hydroxymethyl)biphenyloxyacetate (316 mg); NMR (d₆DMSO) δ 3.7(s,3H), 4.5(s,2H), 4.85(s,2H), 7.0(d,2H), 7.35(d,2H), 7.5–7.6(dd,4H); me 273(M+H)⁺ iii) To a solution of the product from step ii) (300 mg) in dichloromethane (15 ml) cooled to 5° C. was added triethylamine (0.17 ml) followed by methanesulphonyl chloride (0.19 ml). The resulting mixture was stirred for 72 hours. Water (10 ml) was added and the mixture was extracted with dichloromethane (3×5 ml). The organic extracts were combined, dried (MgSO4) and evaporated to give a gum. Purification by flash column chromatography on silica, eluting with ethyl acetate/hexanie (25:75 v/v) gave methyl 4-(4'-chloromethyl)biphenyloxyacetate (230 mg) as a solid: NMR (d₆DMSO) δ 3.75(s,3H), 4.8(s,2H), 4.85(s,2H), 7.05(d,2H), 7.5(d,2H), 7.6–7.65 (dd,4H); m/e 290 M⁺.

iv) To a solution of 4-methylaminopyridine (142 mg) in acetonitrile (5 ml) was added slowly a solution of the product of step iii) (230 mg) in acetonitrile (5 ml). Tricthylaminie (0.18 ml) was added and the resulting mixture was stirred for 72 hours. The mixture was partitioned between water (20 ml) and dichloromethane (50 ml). The organic layer was separated, dried (MgSO₄) and evaporated to give a solid, which was recrystallised from isopropanol to give methyl 4-[4'-[N-methyl-N-(4-pyridyl) aminomethyl]biphenyloxyacetate (50 mg): NMR (d₆DMSO) δ 2.9(d,3H), 3.7(s,3H), 4.85(s,2H), 5.4(s,2H), 6.85–6.95(m,2H),7.0(d,2H), 7.45(d,2H), 7.55–7.7(dd, 4H), 8.25(d, 1H), 8.5(d, 1H); m/e 363(M+H)⁺.

EXAMPLE 76

5-[[4-(4-Pyridyl)piperazin-1-yl]methylene]naphth-2-yloxyacetic acid

In a similar manner to Example 67, but starting from methyl 5-[[4-(4-pyridyl)piperazin-1-yl]methylene]naphth- 2-yloxyacetate was prepared the title compound: NMR (d$_6$DMSO) δ 2.75(m,4H), 3.7(m,4H), 4.1 (s,2H), 4.8(s,2H), 7.15–7.5(m,6H), 7.8(d,1H), 8.2–8.3(m,3H); m/e 378 (M+H)$^+$.

The starting material was prepared as follows:

i) A solution of 6-methoxy-1-tetralone (15 g) in diethyl ether (250 ml) was added slowly to a mixture of methyl magnesium iodide (37 ml of a 3M solution in diethyl ether) and diethyl ether (100 ml) whilst maintainiig the temperature below 10° C.. After stirring at 5° C. for 30 minutes, the mixture was refluxed for 2 hours. The reaction was quenched with saturated ammoniumn chloride. The organic layer was separated dried(MgSO$_4$) and evaporated. Purification by flash column chromatography, eluting with ethyl acetatc/hexane (1:99 v/v) gave 1-methyl-7-methoxy-1,2-dehydrodecalin (11.58 g) as an oil: NMR (d$_6$DMSO) δ 1.95(m,3H), 2.1–2.25(m,2H), 2.7(d,2H), 3.75(s,3H), 5.65–5.75(m,1H), 6.7–6.8(m,2H), 7.1(d, 1H); m/e 175(M+H)$^+$.

ii) 2,3-Dichloro 5,6 dicyano-1,4 benzoquinone (17.85 g) was added in one portion to a solution of the product from step i) (11.56 g) in toluene (500ml). After stirring for 1 hour the mixture was filtered and an equal volume of hexane was added. The diluted filtrate was passed down a short alumina column. Removal of the solvent gave 6-methoxy-1-methylnaphthalene (6.4 g) as an oil: NMR (d$_6$DMSO) δ 2.6(s,3H), 3.7(s,3H), 7.15–7.25(m,2H), 7.3–7.35(m, 2H), 7.65(d,1H), 7.9(d,1H); m/e 173(M+H)$^+$ iii) To a solution of 6-methoxy-1-methylnaphthalene (6.4 g) in dichloromethanie (500 ml), cooled to –60° C., was added boron tribromide (45 ml of a 1M solution in dichloromethane). The resulting mixture was stirred at –60° C. for 3 hours. The reaction was quenched with water (500 ml) and extracted with dichloromethane (2×500 ml). The organic extracts were combined, dried (MgSO$_4$) and evaporated to give a solid. Purification by flash column chromatography on silica, eluting with ethyl acctate/hexane (5:95 v/v) gave 6-methyl-2-naphthol (3.76 g) as a white solid. This was used without further characterisation.

iv) To a solution of 6-methyl-2-naphthol (3.15 g) in acetone (100 ml) was added anhydrous potassium carbonate (6.0 g) followed by methyl bromoacetate (2.0 ml). The mixture was stirred for 18 hours and then filtered. The solvent was removed by evaporation to give an oil. Purification by flash column chromatography on silica, eluting with ethyl acetate/hexane (5:95 v/v) gave methyl 2-(5-methyl) naphthoxyacetate (3.8 g) as a white solid: NMR (d$_6$DMSO) δ 2.6(s,3H), 3.7(s,3H), 4.9(s,2H), 7.15–7.4(m, 4H), 7.65(d,1H), m/e 23 1(M+H)$^+$.

v) To a solution of the product from step iv) (1.5 g) in carbon tetrachloride (100 ml) was added N-bromosuccinimide (1.16 g) followed by a catalytic amount of AIBN. The resulting mixture was refluxed for 2 hours. The solvent was removed by evaporation to give an oil, which was purified by flash column chromatography on silica eluting with ethyl acetate/hexane (5:95 v/v) to give methyl 2-(5-bromomethyl)naphthoxyacetate (1.16 g) as a gum: NMR (d$_6$DMSO) δ 3.75(s,3H), 4.95(s,2H), 5.2(s,2H), 7.3–7.6 (m,4H), 7.8(d,1H), 8.15(d,1H); m/e 309/311 (M+H)$^+$Br pattern.

vi) In a similar manner to Example 66, but starting from the product of step v) was prepared methyl 5-[[4-(4-pyridyl) piperazin-1-yl]methylenelnaphth-2-yloxyacetate: NMR (d$_6$DMSO) δ 3.2–3.35(m,8H), 3.7(s,3H), 3.9(s,2H), 4.9 (s,2H), 6.8(d,2H), 7.2–7.45(m,4H), 7.75(d, 1H), 8.15(d, 2H), 8.25(d, 1H); mie 392(M+H)$^+$.

EXAMPLE 77

4-[[4-(4-Pyridyl)piperazin-1-yl]methylene]cinnamic acid $^t$Butyl 4-[[4-(4-pyridyl)piperazin-1-yl]methylene] cinnamate (200 mg) was stirred in trifluoroacetic acid (5 ml) for 2 hours. The solvent was removed by evaporation and the resulting oil was titriated with anhydrous ether to give the title compound (210 mg) as a white solid: NMR (d$_6$DMSO) δ 3.05–3.25(m,4H), 3.7–4.1(bm,4H), 4.25(s,2H), 6.6(d,1H), 7.25(d,2H), 7.5(d,2H), 7.6(d,1H), 7.75(d,2H), 8.35(d,2H); m/e 324(M+H)$^+$; calculated for C$_{19}$H$_{21}$N$_3$O$_2$.2CF$_3$COOH.0.5H$_2$O: C, 49.5; H, 4.25; N, 7.4. Found: C, 49.1; H, 4.2; N, 7.1.

The starting material was prepared as follows:

i) In a similar to Example 66, but starting from $^t$butyl 4-bromomethyl cinnamate was prepared $^t$butyl 4-[[4-(4-pyridyl)piperazin-1-yl]methylenel cinnamate: NMR (d$_6$DMSO) δ 1.45(s,9H), 3.55(s,2H), 6.5(d,1H), 6.8(d, 2H), 7.35(d,2H), 7.55(d,1H), 7.65(d,2H), 8.15(d,2H).

EXAMPLE 78

Dimethyl 4-[2-[4-(4-pyridyl)piperazin-1-yl)-2-methyl]acetyl]-1,2-diphenoxydiacetate In a similar manner to Example 66, but starting from dimethyl 4-[(2'-bromopropionyl)-phenylene-1,2-dioxy] diacetate was prepared the title compound: NMR (d$_6$DMSO) δ 1.15(d,3H), 2.55–2.7(m,4H), 3.2–3.35(m,4H), 3.68(s,3H), 3.70(s,3H), 4.25(q,1H), 4.9(s,2H), 4.95(s,2H), 6.75(d,2H), 7.0(d,1H), 7.65(d,1H), 7.75(dd,1H), 8.15(d,2H); m/e 472 (M+H)$^+$. The starting material was prepared as follows:

i) To a solution of 3,4 dihydroxypropiophenone (1.24 g) in DMF (1Smi) was added anhydrous potassium carbonate (3.09 g) followed by methyl bromoacetate (1.4 ml). The resulting mixture was stirred for 24 hours. Water (50 ml) was added and the mixture was extracted with ethyl acetate (3×100 ml) The organic extracts were combined, dried (MgSO$_4$) and evaporated to give a gum. Purification by flash column chromatography on silica eluting with ethyl acetate/hexane (1:1 v/v) gave dimethyl 4-propionyl-phenylene-1,2-dioxydiacetate (1.79 g) as an oil: NMR (d$_6$DMSO) δ 1.05(t,3H), 3.0(q,2H), 3.7(s,6H), 4.9(s,2H), 4.95(s,2H), 7.05(d,d,1H), 7.45(d,1H), 7.6(dd,1H); m/e 311 (M+H)$^+$.

ii) To a solution of the product from step i) (1.79 g) in chloroform (15 ml) was added dropwise a solution of bromine (0.3 ml) in chloroform (5 ml) and the resulting mixture was stirred for 3 hours. The solvent was removed by evaporation to give a gum which was purified by flash column chromatography on silica, eluting with ethyl acetate/hexane (2:3 v/v) to give dimethyl 4-[(2'-bromopropionyl)-phenylene-1,2-dioxy)diacetate (1.95 g), which solidified on standing: NMR (d$_6$DMSO) 8 1.75(d, 3H), 3.7(s,6H), 4.9(s,2H), 4.95(s,2H), 5.8(q,1H), 7.05(d, 1H), 7.5(d, 1H), 7.7(dd, 1H); m/e 389/391 (M+H)$^+$Br pattern.

EXAMPLE 79

4-[2-[(4-Pyridyl)piperazin-1-yl]-2-methyl]acetyl-1, 2-diphenoxydiacetic acid

In a similar manner to Example 67, but starting from the product of Example 78 was prepared the title compound: NMR (d$_6$DMSO) δ 1.4(d,3H), 3.0–3.2(m,4H), 3.75–3.9(m, 4H), 4.75.5.0(m, 1H), 4.8(s,2H), 4.85(s,2H), 7.05(d, 1H), 7.25(d,2H), 7.55(d, 1H), 7.75(dd, 1H), 8.3(d,2H); m/e 444 (M+H)$^+$. Calculated for $C_{22}H_{25}N_3O_7.2.25CF_3COOH.H_2O$ C, 44.3; H, 4.1; N, 5.85; TFA, 35.7. Found C, 44.2; H, 3.9; N, 5.7; TFA, 36.2.

EXAMPLE 80

Methyl 2-[4-(4-pyridyl)piperazin-1-yl]tetralone-6-oxyacetate

In a similar manner to Example 66, but starting from methyl 2-bromotetralone-6-oxyacetate was prepared the title compound: NMR ($d_6$DMSO+$CD_3$COOD) δ 2.05–2.4(m, 2H), 2.9–3.05(m,2H), 3.1 –3.25(m,4H), 3.6(s,3H), 3.75–3.9 (m,4H), 4.05(dd,1H), 4.75(s,2H), 6.75(d,1H), 6.85(dd,1H), 7.05(d,2H), 7.85(d,1H), 8.1 (d,2H); m/e 396(M+H)$^+$. The starting material was prepared as follows:

i) A solution of 6-methoxy- 1-tetralone (5.0 g) in 48% hydrobromic acid (62 ml) was refluxed for 8 hours. The mixture was cooled, filtered and washed with water (50 ml) to give 6-hydroxy-1-tetralone (3.91 g): NMR ($d_6$DMSO) 1.9–2.05(m,2H), 2.4–2.55(m,2H), 2.8–2.9(m, 2H), 6.65(d, 1H), 6.7(dd,1H), 7.75(d,1H), m/e 163(M+H)$^+$.

ii) To a solution of 6-hydroxy-1-tetralone (2.62 g) in acetone (50 ml) was added anhydrous potassium carbonate (2.23 g) followed by methyl bromoacetate (1.52 ml) and the resulting mixture was stirred for 18 hours. The mixture was filtered and the solvent was evaporated to give a yellow solid. Recrystallisation from ethyl acetate gave methyl tetralone-6-oxyacetate (2.28 g): NMR ($d_6$DMSO) δ 1.95–2.05(m,2H), 2.45–2.55(m,2H), 2.9(t,2H), 3.7(s, 3H), 4.9(s,2H), 6.85–6.9(m,2H), 7.8(d,1H); m/e 235(M+H)$^+$.

iii) To a solution of the product from step ii) (1.3 g) in chloroform (15 ml) was added dropwise a solution of bromine (0.29 ml) in chloroform (1 ml) and the resulting mixture was stirred for 4 hours. The solvent was evaporated to give an oil. Purification by flash column chromatography on silica, eluting with ethyl acetate/hexane (30:70 v/v) gave methyl 2-bromotetialone-6-oxyacetate (1.55 g) as an oil: NMR ($d_6$DMSO) δ 2.3–2.6(m,2H), 2.9–3.1(m,2H), 3.7(s,3H), 4.9(s,2H), 4.9–5.0(m,1H), 6.9–7.0(m,2H), 7.9(d,1H); m/e 313/315(M+H)$^+$Br pattern.

EXAMPLE 81

Methyl 2-S-(n-butylsulphonylamino)-3-[4-[3-[1-(4-pyridyl)piperidin-4-yl]propoxy]phenyl]propionate Using a procedure similar to that described in Example 35, but starting from the appropriate amino ester, the title compound was prepared; NMR ($d_6$DMSO) 0.75(t,3H), 1.0–1.44(m,8H), 1.44–1.64(m, 1H), 1.75(brd,4H), 2.5–3.02 (m,6H), 3.64(s,3H), 3.85–4.1 (m,5H), 6.81 (d,2H), 6.84(d, 2H), 7.19(d,2H), 7.78(d, 1H), 8. 12(d,2H); mass spectrum (+ve FAB, MeOH/NBA): 518 (M+H)$^+$.

The starting material was prepared using similar procedures to those described in Example 33. There was thus prepared the following intermediates i) and ii) which were themselves prepared starting from 4-(4-hydroxypropylpiperidin- 1 -yl) pyridine iii).

i) Methyl 2-S-(benzyloxycarbonylamino)-3- [4- [3-[1 -(4-pyridyl)piperidin-4-yl]-propoxy]phenyl]propionate; NMR ($d_6$DMSO) 1.18–1.24(m,2H), 1.3–1.43(m,2H), 1.44–1.65(m,1H), 1.65–1.83(m,4H), 2.7–2.88(m,3H), 2.96(dd,1H), 3.61(s,3H), 3.92(t,4H), 4.14–4.25(m, 1H), 4.98(s,2H), 6.8(d,2H), 6.82(d,2H), 7.14(d,2H), 7.2–7.4 (m,5H), 7.74(d,1H), 8.12(d,2H); mass spectrum(+ve FAB, MeOH/NBA): 532(M+H)$^+$.

ii) Methyl 2-S-amino-3- [4- [3-[1-(4-pyridyl)piperidin-4-yl] propoxy]phenyl]propionate;

NMR ($d_6$DMSO) 1.03–1.2(m,2H), 1.28–1.40(m,2H), 1.42–1.62(m, 1H), 1.64–1.80(m,4H), 2.65–2.9(m,4H), 3.58 (s,3H), 3.45–3.6(m, 1 H), 3.85–3.98(mn,4H), 6.78(d,2H), 6.8(d,2H), 7.06(d,2H), 8.11 (d,2H); mass spectrum(+ve FAB, MeOH/NBA): 398(M+H)$^+$.

iii) 4-(4-Hydroxypropylpiperidin-1-yl)pyridine.

A solution of N-(2-carbamoylethyl)-4-cyanopyr-idinium chloride (2.1 g) in water (5 ml) was added dropwise to a stirred mixture of 4-hydroxypropylpiperidine (2.4 g), water (10 ml) and 2.5M sodium hydroxide solution (4.6 ml) cooled in an ice-bath. The mixture was stirred at 0–5° C. for 1 hour. 2.5M sodium hydroxide solution (7 ml) was added and the mixture heated at reflux for 3 hours. The mixture was cooled in an ice-bath and gummy solid separated out. The aqueous layer was decanted off and the gummy solid dissolved in dichloromethane (75 ml). The solution was washed with saturated sodium chloride solution (10 ml) and dried ($MgSO_4$). The solvent was removed by evaporation to give a gummy solid (880 mg) which on trituration with ether gave a solid; NMR ($d_6$DMSO) 1.0–1.35(m,4H), 1.35–1.6(m,3H), 1.7(dd,2H), 2.70–2.88(dt,2H), 3.38(t,2H), 3.89(brd,2H), 4.35(brs, 1H), 6.78(d,2H), 8.1 (d,2H); mass spectrum(Cl$^+$): 221 (M+H)$^+$.

EXAMPLE 82

2-S-(n-Butylsulphonylamino)-3-[4-[3-[1-(4-pyridyl) piperidin-4-yl]propoxy]phenyl]propionic acid Using a similar procedure to that described in Example 34, but starting from the product of Example 81, the title compound was obtained as an amorphous solid; NMR ($d_6$DMSO/$CD_3CO_2D$) 0.73(t,3H), 1.0–1.5(m,8H), 1.55–1.85(m,5H), 2.54–2.78(m,3H), 2.9–3.2(m,3H), 3.8–3.98(m,3H), 4.15(brd,2H), 6.8(d,2H), 7.09(d,2H), 7.15 (d,2H), 8.1(d,2H); mass spectrum(+ve FAB, MeOH/NBA): 504(M+H)$^+$; microanalysis found C,60.3; H,7.2; N,7.9%; $C_{26}H_{37}N_3O_5S.H_2O$ requires C,59.9; H,7.5; N,8.1%.

EXAMPLE 83

Methyl 2-S-(butylsulphonylamino)-3-[4-[4-[1-(4-pyridyl)piperidin-4-yl]-butoxy]phenyl]propionate Using, a similar procedure to that described in Example 35, but starting from the appropriate amino ester, the title compound was prepared; NMR (CDCl$_3$) 0.87(t,3H), 1.14–1.4(m,6H), 1.42–1.7(m,5H), 17–1.9(m,4H), 2.7–3.18 (m,6H), 3.78(s,3H), 3.9(brd,2H), 3.93(t,2H), 4.32(brs,1H), 4.82(brs,1H), 6.66(d,2H), 6.83(d,2H), 7.09(d,2H), 8.22(d, 2H); mass spectrum(+ve FAB, McOH/NBA): 532 (M+H)$^+$.

The starting material was prepared using similar procedures to those described in Examples 33 and 81iii). There was thus prepared the following intermediates:

i) 4-(4-hydroxybutylpipeidin-1-yl)pyridine; NMR ($d_6$DMSO) 0.97–1.58(m,9H), 1.7(dd,2H), 2.78(dt,2H), 3.38(m,2H), 3.88(brd,2H), 4.29(t, 1H), 6.78(d,2H), 8.10 (d,2H); mass spectrum(Cl$^+$): 235(M+H)$^+$.

ii) Methyl 2-S-(benzylcarbonylamino)-3-[4-[4-[1-(4-pylridyl)piperidin-4-yl]butoxy]phenyl]propionate; NMR ($d_6$DMSO) 1.0–1.35(m,4H), 1.35–1.60(m,3H), 1.62–1.80 (m,4H), 2.8(dt,3H), 2.96(dd,1H), 3.62(s,3H), 3.85–3.97 (m,4H), 4.15–4.28(m,1H), 4.99(s,2H), 6.78(d,2H), 6.81

(d,2H), 7.13(d,2H), 7.2–7.4(m,5H), 7.74(d,lH), 8.11(d, 2H); mass spectrum(Cl⁺): 546(M+H)⁺.

iii) Methyl 2-S-amino-3-[4- [4- [1-(4-pyridyl)-piperidin-4-yl]butoxy ]phenyl]propionate; NMR (d₆DMSO) 1.05–1.35(m,4H), 1.35–1.58(m,3H), 1.6–1.8(mn,4H), 2.65–2.9(m,4H), 3.51(t,1H), 3.58(s,3H), 3.8–3.98(m,4H), 6.78(dd,2H), 6.8 1(d,2H), 7.05(d,2H), 8.1(dd,2H); mass spectrum(Cl⁺): 412(M+H)⁺.

EXAMPLE 84

2-S-(n-Butylsulphonylamino)-3-[4-[4-[1-(4-pyridyl) piperidin-4-yl]butoxy]phenyl]propionic acid Using a similar procedure to that described in Example 34 but starting from the product of Example 83, the title compound was obtained as an amorphous solid; NMR (d₆DMSO) 0.78(t,3H), 1.0–1.6(m,l 1H), 1.6–1.82(brt,4H), 2.5–3.04(m,6H), 3.8–4.0(m,5H), 6.8(m,4H), 7.19(d,2H), 8.1 (brd,2H); mass spectrum(+ve FAB,MeOH/NBA): 518(M+H)⁺; microanalysis found C,62.4; H,7.8; N,7.9%; C₂₇H₃₉N₃O₅S requires C,62.6; H,7.6; N,8.1%.

EXAMPLES 85–87

Using a procedure similar to that described in Example 35, but starting, from the appropriate substituted suliphonyl chloride and methyl 2-S-amino-3-[4-[2-[1-(4-pyridyl) piperidin-4-yl]ethoxylphenyl]propionate there was obtained the following compounds:

EXAMPLE 85

Methyl 2-S-(methsulphonylamino)-3-[4-[2-[1-(4-pyridyl)piperidin-4-yl]ethoxy]phenyl]propionate NMR (d₆DMSO) 1.08–1.34(m,2H), 1.6–1.85(m,5H), 2.6 (s,3H), 2.7–3.0(m,4H), 3.63(s,3H), 3.84–4.2(m,5H), 6.80(d, 2H), 6.85(d,2H), 7.18(d,2H), 8.12(d,2H); mass spectrum(+ve FAB, McOH/NBA): 462(M+H)⁺.

EXAMPLE 86

Methyl 2-S-(benzylsulphonylamino)-3-[4-[2-[1-(4-pyridyl)piperidin-4-yl]ethoxy]phenyl]propionate NMR (d₆DMSO) 1.05–1.28(m,2H), 1.57–1.82(m,5H), 2.68–2.95(m,4H), 3.58(s,3H), 3.8–4.15(m,7H), 6.79(d,2H), 6.88(d,2H), 7.12(d,2H), 7.17(m,2H), 7.3(m,3H), 7.79(brd, 1H), 8.1(d,2H); mass spectrum(+ve FAB, MeOH/NBA): 538(M+H)+.

EXAMPLE 87

Methyl 2-S-(4-methylphenylsulphonylamino)-3-[4-[2-[1-(4-pyridyl)piperidin-4-yl]ethoxy]phenyl] propionate NMR (d₆DMSO) 1.1–1.33(m,2H), 1.6–1.88(m,5H), 2.35 (s,3H), 2.6–2.75(dd,1H), 2.75–2.92(m,3H), 3.38(s,3H), 3.8–4.1(m,5H), 6.76(d,2H), 6.81(d,2H), 7.0(d,2H), 7.28(d, 2H), 7.47(d,2H), 8.12(d,2H), 8.32(d, 1H); mass spectrum(+ve FAB, MeOH/NBA): 538(M+H)⁺.

EXAMPLES 88–90

Following the method of Example 34, but using the products of Examples 85–87, there was obtained the following compounds:

EXAMPLE 88

2-S-(Methylsulphonylamino)-3-[4-[2-[1-(4-pyridyl) piperidin-4-yl]ethoxy]phenyl]propionic acid NMR (d₆DMSO) 1.05–1.35(m,2H), 1.6–1.95(m,5H), 2.61(s,3H), 2.65–3.1(m,4H), 3.88–4.1(m,5H), 6.84(d,2H), 6.9(d,2H), 7.18(d,2H), 8.14(d,2H); mass spectrum(+ve FAB, MeOH/NBA): 448(M+H)⁺.

EXAMPLE 89

2-S-(Benzylsulphonylamino)-3-[4-[2-[1-(4-pyridyl) piperidin-4-yl]ethoxy]phenyl]propionic acid NMR (d₆DMSO/CD₃CO₂D) 1.07–1.35(m,2H), 1.60–1.88(m,5H), 2.7–3.2(m,4H), 3.85–4.25(m,7H), 6.87(d, 2H), 7.1 (d,2H), 7.13–7.45(m,7H), 8.15(d,2H); mass spectrum(+ve FAB,MeOH/NBA): 524(M+H)⁺; microanalysis found C,61.8; H,6.8; N,7.6%; C₂₈H₃₃N₃O₅S.H₂O requires C,62. 1; H,6.5; N,7.8%.

EXAMPLE 90

Lithium 2-S-(4-methylphenylsulphonylamino)-3-[4-[2-[1-(4-pyridyl)piperidin-4-yl]ethoxy]phenyl] propionate NMR (d₆DMSO/CD₃CO₂D) 1.15–1.38(m,2H), 1.67–1.78(m,2H), 1.82–2.0(m,3H), 2.36(s,3H), 2.65–2.8 (dd, 1H), 2.85–2.95(dd, 1H), 3.14(t,2H), 3.78(m, 1H), 4.0 (t,2H), 4.18(d,2H), 6.77(d,2H), 7.04(d,2H), 7.1 1(d,2H), 7.24(d,2H), 7.51(d,2H), 8.15(d,2H); mass spectrum(+ve FAB, MeOH/NBA): 536(M+Li)⁺; microanalysis found C,63.2; H,6.5; N,7.9%; C₂₈H₃₂N₃O₅SLi requires C,63.5; H,6.1; N,7.9%.

EXAMPLE 91

Methyl 2-S-(pentanoylamino)-3-[4-[2-[1-(4-pyridyl) piperidin-4-yl]ethoxy]phenyl]propionate Valeryl chloride (0.25 ml) was added dropwise to a solution of methyl 2-S-amino-3-[4-[2- [1-(4-pyridyl) piperidin-4-yl]ethoxy ]phenyl]propionate (640 mg) and triethylamine (0.7 ml) in dichloromethane (17 ml) at ambient temperature. The reaction mixture was stirred for 5 hours and then diluted with dichloromethane (20 ml) and washed with water (20 ml), saturated sodium chloride solution (10 ml) and dried (MgSO₄). The solvent was evaporated and the residue purified by flash chromatography eluting with methanol/dichloromethane (1:9 v/v) to give the title compound (660 mg) as a gum; NMR (d₆DMSO) 0.81 (t,3H), 1.05–1.3(m,4H), 1.3–1.45(m,2H), 1.60–1.85(m,5H), 2.04(t, 2H), 2.7–3.0(m,4H), 3.6(s,3H), 3.92(d,2H), 3.99(t,2H), 4.35–4.48(m,1H), 6.8(d,2H), 6.83(d,2H), 7.11(d,2H), 8.12 (d,2H), 8.18(d,1H); m/e +ve FAB,MeOH/NBA): 468(M+H)⁺.

EXAMPLE 92

Methyl 2-S-(pentanoylamino)-3-[4-[1-(4-pyridyl) piperidin-4-yl]methoxyphenyl]propionate Using a procedure similar to that described in Example 91, but starting from the appropriate amino ester, the title compound was prepared, NMR (d₆DMSO) 0.8(t,3H), 1.05–1.45(m,6H), 1.83(dd,2H), 1.9–2.1 (m, 1H), 2.04(t,2H), 2.7–3.0(m,4H), 3.59(s,3H), 3.82(d,2H), 3.96(d,2H), 4.35–4.48(m, 1H), 6.80(d,2H), 6.83(d,2H), 7. 10(d,2H), 8.12(d,2H), 8.17(d, 1lH); mass spectrum(+ve FAB, MeOH/ NBA): 454(M+H)⁺.

EXAMPLE 93

2-S-(Pentanoylamino)-3-[4-[2-[1-(4-pyridyl) piperidin-4-yl]ethoxy]phenyl]propionic acid Using a procedure similar to that described in Example 34, but starting from the product of Example 91, the title compound was prepared. NMR (d₆DMSO) 0.8(t,3H), 1.08–1.3(m,4H), 1.3–1.45(m,2H), 1.6–1.87(mn,5H), 2.05(t, 2H), 2.7–3.05(m,4H), 3.9–4.05(m,4H), 4.3–4.43(m, 1 H), 6.82(d,2H), 6.85(d,2H), 7.11 (d,2H), 7.97(d, 1H), 8.12(brd, 2H); mass spectrum(+ve FAB, MeOH/NBA): 454(M+H)⁺; microanalysis found C,63.1 H,7.8; N,8.3%; $C_{26}H_{35}N_3O_4 \cdot 2H_2O$ requires C,63.8; H,8.0; N,8.6%.

EXAMPLE 94

2-S-(Benzyloxycarbonylamino)-3-[4-[2-[1-(4-pyridyl)piperidin-4-yl]ethoxy]phenyl]propionic acid Using a procedure similar to that described in Example 34, but starting from the product of Example 35i), the title compound was prepared. NMR (d₆DMSO) 1.1–1.35(m,2H), 1.6–1.9(m,5H), 2.65–3. 1(m,4H1), 3.85–4.2(m,5H), 4.96(s, 2H), 6.75–6.9(m,4H), 7.14(d,2H), 7.2–7.35(m,5H), 7.5(d, 1H), 8.1 (d,2H); mass spectrum(+ve FAB, MeOH/NBA): 504(M+H)⁺.

EXAMPLE 95

Methyl-2-S-(n-butylsulphonylamino)-3-[3-(N-methyl-N-4-pyridyl)aminopropoxy] phenylpropionate Using a procedure similar to that described in Example 33, but starting from methyl 2-S-amino-3-[3-(N-methyl-N-4-pyridyl)aminopropoxy]phenylpropionate, the title compound was prepared. NMR (CDCl₃) 0.89(t,3H), 1.25–1.4 (m,2H), 1.55–1.75(m,2H), 2.0–2.15(m,2H), 2.80(dd,2H), 2.9–3.15(m,2H), 3.05(s,3H), 3.63(t,2H), 3.77(s,3H), 3.95(t, 2H), 4.28–4.38(m,1H), 6.57(d,2H), 6.80(d,2H), 7.10(d,2H), 8.14(d,2H); mass spectrum (Cl⁺); 464(M+H)⁺.

The starting material was prepared as follows:
i) Using a procedure similar to that described in Example 33i), but starting from N-methyl-N-(4-pyridyl) aminopropanol and N-t-butyloxycarbonyl-S-tyrosine methyl ester, there was obtained, methyl 2-S-(t-butyloxycarbonylamino)-3-[3-N-methyl-N-(4-pyridyl) aminopropoxy]phenyl propionate, as a gum, NMR (CDCl₃) 1.43(s,9H), 2.0–2.15(mi,2H), 3.04(s,3H), 2.95–3.10(m,2H), 3.62(t,2H), 3.73(s,3H), 3.98(t,2H), 4.54(brd, 1H), 4.98(brd, 1H), 6.56(d,2H), 6.80(d,2H), 7.04(d,2H), 8.17(d,2H).
ii) The product from step i) (500 mg) and 5M methaniolic hydrochloric acid solution (4 ml) was stirred at ambient temperature for 16 hours. The solvent was evaporated to give the corresponding amino compound as the dihydrochloride salt which was used without further purification.

EXAMPLE 96

2-S-(n-Butylsulphonylamino)-3-[3-(N-4-pyridyl-N-methyl)aminopropoxylphenyl propionic acid Using a procedure similar to that described in Example 34, but starting from the product of Example 95, the title compound was prepared, NMR (d₆DMSO/CD₃CO₂D) 0.8 (t,3H), 1.1–1.28(m,2H), 1.28–1.55(m,2H), 2.0–2.1 5(m,2H), 2.6–2.8(m,3H), 2.93–3.08(dd,1H), 3.18(s,3H), 3.75(t,2H), 3.9–4.05(m,3H), 6.86(d,2H), 7.0(d,2H), 7.2(d,2H), 8.15(d, 2H); mass spectrum (+ve FAB,MeOH/NBA): 450(M+H)⁺; microanalysis found C,53.9; H,6.9; N,8.4%; $C_{22}H_{31}N_3O_5S \cdot 2H_2O$ requires C,54.4; H,7.2; N,8.6%.

EXAMPLE 97

Methyl 3-(n-butylsulphonylamino)-3-[4-[1-(4-pyridyl)piperidin-4-yl]-methoxyphenyl]propionate Using a procedure similar to that described in Example 33, but starting from methyl 3-amino-3-[4-[1-(4-pyridyl) piperidin-4-yl]methoxyphenyl]propionate, dihydrochloride, the title compound was prepared; NMR (CDCl₃) 0.84(t,3H), 1.2–1.4(m,2H), 1.4–1.55(m,2H), 1.55–1.75(m,2H), 1.97 (brd,2H), 2.02–2.2(m,1H), 2.65–2.85(m,2H), 2.88(d,2H), 3.0(dt,2H), 3.67(s,3H), 3.84(d,2H), 4.0(brd,2H), 4.85(q,1H), 5.40(d,1H), 6.71(d,2H), 6.86(d,2H), 7.27(d,2H), 8.25(d, 2H); mass spectrum(+ve FAB,MeOH/NBA): 490(M+H)⁺.

The starting material was prepared as follows:
i) Thionyl chloride (4.3 ml) was added to methanol (50 ml) cooled in an ice-salt bath. 3-Amino-3-(4-hydroxyphenyl) propionic acid (9.7 g) was added and the mixture allowed to reach ambient temperature and then refluxed for 2 hours. The solvent was removed by evaporation in vacuo to give a gummy solid (12.8 g) which was used without further purification. A solution of di-t-butyldicarbonate (5.8 g) in dichloromethane (50 m) was added to a stirred mixture of the gummy solid (5.75 g) and potassium hydrogen carbonate (6.2 g) in water (20 ml). The mixture was stirred at ambient temperature for 4 hours. The organiic layer was separated and washed with water (10 ml), 1M hydrochloric acid solution (10 ml), saturated sodium hydrogen carbonate solution (10 ml), water (10 ml) and dried (MgSO₄). The solvent was evaporated to give methyl 3-(t-butyloxycarbonylamino)-3-(4-hydroxyphenyl)propionate as a solid; m.p. 119°–120° C.; NMR (d₆DMSO) 1.34(s,9H), 2.54–2.78(m,2H), 3.53(s, 3H), 4.7–4.9(q, 1H), 6.67(d,2H), 7.08(d,2H), 7.28(brd, 1H), 9.24(brs,1H).
ii) Using a procedure similar to that described in Example 33i), but using the product of step i), methyl 3-(t-butyloxycarbonylamino)-3-[4-[1-(4-pyridyl)piperidin-4-yl]-methoxyphenyl]propionate was prepared as a gum; NMR (CDCl₃) 1.33–1.55(m,2H), 1.44(s,9H), 1.95(brd, 2H), 1.95–2.15(m, 1 H), 2.7–3.0(m,4H), 3.61 (s,3H), 3.80(d,2H), 3.95(brd,2H), 4.95–5.1(m,1H), 5.25–5.40(m, 1H), 6.68(d,2H), 6.85(d,2H), 7.2(d,2H), 8.25(d,2H).
iii) The product of step ii) (550 mg) and 5M methanolic hydrochloric acid solution (4 ml) was stirred at ambient temperature for 18 hours. The solvent was evaporated to give methyl 3-amino-3-[4-[1 -(4-pyridyl)piperidin-4-yl] methoxyphenyl]propionate dihydrochloride as a foam; NMR (d₆DMSO/CD₃CO₂D) 1.23–1 45(m,2H), 1.92(brd, 2H), 2.05–2.25(m, 1H), 3.0–3 25(m,4H), 3.52(s,3H), 3.85 (d,2H), 4.2(brd,2H), 4.54(t,1H), 6.92(d,2H), 7.1(d,2H), 7.39(d,2H), 8.10(d,2H).

EXAMPLE 98

3-(n-Butylsulphonylamino)-3-[4-[1-(4-pyridyl) piperidin-4-yl]methoxyphenyl]propionic acid Using a procedure similar to that described in Example 34, but using the product of Example 97, the title compound was prepared; NMR (d₆DMSO/CD₃CO₂D) 0.78(t,3H), 1.05–1.3(m,2H), 1.3–1.57(m,4H), 1.98(brd,2H), 2.1 –2.33 (m, 1 H), 2.45–2.85(m,4H), 3.25(t,2H), 3.89(d,2H), 4.25 (brd,2H), 4.68(t,1H), 6.90(d,2H), 7.14(d,2H), 7.33(d,2H), 8.14(d,2H); mass spectrunm(+ve FAB,MeOHINBA): 490 (M+H)+.

EXAMPLE 99

Methyl 3-(4-methylphenylsulphonylamino)-3-[4-[1-(4-pyridyl)piperidin-4-yl]methoxyphenyl]propionate Using a procedure similar to that described in Example 33, but starting from the product of Example 97iii) and p-tolluenesulphonyl chloride, the title compound was prepared; NMR (CDCl$_3$) 1.34–1.55(m,2H), 1.95(d,2H), 2.0–2.2 (m,1H), 2.38(s,3H), 2.62–3.05(m,4H), 3.55(s,3H), 3.78(d, 2H), 3.96(d,2H), 4.65(m,1H), 5.65(brs,1H), 6.7(d,2H), 6.72 (d,2H), 7.05(d,2H), 7.2(d,2H), 7.65(d,2H), 8.25(d,2H); mass spectrum(+ve FAB,MeOH/NBA): 524(M+H)$^+$

EXAMPLE 100

Methyl 2-R-(n-butylsulphonylamino)-3-[4-[1-(4-pyridyl)piperidin-4-yl]methoxyphenyl]propionate Using a procedure similar to that described in Example 33,but starting from methyl 2-R-amino-3-[4-[1-(4-pyridyl) piperidin-4-yl]-methoxyphenyl]propionate,the title compound was prepared; NMR (CDCl$_3$) 0.88(t,3H), 1.2–1.7(m, 6H), 1.96(d,2H), 2.0–2.2(m,1H), 2.7–2.83(m,2H), 2.85–3.15(m,4H), 3.77(s,3H), 3.79(d,2H), 3.96(d,2H), 4.32 (m,1H), 4.85(brd,1H), 6.7(d,2H), 6.83(d,2H), 7.08(d,2H), 8.25(brd,2H); mass spectrum(+ve FAB,MeOH/NBA): 490 (M+H)$^+$.

The starting material was prepared as follows:
i) Using a similar procedure to that described in Example 33i),but starting from N-t-butyloxycarbonyl-S-tyrosine methyl ester,there was obtained,methyl 2-R-(t-butyloxycarbonylamino)-3-[4-[1-(4-pyridyl)piperidin-4-yl]methoxyphenyl]propionate as a gum,NMR (CDCl$_3$) 1.43(s,9H), 1.36-1.55(m,2H), 1.96(brd,2H), 2.0–2.15(m, 1H), 2.95(dt,2H), 3.03(d,2H), 3.71 (s,3H), 3.81 (d,2H), 3.95(brd,2H), 4.52(brd, 1H), 4.95(brd,1H), 6.70(d,2H), 6.80(d,2H), 7.01(d,2H), 8.24(d,2H).
ii) Using a similar procedure to that described in Example 95ii),but starting from the product obtained in step i),there was obtained,methyl 2-R-amino-3-[4-[1-(4-pyridyl)-piperidin-4-yl]methoxyphenyl]propionate dihydrochloride as a foam, NMR (d$_6$DMSO/CD$_3$CO$_2$D) 1.26–1.48 (m,2H), 1.96(brd,2H), 2.1–2.3(m,1H), 3.09(dd,2H), 3.21 (t,2H), 3.70(s,3H), 3.84(d,2H), 4.15–4.3(m,3H), 6.88(d, 2H), 7.14(m,4H), 8.14(d,2H).

EXAMPLE 101

2-R-(n-Butylsulphonylamino)-3-[4-[1-pyridyl) piperidin-4-yl]-methoxyphenyl]propionic acid Following the method of Example 34,but using the product of Example 100,the title compound was prepared; NMR (d$_6$DMSO) 0.75(t,3H), 1.03–1.45(m,6H), 1.87(d,2H), 1.95–2.2(m,1H), 2.45–2.78(m,3H), 2.88–3.08(m,3H), 3.82 (d,2H), 3.8–3.95(m,1H), 4.05(brd,2H), 6.84(d,2H), 6.92(d, 2H), 7.18(d,2H), 8.13(brs,2H); mass spectrum(-ve FAB, MeOH/NBA): 474(M-H)- ; microanalysis found C,55.1; H,6.8; N, 7.8%; C$_{24}$H$_{33}$N$_3$O$_5$S.2.5H$_2$O requires C,55.4; H, 7.3; N, 8.1%.

EXAMPLE 102 cis-1-Hydroxy-4[4-(4-pyridyl )piperazin-1-yl]cyclohexaneacetic acid

A mixture of cis-1,1-dimethylethyl-1-hydroxy-4-[4-(4-pyridyl)piperazin-1-yl]cyclohexane acetate (120 mg),water (0.2 ml) and trifluoroacetic acid (2 ml) was stirred for 30 minutes at ambient temperature. The mixture was concentrated in vacuo to give a gum which was triturated with ether to give the title compound as a white solid; m.p. 197°–200° C.(dec.); NMR (d$_6$DMSO/CD$_3$CO$_2$D) 1.45–1.68(m,2H), 1.8°–2.0(m,6H), 2.43(s,2H), 3.15–3.34(m,1H), 3.48(brs, 4H), 4.0(brs,4H), 7.23(d,2H), 8.3(d,2H); mass spectrum(+ve FAB,MeOH/NBA): 320(M+H)$^+$; microanalysis found C, 45.6; H, 5.0; N, 7.2; CF$_3$CO$_2$H, 42.6%; C$_{17}$H$_{25}$N$_3$O$_3$.2.1CF$_3$CO$_2$H requires C,45.6; H, 4.9; N, 7.5; CF$_3$CO$_2$H, 42.8%.

The starting material was prepared as follows: i) Sodium cyanoborohydride (280 mg) was added to a stirred mixture of 1,1-dimethylethyl 1-hydroxy-4-oxocyclohexane acetate (1.0 g), 1-(4-pyridyl)piperazine (830 mg),1M hydrochloric acid solution in methanol (1.5 ml) and 3A molecular sieve (500 mg) in methanol (25 ml) at ambient temperature. The mixture was stirred for 72 hours,filtered and the filtrate concentrated in vacuo. Saturated sodium hydrogen carbonate solution (10 ml) and saturated sodium chloride solution (10 ml) was added to the residue and extracted with ethyl acetate (2×25 ml). The combined ethyl acetate extracts were washed with saturated sodium chloride solution (10 ml) and dried(MgSO$_4$). The solvent was removed by evaporation and the residue (1.7 g) purified by flash chromatography eluting with methanol/dichloromethane/ triethylamine (1:9:0.2 v/v/v) to give cis- 1,1-dimethylethyl- 1-hydroxy-4-[4-(4-pyridyl)piperazin-1-yl]cyclohexane acetate as a white amorphous solid; NMR (CDCl$_3$) 1.25–1.4(m,2H), 1.47(s, 9H), 1.6–1.9(m,6H), 2.35(s,2H), 2.26–2.42(m,1H), 2.69–2.73(m,4H), 3.31–3.35(m,4H), 3.56(brs,1H), 6.65(d, 2H), 8.25(d,2H).

EXAMPLE 103

Tert-butyl 1-[2-[4-(4-pyridyl)piperazin-1in-1-yl] acetyl]piperidin-3-yloxyacetate A solution of t-butyl 1-(bromoacetyl)piperidin-3-yloxyacetate (1.2 g) in acetonitrile (20 ml) was added dropwise to a stirred solution of 1-(4-pyridyl)piperazine (1.6 g) in acetonitrile (30 ml) and stirring was continued for 1 hour. The mixture was filtered and the filtrate was concentrated. The residue was purified by flash column chromatography, eluting with triethylamine (1%) in ethyl acetate, to give a colourless gum, which on crystallisation from cyclohexane, afforded the title compound (350 mg) as colourless prisms m.p. 93°–95°; NMR (d$_6$DMSO) δ1.4(9H, d); 1.3–2.0(4H,m); 2.7(4H,brs); 3.2–3.9(11H,m); 4.0(2H,d); 7.1(2H,d); 8.2(2H,d); m/e 419(M+H)$^+$; calculated for C$_{22}$H$_{34}$N$_4$O$_4$: C, 63.1;H, 8.2; N, 13.4; found: C,63.4;H, 8.2; N, 13.3%.

The starting material was prepared as follows:
i) Benzylchloroformate (15 ml) was added dropwise to a stirred suspension of 3-hydroxypiperidine hydrochloride (13.7 g) and triethylamine (30 ml) in dichloromethane (150 ml),maintaining the temperature below 15° C. throughout. Stirring was continued for three hours,then the solution was washed with water (4×100 ml) and saturated aqueous sodium chloride (100 ml),dried (PS paper) and concentrated. The residual oil was dissolved in ether (300 ml),washed with dilute hydrochloric acid (2×100 ml) and water (100 ml),dried (PS paper) and concentrated. The residue was purified by flash column chromatography,eluting first with hexane/ether (1: 1) then ether to give 1-benzyloxycarbonylpiperidine-3-ol (7.1 g) as a colourless oil. NMR (d$_6$DMSO) δ1.2–1.4(2H,m); 1.6–1.9(1 H,m +1 H,m); 2.8(1H,br s); 2.95(1 H,m); 3.45(1 H,m); 3.65(1H,brd); 3.8(1H,dd); 4.85(1H,d); 5.1(2H,s); 7.3(5H,m); m/e 236(M+H)$^+$.
ii) A solution of the product of step i) (4.7 g) in THF (100 ml) was cooled to −30° C. and treated with a solution of lithium hexamethyldisilazide (22 ml 1M in THF). The mixture was stirred for 2 minutes,cooled to −70° C., treated with t-butylbromoacetate (3.5 ml) and allowed to warm to room temperature over four hours. The mixture was diluted with ether (100 ml) and washed with water (3×100 ml) and saturated aqueous sodium chloride (100 ml),dried (PS paper) and concentrated. The residual oil was purified by flash column chromatography, eluting with hexane/ethyl acetate (first 90:10 then 85:15) to give t-butyl 1-benzyloxycarbonyl-piperidin-3-yloxyacetate (1.6 g) as a pale yellow oil.NMR ($d_6$DMSO)δ1.4(9H,s); 1.3–1.6(2H,m), 1.65(1H,m); 1.85(1H,m); 3.25(2H,m); 3.4(2H,m); 3.6(1H,d); 4.0(2H,s); 5.0(2H,s); 7.2–7.4(5H, m); m/e 350 (M+H)$^+$.

iii) A solution of the product of step ii) (1.6 g) in isopropanol (50 ml) was hydrogenolysed over palladium on carbon catalyst (10%, 200mg). The mixture was filtered and the filtrate was concentrated to give t-butyl piperidin-3-yloxyacetate as an oil which was used without further purification.

iv) The product of step iii) was dissolved in ether (25 ml),treated with triethlylamine (0.65 ml) and added to a stirred cooled solution of bromoacetylbromide (0.42 ml) in ether (25 ml). Stirring was continued for two hours and the mixture was allowed to warm to room temperature. Ether (50 ml) was added and the solution was washed sequentially with water (50 ml), dilute aqueous sodium hydrogen carbonate (50 ml), water (50 ml) and saturated aqueous sodium chloride (50 ml) then dried (PS paper) and concentrated to give t-butyl (1-bromoacetyl) piperidin-3-yloxyacetate (1.2 g) as a pale brown oil which was used without further purification. NMR (CDCl$_3$) δ1.5(9H,s); 1.4–2.0(4H,m); 3.2–4.0(9H,m); m/e 336(M+H)$^+$.

EXAMPLE 104

1[2-[4-(4-Pyridyl)piperazin-1yl]acetyl]piperidin-3-yloxyacetic acid

The product of Example 103 (340 mg) was dissolved in a mixture of trifluoroacetic acid (10 ml) and dichloromethane (10 ml) and the solution was allowed to stand for 1.5 hours. The solution was concentrated and the residue was azeotroped successively with dichloromethane and ether,then concentrated. The residual gum was passed down a Mega-bond elut column, eluting with dichloromethane/methanol/water (5:4: 1),concentrated, dissolved in water (25 ml) and freeze-dried to give the title compound (250 mg) as a foam. NMR ($d_6$DMSO) δ1.2–1.8(4H,m); 3.0–4.2(15H,m); 4.35(2H,d); 7.2(2H,d); 8.2(2H,d); m/e 363(M+H)$^+$.

EXAMPLE 105

3RS, 4RS1-[2-[4-(4-Pyridyl)piperazin-1-yl] acetylpiperidin3,4-dioxydiacetic acid In a similar manner to Example 104 there was obtained the title compound as a pale yellow solid. NMR ($d_6$DMSO+ $d_4$AcOH) δ1.6(1H,m); 1.8(1H,m); 3.1–4.5(20H,m), 7.2(2H, d); 8.25(2H,d); m/e 437(M+H)$^+$.

The starting material was obtained using similar procedures to those described in Example 103. The following intermediates were prepared:

1-benzyloxycarbonylpiperidine-3,4-diol. NMR ($d_6$DMSO) δ1.2–1.4(1H,m); 1.7–1.9(1 H,m); 2.8–3.4(5H, m); 3.6–3.8(2H,m); 4.8(1 H,d); 4.9(1 H,d); 5.1 (2H,s); 7.3(5H,m); m/e 252(M+H)$^+$.

di-t-butyl 1-benzyloxycarbonylpiperidin-3,4-dioxydiacetate NMR ($d_6$DMSO+$d_4$ACOH)δ1.4(18H,s); 1.4–1.5(1 H,m); 1.9(1 H,m); 3.2–3.7(6H,m); 4.0(4H,d); 5.1 (2H,s); 7.3(5H,m); m/e 480(M+H)$^+$and 502(M+Na$^+$).

di-t-butyl-1-bromoacetylpiperidine-3,4-dioxydiacetate m/e 466(M+H)$^+$and 356(s) (M-2$^t$Bu).

di-t-butyl 1-[2-[4-(4-pyridyl)piperazin-1-yl]acetyl-piperidin-3,4-dioxydiacetate: used immediately without characterisation.

EXAMPLE 106 t-Butyl 1[2-[4-(4-pyridyl)piperazin-1-yl] acetylpiperidin-4-yloxyacetate

In a similar manner to Example 103 there was obtained the title compound as a gum. NMR ($d_6$DMSO)δ1.3(9H,s); 1.3–1.5(2H,m); 1.6–1.8(2H,m); 3.0–3.3(6H,m); 3.5(3H,m); 3.6–3.9(7H,m); 3.9(2H,s); 7.05(2H,d); 8.1(2H,d), m/e 419 (M+H)$^+$.

The starting material was obtained using similar procedures to those described in Example 103. The following intermediates were obtained:

1-benzyloxycarbonylpiperidine-4-ol NMR ($d_6$DMSO) δ1.2–1.4(2H,m); 1.6–1.8(2H,m); 3.0–3.2(2H,m); 3.6–3.8 (3H,m); 4.7(1H,d); 5.1(2H,s); 7.35(5H,m). m/e 236(M+H)$^+$.

t-butyl 1-benzyloxycarbonylpiperidine-4-oxyacetate NMR ($d_6$DMSO) δ1.3–1.5(2H,m); 1.4(9H,s); 1.7–1.9(2H, m); 3.0–3.2(2H,m); 3.5–3.6(1H,m); 3.6–3.8(2H,m); 4.0(2H, s); 5.1(2H,s); 7.3(5H,m). m/e 350(M+H)$^+$..

t-butyl 1-bromoacetylpiperidine-4-oxyacetate NMR (CDCl$_3$) δ1.45(9H,s); 1.6–2.0(4H,m); 3.4(1 H,m); 3.5(1H, m); 3.6–3.8(3H,m); 3.9(2H,s); 4.0(2H,s). m/e 336/338(M+H)$^+$; 358/360(M+Na)+; 280/282 (M-$^t$Bu)+.

EXAMPLE 107

N-2-Methoxyethyl 1-[2-[4-(4-pyridyl)piperazin-1-yl]acetyl]-piperidin-4-yloxyacetamide A solution of N-2-methoxyethyl 1-bromoacetylpiperidine-4-oxyacetamide (350 mg) in acetonitrile (10 ml) was added to a stirred solution of N-(4-pyridyl)piperazine (400 mg) in acetonitrile (10 ml) and the mixture was allowed to stand for 16 hours. The precipitate was removed by filtration and the filtrate was concentrated. The residue was dissolved in ethyl acetate, (15 ml) and extracted with water (3×10 ml). The combined aqueous extracts were extracted with dichloromethane (3×15 ml) and the combined organic extracts were dried (PS paper) and concentrated. The residual gum was purified by flash column chromatography (grade II alumina) eluting first with dichloromethane and then with methanol/dichloromethane (1:200) to give the title compound (110 mg) as a colourless gum; NMR ($d_6$DMSO) δ1.3–1.6(2H,m); 1.6–1.9(2H,m); 3.0(4H, m); 3.05–3.25(2H,m); 3.15(3H,s); 3.25–3.4(5H,m); 3.7–3.9 (7H,m); 3.9(2H,s); 7.0(2H,d); 8.1(2H,d) m/e 420 (M+H)+; m/e 442(M+Na)$^+$.

The starting material was prepared as follows:

i) A mixture of ethyl 1-benzyloxycarbonylpiperidine-4-oxyacetate (2.4 g) and 2-methoxyethylamine (5 ml) was heated on a steam bath for 6 hours. The amine was evaporated under reduced pressure and the residue was dissolved in ethyl acetate (10 ml), washed sequentially with dilute citric acid solution (5 ml), water (5 ml) and saturated aqueous sodium chloride (5 ml), dried (MgSO$_4$) and concentrated. The residual oil was purified by flash column chromatography,eluting with hexane/ethyl acetate (1:3) to give N-2-methoxyethyl-1-benzyloxycarbonylpipenidine-4-oxyacetamide (500 mg) as a colourless oil; NMR ($d_6$DMSO)δ1.4–1.5(2H,m);

1.75–1.9(2H,m); 3.0–3.4(9H,m); 3.55(1 H,m); 3.65–3.8 (2H,m); 3.9(2H,s); 5.1(2H,s); 7.3(5H,m); 7.6(1H,brt); m/e 351(M+H)⁺, 373 (M+Na)⁺.

In a similar manner to that described in Example 103, N-2-methoxyethyl 1-benzyloxycarbonylpiperidine-4-oxyacetamide was converted to N-2-methoxyethyl-1-bromoacetylpiperidine-4-oxyacetamide; NMR (CDCl₃)δ1.5–2.0(4H,m); 3.2–3.5(5H,m); 3.5(4H,m); 3.6–3.8(2H,m); 3.8–4.0(1H,m); 3.9(2H,s); 4.0(2H,s); 6.9 (1H,brs), m/e 337/339 (M+H)⁺ 359/361(M+Na)⁺.

EXAMPLE 108

4-[2-[3-[4-(1-Pyrrolidinyl)pyridin-3yl]methylidene] pyrrolidin-1-yl]-acetylphenoxyacetic acid A solution of methyl 4-[2-[3-[4-(1-pyrrolidinyl)pyridin-3-yl]methylidene]-pyrrolidin-1-yl]acetyl]phenoxyacetate (300 mg) in a mixture of concentrated hydrochloric acid (2 ml) and dioxan (8 ml) was heated and stirred at 50° C. for 30 minutes. The solution was concentrated and the residue was dissolved in water (20 ml),washed with ether (2×5 ml), treated with decolourising charcoal, filtered and concentrated to give the title compound (161 mg) as a pale brown foam. NMR (d₆DMSO)+d₄AcOH) δ2.0(4H,brs); 2.6–4.6 (10H,m); 4.85(2H,s); 5.15(2H,s); 6.8(1 H,m); 6.85(1H,d); 7.1(2H,d); 8.0(2H,d); 7.9–8.1(1H,m); 8.1(1H,d); m/e 422 (M+H)⁺.

The starting material was prepared as follows:

i) A mixture of 4-chloropyridine-3-carboxaldehyde (10 g), prepared according to the method described in J.Het.Chem, 25,81), pyrrolidine (25 ml) and ethanol (100 ml) was heated under reflux for 5 hours, then concentrated. The residue was purified by flash column chromatography (grade II alumina) eluting first with dichloromethane and then with methanol/dichloromethane (1:200) to give 3-[[4-(pyrrolidin-1-yl)pyridin-3-yl] methylidene]-1-pyrroline (900 mg) as a white solid. NMR (d₆DMSO) δ1.8(4H,m); 2.5(2H,m); 3.3(4H,m); 3.95(2H, m); 6.6(1H,d); 7.0(1H,t), 7.9(1H,t), 8.0(1H,d); 8.15(1H, s); m/e 228(M+H)⁺; calculated for C₁₄H₁₇N₃: C,74.0;H, 7.5; N, 18.5; found C,74. 1;H, 7.7; N, 18.4%.

ii) A solution of the product of step i) (650 mg) in ethanol (20 ml) was treated with sodium borohydride (150 mg) and the mixture was stirred for 4 hours. Glacial acetic acid (2 ml) was added and the mixture was concentrated. The residue was treated with saturated aqueous sodium chloride (20 ml) and saturated sodium hydrogen carbonate solution (10 ml) and extracted with ethyl acetate (2×10 ml). The aqueous solution was basified with aqueous sodium hydroxide (2.5M) and extracted with dichloromethane (4×20 ml). The combined organic extracts were concentrated to give 3-[[4-(pyrrolidin-1-yl)pyridin-3-yl]methylidine]pyrrolidine (350 mg) as a yellow paste which was used without further purification. Conversion to the hydrochloride salt using hydrogen chloride in ether/ethanol followed by crystallisation from isopropanol gave pale yellow prisms, m.p. 250°, NMR (d₆DMSO) δ1.95(4H,brs); 2.55(2H,m); 3.3(2H,m); 3.5–3.7(4H,brs); 3.95(2H,brs); 6.75(1H,brs); 6.85(1H,d); 8.0(1H,s); 8.15(1H,dd); 9.6–10.0(2H,brs); m/e 230 (M+H)⁺; calculated for C₁₄HCl₁₉N₃.2HCl. 0.1H₂O: C, 55.3; H, 7.0; N, 13.8; H₂O, 0.6; found: C,55.7; 55.5; H. 7.2, 7.1; N, 13.6; 13.5; H₂O 0.8%.

iii) A solution of methyl 4-bromoacetyl-phenoxyacetic ester (1.2 g) in acetonitrile (20 ml) was added dropwise to a stirred mixture of the product of step ii) (1.0) and triethylamine (0.6 ml) in acetonitrile (20 ml),and stirring was continued for 3 hours. The mixture was concentrated and the residue was dissolved in ethyl acetate (50 ml). The solution was washed with water (3×20 ml) and saturated sodium chloride solution (10 ml),dried (MgSO₄) and concentrated to give a gum. Methanol (20 ml) was added and the solution was acidified with ethereal HCl. Concentration gave methyl 4-[2-[3-(4-[1-pyrrolidinyl) pyridin-3-yl]-methylidene]pyrrolidin-1-yl]- acetyl] phenoxyacetate (650 mg) as an orange solid which was used without further purification.

EXAMPLE 109

3-[1-[2-[4-(4-Pyridyl)piperazin-1-yl]acetyl] piperidin-4-yl]propanoic acid

A mixture containing ethyl 3-[1-[2-[4-(4-pyridyl) piperazin-1-yl]acetyl]piperidin-4-yl]propanoate (50 mg), concentrated hydrochloric acid (1 ml) and dioxan (4 ml) was stirred at 50°–60° C. for 1 hour,then concentrated to give a foam which was triturated with hot isopropanol. Filtration gave the title compound (48 mg) as pale cream prisms, m.p. 188°–190° C. NMR (d₆DMSO+d₄AcOH) δ1.0–1.3(2H,m); 1.5–1.6(3H,m); 1.8(2H,d); 2.3(2H,t); 2.6–2.8(1H,m); 2.95–3.15(1H,m); 3.5(4H,brs); 3.6–3.7(1H,m); 4.0–4.2(4H, brs); 4.3–4.5(3H,m); 7.25(2H,d); 8.35(2H,d); m/e 361(M+ H)⁺; calculated for C₁₉H₂₈N₄O₃2HCl. H₂O: C,50.6;H, 7.2; N, 12.4; H₂O, 4.0; found: C,50.3; H, 7.2; N, 12.2; H₂O, 4.0%.

The starting material was prepared as follows:

i) Diethylazodicarboxylate (24.6 ml) was added dropwise to a stirred solution of triphenylphosphine (39.3 g) in THF (120 ml) at 0° C. under argon. The mixture was stirred for 20 minutes,then treated sequentially with lithium bromide (26.1 g) and a solution of 1-benzyloxycarbonylpiperidine-4-ol (7.1 g) in THF (50 ml). The mixture was allowed to warm to room temperature and stirring was continued for 1 hour. The mixture was concentrated, the residue treated with ether 100 (ml) and silica (60 ml), and the solvent was evaporated under reduced pressure. The resulting powder was added to the top of a flash column and the column was eluted with hexane/ether (4:1) to give 1-benzyloxycarbonyl-4-bromopiperidine (3.6 g) as a colourless oil; NMR (CDCl₃) δ1.8–2.0(2H,m); 2.0–2.2 (2H,m); 3.3–3.5(2H,m); 3.6–3.8(2H,m); 4.35(1H,m); 5.1 (2H,s); 7.3(5H,m). m/e 298/300(M+H)⁺; 320/322 (M+Na)⁺.

ii) A solution of the product of step i) (2.6 g) in toluene (100 ml) was stirred at 95° C. under argon and treated with a solution of tributyltin hydride (5.9 ml) in toluene (50 ml), added via a syringe pump over 6 hours. Samples of ethyl acrylate (4.7 ml each) and azobisisobutyronitrile (10 mg) were added at periods of 0 h, 2 h and 4 h during the addition of the tin hydride. The mixture was cooled, concentrated and purified by flash column chromatography, eluting with hexane/ethyl acetate (4:1) to give ethyl 3-(1-benzyloxycarbonyl) piperidin-4-yl) propanoate (1.7 g). NMR (d₆DMSO) δ0.9–1.1(2H,m); 1.15(3H,t); 1.3–1.5(3H,m); 1.6–1.7(2H,m); 2.3(2H,t); 2.6–2.8(2H,brt); 3.9–4.1(2H,brt+2H,q); 5.05(2H,s); 7.3 (5H,m), m/e 320 (M+H)⁺, 342(M+Na)⁺, and ethyl 3-(1-benzyloxycarbonylpiperidin-4-yl)-2-(2-ethoxycarbonylethyl)propanoate (0.7 g) NMR (d₆DMSO) δ1.2(6H, 2t); 1.0–1.8(9H,m); 2.3(2H,t); 2.45(1H,m); 2.6–2.9(2H,brt); 3.8–4.0(2H,brt); 4.0–4.2(4H, 2q); 5.05 (2H,s); 7.3(5H,m); m/e 420(M+H)+,442(M+Na)⁺.

iii) In a similar manner to that described in Example 103,ethyl 3-(1-benzyloxycarbonylpiperidin-4-yl)

propanoate was converted to ethyl 3-[1-[2-[4-(4-pyridyl) piperazin-1-yl]acetyl]piperidin-4-yl]propanoate. The following intermediates were isolated: ethyl-1-bromoacetylpiperidin-4-ylpropanoate. NMR (CDCl$_3$) δ1.1–1.4(2H,m); 1.25(3H,t); 1.5–1.7(3H,m); 1.7–1.9(2H, t); 2.3(2H,t); 2.5–2.7(1 H,td); 3.0–3.2(1H,td); 3.8–4.0 (2H,d)+1 H,m); 4.15(2H,q); 4.55(1H,m); m/c 306/308 (M+H)$^+$. ethyl 3-[1- [2-[4-(4-pyridyl)piperazin- 1-yl] acetyl]piperidin-4-yl]propanoate. m.p. 90°–92° C.; NMR (d$_6$DMSO) δ0.85–1.0(1 H,m); 1.05–1.2(1H,m); 1.2(3H, t); 1.5(3H,m); 1.7(2H,m); 2.3(2H,t); 2.5(4H,brs); 2.8–3.0(1 H,t); 3.1(1H,d); 4.05(2H,q+1 H,m); 4.3(1 H,d); 6.8(2H,d); 8.15(2H,d); m/e 389 (M+H)$^+$411 (M+Na)+; calculated for C$_{21}$H$_{32}$N$_4$O$_3$; C, 64.9; H, 8.3; N, 14.4; found: C, 65.0; H, 8.5; N, 14.4%.

EXAMPLE 110

Ethyl 2RS-(n-butylsulphonylamino)-3-[1-[2-[4-(4-pyridyl)piperazin-1yl]-acetyl]piperidin-4-yl] propanoate A mixture containing ethyl (2-n-butylsulphonylamino)-3-[1-(2-bromoacetyl)piperidin-4-yl]propanoate (330 mg), 1-(4-pyridyl)piperazine (150 mg), triethylamine (0.13 ml) and acetonitrile (20 ml) was stirred for 16 hours. The mixture was concentrated and the residue was dissolved in ethyl acetate (50 ml). The solution was washed with water (2×20 ml) and saturated aqueous sodium chloride (20 ml), dried (MgSO$_4$) and concentrated. The residue was dissolved in ethanol (20 ml), treated with decolourising charcoal, filtered and concentrated to give the title compound (136 mg) as a colourless glass. NMR (d$_6$DMSO+d$_4$AcOH) δ0.8 (3H,t); 1.0(1 H,m); 1.1(3H,t); 1.3(2H,m); 1.5–1.8(8H,m); 2.9(4H,m); 3.2(4H,brs); 3.65(1 H,m); 3.8–4.1(4H,brs+3H, m+2H,q); 4.35(1H,m); 7.1(2H,d); 8.1 (2H,d); m/e 524(M+H)$^+$.

The starting material was prepared as follows:

i) A solution of methanesulphonylchloride (7.7 ml) in dichloromethane (50 ml) was added dropwise to a stirred solution of 1-benzyloxycarbonyl-4-hydroxymethylpiperidine (23.4 g) in dichloromethane (350 ml) cooled to 5° C. Stirring was continued for 1 hour, then the solution was washed with water (4×150 ml) and saturated aqueous sodium chloride (100 ml), dried and concentrated. The residue was crystallised from tetrachloromethane (250 ml) to give 1-benzyloxycarbonyl-4-methanesulphonyloxymethylpiperidine (20 g) as colourless prisms, m.p. 72°–74° C. NMR (CDCl$_3$) δ1.1–1.4(2H, m); 1.7–1.8(2H,d); 1.9–2.1(1H,m); 2.7–2.9(2H,t); 3.0 (3H,s); 4.05(2H,d); 4.1–4.4(2H,d); 5.1(2H,s); 7.3(5H,m); m/e 328(M+H)+350 (M+Na)$^+$; calculated for C$_{15}$H$_{21}$N$_5$O$_5$: C, 55.0;H, 6.5; N, 4.3; found: C, 54.8; H, 6.6; N, 4.2%.

ii) A mixture containing triethylbenzylammonium bromide (0.3 g), the product of step i) (3.27 g),ethyl N-diphenylmethylidene glycine ester (3.0 g), potassium carbonate (4.2 g) and acetonitrile (45 ml) was heated under reflux for 48 hours, concentrated, and the residue was partitioned between ethyl acetate (100 ml) and water (100 ml). The ethyl acetate fraction was washed with water (2×50 ml) and saturated aqueous sodium chloride (50 ml), dried (MgSO$_4$) and concentrated. The residue was purified by flash column chromatography, eluting with hexane/ether (3: 1) to give ethyl 2RS-(diphenylmethylidene amino)-3-(1-benzyloxycarbonylpiperidin-4-yl)propanoate (650 mg) as a pale yellow oil. NMR (d$_6$DMSO) δ0.8–1.6(5H,m); 1.2(3H,t); 1.8(2H,t); 2.6–2.8(2H,m); 3.8–4.0(3H,m); 4.1(2H,q); 5.05(2H,s); 7.1–7.6(15H,m); m/e 499(M+H)$^+$; 42 1 (M+Na)$^+$.

iii) A mixture of the product of step ii) (1.1 g), saturated hydrogen chloride in ether solution (15 ml) and ethanol (50 ml) was allowed to stand for 1 hour. The solution was concentrated and the residue was stirred with ether (30 ml) to give a colourless solid. The solid was filtered off, washed with ether (30 ml) and dried to give ethyl 2RS-amino-3-(1-benzyloxycarbonylpiperidin-4-yl)propanoate hydrochloride (700 mg) as a colourless solid which was used without further purification. A sample (50 mg) was recrystallised from ethyl acetate (10 ml) to give colourless prisms (30 mg), m.p. 122°. NMR (d$_6$DMSO) δ0.9–1.1 (2H,br.m); 1.25(3H,t); 1.6–1.8(5H,br.m); 2.6–2.9(2H, br.m); 3.9–4.1(3H,br.m); 4.2(2H,dq); 5.1(2H,s); 7.3(5H, m); 8.4–8.7(3H,br.s); m/e 335(M+H)$^+$; calculated for C$_{18}$H$_{26}$N$_2$O$_4$.HCl: C, 58.3; H, 7.3; N, 7.6; found: C, 58.2;H, 7.7; N, 7.5%.

iv) A mixture of the product of step iii) (650 mg), n-bitylsulphonylchloride (0.25 ml), triethylamine (0.55 ml) and dichloromethane (30 ml) was stirred for 4 hours at room temperature, then diluted with dichloromethane (50 ml), washed with water (3×50 ml) and saturated aqueous sodium chloride (50 ml), dried (PS paper) and concentrated. The residue was purified by flash column chromatography, eluting with hexane/ethyl acetate (3: 1) to give ethyl 2RS-(n-butylsulphonylamino)-3-(1-benzyloxycarbonylpiperidin-4-yl)propanoate (400 mg) as a colourless gum. NMR (d$_6$DMSO) δ0.9(3H,t); 1.0–1.2 (2H,m); 1.25(3H,t); 1.3–1.5(2H,m); 1.5–1.8(7H,m); 2.6–2.9(2H,m); 2.8–3.1 (2H1,m); 3.8–4.1(3H,m); 4.1 5(2H,q); 5.1(2H,s); 7.3(5H,m); 7.7(1H,d); m/e 455 (M+H)$^+$; 477(M+Na)$^+$.

In a similar manner to that described in Example 103,the carbonyl-protected piperidine was converted to the N-bromoacetyl analogue, which was isolated as a colourless gum and used without further purification.

EXAMPLE 111

2-RS-(n-Butylsulphonylamino)-3-[1-[2-[4-(4-pyridyl)-piperazin-1-yl]acetyl]propanoic acid A mixture of the product of Example 110 (50 mg), concentrated hydrochloric acid (1 ml) and dioxan (4 ml) was stirred at 50° C. for one hour, then concentrated, triturated with acetone and dried under vacuum. The residual solid was stirred with dioxan (3 ml) and concentrated hydrochloric acid (2 ml) at 70° C. for 1 hour then concentrated and dried under vacuum to give the title compound (34.3 mg) as a pale yellow solid. NMR (d$_6$DMSO +d$_4$ AcOH) δ0.8 (3H,t); 1.0–1.2(1H,m); 1.3(2H,m); 1.5–1.8(8H,m); 2.8–3.0(4H,m); 3.4–3.6(6H,m); 4.0(4H,brs); 4.1–4.4(3H,m); 7. 1(2H,d); 8.1 (2H,d); m/e 496 (M+H)$^+$; 518 (M+Na)$^+$.

EXAMPLE 112

3-[2-[4-(4-Pyridyl)piperazin-1-yl]acetyl]piperidin-4-yl]-3- 2-(2-carboxyethyl)]propanoic acid A mixture containing ethyl 3-[1-[2-[4-(4-pyridyl) piperazin-1-yl]acetyl]piperidin-4-yl]-3-[2-(2-ethoxycarbonylethyl)]- propanoate, concentrated hydrochloric acid (2 ml) and dioxan (3 ml) was stirred at 70° C. for 1 hour, concentrated and dried under vacuum. The residue was triturated with acetone and redried to give the title compound (52 mg) as a pale yellow foam. NMR (d$_6$DMSO +d$_4$AcOH) δ0.9–1.1 (1 H,m); 1.2–1.3(1 H,m);

1.5(3H,m); 1.7(2H,t +2H,m); 2.2(2H,t); 2.35(1 H,m); 2.6(1 H,m); 2.7–3.0(2H,m); 3.2(1 H,m); 3.5(4H,m); 4.0(4H,m); 4.8(2H,d); 7.1(2H,d); 8.2(2H,d); m/e 433(M+H)$^+$.

The starting material was prepared as a pale yellow gum from ethyl 3-(1-benzyloxycarbonylpiperidin-4-yl)-2-(2-ethoxycarbonylethyl)propanoate using a similar procedure to that described for the monoester in Example 109.

EXAMPLE 113

4-[4-[(4-Dimethylaminopyrid-3-yl)methoxy]phenoxy]butanoic acid

A mixture containing ethyl 4-14-[(4-dimethylaminopyrid-3-yl)methoxy]phenoxy]-butanoate (25 mg), aqueous sodium hydroxide (1M, 0.2 ml), methanol (0.5 ml) and water (0.5 ml) was stirred for 3 hours then neutralised with hydrochloric acid (1M, 0.2 ml) and concentrated. The residue was dissolved in dichloromethane (5 ml), filtered, and the filtrate was concentrated to give the title compound (17 mg) as a colourless gum. NMR (d$_6$DMSO +d$_4$AcOH) δ2.0(2H,q); 2.4(2H,t); 3.35(6H,s); 3.95(2H,t); 5.1(2H,s); 6.8–7.0(4H,dd +1 H,m); 8.15(1 H,dd); 8.3(1 H,d); m/e 331 (M+H)$^+$.

The starting material was prepared as follows:

i) A solution of 4-dimethylaminopyridine-3-carboxaldehyde (J. Het. Chem. 25, 81) (1.5 g) in ethanol (25 ml) was treated with sodium borohydride (200 mg) and the mixture was stirred for 4 hours. Concentrated hydrochloric acid (1 ml) was added and the mixture was concentrated. The residue was treated with saturated aqueous sodium chloride (40m) and concentrated aqueous sodium hydroxide (2 ml) and the mixture was extracted with dichloromethane (4×20 ml). The combined organic extracts were washed with saturated aqueous sodium chloride (40 ml), dried (PS paper) and concentrated. The residue was dissolved in methanol, treated with decolourising charcoal, filtered and concentrated to give 4-dimethylaminopyridine-3-methanol (1.1 g) as a pale yellow oil. NMR (d$_6$DMSO) δ2.9 (6H,s); 4.5(2H,s); 4.0–4.8(1H.br.s); 6.7(1H,d); 8.15(1H,d); 8.3(1H,s); m/e 153 (M+H)$^+$; 135(M+H–H$_2$O)$^+$.

ii) A mixture containing the product of step i) (300 mg), ethyl 4-(4-hydroxyphenoxy)butanoate (450 mg), triphenylphosphine (0.58 g) and dichloromethlhane (5 ml) was stirred for 30 minutes then treated dropwise with diethylazodicarboxylate (0.35 ml). The mixture was stirred for 2 hours then diluted with ether (50 ml), washed with water (2×25 ml) and saturated aqueous sodium chloride (25 ml), dried (MgSO$_4$) and concentrated. The residue was purified by flash column chromatography eluting with ethanol/dichloromethane (3:97) to give ethyl 4–14-(4-dimethylamilopyrid-3-yl)methoxylphenoxybutanoate (200 mg) as a colourless solid. NMR (d$_6$DMSO +d$_4$AcOH) δ1.1(3H,t); 1.9(2H,q); 2.3(2H,t); 3.2(6H,s); 3.8(2H,t); 3.95(2H,q); 5.0(2H,s); 6.7–6.9(2H,d +1H,d +2H,d); 8.0(1H,dd); 8.15(1H,d); m/e 359 (M+H)$^+$.

EXAMPLE 114

Methyl3-(4-dimethylamninopyrid-3-yl)methoxyphenoxyl-2-benzyloxycarbonylaminopropanoate A stirred mixture containing 4-dimethylaminopyridine-3-methanol (700 mg), triphenylphosphine (1.3 g), N-benzyloxycarbonyltyrosine methyl ester (1.66 g) and THF (50 ml) was treated dropwise with diethylazodicarboxylate (1.3 g) and the mixture was stirred for 4.5 hours and concentrated. The residue was purified by flash column chromatography eluting with methanol/dichloromethane (first 1:99, then 2:98) to give the title compound (900 mg) as a colourless foam. NMR (d$_6$DMSO) δ2.7–3.1(2H,m); 2.9(6H,s); 3.6(3H,s); 4.2(1 H,m); 4.95(2H,s); 5.05(2H,s); 6.8(1H,d); 6.9(2H,d); 7.15(2H,d); 7.2–7.4(5H,m); 7.75)1H, d); 8.3(1 H,s); m/e 464(M+H)$^+$.

EXAMPLE 115

N-[1-[2-[4-(4-Pyridiyl)piperazin-1-yl]acetyl]piperidin-4-ylmethyl]-1-butanesulphonamide A mixture containing 4-n-butylsulphonylaminomethyl-N-bromoacetylpipelidine (250 mg),1-(4-pyridyl)piperazine (125 mg),triethylamine (0.11 ml) and acetonitrile (10 ml) was stirred for 16 h and concentrated. The residue was purified by flash column chromatography, eluting with dichloromethanolmethanol/triethylamine (95:5:0.5), to give a colourless solid (280 mg). The solid was dissolved in water (5 ml) and extracted with ethyl acetate (3×5 ml). The combined organic extracts were washed with saturated aqueous sodium chloride (5 ml), dried (MgSO$_4$) and concentrated to give the title compound (90 mg) as a colourless oil. NMR (d$_6$DMSO +d$_4$AcOH) δ0.8(3H,t); 1.4(2H,m); 0.9–1.8 (2H,m +2H,m +2H,m +1 H,m); 2.6(1H,t); 2.7–3.0(2H,d +2H,m +1H,t); 3.3(4H.brs); 3.6(1H,brd); 3.9(4H,brs); 3.9–4.2(2H,dd); 4.3(1H,brd), 7.1(2H,d); 8.15(2H,d); m/e 438(M+H)$^+$.

The starting material was prepared as follows:

i) A solution of n-butylsulphonamide (500 mg) in DMF (5 ml) was added dropwise to a suspension of sodium hydride (150 mg, 60% dispersion in mineral oil) in DMF (10 ml) and the mixture was stirred for 10 minutes. 4-Methanesulphonyloxymethyl-N-benzyloxycarbonylpiperidine (1.09 g) was added and the mixture heated at 80° C. for 16 hours. The mixture was cooled, poured into water (100 ml) and extracted with ethyl acetate (3×50 ml). The combined organic extracts were washed with water (3×50 ml) and saturated aqueous sodium chloride (50 ml), dried (MgSO$_4$) and concentrated. The residual oil was purified by flash column chromatography, eluting with methanol/dichloromethane (1:99) to give a colourless semi-solid. This mixture was dissolved in warm tetrachloromethane (6 ml) and cooled to give 4-n-butylsulphonylaminomethyl-N-benzyloxycarbonylpiperidine (230 mg) as colourless prisms, mp 83°–85° C. NMR (d$_6$DMSO) δ0.9(3H,t), 0.9–1.1(2H,m); 1.3–1.5(2H,m); 1.5–1.8(5H,m); 2.7–2.9 (4H,m); 2.95(2H,m); 4.0(2H,d); 5.1(2H,s); 7.0(1H,t); 7.3 (5H,m). m/e 369(M+H)$^+$; 391(M+Na)$^+$; calculated for C$_{18}$H$_{28}$N$_2$SO$_4$: C, 58.7; H, 7.7; N, 7.6; found: C, 58.5; H, 7.8; N, 7.6%.

The N-benzyloxycarbonyl-protected piperidine was converted to the N-bromoacetyl analogue using a similar procedure to that described in Example 103. The N-bromoacetyl compound was used immediately in the preparation of product.

EXAMPLE 116

Methyl 4-[2-[4-(4-pyridyl)piperazin-1-yl]-2,6-dichlorophenoxyacetate

Prepared in a similar manner to Example 5,but starting from methyl 4-bromoacetyl-2,6-dichlorophenoxyacetate, however stirring for only 6 hours and purification by flash chromatography on silica, eluting first with dichloromethane then successively 2,3,4 and 5% v/v methanol/dichloromethane. Concentration of the fractions in vacuo and recrystallisation of the residue from methanol gave the title compound in 24% yield as a pale orange solid: m.p. 149°–150° C.; NMR (d$_6$DMSO) δ8.14(2H,d), 8.06(2H,s), 6.81(2H,d), 4.82(2H,s), 4.05(0.5H,b), 3.94(2H,s), 3.73(3H,s), 3.32(4H,t), 3.18(1.5H,s), 2.64(4H,t); m/e 438 (M+H)$^+$, 3207 2×Cl pattern; calculated for C$_{20}$H$_{21}$Cl$_2$N$_3$O$_4$.0.5CH$_3$OH: C, 54.1; H, 5.1; N, 9.2. found: C, 53.7; H, 5.4; N, 8.9%.

The starting material was prepared as follows:

i) Sodium hydride (50% w/w dispersion in mineral oil, 1.32 g) was treated under argon with repeated washes of hexane. The oil-free residue was suspended in dry DMF (10 ml) and, with stirring and cooling (ice-bath), a solution of 3,5-dichloro-4-hydroxyacetophenone (5.13 g) in dry DMF (15 ml) was added dropwise. Stirring was continued for 30 minutes when methyl bromoacetate (3.06 ml) was added dropwise and stirring was continued for a further 18 hours at ambient temperature. The reaction mixture was added to water, the mixture was extracted twice with ethyl acetate, the organic phases dried (MgSO$_4$), filtered and then evaporated. The residue, after recrystallisation from hexane (250 ml), gave methyl 4-acetyl-2,6-dichlorophenoxyacetate, 4.25 g, as white crystals: NMR (d$_6$DMSO) δ8.00(2H,s), 4.80(2H,s), 3.73 (3H,s), 2.59(3H,s).

ii) A solution of bromine (0.77 ml) in chloroform (10 ml) was added dropwise over 15 minutes to a stirred solution of the product from step i) (4.16 g) in chloroform (40 ml) at 25° C. The temperature was raised to 40° C. for 1 hour and then stirring continued for a further 18 hours at ambient temperature. The solvent was removed in vacuo and the residual oil purified by flash chromatography on silica, eluting with dichloromethane, to give a crystalline solid. Recrystallisation from methanol gave methyl 4-bromoacetyl-2,6- dichlorophenoxyacetate, 1.88 g, as white crystals: m.p. 89°–90° C.; NMR (d$_6$DMSO) δ 8.06(2H,s), 4.93(2H,s), 4.82(2H,s), 3.72(3H,s); m/e 355/357 (M+H)$^+$, 1 Br pattern; calculated for C$_{11}$H$_9$BrCl$_2$O$_4$: C, 37.1; H, 2.3. found: C, 36.8; H, 2.4%.

EXAMPLE 117

Methyl4-[2-[4-(4-pyridyl)piperazin-1-acetyl]-1-naphthoxyacetate

Prepared in a similar manner to Example 5,but starting from methyl 4-bromoacetylnaphthoxyacetate and purification by flash chromatography on silica, eluting with dichloromethane then increasing concentrations of methanol to 5% v/v methanol/dichloromethane. Trituration with ether gave the title compound in 13% yield, as a solid: m.p. 140°–142° C.; NMR (d$_6$DMSO) δ 8.70(1H,dd), 8.32(1H,dd), 8.23(1H,d), 8.16(2H,bd), 7.64(2H,m), 7.00(1H,d), 6.80(2H,d), 5.14 (2H,s), 3.92(2H,s), 3.75(3H,s), 3.31(4H,t), 2.67(4H,t); m/e 420 (M+H)$^+$; calculated for C$_{24}$H$_{25}$N$_3$O$_4$.0.25 H$_2$O: C, 67.9; H, 6.0; N, 9.9. found: C, 67.8; H, 6.0; N, 9.7%.

The starting material was prepared as follows:

i) In a similar manner to Example 116i), but starting from 4-acetyl-1-naphthol, there was obtained methyl 4-acetyl-1-naphthoxyacetate in 62% yield as a white crystalline solid: m.p. 123°–125° C.; NMR (d$_6$DMSO) δ 8.89(1H,dd), 8.31(1H,dd), 8.19(1H,d), 7.63(2H,m), 7.00(1 H,d), 5.14(2H,s), 3.76(3H,s), 2.68(3H,s); m/e 259 (M+H)$^+$; calculated for C$_{15}$H$_{14}$O$_4$: C, 69.8; H, 5.5. found: C, 69.7; H, 5.4%.

ii) A mixture of the product from step i) above (2.0 g) and cupric bromide (3.45 g) in ethyl acetate (35 ml) was heated at reflux temperature for 24 hours. On cooling, the mixture was filtered,concentrated in vacuo and the residue purified by flash chromatography on silica eluting with dichloromethane. Evaporation of the fractions gave methyl 4-bromoacetyl-1-naphthoxyacetate as a white solid: m.p. 99°–101° C.; NMR (d$_6$DMSO) δ 8.73(1 H,d), 8.34(1H,d), 8.26(1H,d), 7.59 to 7.82(2H,m), 7.02(1H,d), 5.15(2H,s), 4.97(2H,s), 3.76(3H,s); m/e 337/339 (M+H)$^+$, 1 Br pattern.

EXAMPLE 118

Methyl 4-[2-|4-(4-pyridyl)piperazin-1-yl]acetyl]-3-methylphenoxyacetate

In a similar manner to Example 5,but starting from methyl 4-bromoacetyl-3-methylphenoxyacetate and with purification by flash chromatography on silica, eluting with 0 to 5% v/v methanol/dichloromethane,and then by flash chromatography on neutral alumina, eluting first with dichloromethane and then 1% v/v methanol/dichloromethane there was obtained the title compound in 9% yield as a yellow oil: NMR (d$_6$DMSO) δ 8.15(2H,d), 7.38(1H,d), 6.82(4H,m), 4.88(2H,s), 3.75(2H,s), 3.71(3H,s), 3.32(4H,t), 2.61(4H,t), 2.43(3H,s), m/e 384 (M+H)$^+$; calculated for C$_{21}$H$_{25}$N$_3$O$_4$.0.5H$_2$O.0.1CH$_2$Cl$_2$: C, 63.1; H, 6.5; N, 10.5. found: C, 62.6; H, 6.6; N, 10.2%.

The starting material was prepared as follows:

i) A mixture of 4-hydroxy-2-methylacetophenone (4.8 g), anhydrous potassium carbonate (5.3 g) and methyl bromoacetate (3.55 ml) in anhydrous acetone (100 ml) was stirred for 2 days. The mixture, after filtration and evaporation of the solvent, gave methyl 4-acetyl-3-methylphenoxyacetate, 6.6 g, as a crystalline solid: m.p. 49°–50° C.; NMR (d$_6$DMSO) δ 7.84(1H,d), 6.83(2H,m), 4.87(2H,s), 3.71(3H,s), 2.50(3H,s), 2.45(3H,s).

ii) Prepared in a similar manner to Example 117ii), but starting from the product of i) above and purification by flash chromatography on silica eluting with 10 to 17.5% v/v ethyl acetate/hexane. Recrystallisation from ethanol gave methyl 4-bromoacetyl-3-methylphenoxyacetate, in 35% yield, as white needles: NMR (d$_6$DMSO) δ 7.90(1H,d), 6.90(1H,s), 6.88(1H,d), 4.90(2H,s), 4.78(2H,s), 3.71(3H,s), 2.43(3H,s).

EXAMPLE 119

Methyl 3-[2-[4-(4-pyridyl)piperazin-1-yl] phenoxyacetate

Prepared in a similar manner to Example 5,but starting from methyl 3-bromoacetylphenoxyacetate and with purification by flash chromatography on silica, eluting with 10% v/v methanol/dichloromethane. Trituration with ether gave the title compound in 20% yield: m.p. 114°–116° C.; NMR (d$_6$DMSO) δ 8.15(2H,b), 7.61(1H,dd), 7.50(1H,m), 7.43 (1H,t), 7.21(1H,dd), 6.83(2H,d), 4.87(2H,s), 3.91(2H,s), 3.70(3H,s), 3.35(4H,t), 2.64(4H,t); m/e 370 (M+H)$^+$; calculated for C$_{20}$H$_{23}$N$_3$O$_4$.0.5H$_2$O: C, 63.5; H, 6.4; N, 11.1. found: C, 63.5; H, 6.5; N, 10.6%.

The starting material was prepared as follows:

i) In a similar manner to Example 116ii), but starting from the methyl 3-acetylphenoxyacetate and purification by flash chromatography on silica, eluting with ethyl acetate/hexane (1:1 v/v) there was obtained methyl 3-bromoacetylphenoxyacetate in 64% yield as a pale fawn solid: NMR (CDCl₃) γ 7.61(1H,d), 7.50(1H,m), 7.43(1H, t), 7.20(1H,dm), 4.70(2H,s), 4.44(2H,s), 3.82(3H,s); m/e 287/289 (M+H)⁺, 1 Br pattern.

EXAMPLE 120

Mixture of methyl 4-[2-[4-(4-pyridyl)piperazin-1-yl]acetyl]-2-methylphenoxyacetate and ethyl 4-[2-[4 (4-pyridyl)piperazin-1-yl]acetyl]-2-methylphenoxyacetate (3:2)

A mixture of methyl 4-acetyl-2-methylphenoxyacetate (3.33 g) and cupric bromide (7.0 g) in ethyl acetate (50 ml) was heated on a steam bath for 18 hours. After filtration, the solvent was evaporated and the residual solid purified by flash chromatography on silica eluting with 10% v/v ethyl acetate/hexane to give an off-white solid. Recrystallisation from ethanol save white needles, 2.37 g, shown by NMR (d₆DMSO) to be a mixture of methyl 4-bromoacetyl-2-methylphenoxy- acetate and ethyl 4-bromoacetyl-2-methylphenoxyacetate which was used without further purification. The mixture (2.25 g) was added portionwise to a stirred solution of 1-(4-pyridyl)piperazine (2.45 g) in acetonitrile (50 ml) and the mixture stirred for 18 hours. The reaction mixture was filtered and the filtrate evaporated to give an orange oil. Purification by flash chromatography on silica eluting with dichloromethane then 1 to 3% v/v methanol/dichloromethane gave the title mixture of compounds, 0.87 g, as a solid: m.p. 136°–138° C.; NMR (d₆DMSO) δ 8.04(2H,d), 7.85(1H,d), 7.82(1H,s), 6.95(1H, d), 6.81(2H,d), 4.96 and 4.93(2H,s,s), 4.18(0.7H,q), 3.84 (2H,s), 3.72(1.7H,s), 3.30(4H,t), 2.60(4H,t), 2.25(3H,s), 1.21(1.3H,t), [Ratio of methyl to ethyl ester 3:2]; m/e 384 (M+H)⁺ for methyl ester, 398 (M+H)⁺ for ethyl ester; calculated for $C_{21}H_{25}N_3O_4$: $C_{22}H_{27}N_3O_4$ (3:2): C, 66. 1;H. 6.6; N, 10.8. found: C, 65.8; H. 6.7; N, 10.5%.

The starting material was prepared as follows:

i) A mixture of 4-hydroxy-3-methylacetophenone (5 g), methyl bromoacetate (3.70(ml) and anhydrous potassium carbonate (5.52 g) in acetone (100 ml) was stirred for 66 hours. The mixture was filtered and the filtrate evaporated to give an oil which crystallised on standing to give methyl 4-acetyl-2-methylphenoxyacetate, 7.2 g: m.p. 51°–53° C.; NMR (d₆DMSO) δ 7.79(1H,s), 7.77(1H,d), 6.94(1H,d), 4.93(2H,s), 3.71(3H,s), 2.50(3H,s +DMSO), 2.24 (3H,s).

EXAMPLE 121

Mixture of methyl 4-[2-[4-(4-pyridyl)piperazin-1-yl]acetyl]-3-methoxyphenoxyacetate and ethyl4-[2-[4-(4-pyridyl)piperazin-1-yl]acetyl]-3-methoxyphenoxyacetate (3:1)

In a similar manner to Example 120,but starting from methyl 4-acetyl-3-methoxyphenoxyacetate there was prepared, after flash chromatography on silica eluting with dichloromethane, a mixture of methyl 4-bromoacetyl-3-methoxyphenoxyacetate and ethyl 4-bromoacetyl-3- methoxyphenoxyacetate in 60% yield: m.p. 84°–86° C. Treatment of this mixture, as in Example 120, followed by chromatography on silica eluting with 1 to 5% v/v methanol/dichloromethane gave the title mixture of compounds in 24% yield as a solid: NMR (d₆DMSO) δ 8.13(2H,d), 7.63 (1H,d), 6.80(2H,d), 6.67(1H,d), 6.59(1H,dd), 4.90 and 4.88 (2H,2s), 4.18(0.5,q), 3.88(3H,s), 3.75(2H,s), 3.71(2.3H,s), 3.32(4H,t), 2.62(4H,t), 1.22(0.7H,t) [Ratio of methyl to ethyl ester 3:1]; m/e 400 (M+H)⁺ for methyl ester, 414 (M+H)⁺ for ethyl ester; calculated for $C_{21}H_{25}N_3O_5$: $C_{22}H_{27}N_3O_5$ (3: 1): C, 63.3;H, 6.5; N, 10.4. found C, 63.1; H, 6.5, N, 10.3%.

The starting material was prepared as follows:
i) In a similar manner to Example 120i), but starting from 4-hydroxy-2-methoxy-acetophenone there was obtained, after evaporation of the solvent and trituration with diethyl ether, methyl 4-acetyl-3-methoxyphenoxyacetate in 91% yield as a white solid: m.p. 95°–96° C.; NMR (d₆DMSO) δ 7.64(1H,d), 6.70(1H,d), 6.60(1H,dd), 4.91 (2H,s), 3.89(3H,s), 3.72(3H,s), 2.49(3H,s).

EXAMPLE 122

Mixture of dimethyl 2,2'-[4-[2-[4-(4-pyridyl) piperazin-1-yl]acetyl]-phenylene-1,3-dioxy]diacetate and diethyl 2,2'-[4-[2-[4-(4-pyridyl)piperazin-1-yl] acetyl]phenylene-1,3-dioxy]- diacetate(1:1)

In a similar manner to Example 120, but starting from dimethyl 2,2'-[(4-acetyl)phenylene-1,3-dioxy]diacetate there was prepared, after flash chromatography on silica eluting with dichloromethane, a mixture of dimethyl 2,2'-[(4-bromoacetyl)phenylene-1,3-dioxy]diacetate and diethyl 2,2'-[(4-bromoacetyl)phenylene-1,3-dioxy]diacetate in 28% yield. Treatment of the mixture,as in Example 120, followed by chromatography on silica eluting with 1 to 5% v/v methanol/dichloromethane gave the title mixture of compounds in 44% yield as a solid: NMR (d₆DMSO) δ 8.14 (2H,d), 7.63(1H,d), 6.82(2H,d), 6.65(2H,d), 4.96+4.93(2H, 2s), 4.49 and 4.47(2H,2s), 4.20(2H,m), 3.91(2H,s), 3.75 and 3.71(3H, 2s), 3.32(4H +H₂O), 2.61(4H,t), 1.23(3H,m) [Ratio of methyl to ethyl esters 1:1]; m/e 458 (M+H)⁺for dimethyl ester and 486 (M+H)⁺ for diethyl ester; calculated for $C_{23}H_{27}N_3O_7$: $C_{25}H_{31}N_3O_7$ (1:1), H₂O: C, 60.0;H, 6.3; N, 8.7. found: C, 60.3;H, 6.2; N, 8.5%.

The starting material was prepared as follows:
i) In a similar manner to Example 120i),but starting from 2,4-dihydroxy-acetophenone and using 2.4 equivalents of methyl bromoacetate and 2.4 equivalents of anhydrous potassium carbonate there was obtained, after evaporation and trituration with diethyl etherhexane (1:1 v/v), dimethyl 2,2'-[(4-acetyl)phenylene-1,3-dioxy]diacetate in 82% yield as a white solid: m.p. 119°–120° C.; NMR (d₆DMSO) δ 7.64(1H,d), 6.56(2H,m), 4.99(2H,s), 4.90 (2H,s), 3.73(3H,s), 3.71(3H,s), 2.57(3H,s).

EXAMPLE 123

4-[2-[4-(4-Pyridyl)piperazin-1-yl]acetyl]-2,6-dichlorophenoxyacetic acid, dihydrochloride A solution of the product Example 116 (190 mg) in dioxane (1.7 ml) was treated with 1N hydrochloric acid (1.7 ml) and the mixture heated at 100° C. for 1.5 hours. The mixture was cooled, diluted with water and freeze-dried. The solid residue,on treatment with a small volume of ethanol, gave the title compound, 120 mg, as a white solid: m.p. 174°–176° C.; NMR (D₂O) δ 8.42(2H,d), 8.26(2H,s), 7.41(2H,s), 5.24(2H,s), 4.98(2H,s), 4.34(4H,t), 3.90(4H,t); m/e 424 (M+H)⁺, 2×Cl pattern; calculated for $C_{19}H_{19}Cl_2N_3O_4.2HCl.H_2O$: C, 44.4;H, 4.5; N, 8.2. found: C, 44.8; H, 4.2; N, 8.1%.

EXAMPLES 124 TO 129

In a similar manner to Example 123, but starting from the product of Examples 117 to 122 the following compounds were prepared:

EXAMPLE 124

4-[2-[4-(4-Pyridyl)piperazin-1-yl]acetyl] naphthoxyacetic acid, dihydrochloride

The title compound was prepared from the product of Example 117 in 84% yield: m.p. 253°–255° C.; NMR (D$_2$O) δ 9.16(1H,d), 8.63(1H,d), 8.42(2H,d), 8.28(1H,d), 8.00(1H,t), 7.78(1H,t), 7.41(2H,d), 7.08(1H,d), 5.27(2H,s), 5.15(2H,s), 4.34(4H,bs), 3.94(4H,bs); m/e 406 (M+H)$^+$; calculated for C$_{23}$H$_{23}$N$_3$O$_4$.2HCl.0.5H$_2$O: C, 56.7;H, 5.4; N, 8.6. found: C, 56.8; H, 5.6; N, 8.1%.

EXAMPLE 125

4-[2-[4-(4-Pyridyl)piperazin-1-yl]acetyl]-3-methylphenoxyacetic acid, dihydrochloride The title compound was prepared from the product of Example 118 in 78% yield: m.p. 242°–244° C.; NMR (D$_2$O) δ 8.38(2H,d), 8.00(1H,d), 7.36(2H,d), 7.14(1H,s), 7.10(1H,d), 5.12(2H,s), 4.97(2H,s), 4.30(4H,bs), 3.84(4H,bs), 2.75 (3H,s); m/e 370 (M+H)$^+$; calculated for C$_{20}$H$_{23}$N$_3$O$_4$.2HCl.0.5H$_2$O: C, 53.4; H, 5.3; N, 9.3. found C, 53.2; H, 5.8; N, 8.8%.

EXAMPLE 126

3-[2-[4-(4-Pyridyl)piperazin-1-yl]acetyl] phenoxyacetic acid, dihydrochloride

The title compound was prepared from the product of Example 119 in 57% yield: m.p. 190°–193° C.; NMR (D$_2$O) δ 8.41(2H,d), 7.86(1H,dt), 7.75(1H,t), 7.72(1H,t), 7.57(1H,dm), 7.40(2H,d), 5.26(2H,s), 4.98(2H,s), 4.98(2H,s), 4.32 (4H,bs), 3.89(4H,t); m/e 356 (M+H)$^+$; calculated for C$_{19}$H$_{21}$N$_3$O$_4$.2HCl.0.75H$_2$O: C, 51.7; H, 5.6; N, 9.5. found: C, 51.6; H, 5.8; N, 9.3%.

EXAMPLE 127

4-[2-[4-(4-Pyridyl)piperazin-1-yl]acetyl]-2-methyl-phenoxyacetic acid, dihydrochloride The title compound was prepared from the product of Example 120 in 98% yield: m.p. 259° to 263° C.; NMR (d$_6$DMSO+D$_2$O) δ 8.46(2H,d), 7.95(2H,m), 7.38(2H,d), 7.15(1H,d), 5.17(2H,s), 5.00(2H,s), 4.19(4H,s), 3.62(4H,s), 2.39(3H,s); m/e 370 (M+H)$^+$; calculated for C$_{20}$H$_{23}$N$_3$O$_4$.2HCl.0.5H$_2$O: C, 53.5; H, 5.8; N, 9.4. found: C, 53.6;H, 5.7; N, 9.5%.

EXAMPLE 128

4-[2-[4-(4-Pyridyl)piperazin-1-yl]acetyl]-3-methoxy-phenoxyacetic acid, dihydrochloride The title compound was prepared from the product of Example 121 in 69% yield: m.p. 168°–170° C.; NMR (d$_6$DMSO+d$_4$ acetic acid) δ 8.36(2H,d), 7.93(1H,d), 7.28 (2H,d), 6.76(1H,d), 6.72(1H,dd), 4.86(2H,s), 4.78(2H,s), 4.08(4H,bs), 3.98(3H,s), 3.54(4H,bs); m/e 386 (M+H)$^+$; calculated for C$_{20}$H$_{23}$N$_3$O$_5$.2HCl.2H$_2$O; C, 48.7; H, 5.9; N, 8.5. found: C, 48.5; H, 5.7; N, 8.3%.

EXAMPLE 129

2,2'-[4-[2-[4-(4-Pyridyl)piperazin-1-yl]acetyl] phenylene-1,3-dioxy]diacetic acid, dihydrochloride The title compound was prepared from the product of Example 122 in 79% yield: m.p. 257°–258° C.; NMR (D$_2$O) δ8.39(2H,d), 8.18(1H,d), 7.48(2H,d), 6.94(1H,dd), 6.76(1H,d), 5.18(2H,s), 5.09(2H,s), 5.01(2H,s), 4.29(4H,b), 3.34(4H,b); m/e 430 (M+H)$^+$; calculated for C$_{21}$H$_{24}$N$_3$O$_7$.2HCl.0.5H$_2$O: C, 49.5; H, 5.3; N, 8.2. found, C, 49.4; H, 5.3; N, 7.8%.

EXAMPLE 130

4-[2-[4-(4-Pyridyl)piperazin-1-yl]acetyl]-2,6-di-tert-butylphenoxyacetic acid

A solution of methyl 4-(2-[4-(4-pyridyl)piperazin-1-yl] acetyl)-2,6-di-tert-butylphenoxyacetate (241 mg) in dioxane (2.0 ml) was treated with 1N hydrochloric acid and the mixture heated at 100° C. for 20 hours. The mixture was cooled, diluted with water, filtered and the filtrate freeze-dried. The solid residue was purified by flash chromatography on silica eluting with toluene/ethyl acetate/0.880 ammonia/ethanol (60:20:10:35 v/v/v/v). The fractions containing the desired product were evaporated, the residue treated with dioxane, filtered and the filtrate diluted with water and freeze dried to give a white foam, which on drying at 55° C. gave the title compound, 90 mg: NMR (d$_6$DMSO) δ8.16(2H,d), 7.97(2H,s), 6.84(2H,d), 4.22(2H,s), 3.86(2H,s), 3.37(4H,t), 2.64(4H,t), 1.39(18H,s); m/e 468 (M+H)$^+$; calculated for C$_{27}$H$_{37}$N$_3$O$_4$.2H$_2$O: C, 64.4; H, 8.2; N, 8.3. found C, 64.6; H, 7.9; N, 7.9%.

The starting material was prepared as follows:

i) In a similar manner to Example 116i), but starting from 2,5-di-tert-butyl-4-hydroxyacetophenone there was obtained from the ethyl acetate extracts a brown oil. Flash chromatography on silica, eluting with successively hexane, then 2% v/v ethyl acetate/hexane and finally 5% v/v ethyl acetate/hexane gave methyl 4-acetyl-2,6-di-tert-butylphenoxyacetate in 50% yield as an oil: NMR (d$_6$DMSO) δ7.84(2H,s), 4.38(2H,s), 3.76(3H,s), 2.55(3H,s), 1.40(18H,s); m/e 321 (M+H)$^+$; calculated for C$_{19}$H$_{28}$O$_4$:C, 71.2; H, 8.8. found C, 71.5; H, 9.0%.

ii) In a similar manner to Example 117ii), but starting from the product of step i) above and with purification by flash chromatography on silica eluting with 5% v/v ethyl acetate/hexane there was obtained methyl 4-bromoacetyl-2,6-di-tert-butylphenoxyacetate in 82% yield as a yellow oil: NMR (d$_6$DMSO) δ7.90(2H,s), 4.92(2H,s), 4.40(2H,s), 3.76(3H,s), 1.41(18H,s).

iii) In a similar manner to Example 5, but starting from the product of step ii) above and with purification by flash chromatography on silica eluting successively with dichloromethane then 2 to 5% v/v methanol/dichloromethane there was obtained a solid. Trituration with ether gave methyl 4-[2-[4-(4-pyridyl)piperazin-1-yl] acetyl]-2,6di- tert-butylphenoxyacetate in 33% yield: m.p. 140°–142° C.; NMR (d$_6$DMSO) δ7.97(2H,s), 6.82 (2H,d), 4.39(2H,s), 3.85(2H,s), 3.75(3H,s), 3.33(4H,t), 2.64(4H,t), 1.39(18H,s) m/e 482 (M+H)$^+$; calculated for C$_{28}$H$_{39}$N$_3$O$_4$: C, 69.8; H, 8.2; N, 8.7. found:C, 69.7; H, 8.6; N, 8.1%.

EXAMPLE 131

Ethyl 4-[2-[4-(4-pyridyl)piperazin-1-yl]acetyl] benzoate

Prepared in a similar manner to Example 5, but starting from ethyl 4-bromoacetylbenozate; recrystallisation from methanol gave the title compound in 32% yield as pale yellow crystals: m.p. 147°–149° C.; NMR (d$_6$DMSO) δ8.14 (2H,d), 8.08(4H,q), 6.78(2H,d), 4.35(4H,q,AB pattern), 3.98

(2H,s), 3.31(4H,t), 2.63(4H,t), 1.35(3H,t); m/e 354 (M+H)³⁰; calculated for $C_{20}H_{23}N_3O_3$: C, 68.0; H, 6.6; N, 11.9. found: C, 68.0;H, 6.5; N, 11.7%.

EXAMPLE 132

Sodium 4-[2-[4-(4-pyridyl)piperazin-1-yl]acetyl] benzoate

A stirred suspension of the product of Example 131 (353 mg) in methanol (5 ml) was treated with a 1 molar sodium hydroxide solution (3 ml). After 2 hours, the cream coloured solid was collected, washed with a little methanol and dried to give the title compound, 240 mg, m.p. <300° C.; NMR (d₆DMSO) δ8.15(2H,d), 8.05(4H,t,AB pattern), 6.85(2H,d), 3.97(2H,s), 3.38(4H,t), 2.65(4H,t), m/e 348 (M+H)⁺; calculated for $C_{18}H_{18}N_3NaO_3 \cdot 0.25H_2O$: C, 61.4; H, 5.3; N, 11.9. found: C, 61.3; H, 5.2; N, 11.7%.

EXAMPLE 133

Dimethyl 2,2'-[5-[2-[4-(4-pyridyl)piperazin-1-yl] acetyl]phenylene-1,3-dioxy]diacetate In a similar manner to Example 5, but starting from dimethyl 2,2'-[(5-bromoacetyl)phenylene-1,3-dioxy] diacetate and with purification by flash chromatography on silica, eluting with 10% v/v methanol/dichloromethane, there was obtained a gum. Trituration with diethyl ether gave the title compound in 14% yield as a yellow solid: m.p. 105°–108° C.; NMR (d₆DMSO) δ8.16(2H,d), 7.15(2H,d), 6.82(3H,m), 4.87(4H,s), 3.89(2H,s), 3.70(6H,s), 3.31(4H,t), 2.63(4H,t); m/e 458 (M+H)⁺; calculated for $C_{23}H_{27}N_3O_7 \cdot 0.75H_2O$:C, 58.7; H, 6.1; N, 8.9. found: C, 58.6; H, 6.0; N, 8.5%.

The starting material was prepared as follows:

i) In a similar manner to Example 116i), but starting from 3,5-dihydroxyacetophenone and using 2.2 equivalents of sodium hydride and methyl bromoacetate there was obtained, after recrystallisation from iso-propanol, dimethyl 2,2'-[(5-acetyl)phenylene-1,3-dioxy]diacetate in 56% yield as a fawn solid: m.p. 96°–98° C.; NMR (CDCl₃) δ7.14 (2H,d), 6.70(1H,t), 4.66(4H,s), 3.81(6H,s), 2.56(3H,s); m/e 296 (M⁺), calculated for $C_{14}H_{16}O_7$: C, 56.8; H, 5.4. found: C, 57.0; H, 5.7%.

ii) In a similar manner to Example 116ii) but starting from the product of step i) above and with purification by flash chromatography on silica eluting with ethyl acetate/hexane (1:2 v/v) there was obtained dimethyl 2,2'-[5-(bromoacetyl)phenylene-1,3-dioxy]diacetate in 47% yield as a sticky solid: NMR (CDCl₃) δ7.14(2H,d), 6.73 (1H,t), 4.66(4H,s), 4.38(2H,s), 3.81(6H,s); m/e 375/377 (M+H)⁺, 1 Br pattern.

EXAMPLE 134

Disodium 2,2'-[5-[2-[4-(4-pyridyl)piperazin-1-yl] acetyl]phenylene-1,3-dioxy]diacetate A stirred solution of the product from Example 133 (100 mg) in methanol (5 ml) was treated with 1 molar sodium hydroxide solution (0.44 ml) and stirring continued for 18 hours. Evaporation of the solvent in vacuo and trituration of the residue with diethyl ether gave the title compound, 86 mg, as a yellow solid: m.p. 184°–206° C.; NMR (D₂O) δ8.36 (2H,d), 7.29(2H,d), 7.12(2H,d), 6.98(1H,t), 4.72(4H, s), 4.28(2H,s), 3.71(4H,bt), 2.98(4H,bt); m/e 4.74(M+H)⁺.

EXAMPLE 135

2-[4-[2-[4-(4-Pyridyl)piperazin-1-yl]acetyl]phenoxy] isobutyric acid, dihydrobromide A mixture of methyl 2-[4-[2-[4-(4-pyridyl)piperazin-1-yl] acetyl]phenoxy]-isobutyrate (50 mg) 48% w/v hydrobromic acid (0.74 ml), dioxane (1 ml) and water (3 ml) was heated at 95° C. for 4 hours. The solution was cooled, diluted with water and freeze-dried to give the title compound, 40 mg, as a pale yellow solid: m.p. 163°–167° C.; NMR (D₂O) δ8.40 (2H,d), 8.16(2H,d), 7.40(2H,d), 7.21(2H,d), 5.21(2H,s), 4.32(4H,b), 3.89(4H,bt), 1.86(6H,s), m/e 384 (M+H)⁺; calculated for $C_{21}H_{25}N_3 \cdot 2HBr \cdot 2H_2O$: C, 43.3; H, 5.3; N, 7.2. found: C, 43.6; H, 5.3; N, 7.3%.

The starting material was prepared as follows:

i) In a similar manner to Example 116ii) but starting from methyl 2-(4-acetylphenoxy)isobutyrate and purification by flash chromatography on silica, eluting with ethyl acetate/hexane (1:2 v/v), there was obtained methyl 2-(4-bromoacetylphenoxy)-isobutyrate in 45% yield as an orange oil: NMR (CDCl₃) δ7.91(2H,d), 6.85(2H,d), 4.48 (2H,s), 3.76(3H,s), 1.67(6H,s). m/e 315/317 (M+H)⁺ 2 Br pattern.

ii) The product from step (i) above (2.00 g) in acetonitrile (10 ml) was added dropwise over 15 minutes to a stirred solution of 1-(4-pyridyl)piperazine (1.04 g) and triethylamine (0.89 ml) in acetonitrile (15 ml) and the mixture stirred overnight. The precipitated solid was removed by filtration and the filtrate evaporated. Purification of the residue by flash chromatography on silica, eluting with 0 to 5% v/v methanol/dichloromethane, gave a yellow gum. Trituration of this gum with diethyl ether gave methyl 2-[4-[2-[4-(4-pyridyl)piperazin-1-yl]acetyl]phenoxy] isobutryate, 170 mg, as a white solid: m.p. 88°–90° C.; NMR (d₆DMSO)δ8.15(2H,d), 7.96(2H,d), 6.82(4H,m), 3.92(2H,s), 3.70(3H,s), 3.33(4H,t), 2.63(4H,t), 1.60(6H, s); m/e 398 (M+H)⁺; calculated for $C_{22}H_{27}N_3O_4 \cdot 0.25H_2O$: C, 65.8; H, 6.8; N, 10.5. found: C, 65.8 H, 7.1; N, 10.4%.

EXAMPLE 136

Ethyl-4-[2-[4-(4-pyridyl)piperazin-1-yl]acetyl] phenoxyacetate

Ethyl 4-bromoacetylphenoxyacetate (6.0 g) was added to a stirred, cooled (4° C.) solution of 1-(4-pyridyl)piperazine (6.5 g) in acetonitrile (225 ml). Stirring was continued for 1 hour at 4° C., then overnight at ambient temperature when the precipitated solid was removed by filtration. The filtrate was evaporated in vacuo and the solid residue triturated with water, filtered, then washed with water and dried. Recrystallization from a small volume of ethanol gave the title compound, 1.71 g, as a cream coloured solid: m.p. 113°–114° C.; NMR (d₆DMSO) δ8.15(2H,d), 7.98(2H,d), 7.02(2H,d), 6.80(2H,d), 4.89(2H,d), 4.17(2H,q), 3.84(2H,s), 3.32(4H,t), 2.62(4H,t) 1.22(3H,t); m/e 384 (M+H)⁺; calculated for $C_{21}H_{25}N_3O_4$: C, 65.8; H, 6.6; N, 11.0. found: C, 65.5; H, 6.6; N, 10.8%.

The starting material was prepared as follows:

i) In a similar manner to Example 118i), but starting from ethyl bromoacetate there was prepared ethyl 4-acetylphenoxyacetate as a crystalline solid in quantitative yield. The product was used without further purification.

ii) In a similar manner to Example 117ii), but starting from the product of step i) above there was prepared ethyl 4-bromoacetylphenoxyacetate in 47% yield as a solid: m.p. 41°–42° C.; NMR (d₆DMSO) δ7.90(2H,d), 7.05(2H, d), 4.90(2H,s), 4.72(2H,s), 4.18(2H,q), 1.33(3H,t).

EXAMPLE 137 iso-Propyl 4-[2-[4-(4-pyridyl)piperazin-1-yl]acetyl] phenoxyacetate iso-Propyl 4-bromoacetylphenoxyacetate (6.3 g) was added to a stirred, cooled (4° C.) solution of 1-(4-pyridyl)

piperazine (6.5 g) in acetonitrile (225 ml). Stirring was continued for 1 hour at 4° C., then overnight at ambient temperature when the precipitated solid was removed. The filtrate was evaporated in vacuo and the residue positioned between ethyl acetate and water. The organic phase was dried (MgSO$_4$) and evaporated. Purification by flash chromatography on silica, eluting firstly with 0 to 10% v/v methanol/dichloromethane and then toluene/ethyl acetate/ 0.880 ammonium hydroxide/ethanol (60:20:10:35 v/v/v/v), gave a cream solid. Recrystallisation from iso-propanol gave the title compound, 2.1 g; m.p. 121°–122° C.; NMR (d$_6$DMSO) δ8.14(2H,d), 7.98(2H,d), 7.02(2H,d), 6.80(2H, d), 4.99(1H,m), 4.85(2H,s), 3.84(2H,s), 3.33(4H,t), 2.62 (4H,t), 1.22(6H,d); m/e 398 (M+H)$^+$; calculated for C$_{22}$H$_{27}$N$_3$O$_4$: C, 66.5; H, 6.9; N, 10.6. found: C, 65.8; H, 6.8; N, 10.4%.

The starting material was prepared as follows:

i) In a similar manner to Example 118i), but starting from iso-propyl bromoacetate there was prepared iso-propyl 4-acetylphenoxyacetate as a crystalline solid in quantitative yield. The product was used without further purification.

ii) In a manner similar to Example 117ii), but starting from the product of step i) above and using iso-propyl acetate in place of ethyl acetate as solvent, there was prepared iso-propyl 4-bromoacetylphenoxyacetate as a crystalline solid in 69% yield: m.p. 64°–66° C.; NMR (d$_6$DMSO) δ7.98(2H,d), 7.06(2H,d), 4.99(1H,m), 4.88(2H,s), 4.83 (2H,s), 1.22(6H,d).

EXAMPLE 138 tert-Butyl 4-[2-[4-(4-pyridyl)piperazin-1-yl]acetyl]-phenoxyacetate

Prepared in a similar manner to Example 136, but starting from tert-butyl 4-bromoacetylphenoxyacetate. After evaporation of the acetonitrile solution the residue was purified by column chromatography on silica, eluting with 0 to 5% v/v methanol/dichloromethane, to give a yellow oil. Trituration with diethyl ether gave the title compound in 35% yield as a solid: m.p. 103°–104° C.; NMR (d$_6$DMSO) δ8.15(2H,d), 7.98(2H,d), 7.00(2H,d), 6.82(2H,d), 4.76(2H,s), 3.84(2H,s), 3.37(4H,t), 2.62(4H,t), 1.43(9H,s); m/e 412 (M+H)$^+$ calculated for C$_{23}$H$_{29}$N$_3$O$_4$: C, 67.1; H, 7.1; N, 10.2. found: C, 66.9; 7.3; N, 10.0%.

The starting material was prepared as follows:

i) In a similar manner to Example 118i), but starting from tert-butyl bromoacetate there was prepared tert-butyl 4-acetylphenoxyacetate as a crystalline solid in 90% yield: m.p. 59°–61° C.; NMR (d$_6$DMSO+d$_4$ acetic acid) δ7.94(2H,d), 6.98(2H,d), 4.21(2H,s), 2.52(3H,s), 1.44 (9H,s).

ii) A solution of the product from step i) above (3.3 g) and N-bromosuccinimide (2.35 g) in carbon tetrachloride was heated at reflux temperature for 80 hours. After cooling, the precipitate was removed by filtration and the filtrate concentrated in vacuo. Purification of the residual oil by flash chromatography on silica, eluting with 5% v/v ethyl acetate/toluene, gave tert-butyl 4-bromoacetylphenoxyacetate, 1.9 g, as a crystalline solid: m.p. softens at 110°–116° C.; NMR (d$_6$DMSO) δ7.97(2H,d), 7.04(2H,d), 4.84(2H,s), 4.80(2H,s), 1.43 (9H,s).

EXAMPLE 139

Neopentyl 4-[2-[4-(4-pyridyl)piperazin-1-yl]acetyl]phenoxyacetate

Prepared in a similar manner to Example 136, but starting from neopentyl 4-bromoacetylphenoxyacetate. After evaporation of the acetonitrile filtrate, the residue was purified by flash chormatography on silica, eluting with 0 to 5% v/v methanol dichloromethane, to give an oil. Trituration with diethyl ether/hexane gave the title compound in 23% yield as a solid: m.p. 88°–90° C.; NMR (d$_6$DMSO) δ8.14(2H,d), 7.98(2H,d), 7.04(2H,d), 6.81(2H,d), 4.97(2H,s), 3.83(4H,s), 3.32(4H,t), 2.61(4H,t), 0.86(9H,s); m/e 426 (M+H)$^+$; calculated for C$_{24}$H$_{31}$N$_3$O$_4$: C, 67.7; H, 7.3; N, 9.9. found: C, 68.1; H, 7.4; N, 9.9%.

The starting material was prepared as follows:

i) To a stirred suspension of 4-acetylphenoxyacetic acid (4.36 g) in dichloromethane (50 ml) was added oxalyl chloride (2.36 ml) and DMF (one drop). The mixtutre was stirred for one hour and then the solvent removed in vacuo to give a yellow oil (4.8 g). A solution of this oil in diethyl ether was added dropwise to a stirred solution of neopentyl alcohol (2.18 g) and triethylamine (3.4 ml) in diethyl ether (50 ml). After the addition, stirring was continued for a further 18 hours when the precipitated solid was removed by filtration. Evaporation of the filtrate and purification of the residue by flash chromatography on silica, eluting with dichloromethane, gave neopentyl 4-acetylphenoxyacetate, 5.1 g, as a pale yelow oil: NMR (CDCl$_3$) δ7.94(2H,d), 6.95(2H,d), 4.72(2H,s), 3.91(2H, s), 2.56(3H,s), 0.93(9H,s).

ii) To a stirred solution of the product step i) above (2.64 g) in chloroform (25 ml), was added slowly over 10 minutes, a solution of bromine (0.52 ml) in chloroform (10 ml). Stirring was continued for a further hour and the solvent removed in vacuo. Trituration of the residue with diethyl ether/hexane gave neopentyl 4-bromoacetylphenoxyacetate, 2.3 g, as a crystalline solid: m.p. 85°–87° C.

EXAMPLE 140

Dimethyl 4-[2-[4-(4-pyridyl)piperazin-1-yl]acetyl]phenoxymalonate

Prepared in a similar manner to Example 136, but starting from dimethyl 4-bromoacetylphenoxymalonate and after evaporation of the aceonitrile filtrate the residue was partitioned between water/ dichloromethane. The organic solution was dried (MgSO$_4$), concentrated and purification by flash chromatography, eluting with 0 to 5% v/v methanol/ dichloromethane, then trituration with diethyl ether gave the title compound in 31% yield as a pale yellow solid: m.p. 115°–116° C.; NMR (d$_6$DMSO) δ8.16(2H,d), 8.02(2H,d), 7.09(2H,d), 6.82(2H,d), 5.95(1H,s), 3.86(2H,s), 3.80(6H,s), 3.34(4H,t), 2.63(4H,t), m/e 428 (M+H)$^+$; calculated for C$_{22}$H$_{25}$N$_3$O$_6$: C, 61.8; H, 5.9; N, 9.8. found C, 61.3; H, 5.9; N, 9.2%.

The starting material was prepared as follows:

i) In a similar manner to Example 118i), but starting from dimethyl bromomalonate and purification by flash chromatography on silica, eluting with 50 to 75% v/v diethyl ether/hexane, there was prepared dimethyl 4-acetylphenoxymalonate in 53% yield as a white crystalline solid: m.p. 71°–72° C.; NMR (d$_6$DMSO) δ7.95 (2H,d), 7.09(2H,d), 5.95(1H,s), 3.78(6H,s), 2.53(3H,s); m/e 267 (M+H)$^+$; calculated for C$_{13}$H$_{14}$O$_6$: C, 58.6; H, 5.3. found: C, 58.9; H, 5.3%.

ii) In a similar manner to Example 117ii), but starting from the product of step i) above and using methyl acetate in place of ethyl acetate as solvent, there was prepared methyl 4-bromoacetylphenoxymalonate in 59% yield as a white crystalline solid: m.p. 114°–115° C.; NMR (d$_6$DMSO) δ7.99(2H,d), 7.12(2H,d), 5.99(1H,s), 4.86 (2H,s), 3.80(6H,s).

EXAMPLE 141

5-[4-[2-[4-(4-Pyridyl)piperazin-1-yl]acetyl] phenoxymethyl]tetrazole

A mixture of 5-(4-chloroacetylphenoxymethyl)tetrazole (166 mg) and 1-(4-pyridyl)piperazine (214 mg) in acetonitrile (10 ml) was stirred overnight. The precipitate was collected, washed with acetonitrile and dried. A solution of this material in a small volume of 50% v/v acetic acid/water was transfered to a 1 inch preparative reverse phase hplc column (DYNAMAX (Trade Mark) C18 83-221-C) and eluted with water/acetonitrile/ trifluoroacetic acid in a gradient from 98:2:0.1 v/v/v to 60:40:0.1 v/v/v. The pure fractions, on freeze-drying, gave the title compound, 8.1 mg, as a white powder: NMR ($D_2O$) $\delta$8.39 (2H,d), 8.18(2H,d), 7.40(4H,m), 5.84(2H,s), 5.20(2H,s), 4.31(4H,bt), 3.87(4H, bt); m/e 380 $(M+H)^+$ The starting material was prepared as follows:

ii) A mixture of phenoxyacetonitrile (26.6 g), sodium azide 13.0 g and ammonium chloride (10.6 g) in DMF (80 ml) was heated at reflux temperature for 18 hours. The solvent was removed in vacuo and the black solid triturated with diethyl ether, collected and dissolved in 4 molar sodium hydroxide solution. This solution was extracted with diethyl ether, then treated with charcoal and filtered. The filtrate, on acidification with concentrated hydrochloric acid, gave a white precipitate. Recrystallisation from toluene gave 5-(phenoxymethyl)tetrazole, 12.05 g, as white plates: m.p. 128°–131° C.; NMR ($d_6$DMSO)$\delta$7.31 (2H,m), 7.02(3H,m), 5.47(2H,s); m/e 177 $(M+H)^+$; calculated for $C_8H_8N_4O$: C, 54.5; H, 4.6; N, 31.8. found: C, 54.6; H, 4.6; N, 32.0%.

ii) Aluminum chloride (30.3 g) was added to a stirred mixture of the product of step i) above (10 g) and chloroacetyl chloride (19.3 g) in dry 1,2-dichloroethane and stirring continued overnight. The mixture was concentrated to about half volume on the steam bath, cooled and added to an ice/hydrochoric acid mixture. After stirring for 15 minutes the solid was collected and, on recrystallisation from methanol/water, gave 5-(4-chloroacetylphenoxymethyl)tetrazole, 7.5 g: m.p. 194°–196° C.; NMR ($d_6$DMSO) $\delta$7.99(2H,d), 7.20(2H,d), 5.61(2H,s), 5.11(2H,s); m/e 251 (M–H)–, 1 Cl pattern; calculated for $C_{10}H_9ClN_4O_2$: C, 47.5; H, 3.6; N, 22.2. found: C, 43.7; H, 3.7; N, 22.2%.

EXAMPLE 142

4-[2-[4-(4-Pyridyl)piperazin-1-yl]acetyl] phenoxyacetamide

A solution of the product of Example 1 (200 mg) in methanol (10 ml), prepared under argon, was cooled to 4° C. and saturated with dry ammonia gas, then sealed in a pressure bottle and kept for 2 days. The orange crystals which formed, after filtration and washing with a little methanol, gave the title compound, 140 mg: m.p. 247° to 248° C.; NMR ($d_6$DMSO)$\delta$8.16(2H,d), 7.99(2H,d), 7.55 (1H,bs), 7.37(1H,bs), 7.02(2H,d), 6.81(2H,d), 4.54(2H,s), 3.85(2H,s), 3.33(4H,t), 2.60(4H,t); m/e 355 $(M+H)^+$; calculated for $C_{19}H_{22}N_4O_3$: C, 64.4; H, 6.3; N, 15.8. found: C, 64.4; H, 6.4; N, 15.6%.

EXAMPLE 143

2-[4-[2-[4-(4-Pyridyl)piperazin-1-yl]acetyl]-phenoxy]-N-methylacetamide

A suspension of the product of Example 1 (100 mg) in a 33% w/v solution of methylamine in ethanol (3 ml) was stirred for 18 hours. The solid formed, after filtration and washing with a little ethyl acetate, gave the title compound, 65 mg: m.p. 169°–171° C.; NMR ($d_6$DMSO)$\delta$8.14(2H,d), 8.06(1H,bq), 8.00(2H,d), 7.05(2H,d), 6.80(2H,d), 4.56(2H, s), 3.82(2H,s), 3.30(4H,t), 2.66(3H,d), 2.61(4H,t); m/e 369 $(M+H)^+$; calculated for $C_{20}H_{24}N_4O_3$: C, 65.2; H, 6.6; N, 15.2. found: C, 65.0; H, 6.8; N, 15.1%.

EXAMPLE 144

2-[4-[2-[4-(4-Pyridyl)piperazin-1-yl]acetyl]-phenoxy]-N-(2-methoxymethyl)-acetamide A suspension of the product of Example 1, (100 mg) in 2-methoxyethylamine (1 ml) was stirred for 18 hours. Filtration of the solid and washing with ethyl acetate gave the title compound, 70 mg, as a white crystalline solid: m.p. 142°–145° C.; NMR ($d_6$DMSO+$d_4$ acetic acid) $\delta$8.20(2H,d), 8.00(2H,d), 7.14(2H,d), 7.06(2H,d), 4.62(2H,s), 3.72(4H,t), 3.38(4H,m), 3.26(3H,s), 2.78(4H,t); m/e 413 $(M+H)^+$; calculated for $C_{22}H_{28}N_4O_4$: C, 64.1; H, 6.8; N, 13.6. found: C, 63.9; H, 6.8; N, 13.3%.

EXAMPLE 145

2-[4-[2-[4-(4-Pyridyl)piperazin-1-yl]acetyl]-phenoxy]-N-(phenylmethyl)-acetamide A solution of 2-[4-(bromoacetyl)phenoxy]-N-(phenylmethyl)acetamide (1.40 g) (preparation described in EPO 052442) in acetonitrile (5 ml) was added to a stirred solution of 1-(4-pyridyl)piperazine (1.14 g) in acetonitrile (20 ml). After stirring overnight the liquors were decanted from the residual gum, then concentrated in vacuo. Purification by flash chromatography on silica, eluting with 2 to 5% v/v methanol/dichloromethane, gave a solid. Trituration of this solid with diethyl ether gave the title compound, 95 mg: m.p. 150°–151° C.; NMR ($d_6$DMSO) $\delta$8.67(1H,bt) 8.15(2H,d), 8.00(2H,d), 7.26(5H,m), 7.06(2H,d), 6.81(2H, d), 4.66(2H,s), 4.34(2H,d), 3.84(2H,s), 3.33(4H,t), 2.54(4H, t); m/e 445 $(M+H)^+$; calculated for $C_{26}H_{28}N_4O_3$. 0.25$H_2O$: C, 69.5; H, 6.4; 12.5. found: C, 69.6; H, 6.4; N, 12.3%.

EXAMPLE 146

Methyl N-[4-[2-[4-(4-pyridyl)piperazin-1-yl]acetyl] phenoxyacetyl]glycinate

A solution of methyl N-[4-(bromoacetyl)phenoxyacetyl] glycinate (0.85 g) in acetonitrile (10 ml) was added to a stirred solution of 1-(4-pyridyl)piperazine (0.81 g) in acetonitrile (30 ml). After stirring overnight the solvent was removed in vacuo and the residue partitioned between water/ethyl acetate. The organic phase was washed with water, then dried ($MgSO_4$) and evaporated. The residue was purified by flash chromatography on silica, eluting with 0 to 7.5% v/v methanol/dichloromethane. Evaporation of the fractions gave the title compound, 130 mg, as a foam: NMR ($d_6$DMSO) $\delta$8.58(1H,t) 8.16(2H,d), 8.01(2H,d), 7.08(2H,d), 6.83(2H,d), 5.75(1H,s), 4.68(2H,s), 3.92(2H,d), 3.84(2H,s), 3.65(3H,s), 3.34(4H,t+$H_2O$), 2.65(4H,t); m/e 427 $(M+H)^+$; calculated for $C_{22}H_{26}N_4O_5$. 0.5$CH_2Cl_2$: C, 57.6; H, 5.8; N, 11.9. found: C, 57.8; H, 5.7; N, 12.0%.

The starting material was prepared as follows:

i) To a stirred suspension of 4-(acetyl)phenoxyacetic acid (3.00 g) in dichloromethane (40 ml) was added oxalyl chloride (1.62 ml) and 1 drop of DMF. Stirring was continued for 1.5 hours and the clear solution on evaporation gave an oil (I). Triethylamine (4.30 ml) was added slowly to a stirred, cooled (4° C.) suspension of methyl glycinate hydrochloride (1.95 g) in dichloromethane (25 ml) under argon. After stirring for 10 minutes, a solution of (I) in dichloromethane (10 ml) was added and stirring continued for a further 2 hours. The precipitate was removed by filtration and the filtrate concentrated in vacuo. Purification of the residue by flash chromatography on silica, eluting with 2% v/v methanol/dichloromethane, gave a solid. Trituration with ether/hexane gave methyl N-[4-(acetyl)phenoxyacetyl] glycinate, 3.1 g, as white crystals: m.p. 120°–121° C.; NMR ($d_6$DMSO)$\delta$8.57(1H,t), 7.94(2H,d), 7.07(2H,d), 4.66(2H,s), 3.92(2H,s), 3.64(3H,s), 2.52(3H,s); m/e 266 (M+H)$^+$; calculated for $C_{13}H_{15}NO_5$: C, 58.9; H, 5.7; N, 5.3. found: C, 58.4; H, 5.5; N, 5.0%.

ii) The product of step i) (3.00 g) and N-bromosuccinimide (2.02 g) in carbon tetrachloride (50 ml) was heated at reflux temperature for 64 hours. The solvent was evaporated and the black residue dissolved in methanol/ethyl acetate, treated with charcoal, filtered and then evaporated. The resulting brown oil was purified by flash chromatography on silica, eluting with dichloromethane. Trituration with hexane gave methyl N-[4-(bromoacetyl)phenoxyacetyl]glycinate, 0.85 g, as a solid: mp softens 109°–111° C.; NMR ($d_6$DMSO) $\delta$8.60(1H,bt), 7.99(2H, d), 7.09(2H,d), 4.84(2H,s), 4.69(2H,s), 3.91(2H,d), 3.64 (3H,s).

EXAMPLE 147

Methyl 4-[2-[4-(4-pyridyl)piperazin-1-yl]ethyl] phenoxyacetate

A mixture of methyl 4-[1-(2-methanesulphonyloxyethyl)]-phenoxyacetate (2.0 g) and 1-(4-pyridyl)piperazine (2.26 g) in acetonitrile was heated at reflux temperature for 25 hours. The solvent was removed in vacuo and the residue purified by flash chromatography on silica, eluting with successively 2.5, 3, 3.5, and 4% v/v methanol/dichloromethane. Isolation of the desired fractions and trituration with diethyl ether gave the title compound, 600 mg; recrystallisation from methanol gave white crystals, m.p. 104°–105° C.; NMR ($d_6$DMSO)$\delta$8.15(2H,d), 7.15(2H,d), 6.86(2H,d), 6.82(2H,d), 4.74(2H,s), 3.69(3H,s), 3.30(4H,t, 2H, m. +$H_2$O), 2.71(2H,m), 2.54(4H,t), m/e 356 (M+H)$^+$, calculated for $C_{20}H_{25}N_3O_3$. 0.25$H_2$O: C, 66.7; H, 7.1; N, 11.7. found: C, 67.0; H, 7.2; N, 11.4%.

The starting material was prepared as follows:
i) A mixture of 4-hydroxyphenethyl alcohol (5.37 g), anhydrous potassium carbonate (5.37 g) and methyl bromoacetate (3.80 ml) in anhydrous acetone (50 ml) was stirred for 18 hours. The mixture, after fitration, was evaporated and the residue after purification by flash chromatography on silica, eluting with 2% v/v methanol/dichloromethane, gave methyl 4-[1-(2-hydroxyethyl)]phenoxyacetate, 5.05 g, as an oil: NMR (CDCl$_3$) $\delta$7.15(2H,d), 6.86(2H,d), 4.62(2H,s), 3.84(2H,m), 3.80(3H,s), 2.81(2H,t), 1.40(1H, bt); m/e 210 (M)$^+$; calculated for $C_{11}H_{14}O_4$: C, 62.8; H, 6.7. found: C, 62.8; H, 6.8%.

ii) Methanesulphonyl chloride (0.98 ml) was added dropwise, over 30 minutes, to a stirred, cooled (4° C.) solution of the product from step i) (2.22 g) and triethylamine (1.91 ml) in dichloromethane (35 ml) under argon. After 2 hours, the solvent was evaporated and the residue partitioned between ethyl acetate (75 ml) and water (20 ml). The organic phase was separated, washed with saturated sodium chloride solution (3×15 ml), dried and evaporated. The residue on purification by flash chromatography on silica, eluting with 45% v/v ethyl acetate/hexane, gave methyl 4-[1-(2-methanesulphonyloxyethyl) ]phenoxyacetate, 2.85 g, as an oil: NMR (CDCl$_3$)$\delta$7.16 (2H,d), 6.87(2H,d), 4.62(2H,s), 4.38(2H,t), 3.81(3H,s), 3.00(2H,t), 2.85(3H,s); m/e 288 (M$^+$); calculated for $C_{12}H_{16}O_6S$: C, 50.0; H, 5.6; S, 11.1 found: C, 50.1; H, 5.5; S, 11.0%.

EXAMPLE 148

4-[2-[4-(4-Pyridyl)piperazin-1-yl]ethyl] phenoxyacetate acid dihydrochloride

In a similar manner to Example 123, but starting from the product of Example 147, there was obtained the title compound in 95% yield: m.p. 270°–273° C.; NMR ($d_6$DMSO +$d_4$ acetic acid) $\delta$8.34(2H,d), 7.30(2H,d), 7.22(2H,d), 6.91 (2H,d), 4.67(2H,s), 4.06(4H,b), 3.46(4H,b), 3.35(2H,m), 3.05(2H,m); m/e 342 (M+H)$^+$; calculated for $C_{19}H_{22}N_3O_3$.2HCl: C, 55.0; H, 6.5; N, 10.1. found: C, 54.8; H, 6.2; N, 9.8%.

EXAMPLE 149

Tertiary butyl 4-[2-[4-(4-pyridyl)piperazin-1-yl] carbonylmethyl]-phenoxyacetate In a similar manner to Example 18iv) but starting from tertiary butyl 4-(carboxymethyl)phenoxyacetate, there was obtained after flash chromatography on silica, eluting with 0 to 5% v/v methanol/dichloromethane, a gum. Further purification by flash chromatography on neutral alumina, eluting with 1% v/v methanol/dichloromethane followed by trituration with diethyl ether gave the title compound in 17% yield as a white solid: m.p. 110°–112° C.; NMR ($d_6$DMSO) $\delta$8.22(2H,d), 7.15(2H,d), 7.06(2H,d), 6.83(2H,d), 4.60(2H, s), 3.70(2H,s), 3.62(4H,bt), 3.38(4H, bt +$H_2$O) 1.42(9H,s), m/e 412 (M+H)$^+$; calculated for $C_{23}H_{29}N_3O_4$.0.25$H_2$O: C, 66.4; H, 7.1; N, 10.1. found: C, 66.4; H, 7.2; N, 10.1%.

The starting material was prepared as follows:
ii) Sodium hydride (50% w/w dispersion in mineral oil, 3.7 g) was treated under argon with repeated washes of hexane. The oil-free residue was suspended in dry DMF (100 ml) and 4-hydroxyphenylacetic acid (13.0 g) was added portionwise to the stirred cooled (4° C.) mixture. After 30 minutes, benzyl bormide (9.2 ml) was added dropwise and, after a further 1 hour at 4° C., stirring was continued overnight at ambient temperature. The solvent was evaporated in vacuo and the residue partitioned between ethyl acetate and water. The aqueous phase was re-extracted with further ethyl acetate and the combined organic extracts washed with water and brine, then dried (MgSO$_4$) and evaporated. The crystaline residue gave benzyl 4-hydroxyphenylacetate, 17.8 g, as off-white crystals: m.p. 70°–72° C. NMR (CDCl$_3$) $\delta$7.32(5H,m), 7.14 (2H,d), 6.76(2H,d), 5.12(2H,s), 3.59(2H,s); m/e 242 (M·)$^+$.

ii) Sodium hydride (50% w/w dispersion in mineral oil, 2.1 g) was treated under argon with repeated washes of hexane. The oil-free residue was suspended in dry DMF (130 ml) and the product from step i) (10 g) added in three portions to the cooled (4° C.) stirred mixture. Stirring was continued for a further 15 minutes when tertiary butyl bromoacetate (7.0 ml) was added dropwise over 15 minutes. After 1 hour at 40° C., the mixture was stirred for 6 hours at ambient temperature. The solvent was evaporated in vacuo and the residue partitioned between ethyl acetate and water. The aqueous phase was re-extracted with further ethyl acetate and the combined organic phases washed with water and brine, then dried (MgSO$_4$) and evaporated. The residue, after purification by flash chromatogrpahy on silica eluting with dichloromethane, gave tertiary butyl 4-(benzyloxycarbonylmethyl) phenoxyacetate, 7.5 g, as a colourless oil: NMR (CDCl$_3$) 7.31(5H,m), 7.20 (2H,m), 5.12(2H,s), 4.49(2H,s) 3.60 (2H,2), 1.48(9H,s); m/e 356 (M·)$^+$.

iii) In a similar manner to Example 18iii) but starting from the product of step ii) above was prepared tertiary butyl 4-(carboxymethyl)phenoxyacetate in 96% yield as a white crystalline solid: m.p. 78°–80° C. NMR (d$_6$DMSO) δ7.15(2H,d), 6.82(2H,d), 4.60(2H,s), 3.48(2H,s), 1.43 (9H,s); m/e 266 (M·)$^+$; calculated for C$_{14}$H$_{18}$O$_5$.0.75H$_2$O: C, 60.1; H, 7.0. found: C, 59.9; H, 7.2%.

EXAMPLE 150

4-[2-[4-(4-Pyridyl)piperazin-1-yl]carbonylmethyl] phenoxyacetic acid, dihydrochloride A solution of the product from Example 149 (50 mg) in a mixture of dioxane (1 ml), water (2 ml) and 1 molar hydrochloric acid solution (0.61 ml) was heated overnight at 90° C. The resulting solution, on dilution with water and freeze-drying, gave the title compound, 30 mg, as a yellow foam: NMR (d$_6$DMSO+d$^4$ acetic acid) δ 8.31 (2H,d), 7.24 (2H,d), 7.18(2H,m), 6.87(2H,m), 4.64(2H,s), 3.96(4H,t), 3.72(2H,s), 3.32(4H,t); m/e 356 (M+H)$^+$; calculated for C$_{19}$H$_{21}$N$_3$O$_4$.2HCl.2.5H$_2$O; C, 48.2; H, 5.9; N, 8.9. found C, 48.5; H, 6.0; N, 8.8%.

EXAMPLE 151

Methyl 4-[2-[4-(2-methylpyrid-4-yl)piperazin-1-yl] acetyl]phenoxyacetate

Methyl 4-bromoacetylphenoxyacetate (1.72 g) was added to a stirred mixture of 1-[4-(2-methylpyridyl)]piperazine dihydrochloride (1.5 g) and triethylamine (2.5 ml) in acetonitrite (25 ml). Stirring was continued overnight when the solvent was removed in vacuo. Purification by flash chromatography, first on silica eluting with 10% v/v methanol/dichloromethane and then on neutral alumina eluting with 1% methanol/dichloromethane, gave the title compound, 418 mg, as a white solide: m.p. 155°–157° C; NMR (d$_6$DMSO)δ8.00(3H,m), 7.04(2H,d), 6.70(1H,d), 6.64 (1H, dd), 4.92(2H,s), 3.83(2H,s), 3.71(3H,s), 3.30(4H b+H$_2$O), 2.61)4H,t), 2.32(3H,s); m/e 384 (M+H)$^+$; calculated for C$_{21}$H$_{25}$N$_3$O$_4$: C, 65.8; H, 6.6; N, 11.0. found: C, 65.4; H, 6.8; N, 10.9%.

The starting material was prepared as follows:
i) A mixture of 4-chloro-2-picoline (5 g) and 1-benzylpiperazine (13.6 ml) in xyelen (50 ml was heated at reflux temerature for 18 hours. The solution was cooled and the solid precipitate removed by filtration and the filtrate concentrated in vacuo. Purification by flash chromatography on silica, eluting with 20% v/v methanol/ dichloromethane gave 4-[4-(2-picoyly)]-1-benzylpiperazine, 9.54 g, as a light fawn crystalline solid: m.p. 94°–95° C.; NMR (CDCl$_3$)δ8.15(1H,d), 7.30(5H,m), 6.51(2H,m), 3.57(2H,s), 3.44(4H,t), 2.57(4H,t), 2.46(3H, s); m/e 268 (M+H)$^+$; calculated for C$_{17}$H$_{21}$N$_3$: C, 76.4; H, 7.9; N, 15.7. found: C, 75.7; H, 8.1; N, 15.7%.

ii) 10% w/w Palladium on charcoal (1.5 g) was added to a stirred solution of the product of step i) (9.00 g) and 2 molar hydrochloric acid (34 ml) in methanol 180 ml) and the mixture was hydrogenated at room temperature and pressure until the theoretical amount of hydrogen had been taken up. Charcoal was added, the mixture stirred for 5 minutes then filtered through diatomaceous earth and the filtrate on evaporation to dryness gave 1-[4-(2-methylpyridyl)]piperazine dihydrochloride, 10.6 g, as a fawn solid: m.p 64°–68° C. NMR (d$_6$DMSO)δ8.20(1H, d), 7.18(1H,d), 7.12(1H,dd), 3.92(4H,t), 3.19(4H,t), 2.51 (3H,s+DMSO); m/e 178 (M+H)$^+$; calculated for C$_{10}$H$_{15}$N$_3$.2HCl.0.75H$_2$O: C, 45.5; H, 7.0; N, 15.9. found: C, 45.3; H, 7.0; N, 15.8%.

EXAMPLES 152

4-[2-[4-(2-Methylpyrid-4-yl)piperazin-1-yl]acetyl] phenoxyacetic acid, dihydrobromide A mixture of the product of Example 151 (160 mg), 48% w/v hydrobromic acid (0.25 ml) and dioxane (1 ml) in water (3 ml) were heated at 90° C. for 30 minutes. The solution was cooled, further water added and the mixture freeze-dried. Trituration of the residue with absolute ethanol gave the title compound, 50 mg, as a fawn solid: m.p. 146°–148° C.; NMR (d$_6$DMSO+d$_4$ acetic acid)δ8.17(1H,d), 7.95(2H, d), 7.09(4H,m), 4.94(2H,s), 4.78(2H,s), 3.99(4H,b), 3.07 (1H,q), 2.46(3H,s), 1.17(1.5H,t); m/e 370 (M+H)$^+$; calculated for C$_{20}$H$_{23}$N$_3$O$_4$.2HBr.H$_2$O.0.5C$_2$H$_5$H: C, 44.1; H, 5.3; N, 7.3, found: C, 44.0; H, 5.4; N, 7.2%

EXAMPLE 153

Methyl [2-[4-(2,6-dimethylpyrid-4-yl)piperazin-1-yl]acetyl]phenoxyacetate, hydrobromide Prepared in a similar manner to Example 151, but starting from 1-[4-[2,6-dimethylpyridyl)]piperazine and using only one equivalent of triethylamine. Purification by flash chromatography on silica eluting with 0 to 5% v/v methanol/ dichloromethane, followed by trituration with diethyl ether, gave the title compound in 64% yield as a white solid: m.p. 212°–215° C.; NMR (d$_6$DMSO) δ13.0(1H,b), 7.96(2H,d), 7.04(2H,d), 6.96(2H,s), 3.90(2H,s), 3.71(3H,s), 3.65(4H,bt), 2.65(4H,bt), 2.42(6H,s); m/e 398 M+H)$^+$; calculated for C$_{22}$H$_{27}$N$_3$O$_4$.1HBr: C, 55.2; H, 5.9; N, 8.8. found: C, 55.3; H, 5.9; N, 8.6%.

The starting material was prepared as follows:
i) In a similar manner to Example 151i), but starting from 4-chloro-2,6-lutidine there was obtained 4-[4-(2,6-dimethylpyridyl)]-1-benzylpiperazine in 59% yield as a yellow oil: NMR (CDCl$_3$)δ7.31(5H,m), 6.37(2H,s), 3.55 (2H,s), 3.32(4H,t), 2.55(4H,t), 2.55(6H,s); m/e 282 (M+H)$^+$.

ii) In a similar manner to Example 151ii) but starting from the product of step i) above there was prepared the solid dihydrochloride. This was dissolved in water, two equivalents of 2 molar potassium hydroxide added and the solvent evaporated. Purification of the residue by flash chromatography on alumina, eluting with 2% v/v methanol/dichloromethane gave 1-[(4-[2,6-dimethylpyridyl)]piperazine in 51% yield as a white crystalline solid: m.p. 123°–124° C.; NMR (CDCl$_3$) δ6.40 (2H,s), 3.27(4H,t) 2.98(4H,t), 2.43(6H,s); m/e 198 (M+H$^+$; calculated for C$_{11}$H$_{17}$N$_3$; C, 69.1; H, 9.0; N, 22.0 found: C, 69.2; H, 9.2; N, 21.6%.

EXAMPLE 154

4-[2-[4-(2,6-Dimethylpyrid-4-yl)piperazin-1-yl] actyl]phenoxyacetic acid, dihydrobromide Following the method of Example 152, but starting from the product of Example 153, the title compound was prepared in 78% yield as a fawn solid: m.p. 210°–212° C.; NMR (d₆DMSO+d₆acetic acid) δ7.99(2H,d), 7.16(2H,d), 7.08(2H,s), 5.09(2H,s), 4.87(2H,s), 4.07(4H,b), 3.52(4H,b), 2.49(6H,s); m/e 384 (M+H)⁺; calculated for C₂₁H₂₅N₃O₄.2HBr.2.5H₂O: C, 42.7; H, 5.4; N, 7.1 found: C, 42.7; H, 5.1; N, 6.9%.

EXAMPLE 155

Methyl 4-[1-(4-pyridyl)piperidin-4-yl] oxyphenoxyacetate

Diethylazodicarboxylate (0.47 ml) was added dropwise over 30 minutes to a stirred mixture of 1-(4-pyridyl)-4-piperidinol (534 mg), methyl 4-hydroxyphenoxyacetate (546 mg), triphenylphosphine (787 mg) and dry THF (30 ml) in an atmosphere of argon and cooled to 4° C. After 1 hour at 4° C., the mixture was allowed to reach ambient temperature and stirred for 48 hours. The solvent was removed by evaporation and the residue purified by flash chromatography on silica eluting with 5% v/v methanol/dichloromethane. Recrystallisation from ethyl acetate/hexane gave the title compound, 532 mg, as a white solid: m.p. 74°–76° C.; NMR (d₆DMSO) δ8.15(2H,bd), 6.89(6H, m), 4.71(2H,s), 4.50(1H,m), 3.70(2H,m), 3.69(3H,s), 3.23 (2H,m), 1.96(2H,m), 1.62(2H,m); m/e 343 (M+H)⁺; calculated for C₁₉H₂₂N₂O₄: C, 66.7; H, 6.5; N, 8.2. found: C, 66.2; H, 6.7; N, 8.2%.

EXAMPLE 156

4-[1-(4-Pyridyl)piperidin-4-yl]oxyphenoxyacetic acid

Following the method of Example 2, but starting from the period product of Example 155, the title compound was prepared in 85% yield: m.p. 288°–291° C.; NMR (NaOD+d₆DMSO)δ7.97(2H,d), 6.77(4H,m), 6.69(2H,d), 4.35(1H, m), 4.19(2H,s), 3.53(2H,m), 3.08(2H,m), 1.82(2H,m), 1.49 (2H,m); m/e 329 (M+H)⁺; calculated for C₁₈H₂₀N₂O₄: C, 65.8; H, 6.1N, 8.5. found: C, 65.7; H, 6.3; N, 8.4%.

EXAMPLE 157

Methyl 4-[1-(4-pyridyl)piperidin-4-yl] methoxyphenoxyacetate

Following the method of Example 155, but starting from 4-(4-hydroxymethylpiperidin-1-yl)pyridine, the title compound was prepared in 18% yield: m.p. 127°–129° C.; NMR (d₆DMSO) δ8.12(2H,d), 6.84(4H,s), 6.81(2H,d), 4.70(2H, s), 3.96(2H,bd), 3.79(2H,d), 3.70(3H,s), 2.88(2H,dt), 2.01 (1H,m), 1.82(2H,bd), 1.30(2H,m), m/e 357 (M+H)⁺; calculated for C₂₀H₂₄N₂O₅.0.5H₂O: C, 65.7; H, 6.9; N, 7.7. found: C, 66.1; H, 6.9; N, 7.8%.

EXAMPLE 158

4-[1-(4-Pyridyl)piperidin-4-yl] methoxyphenoxyacetic acid.

Following the method of Example 2 but starting from the product of Example 157, the title compound was prepared in 86% yield: m.p. 278°–281° C.; NMR (d₆DMSO+TFA)δ8.09 (2H,t), 7.08(2H,d), 6.78(4H,s), 4.50(2H,s), 4.20(2H,bd), 3.74(2H,d), 3.17(2H,bt), 2.12(1H,m), 1.91(2H,m) 1.32(2H, m), m/e 343 (M+H)⁺; calculated for C₁₉H₂₂N₂O₄.0.25H₂O: C, 65.8; H, 6.5; N, 8.1. found: C, 66.0; H, 6.6; N, 8.0%.

EXAMPLE 159

Methyl 4-[2-[1-(4-pyridyl)piperidin-4-yl]ethoxy] phenoxyacetate

Following the method of Example 155, but starting from 4-(4-hydroxyethylpiperidin-1-yl)pyridine, the title compound was prepared in 65% yield: m.p. 86°–88° C.; NMR (d₆DMSO) δ8.11(2H,d), 6.85(4H,s), 6.79(2H,d), 4.70(2H, s), 3.96(2H,t), 3.92(2H,bd), 3.69(3H,s), 2.81(2H,dt), 1.78 (2H,bd), 1.73(1H,m), 1.65(2H,q), 1.20(2H,m); m/e 371 M+H)⁺; calculated for C₂₁H₂₆N₂O₄: C, 68.1; H, 7.1; N, 7.6. found: C, 67.5; H, 7.3; N, 7.5%.

EXAMPLE 160

4-[2-[1-(4-Pyridyl)piperidin-4-yl]ethoxy] phenoxyacetic acid

Following the method of Example 2, but starting from the product of Example 159, the title compound was prepared in 74% yield; m.p. 247°–249° C.; NMR (d₆DMSO+TFA)δ8.19 (2H,t), 7.19(2H,d), 6.38(4H,s), 4.60(2H,s), 4.25(2H,bd), 4.01(2H,t), 3.20(2H,dt), 1.93(3H,m), 1.70(2H,q), 1.28(2H, m); m/e 357 (M+H)⁺; calculated for C₂₀H₂₄N₂O₄: C, 67.4; H, 6.8; N, 7.9 found: C, 67.0; H, 6.8; N, 7.7%.

EXAMPLE 161

Methyl 3-[4-[1-(4-pyridyl)piperidin-4-yl] methoxyphenyl]propionate

Following the method of Example 155, but starting from 4-(4-hydroxymethylpiperidin-1-yl)pyridine and methyl 3-(4-hydroxyphenyl)propionate, the title compound was prepared in 14% yield: m.p. 96.5°–98.5° C.; NMR (d₆DMSO) δ8.13(2H,d), 7.11(2H,d), 6.83(4H,m), 3.97(2H, dm), 3.81(2H,d), 3.56(3H,s), 2.87(2H,dt), 2.77(2H,t), 2.57 (2H,t), 2.01(1H,m), 1.84(2H,m), 1.30(2H,m); m/e 355 (M+H)⁺; calculated for C₂₁H₂₆N₂O₃.0.75H₂O: C, 68.5; H, 7.2; N, 7.8. found: C, 68.5; H, 7.5; N, 7.6%.

EXAMPLE 162

3-[4-[1-(4-Pyridyl)piperidin-4-yl]methoxyphenyl] propionic acid

Following the method of Example 2, but starting from the product of Example 161, the title compound was prepared in 80% yield: m.p. 303°–307° c.; NMR (d₆DMSO+TFA)δ8.20 (2H,d), 7.25(6H,m), 4.31(2H,m), 3.88(2H,d), 3.27(2H,bt), 2.82(2H,t), 2.52(2H,t), 2.25(1H,m), 2.00(2H,bd), 1.40(2H, m); m/e 341 (M+H)⁺; calculated for C₂₀H₂₄N₂O₃.0.25H₂O: C, 69.6; H, 7.2; N, 8.1. found: C, 69.6; H, 7.2; N, 8.0%.

EXAMPLE 163

Methyl 4-[[1-(4-pyridyl)piperidin-4-yl] carboxamido]phenoxyacetate, hydrochloride Thionyl chloride (5 ml) was added dropwise over ten minutes to a stirred suspension of 1-(4-pyridyl)-4-piperidinecarboxylic acid (2.06 g) in dry dichloromethane (20 ml) at 4° C. After 1 hour at 4° C., the mixture was allowed to reach ambient temperature and stirred for 16 hours. The solvent was removed by evaporation and the residue dried under high vacuum to give a solid foam (2.84 g).

Triethylamine (0.70 ml) was added to a stirred suspension of methyl 4-aminophenoxyacetate hydrochloride (544 mg) in dry dichloromethane (10 ml). After stirring for 1 hour, the mixture was cooled to 4° C., and the foam (0.71 g) added. After 1 hour at 4° C. the mixture was allowed to reach ambient temperature and stirred for 16 hours. The precipitated solid was collected, washed with dichloromethane and, on recrystallisation from water, gave the title compound, 744 mg; m.p. 233°–234.5° C.; NMR (d₆DMSO)δ13.56(1H,b), 9.98(1H,s), 8.21(2H,d), 7.51(2H,d), 7.20(2H,d), 6.85(2H,d), 4.72(2H,s), 4.25(2H,bd), 3.69(3H,s), 3.72(2H+$H_2O$), 2.78 (1H,m), 1.97(2H,m), 1.67(2H,m); m/e 370 (M+H)$^+$; calculated for $C_{20}H_{23}N_3O_4$.HCl: C, 59.2; H, 6.0; N, 10.4. found: C, 58.8; H, 6.1; N, 10.3%

EXAMPLE 164

4-[4-[1-4-Pyridyl)piperidin-4-yl]carboxamido] phenoxyacetic acid

Following the method of Example 2, but starting from the product of Example 163, the title compound was prepared in 69% yield: m.p. 285°–287° C.; NMR (NaOD)δ8.30(2H,d), 7.44(2H,d), 7.07(2H,d), 7.04(2H,d), 4.60(2H,s), 4.14(2H, bd), 3.11(2H,dt), 2.81(1H,m), 2.11(2H,bd), 1.88(2H,dq); m/e 356 (M+H)$^+$; calculated for $C_{19}H_{21}N_3O_4.H_2O$: C, 61.1; H, 6.2; N, 11.3. found: C, 60.9; H, 6.2; N, 11.0%.

EXAMPLE 165

Methyl 4-[2-[(1-(4-pyridyl)piperidin-4-yl] acetamido]phenoxyacetate

To a stirred solution of 1-(4-pyridylpiperdin-4-yl)acetic acid hydrochloride (400 mg) in dry DMF (5 ml) was added N,N'-diisopropylethylamine (1.1 ml), HOBT (240 mg), 2-(1H-benzotriazole-1-yl)-1,1,3,3-tetramethyuronium hexafluorophosphate (600 mg). After 15 minutes methyl 4-aminophenoxyacetate (280 mg) was added and stirring contiuned overnight. The reaction mixture was added to ethyl acetate (100 ml) and this mixture washd with water, 10% w/v sodium hydrogen sulphate solution and brine, then dried ($MgSO_4$) and evaporated. Purification of the resulting gum by flash chromatography, first on silica eluting with 0 to 5% v/v methanol/dichloromethane and then on neutral alumina eluting with 2% v/v methanol/dichloromethane gave, on trituration with diethyl ether the title compound, 55 mg, as an off-white solid: m.p. 155°–157° C.; NMR ($d_6$DMSO) δ9.74(1H,s), 8.11(2H,d), 7.48(2H,d), 6.86(2H,d), 6.79(2H,d), 4.73(2H,s), 3.91(2H,bd), 3.70(3H,s), 2.84 (2H,dt), 2.21(2H,d), 2.03(1H,m), 1.72(2H,bd), 1.22 (2H,dq); m/e 384(M+H)$^+$; calculated for $C_{21}H_{25}N_3O_4$. 0.5 $H_2O$: C, 64.5; H, 6.6; N, 10.7. found: C, 64.7; H, 6.8; N, 10.8%.

The starting material was prepared as follows:

i) A mixture of ethyl 4-carboxymethylpiperidine (from Example 29ii) (3.25 g), triethylamine (5.28 ml), 4-chloropyridine hydrochloride (2.85 g) and xylene (100 ml) was heated at reflux temperature overnight. The mixture was cooled, the precipitate removed by filtration and the filtrate evaporated. A solution of the residue in dichloromethane was washed with water, then dried ($MgSO_4$) and evaporated. Purification by flash chromatography on silica, eluting with 10% v/v methanol/dichloromethane, gave ethyl 1-(4-pyridylpiperdin-4-yl) acetate, 2.15 g, as an oil: NMR ($CDCl_3$)δ8.23(2H,d), 6.64(2H,d), 4.26(2H,q), 3.88(2H,dm), 2.89(2H,dt), 2.27 (2H,d), 2.05(1H,m), 1.82(2H,dm), 1.36(2H,dq), 1.27(3H, t); m/e 249(M+H)$^+$.

ii) A mixture of the product from step i) (2.20 g), 1 molar hydrochloric acid (35.5 ml) and dixoane (100 ml) was heated at 95° C. for 3 hours. The resulting solution, on freeze-drying, gave 1-(4-pyridylpiperidin-4-yl)acetic acid hydrochloride, 2.3 g, as a light-brown powder: m.p. 105°–108° C.; NMR ($d_6$DMSO) δ13.57(1H,b), 8.18(2H,d), 7.17(2H,d), 4.21(2H,bd), 3.17(2H,dt), 2.21(2H,d), 2.09(1H,m), 1.83(2H,dm); 1.22(2H,dq); m/e 221(M+H)$^+$; calculated for $C_{12}H_{16}N_2O_2$.HCl. 1.25 $H_2O$: C, 51.6; H, 7.0; N, 10.0; Cl, 12.7. found C, 51.7; H, 7.0; N,9.8; Cl, 12.2%.

EXAMPLE 166

4-[2-[1-(4-Pyridyl)piperidin-4-yl]acetamido] phenoxyacetic acid dihydrochloride

A mixture of the product from Example 165 (30 mg), 1 molar hydrochlori acid (0.40 ml), water (2 ml) and dioxane (1 ml) was heated at 95° C. for 1 hour. The resulting solution, on freeze-drying and trituration of the residue with ether, gave the title compound, 25 mg, as a light brown solid: m.p. 158°–162° C.; NMR ($d^6$DMSO+$d^4$ acetic acid) 8.17 (2H,d), 7.49(2H,d), 7.20(2H,d), 6.85(2H,d), 4.61(2H,s), 4.23(2H,bd), 3.21(2H,bt), 2.21(3H,m); 1.86(2H,bd+acetic acid), 1.28(2H,bq); m/e 370(M+H)$^+$; calculated for $C_{20}H_{23}N_3O_4$. 2HCl. 1.25 $H_2O$: C, 51.7; H, 5.9; N, 6.0. found: C, 51.6; H, 6.0; N, 9.2%.

EXAMPLE 167

4-[[1-(4-Pyridyl)piperidin-4-yl]aminocarbonyl] phenoxyacetic acid dihydrochloride Following the method of Example 166, but starting from tertiary butyl 4-[[1-(4-pyridyl)piperidin-4-yl] aminocarbonyl]phenoxyacetate (50 mg), but with the removal of the insoluble precipitate before freeze-drying, the title compound was prepared in 50% yield: m.p. 278°–280° C.; NMR ($d_6$DMSO+$d_4$ acetic acid) δ8.19(2H,d), 7.82(2H,d), 7.20(2H,d), 6.98(2H,d), 4.74(2H,s), 4.23(3H,m), 3.38(2H,bt), 2.04(2H,m), 1.64(2H,m); m/e 356 (M+H)$^+$; calculated for $C_{19}H_{21}N_3O_4$.2HCl. 1.25 $H_2O$: C, 50.6; H, 5.7; N, 9.3. found: C, 50.6; H, 5.7; N, 9.2%.

The starting material were prepared as follows:

i) Acetyl chloride (3.95 ml) was added dropwise to a stirred solution of 4-aminol-benzylpiperidine (10.0 g) and triethylamine (7.7 ml) in dry dichloromethane (100 ml) at 4° C. The mixture was allowed to reach ambient temperature and stirred for 16 hours. Water was then added, the organic phase separated and dried ($MgSO_4$), and removal of the solvent by evaporation gave 4-acetylamino-1-benzylpiperidine, 10.23 g, as a light brown solid which was used without further purification: NMR ($CDCl_3$) δ7.29)5H,m), 5.29(1H,b), 3.79(1H,m), 3.49(2H,s), 2.80 (2H,dm), 2.12(2H,dt), 1.95(3H,s), 1.91(2H,dm), 1.46(2H, dq); m/e 233 (m+H)$^+$.

ii) 10% w/w Palladium on charcoal (1.5 g) was added to a solution of the product from step i) (10.0 g), 1 molar hydrochloric acid (21.5 ml) and methanol (150 ml) and the mixture hydrogenated at room temperature and pressure until the theoretical amount of hydrogen had been taken up. Charcoal was added, the mixture stirred for 1 hour then filtered through diatomaceous earth and the filtrate evaporated to dryness giving 4-acetylaminopiperidine hydrochloride, 8.64 g, as a sticky foam; NMR ($CDCl_3$+$d_6$DMSO) δ9.72(1H,b), 9.02(1H,b), 7.40(1H,bd), 3.87(1H,m), 3.30(2H,m), 2.81(2H,m), 1.86 (4H,m), 1.80(3H,s); m/e 143 (M+H)$^+$.

iii) A mixture of the product from step ii) (1.79 g), 4-chloropyridine hydrochloride (1.50 g), sodium hydrogen carbonate (2.86 g) in 3-methyl 1-butanol (25 ml) was heated at reflux temperature for 16 hours. The cooled mixture was filtered and the filtrate concentrated in vacuo. Purification of the residue by flash chromatography on silica, eluting with methanol/dichloromethane (1:2 v/v) gave 4-acetylamino-1-(4-pyridyl)piperidine as a foam, 0.69 g: NMR ($d_6$DMSO) δ8.10(2H,d), 7.80(1H,bd), 6.80 (2H,dd), 3.82(3H,m), 2.93(2H,dt), 1.78(3H,s), 1.77(2H,m), 1.33(2H;dq); m/e 220 (M+H)$^+$.

iv) The product from step iii) (0.52 g) in 1 molar hydrochloriac acid (11.9 ml) was heated at 95° C. for 5 hours. The solvent was evaporated and the residue, on drying over potassium hydroxide in vacuo gave 4-amino-1-(4-pyridyl)piperidine trihydrochloride hydrate, 0.70 g as a light brown solid: m.p. >300° C; NMR (d$_6$DMSO) δ8.28 (4H,m), 7.22(2H,d) 4.27(2H,bd), 3.5 to 3.15(3H+H$_2$O), 2.09(2H,m), 1.59(2H,dq); m/e 178(M+H)$^+$; calculated for C$_{10}$H$_{15}$N$_3$.3HCl.0.75 H$_2$O: C, 40.0; H, 6.5; N, 14.0. found: C, 40.4; H, 6.3; N, 13.5%.

v) A mixture of benzyl 4-hydroxybenzoate (4 g), t-butyl bromoacetate (3.7), powdered anhydrous potassium carbonate (2.4 g) and acetone (100 ml) was heated at reflux for 3 days. The reaction mixture was cooled and then filtered and the filtrate evaporated to dryness to give a viscous oil (6.37 g). A portion of this oil (3.4 g) was dissolved in methanol (30 ml) and ammonium formate (4 g) was added. The resultant solution was covered with a blanket of argon before a slurry of 10% Pd on C (100 mg) in methanol (5 ml), also under argon, was added. The reaction mixture was stirred at room temperature for 18 hours then the catalyst was filtered off through a pad of kieselguhr and washed with ethanol and water. The combined filtrate and washings were evaporated to dryness and the residue was partitioned between dichloromethane and aqueous sodium bicarbonate. The aqueous layer was separated, washed with dichloromethane and then carefully acidified with dilute aqueous citric acid solution. A solid precipitated which was collected, washed with water and air-dried to give 4-t-butoxycarbonylmethoxybenzoic acid (1.45 g), as a white crystalline solid: m.p. 119°–121° C.

vi) Following the method of Example 165, but starting from the product of step v) and the product from step iv) and purification by flash chromatography on silica eluting with 0–5% v/v methanol/dichloromethane there was obtained tertiary butyl 4-[[1-(4-pyridyl)piperidin-4-yl]aminocarbonyl]phenoxyacetate hexafluorophosphate in 49% yield as a white solid: m.p. 196°–198° C.; NMR (d$_6$DMSO) δ8.21(2H,d), 8.18(1H,d), 7.80(2H,d), 7.19 (2H,d), 6.95(2H,d), 4.72(2H,s), 4.20(3H,m), 3.5–3.1(4H+H$_2$O), 1.98(2H,m), 1.59(2H,m), 1.42(9H,s); m/e 412 (M+H)$^+$; calculated for C$_{23}$H$_{29}$N$_3$O$_4$. HPF$_6$: C, 4.96; H, 5.4; N, 7.5, found: C, 49.1; H, 5.5; N, 7.3%. The free base was generated by flash chromatography on neutral alumina eluting with 1% v/v methanol dichloromethane and used in the preparation of the acid.

EXAMPLE 168

4-[[1-(4-Pyridyl)piperidin-4-yl]methylaminocarbonyl[phenoxyacetic acid

Following the method of Example 166, but starting from tert-butyl 4-[[1-(4-pyridyl)piperidin-4-yl]methylaminocarbonyl]phenoxyacetate, the title compound was prepared in 95% yield: m.p. 84°–86° C.; NMR (d$_6$DMSO) δ8.38(1H,t), 8.18(2H,d), 7.81(2H,d), 7.19(2H,d), 6.95(2H,d), 4.73(2H,s), 4.20(2H,bd), 3.8–3.0(H$_2$O), 1.99 (1H,m), 1.84(2H,bd), 1.21(2H,m); m/e 370 (M+H)$^+$.

The starting material was prepared as follows:

Following the method of Example 167i), but starting from 1-tert-butyloxycarbonylpiperidin-4-ylmethylamine tosylate there was prepared N-[(1-tertiarybutyloxycarbonylpiperidine-4yl)methyl] acetamide in 95% yield as an oil which slowly crystallised: NMR (CDCl$_3$) δ5.52(1H,b), 4.12(2H,bd), 3.14(2H,m), 2.68(2H,dt), 1.98(3H,s), 1.67(3H,m), 1.44 (9H,s), 1.12(2H,dq); m/e 257 (M+H)$^+$.

The product was used in step ii) without further purification.

ii) A solution of the product from step i) (6.50 g) in trifluoroacetic acid (50 ml) was stirred overnight. The solvent was evaporated and the residue, on purification by flash chromatography on neutral alumina, eluting with 10% v/v methanol/dichloromethane gave N-[4-piperidinylmethyl]acetamide, 3.78 g, as a yellow oil: NMR (d$^4$ acetic acid) δ3.22(2H,bd), 2.96(2H,d), 2.81(2H, dt), 1.83(3H,s), 1.76(2H,bd), 1.67(1H,m), 1.26(2H,dq); m/e 157 (M+H)$^+$.

iii) Following the method of Example 165), but starting from the product of ii) above and purification by flash chromatography on silica eluting with 20 to 33% v/v methanol/dichloromethane there was obtained 4-(4-acetylaminomethylpiperidin-1-yl)pyridine in 28% yield as a gummy solid: NMR (d$_6$DMSO) δ8.18(2H,d), 7.90 (1H,t), 7.07(2H,d), 4.12(2H,bd), 3.05(2H,dt), 2.95(2H,t), 1.80(3H,s), 1.77(3H,m), 1.13(2H,m); m/e 234 (M+H)$^+$.

iv) Following the method of Example 167iv), but starting from the product of iii) above, there was obtained 4-(4-aminomethylpiperidin-1-yl)pyridine in 95% yield as a yellow gum: NMR (d$_6$DMSO) δ8.26(4H,m), 7.21(2H,d), 4.26(2H,bd), 3.19(2H,dt), 2.74(2H,t), 2.05(1H,m), 1.92 (2H,bd), 1.26(2H;dq); m/e 192 (M+H)$^+$.

v) Following the method of Example 165, but starting from the product of Example 167v) and the product from step iv) above and purification by flash chromatography on silica, eluting with 0 to 5% v/v methanol/dichloromethane and trituration with diethyl ether there was obtained tertiary butyl 4-[[1-(4-pyridyl)piperidin-4-yl)]methylaminocarbonyl]-phenoxyacetate hexafluorophosphate in 35% yield as a white solid: m.p. 182°–184° C.; NMR (d$_6$DMSO) δ13.11(1H,b), 8.37(1H,t), 8.17(2H,d), 7.80(2H,d), 7.19(2H,d), 6.95(2H,d), 4.72(3H,s), 4.21(2H, bd), 3.19(4H,m), 2.00(1H,m), 1.86(2H,m), 1.43(9H,s), 1.21(2H,m); m/e 426(M+H)$^+$; calculated for C$_{24}$H$_{31}$N$_3$O$_4$.HPF$_6$.0.5 H$_2$O: C, 49.6; H, 5.7; N, 7.2; P, 5.4. found: C, 49.6; H, 5.7; N, 7.1; P, 5.8%.

EXAMPLE 169

4-[[1-(4-Pyridyl)piperidine-4-yl]carboxyamido] acetic acid

Following the method of Example 2, but starting from methyl 4-[[1-(4-pyridyl)piperidin-4-yl]carboxamido] phenylacetate hydrochloride the title compound was prepared in 93% yield: m.p. 281°–282° C.; NMR (d$_6$DMSO) δ9.87(1H,s), 8.13(2H,d), 7.51(2H,d), 7.16(2H,d), 6.83(2H, dd), 4.00(2H,dm), 3.49(2H,s), 2.90(2H,dt), 2.61(1H,m), 1.87(2H,dd), 1.66(2H,dq); m/e 340 (M+H)$^+$; calculated for C$_{19}$H$_{21}$N$_3$O$_3$: C, 67.2; H, 6.2; N, 12.4. found: C, 67.4; H, 6.2; N, 12.4%.

The starting material was prepared as follows:

i) Following the method of Example 163, but starting from methyl 4-aminophenylacetate hydrochloride, methyl 4-[[1-(4-pyridyl)piperidin-4-yl]carboxamido]-phenylacetate hydrochloride was prepared in 78% yield: m.p. 235°–236.5° C.; NMR (d$_6$DMSO) δ13.61(1H,b), 10.10 (1H,s) 8.21(2H,d), 7.55(2H,d), 7.21(2H,d), 7.16(2H,d), 4.28(2H,dm), 3.60(5H,s), 3.30(2H,m+H$_2$O), 2.81(1H,m), 1.98(2H,m), 1.67(2H;m); m/e 354(M+H)$^+$; calculated for C$_{20}$H$_{23}$N$_3$O$_3$. HCl: C, 61.6; H, 6.2; N, 10.8. found: C, 61.7; H, 6.3; N, 10.6%.

EXAMPLE 170

N-[4-[4-[1-(4-Pyridyl)piperidin-4-yl] carboxamidophenyl]-methyl]-1-butanesulphonamide 4-[1-(4-Pyridyl)piperidin-4-ylcarboxamido]benzylamine dihydrochloride, hydrate (1.09 g) was dissolved in water and treated with 1 molar sodium hydroxide and the mixture stirred for 3 hours. The solid precipitate was collected, washed with water and dried to give 4-[1-(4-pyridyl) piperidin-4-ylcarboxamido]benzylamine (840 mg). 1-Butanesulphonyl chloride (0.08 ml) was added to a stirred solution under argon of the amine (160 mg) and triethylamine (0.09 ml) in dry DMF at 4° C. After 2 hours, the solvent was evaporated in vacuo. The residue was dissolved in water, 1 molar sodium hydroxide added and the precipiate collected and dried. Purification of this solid by flash chromatography on silica, eluting with 15% v/v methanol/ dichloromethane and recrystallisation from methanol gave the title compound, 146 mg: m.p. 98°–101° C. NMR (d$_6$DMSO) δ9.90(1H,s), 8.24(2H,d), 7.56(2H,d), 7.50(1H,t), 7.24(2H,d), 6.82(2H,d), 4.06(2H,d), 3.99(2H,dm), 2.89(4H, m), 2.61(1H,m), 1.85(2H,dd), 1.62(4H,m), 1.30 (2H,m), 0.82(3H,t); m/e 431 (M+H)$^+$; calculated for C$_{22}$H$_{30}$N$_4$O$_3$S.H$_2$O: C, 58.9; H, 7.2; N, 12.5. found: C, 58.5; H, 7.3; N, 12.3%.

The starting material was prepared as follows:

i) A mixture of 4-nitrobenzylamine hydrochloride (5.00 g), triethylamine (25 ml), dry DMF (25 ml) and di-tertiary-butyl dicarbonate (6.07 g) was stirred for 16 hours then the solvent was evaporated in vacuo. The residue was partitioned between ethyl acetate (200 ml) and water (50 ml), separated and the organic phase washed successively with water, 0.5 molar sodium hyroxide, water and brine, dried (MgSO$_4$) and evaporated. Recrystallisation of the solid residue from ethyl acetate/hexane gave N-tertiary-butyloxycarbonyl-4-nitrobenzylamine, 5.65 g: m.p. 110°–111° C.; NMR (d$_6$DMSO) δ8.19(2H,d), 7.52(1H, bt), 7.51(2H,d), 4.24(2H,d), 1.40(9H,s); m/e 253(M+H)$^+$; calculated for C$_{12}$H$_{16}$N$_2$O$_4$: C, 57.1; H, 6.4; N, 11.1. found: C, 56.9; H, 6.3; N, 10.9%.

ii) 10% w/w palladium on charcoal (250 mg) was added to a solution of the product from step i) (5.37 g) in ethanol (100 ml) and the mixture hydrogenated at room temperature and pressure until the theoretical amount of hydrogen had been taken up. Charcoal was added, the mixture stirred for 10 minutes then filtered through diatomaceous earth and the filtrate evaporated to dryness. The solid residue, on recrystallisation from ethyl acetate/hexane gave 4-(N-tertiary-butyloxycarbonylaminomethyl) aniline, 4.20 g; m.p. 80°–82° C.; NMR (d$_6$DMSO) δ7.10 (1H,bt), 6.88(2H,d), 6.49(2H,d), 4.92(2H,s), 3.92(2H,d), 1.38(9H,s); m/e 223(M+H)$^+$; calculated for C$_{12}$H$_{18}$N$_2$O$_2$: C, 64.8; H, 8.2; N, 12.6. found: C, 65.4; H, 8.3; N, 13.0%.

iii) Thionyl chloride (5 ml) was added dropwise over ten minutes to a stirred suspension of 1-(4-pyridyl)-4-piperidinecarboxylic acid (5.15 g) in dry dichloromethane (20 ml) at 4° C. After 1 hour at 4° C., the mixture was allowed to reach ambient temperature and stirred for 16 hours. The solvent was removed by evaporation and the residue dried under high vacuum to give a solid foam (7.06 g). The foam (4.31 g) was added, under argon, to a stirred solution of the product from step (ii) (3.55 g) and triethylamine (4.59 ml) in dry dichloromethane (150 ml) at 4° C. After 1 hour at 4° C., the mixture was allowed to reach ambient temperature and stirred for 16 hours. Dichloromethane (150 ml) was added and the mixture washed with water (3×30 ml), dried (MgSO$_4$) and evaporated. The solid residue on recrystallisation from ethyl acetate gave N-tertiary-butyloxycarbonyl-4-[1-(4-(pyridyl)piperidin-4-ylcarboxamido]-benzylamine, 4.22 g: m.p. 215°–217° C. NMR (d$_6$DMSO) δ9.88(1H,s), 8.15(2H,d), 7.52(2H,d), 7.30(1H,t) 7.14(2H,d), 6.82(2H, d), 4.02(4H,m), 2.90(2H,dt), 2.61(1H,m), 1.87(2H,dd), 1.65(2H,dq); m/e 411 (M+H)$^+$; calculated for C$_{23}$H$_{30}$N$_4$O$_3$: C, 67.2; H, 7.4; N, 13.6. found: C, 67.3; H, 7.4; N, 13.5%.

iv) A hydrogen chloride solution in dry ether (40 ml) was added to a stirred suspension of the product of step iii) (4.10 g) in acetonitrile (100 ml) under argon. After 2.5 hours, the solid was collected, washed with dry ether and dried over potassium hydroxide to give 4-[1-(4-pyridyl) piperidin-4-ylcarboxamido]benzylamine dihydrochloride, 3.78 g, as a white solid: m.p. 286°–289° C.; NMR (d$_6$DMSO) δ13.69(1H,b), 9.96(1H,s), 8.39(3H, b), 8.23(2H,d), 7.66(2H,d), 7.40(2H,d), 7.22(2H,d), 4.27 (2H,bd), 3.93(2H,m), 3.26(2H,m), 2.86(1H,m), 2.00(2H, bd), 1.69(2H,bq); m/e 311 (M+H)$^+$; calculated for C$_{18}$H$_{22}$N$_4$O.2HCl.0.5 H$_2$O: C 55.1; H, 6.4; N, 14.3. found. C, 54.9; H, 6.4; N, 13.9%.

EXAMPLE 171

N-[4[4-[1-(4-Pyridyl)piperidin-4yl] carboxyamidophenyl]methyl]-4-methylphenylsulphonamide 4-Methylphenylsulphonyl chloride (419 mg) was added to a stirred mixture of the product of Example 170 step (iv) (766 mg), triethylamine (0.86 ml) and dry DMF (15 ml) at 4° C. After 1 hours, the mixture was allowed to attain ambient temperature and stirred for 16 hours. Then further 4-methylphenylsulphonyl chloride (210 mg) and triethylamine (0.17 ml) were added and stirring continued for 24 hours. The precipitated solid was collected, washed with dichloromethane and water. This solid was suspended in 1 molar sodium hydroxide, the mixture stirred for 3 hours. The solid was collected, washed well with water and on drying, gave the titled compound, 734 mg: m.p. 124°–127° C.; NMR (d$_6$DMSO) δ9.37(1H,s), 8.15(2H,b), 7.94(1H,t), 7.67 (2H,d), 7.48(2H,d), 7.36(2H,d), 6.32(2H, bd), 3.99(2H,bd), 3.87(2H,d), 2.90(2H,bt), 2.58(1H,m), 2.48(3H,s), 1.84(2H, bd), 1.63(2H,dq); m/e 465 (M+H)$^+$; calculated for C$_{25}$H$_{28}$N$_4$O$_3$S. 1.25 H$_2$O: C, 61.6; H, 6.3; N, 11.5; S, 6.6. found: C, 61.5; H, 6.1; N, 11.2; S, 7.0%.

EXAMPLE 172

4-Methyloxycarbonylmethylamiophenyl [1-(4-pyridyl)piperidin4-yl]acetate

Thionyl chloride (1 ml) was added dropwise to a stirred suspension of [1-(4-pyridyl)piperidin-4-yl]acetic acid (300 mg) in dry dichloromethane (5 ml) and the mixture stirred for 4 hours. The solvent was evaporated and the residue triturated with hexane and dried under high vacuum over potassium hydroxide to give a solid foam. A solution of the foam in dry dichloromethane (5 ml) was added dropwise to a stirred solution of methyl N-(4-hydroxyphenyl)glycinate (210 mg) and triethylamine (0.33 ml) in dry dichloromethane (10 ml) and the mixture stirred for 16 hours. The mixture was diluted with dichloromethane, washed with water, dried and evaporated. Purification by flash chromatography on silica, eluting with 0–10% v/v methanol/ dichloromethane and trituration of the resulting gum with diethyl ether gave the title compound, 80 mg, as a white solid: m.p. 120°–122° C.; NMR (d$_6$DMSO) δ8.13(2H,d), 6.84(2H,d), 6.81(2H,d) 6.54(2H,d), 6.01(1H,t), 3.96(2H, bd), 3.90(2H,d), 3.66(3H,s), 2.90(2H,dt), 2.50(2H,d+ DMSO), 2.07(1H,m), 1.81(2H,bd), 1.30(2H,dq); m/e 384 (M+H)$^+$; calculated for C$_{21}$H$_{25}$N$_3$O$_4$0.5 H$_2$O: C, 64.3; H, 6.6; N, 10.7. found: C, 64.2; H, 6.3; N, 10.7%.

EXAMPLE 173

Methyl 4-[2-[1-(4-pyridyl)piperidin-4-yl]acetyl] phenoxyacetate

Oxalyl chloride (2.40 ml) was added to a stirred suspension of [1-(4-pyridyl)piperidin-4-yl]acetic acid acid hydrochloride hydrate (1.25 g) in dry dichloromethane under argon. A few drops of dry DMF were added and the mixture stirred for 30 minutes to give a clear solution. The solvent was removed in vacuo and the residue dried. The resulting solid foam was suspended in dichloroethane (40 ml), the suspension cooled to 4° C. and with stirring, aluminium chloride (3.21 g) added. After 30 minutes the mixture was allowed to warm to ambient temperature when methyl phenoxyacetate (1.16 ml) was added and stirring continued for a further 2.5 hours. The mixture was added to an ice-water mixture to which was added dichloromethane. The aqueous phase was adjusted to pH7 and the solid removed by filtration. The filtrate was extracted three times with dichloromethane and the extracts dried ($MgSO_4$). Evaporation of the solvent gave a clear oil which crystallised on addition of ether. The solid was collected and on recrystallisation from methyl acetate gave the title compound, 1.06 g: m.p. 137°–138° C.; NMR ($d_6$DMSO) δ8.11(2H,b), 7.94(2H, d), 7.03(2H,d), 6.78(2H,bd), 4.91(2H,s), 3.90(2H,d), 3.71 (3H,s), 2.91(2H,d), 2.85(2H,dt), 2.12(1H,m), 1.75(2H,bd), 1.26(2H,dq); m/e 369 (M+H)$^+$; calculated for $C_{21}H_{24}N_2O_4$: C, 68.5; H, 6.6; N, 7.6. found C, 68.2; H, 6.5; N, 7.5%.

The starting [1-(4-pyridyl)piperidin-4-yl]acetic acid hydrochloride hydrate is described in Example 165i) and ii).

EXAMPLE 174

4-[2-[1-(4Pyridyl)piperidin-4-yl]acetyl] phenoxyacetic acid hydrochloride

A mixture of the product of Example 173 (300 mg), dioxan (10 ml) and 1 molar hydrochloric acid (2.7 ml) were stirred for 80 hours at ambient temperature. The solvent was removed in vacuo and a little water added. The resulting solid was collected, washed with water and, after drying, gave the titled compound, 170 mg; m.p. 239°–241° C.; NMR ($D_2O$) δ8.17(2H,d), 8.15(2H,d), 7.36(2H,d), 7.20(2H, d), 5.01(2H,s), 4.33(2H,d), 3.38(2H,dt), 3.16(2H,d) 2.48 (1H,m), 2.08(2H,d), 1.54(2H,dq); m/e 355 (M+H)$^+$; calculated for $C_{20}H_{22}N_2O_4.HCl.1.5H_2O$; C, 57.4; H, 6.1; N, 6.7. found: C, 57.3; H, 6.1; N, 6.4%.

EXAMPLE 175

Methyl 4-[2-[4-(4-pyridyl)piperazin-1yl]-2,2-dimethylacetyl]-phenoxyacetate

Methyl 4-(2,2-dimethylbromoacetyl)phenoxyacetate (1.58 g) was added to a stirred solution of 1-(4-pyridyl)piperazine (1.63 g) in acetonitrile (40 ml). After 34 days, the solid formed was removed by filtration and the filtrate evaporated to give an oil. Purification by flash chromatography on silica, eluting with 0.5 to 4.0% v/v methanol/dichloromethane gave the title compound, 240 mg, as a white foam: NMR ($d_6$DMSO) δ8.49(2H,d), 8.12(2H,d), 6.96(2H,d), 6.77(2H,d), 4.87(2H,s), 3.69(3H,s), 3.28(4H,t), 2.58(4H,t), 1.25(6H,s); m/e 398 (M+H)$^+$; calculated for $C_{22}H_{27}N_3O_4.0.25H_2O$; C, 65.7; H, 6.8; N, 10.4. found: C, 65.3; H, 6.9; N, 10.4%.

The starting material was prepared as follows:

i) Following the method of Example 118i) but starting from 4-2,2-dimethylacetyl)phenol and only stirring for 18 hours instead of 2 days, there was obtained methyl 4-(2,2-dimethylacetyl)phenoxyacetate, in 90% yield, as an off-white crystalline solid: m.p. 45°–46° C., NMR ($d_6$DMSO) δ7.92(2H,d), 7.02(2H,d), 4.90(2H,s), 3.71 (3H,s), 3.60(1H,m), 1.09(6H,d).

ii) Bromine (2.09 ml) was added dropwise over ten minutes to a stirred solution of the product of step i) above (9.44 g) in carbon tetrachloride (200 ml). The solution was stirred for 16 hours, then the solvent was evaporated in vacuo to give an orange oil. A solution of this oil, in a small volume of dichloromethane, was filtered through silica and the clear filtrate, on evaporation, gave methyl 4-(2-bromo-2,2-dimethylacetyl)phenoxyacetate, 11.3 g, as a white crystalline solid: m.p. 46°–50° C.; NMR ($d_6$DMSO) δ8.09(2H,d), 7.05(2H,d), 4.92(2H,s), 3.72 (3H,s), 2.00(6H,s).

EXAMPLE 176

4-[2-[4-(4-Pyridyl)piperazin-1-yl]-2,2-dimethylacetyl]phenoxyacetic acid

Following the method of Example 2 but starting from the product of Example 175 and stirring for 16 hours instead of 2 hours, the title compound was obtained in 76% yield, as a white crystalline solid: m.p. 278°–279° C.; NMR ($D_2O$) δ8.72(2H,d), 8.20(2H,d), 7.16(4H,d), 4.76(2H,s), 3.80(4H, bt), 2.91(4H,bt), 1.55(6H;s); m/e 406 (M+Na)$^+$, 384 (M+H)$^+$; calculated for $C_{21}H_{25}N_3O_4 0.5NaCl$: C, 61.1; H, 6.1; N, 10.2. found: C, 60.8; H, 5.9; N, 10.0%.

EXAMPLE 177

RS Methyl 4-[3-[4-(4-pyridyl)piperazin-1-yl]-2-methylpropanoyl]-phenoxyacetate

A stirred mixture of methyl 4-(2,2-dimethylbromoacetyl) phenoxyacetate (3.15 g), and 1-(4-pyridyl)piperazine (3.26 g) in acetonitrile (200 ml) was heated at reflux temperature for 4 days. The solvent was removed in vacuo and the residue partioned between dichloromethane/water. The organic phase was dried ($MgSO_4$), evaporated and then purified by flash chromatography on silicon, eluting with 2 to 5% v/v methanol/dichloromethane. Further purification by flash chromatography on neutral alumina, eluting with dichloromethane, gave the title compound, 350 mg, as a clear oil: NMR ($d_6$DMSO) δ8.12(2H,d), 7.98(2H,d), 7.04 (2H,d), 6.75(2H,d), 4.92(2H,s), 3.86(1H,m), 3.71(3H,s), 3.19(4H,t), 2.70(1H,q), 2.49(DMSO+4H), 2.36(1H,q), 1.09 (3H,s), trace of dichloromethane; m/e 398 (M+H)$^+$; calculated for $C_{22}H_{27}N_3O_4 0.1 CH_2Cl_2$: C, 65.3; H, 6.7; N, 10.3. found: C, 65.1; H, 6.9; N, 10.1%.

EXAMPLE 178

Methyl 4-[4-[4-(4-pyridyl)piperazin-1-yl] methylphenyl]butyrate 1-(4-Pyridyl)piperazine (1.63 g) was dissolved in warm acetontrile (25 ml), the solution cooled to 30° C. and with stirring, a solution of methyl 4-(4-bromomethylphenyl) butyrate in acetonitrile (5 ml) added. After 30 minutes the resulting precipitate was removed by filtration and the filtrate concentrated in vacuo to give a yellow oil. Purification by flash chromatography on silica, eluting with 0 to 4% v/v methanol/dichloromethane gave a solid. Trituration with ether and removal of the insoluble solid gave a clear solution. Concentration of this solution gave the title compound, 0.90 g, as a white fluffy solid: m.p. 126°–127° C.; NMR ($d_6$DMSO) δ8.14(2H,d), 7.24(2H,d), 7.14(2H,d), 6.77(2H,d), 3.59(3H,s), 3.48(2H,s), 3.30(4H,t), 2.59(2H,t), 2.47(4H,t), 2.32(2H,t), 1.63(2H,m); m/e 354 (M+H)$^+$; calculated for $C_{21}H_{27}N_3O_2.0.25H_2O$: C, 70.4; H, 7.7; N, 11.7. found: C, 70.6; H, 7.6; N, 11.7%.

EXAMPLE 179

Methyl 5-[4-[4-(4-pyridyl)piperazin-1-yl] methylphenyl]pentanoate

A mixture a methyl 5-(4-bromomethylphenyl)pentanoate and 5-(2-bromometylphenyl)pentanoate, 70:30 w/w by NMR, prepared according to the method for the starting material in Example 178 (2.14 g) was reacted in a similar manner to Example 178. The crude mixture of esters was purified by flash chromatography on silica, eluting with 0–5% v/v methanol/dichloromethane. Evaporation of the appropriate fractions gave the title compound, 605 mg, as a waxy solid: m.p. 53°–54° C.; NMR (d$_6$DMSO) δ8.13(2H,d), 7.23(2H,d), 7.14(2H,d), 6.79(2H,d), 3.58(3H,s), 3.47(2H,s), 3.30(4H,t+H$_2$O), 2.57(2H,t), 2.46(4H,t), 2.32(2H,t), 1.56 (4H,m); m/e 368 (M+H)$^+$; calculated for C$_{22}$H$_{29}$N$_3$O$_2$.0.5H$_2$O: C, 70.1; H, 8.0; N, 11.2. found: C, 70.3; H, 8.2; N, 11.0%.

EXAMPLE 180

4-[4-[4-(4-Pyridyl)piperazin-1yl]methylphenyl] butyric acid, dihydrochloride

Following the method of Example 123 but starting from the product of Example 178 and heating at 100° C. for 4 hours instead of 1.5 hours the title compound was prepared in 88% yield: m.p. 236°–238° C.; NMR (D$_2$O) δ8.40(2H,d), 7.66(2H,d), 7.61(2H,d), 4.61(2H,s), 4.19(4H,b), 3.69(4H,b), 2.94(2H,t), 2.61(2H,t), 2.15(2H,m); m/e 340 (M+H)$^+$; calculated for C$_{20}$H$_{25}$N$_3$O$_2$.2HCl0.5H$_2$O: C, 57.0; H, 6.6; N, 10.0. found: C, 57.2; H, 6.9; N,9.8%.

EXAMPLE 181

Mixture of 5-[4-[4-(4-pyridyl)piperazin-1-yl] methylphenyl]pentanoic acid and 5-[2-[4-(4-pyridyl)piperazin-1-yl]methylphenyl]pentanoic acid, dihydrochloride (4:1)

Following the method of Example 180, but starting from the crude mixture of esters in Example 179, there was obtained the titled mixture of compounds in 59% yield, as a white solid: NMR (D$_2$O) δ8.38(2H,d), 7.62(4H,m), 7.35 (2H,d), 4.70(0.4H,s), 4.61(1.6H,s), 4.18(4H,b), 3.68(4H,b), 2.98(0.4H,t) 2.91(1.6H,t), 2.59(2H,t), 1.82(4H,m); m/e 354 (M+H)$^+$; calculated for C$_{21}$H$_{27}$N$_3$O$_2$.2HCl0.5H$_2$O: C, 57.9; H, 6.9; N, 9.7. found: C, 59.6; H, 7.2; N, 9.4%.

EXAMPLE 182

N-[[4-[1-(4-Pyridyl)piperidin-4-yl]carboxamidophenyl]ethyl]-methanesulphamide

Following the method of Example 170 but starting from methanesulphonyl chloride instead of 1-butanesulphonyl chloride there was obtained after evaporation of the reaction solvent an oily solid. This residue was partitoned between ethyl acetate and a dilute hydrochloric acid solution. Separation and then neutralisation of the aqueous phase with sodium hydroxide solution gave a solid. This was collected by filtration, washed with water and, on drying, gave the title compound in 93% yield: m.p. 238°–240° C.; NMR (d$_6$DMSO) δ9.91(1H,s), 8.13(2H,d), 7.08(2H,d), 7.47(1H, bt), 7.25(2H,d), 6.82(2H,d), 4.08(2H,d), 3.98(2H,bd), 2.89 (2H,bt), 2.82(3H,s), 2.59(1H,m), 187 (2H, bd), 1.65 (2H, dq); m/e 389 (M+H)$^+$; calculated for C$_{19}$H$_{24}$N$_4$O$_3$S.0.25H$_2$O: C, 58.1; H, 6.3; N, 14.3. found C, 58.2; H, 6.5; N, 14.3%.

EXAMPLE 183

N-[2-[4-[1-(4-Pyridyl)piperidin-4-yl]carboxamidophenyl]ethyl]methanesulphonamide Following the method of Example 182, but starting from 4-[1-(4-pyridyl)piperidin -4-ylcarboxamido] phenethylamine, the title compound was prepared in 90% yield: m.p. 193°–195° C.; NMR (d$_6$DMSO) δ9.85(1H,s), 8.16(2H,d), 7.51(2H,d), 7.15(2H,d), 7.03(1H,t), 6.82(2H,d), 4.00(2H,bd), 3.13(2H,q), 2.90(2H,dt), 2.83(3H,s), 2.72(2H, t), 2.60(1H,m), 1.87(2H,dd), 1.65(2H,dq); m/e 403 (M+H)$^+$; calculated for C$_{20}$H$_{26}$N$_4$O$_3$S.0.25H$_2$O: C, 59.0; H, 6.6; N, 13.8. found, C, 59.0; H, 6.7; N, 13.7%.

The starting material was prepared as follows:

i) Following the method of Example 170i), but starting from 4-nitrophenethylamine, there was obtained N-tertiary-butyloxycarbonyl-4-nitrophenethylamine in 82% yield: m.p. 94°–95° C.; NMR (d$_6$DMSO) δ8.14(2H,d), 7.46(2H, d), 6.89(1H,bt), 3.20(2H,q), 2.82(2H,t), 1.33(9H,s); m/e 267 (M+H)$^+$; calculated for C$_{13}$H$_{18}$N$_2$O$_4$: C, 58.6; H, 6.81; N, 10.5. found: C, 58.3; H, 6.9; N, 10.5%.

ii) Following the method of Example 170ii) but starting from the product of step i) above, there was obtained 4-(N-tertiary-butyloxycarbonyl 2-aminoethyl)aniline in 78% yield: m.p. 74°–75° C.; NMR (d$_6$DMSO) δ6.81(2H, d), 6.73(1H,m), 6.47(2H,d), 4.82(2H,s), 3.02(2H,m), 2.50 (2H,m+DMSO), 1.37(9H,s); m/e 237 (M+H)$^+$; calculated for C$_{13}$H$_{20}$N$_2$O$_2$: C, 66.1; H, 8.5; N, 11.9; found C, 65.9; H, 8.9; N, 11.8%.

iii) Following the method of Example 170ii), but starting from the product of step ii) above, was obtained after recrystallisation from methanol, N-tertiary-butyloxycarbonyl 4-[1-(4-pyridyl)piperidin-4-ylcarboxamido]phenethylamine in 62% yield: m.p. 242°–244° C.; NMR (d$_6$DMSO) δ9.82(1H,s), 8.15(2H,d), 7.50(2H,d), 7.09(2H,d), 6.82(2H,d), 6.78(1H,m), 3.99 (2H,bd), 3.10(2H,q), 2.90(2H,dt), 2.63(2H,t), 2.56(1H, m), 1.86(2H,dd), 1.65(2H,dq), 1.48(9H,m); m/e 425 (M+H)$^+$; calculated for C$_{24}$H$_{32}$N$_4$O$_3$.0.5H$_2$O: C, 66.5; H, 7.7; N, 12.9. found: C, 66.5; H, 7.7; N, 12.9%.

iv) Following the method of Example 170iv) but starting from the product of step iii) above there was obtained the dihydrochloride salt, m.p. 286°–289° C. To a stirred solution of the salt in water was added 3 equivalents of 1 molar sodium hydroxide. After 1 hour the precipitated solid was collected by centrifugation, washed with water and on drying, gave 4-[1-(4-pyridyl)piperidin-4-ylcarboxamido]phenethylamine in 92% yield: m.p. 207°–211° C.; NMR (d$_6$DMSO+d$_4$ acetic acid) δ8.18(2H, d), 7.58(2H,d), 7.18(4H,m) 4.22(2H,d), 3.28(2H,t), 3.05 (2H,m), 2.83(3H,m), 2.00(2H,dd), 1.76(2H,dq); m/e 325 (M+H)$^+$; calculated for C$_{19}$H$_{24}$N$_4$O.0.5H$_2$O: C, 68.4; H, 7.6; N, 16.8. found: C, 68.2; H, 7.6; N, 16.7%.

EXAMPLE 184

N-[2-[4-[1-(4-Pyridyl)piperidin-4-yl]carboxamidophenyl]ethyl]-4-methylphenylsulphonamide Following the method of Example 183, but starting from 4-methylphenylsulphonyl chloride instead of methanesulphonyl chloride, the title compound was obtained 81% yield: m.p. 175°–178° C.; NMR (d$_6$DMSO) δ9.81(1H,s), 8.15(2H,d), 7.64(2H,d), 7.55(1H,t), 7.46(2H,d), 7.36(2H,d), 7.03(2H,d), 6.82(2H,d), 3.98(2H,bd), 3.90(4H,m), 2.60(3H, m), 2.37(3H,s), 1.85(2H,dd), 1.65(2H,dq), m/e 479 (M+H)$^+$; calculated for C$_{26}$H$_{30}$N$_4$O$_3$S.H$_2$O: C, 62.9; H, 6.5; N, 11.3. found: C, 63.1; H, 6.3; N, 11.1%.

EXAMPLE 185

N-[4-[2-[4-(4-Pyridyl)piperazin-1-yl]ethyl]phenyl] methyl-1-butanesulphonamide

Triethylamine (0.41 ml) was added to a stirred suspension of 4-[2-[4-(4-pyridyl)piperazin-1-yl]ethyl]benzylamine, trihydrochloride (300 mg) in dry dichloromethane (20 ml). After 5 minutes, 1-butanesulphonyl chloride (0.10 ml) was added and the mixture stirred overnight. Dichloromethane (80 ml) was added and the solution washed with water (2×25 ml), dried (MgSO$_4$) and the solvent removed in vacuo. Trituration of the residue with a small volume of ethyl acetate gave the title compound, 50 mg, as an off-white solid: m.p. 154°–156° C.; NMR (d$_6$DMSO) δ8.16(2H,d), 7.53(1H,t), 7.22(4H,m), 6.37(2H,d), 4.10(2H,d), 3.35(6H, m+H$_2$O), 2.81(4H,m), 2.54(4H,m+DMSO), 1.56(2H,m), 1.29(2H,m), 0.82(3H,t), m/e 417 (M+H)$^+$; calculated for C$_{22}$H$_{32}$N$_4$O$_2$S.0.75H$_2$O: C, 61.5; H, 7.8;, 13.0. found: C, 61.5; H, 7.6; N, 12.7%.

The starting material was prepare as follows:

i) A suspension of di-tert-butyl iminodicarboxylate (4.25 g) and finely powdered anhydrous potassium hydroxide (1.1 g) in dry THF (60 ml) was stirred for 2 hours. 2-(4-Bromomethylphenyl)ethanol (4.2 g) dissolved in THF (40 ml) was added and the mixture stirred for 16 hours when further anion [prepared from di-tert-butyl iminodicarboxylate (4.25 g) and finely powdered anhydrous potassium hydroxide (1.1 g) in dry THF (40 ml) was added and stirring continued for 3 days. Ether (300 ml) was added and the mixture washed with water and saturated sodium chloride solution, then dried (MgSO$_4$) and evaporated to give a colourless oil. Purification by flash chromatography on silica, eluting with 1% v/v methanol/dichloromethane gave N-di-tert-butyloxycarbonyl 4-[1-(2-hydroxyethyl)]benzylamine, 6.1 g, as a clear oil: NMR (CDCl$_3$) δ7.25(2H,d), 7.17(2H,d), 4.75(2H,s), 4.37(1H, b), 3.35(2H,bt), 2.85(2H,t), 1.46(18H,s); m/e 352 (M+H)$^+$.

ii) A stirred, cooled (4° C.), solution of the product from step i) above (6.1 g) in dry dichloromethane (100 ml) was treated under argon with triethylamine (3.1 ml), then methanesulphonyl chloride (1.6 ml) was added dropwise over 15 minutes and stirring continued for 1 hour at 4° C. and 2 hours at ambient temperature. The dichloromethane was removed by evaporation and the residue dissolved in ethyl acetate (250 ml). This solution was washed with water and saturated sodium chloride solution, then dried (MgSO$_4$). Evaporation of the solvent gave N-di-tert-butyloxycarbonyl-4-[1-(2-methanensulphonyl-oxyethyl)] benzylamine, 6.53 g, as an off-white solid: m.p. 66°–68° C.; NMR (CDCl$_3$) δ7.26(2H,d), 7.17(2H,d), 4.75(2H,s), 4.40(2H,t), 3.03(2H,t), 2.84(3H,s), 1.46(18H,s); m/e 452 (M+Na)$^+$.

iii) A mixture of the product from step ii) above (6.5 g) and 1-(4-pyridyl)piperazine (4.95 g) in acetonitrile (100 ml) was heated and stirred at reflux temperature for 16 hours. The solvent was removed in vacuo, the residue dissolved in dichloromethane (300 ml) and this solution washed with water, then dried (MgSO$_4$) and evaporated. The residue, after purification by flash chromatography on silica, eluting with 10% v/v methanol/dichloromethane gave N-di-tert-butyloxycarbonyl 4-[2-[4-(4-pyridyl)piperazin- 1-yl]ethyl]benzylamine, 2.25 g, as a coloured gum: NMR (d$_6$DMSO) δ8.14(2H,d), 7.21(2H,d), 7.12 (2H,d), 6.81(2H,d), 4.63(2H,s), 3.30(6H,m+H$_2$O), 2.75 (2H,t), 2.53(4H,t+DMSO), 1.40(18H,s); m/e 497 (M+H)$^+$.

A solution of the product from step iii) above (2.0 g) dissolved in methanol (40 ml) was treated with a 5 molar solution of dry hydrogen chloride gas in methanol (8.0 ml) and the mixture stirred for 16 hours. The solvent was removed in vacuo and the residue, on trituration with ether, gave 4-[2-[4-(4-pyridyl)piperazin-1-yl]ethyl]benzylamine, trihydrochloride, 1.86 g, as a pale yellow solid: m.p. 297°–299° C. dec; NMR (d$_6$DMSO) δ13.92(2H,b), 12.01 (1H,b), 8.49(4H,m), 7.47(2H,m), 7.31(4H,m), 4.46(2H,b), 4.00(2H,q), 3.70(4H,b), 3.30(6H,m+H$_2$O); m/e 297 (M+H)$^+$; calculated for C$_{18}$H$_{24}$N$_4$.3HCl.3.5H$_2$O: C, 46.1; H, 7.3; N, 11.9. found: C, 45.8; H, 7.1; N, 11.8%.

EXAMPLE 186

N-[4-[2-[4-(4-Pyridyl)piperazin-1-yl]ethyl]phenyl] methyl-4-methylphenylsulphonamide Following the method of Example 185, but starting from 4-methylphenylsulphonyl chloride instead of 1-butanesulphonyl chloride the title compound was obtain in 69% yield, as a white solid: m.p. 180°–182° C.; NMR (d$_6$DMSO+d$_4$acetic acid) δ8.21(2H,d), 7.70(2H,d), 7.47(2H, d), 7.19(6H,m), 3.96(2H,s), 3.80(4H,bt), 2.94(4H,bt), 2.86 (4H,bs), 2.40(3H,s), m/e 451 (M+H)$^+$; calculated for C$_{25}$H$_{30}$N$_4$O$_2$S.H$_2$O: C, 64.1; H, 6.8; N, 11.9. found: C, 63.9; H, 6.6; N, 11.6%.

EXAMPLE 187

Ethyl 6-[4-(4-pyridylamino)phenoxy]hexanoate

Trifluoroacetic acid (3 ml) was added to a stirred solution of ethyl 6-[4-[N-(4-pyridyl)-N-tertiary-butyloxycarbonylamino]phenoxy]-hexanoate (260 mg) dissolved in dichloromethane (3 ml). After 18 hours the solvents were removed in vacuo and the residual gum dissolved in dichloromethane. This solution was treated with a saturated solution of sodium hydrogen carbonate. The organic phase was washed with water, dried and evaporated. Trituration of the residue with hexane gave the title compound, 120 mg, as a white solid: m.p. 104°–106° C.; NMR (CDCl$_3$) δ8.22(2H,d), 7.12(2H,d), 6.90(2H,d), 6.64(2H,dd), 5.82(1H, s), 4.13(2H,q), 3.97(2H,t), 2.34(2H,t), 1.80(2H,m), 1.70(2H, m), 1.53(2H,m), 1.27(3H,t); m/e 329 (M+H)$^+$; calculated for C$_{19}$H$_{24}$N$_2$O$_3$.0.25H$_2$O:C, 68.6; H, 7.4; N, 8.4. found: C, 68.8; H, 7.3; N, 8.2%.

The starting material was prepared as follows:

i) A stirred mixture of 4-chloropyridine hydrochloride (2 g) and 4-methoxyaniline (4.9 g) was heated at 140° C. for 5 hours. After cooling the residue was dissolved in dichloromethane (250 ml), the solution extracted with water (2×100 ml). The aqueous extracts were treated with sodium hydroxide solution and then extracted with ethyl acetate (4×100 ml). The combined organic extracts were washed with water, and saturated sodium chloride solution, then dried and the solvent evaporated. Purification by flash chromatography on silica, eluting with 10% v/v methanol/dichloromethane gave 4-(4-pyridylamino) methoxybenzene, 2 g, as a fawn solid: m.p. 159°–160° C.; NMR (d$_6$DMSO) δ8.47(1H,s) 8.09(2H,d), 7.10(2H,d), 6.92(2H,d), 6.70(2H,dd), 3.73(3H,s); m/e 201 (M+H)$^+$; calculated for C$_{12}$H$_{12}$N$_2$O$_3$: C, 72.0; H, 6.0; N, 14.0. found: C, 71.4; H, 6.1; N, 13.8%.

ii) A mixture of the product from step i) above (2.0 g) and 48% w/v hydrobromic acid (30 ml) was heated at 140° C. for 4 hours. The cooled solution was neutralised with 0.880 ammonia solution and then extracted four times with ethyl acetate. The combined organic extracts ere washed with water and saturated sodium chloride solution, then dried (MgSO$_4$) and evaporated. Purification by flash chromatography on silica, eluting with 10 to 20% v/v methanol/dichloromethane gave 4-(4-pyridylamino) phenol, 0.78 g as an off-white solid: m.p. 246°–248° C.;

NMR (CDCl$_3$+d$_6$DMSO) δ8.92(1H,b), 8.09(2H,d), 7.31 (1H,s), 7.00(2H,d), 6.79(2H,d), 6.67(2H,dd); m/e 187 (M+H)$^+$.

iii) A mixture of the product from step ii) above (0.78 g), di-tertiary-butyl dicarbonate (0.91 g), triethylamine (0.59 ml), 1,2-dimethoxymethane (20 ml) and water (10 ml) was stirred for 18 hours. The solvents were removed in vacuo and the residue partitioned between ethyl acetate and water. The aqueous phase was extracted two times with further ethyl acetate and the combined organic extracts washed with water and brine, dried (MgSO$_4$) and evaporated to a small volume when crystallisation occurred. Collection by filtration gave 4-[N-(4-pyridyl)-N-tertiary-butyloxycarbonylamino]phenol, 1.07 g as a white crystalline solid: m.p. 192°–194° C. (dec); NMR (CDCl$_3$) δ8.28(2H,dd), 7.18(4H,s), 6.76(2H,dd), 6.03 (1H,bs), 1.57(9H,s); m/e 287 (M+H)$^+$.

iv) Sodium hydride (50% w/w dispersion in mineral oil, 55 mg) was added under argon to a stirred solution of the product from step iii) above (300 mg)in dry DMF (5 ml). After five minutes, ethyl 6-bromohexanoate (0.20 ml) was added and the mixture stirred for 16 hours. The DMF was evaporated in vacuo and the residue partitioned between dichloromethane and water. The aqueous phase was extracted with further dichloromethane. The combined organic extracts were washed with water then dried, and evaporated. The residue was purified by chromatography on alumina, eluting with dichloromethane and the 1% v/v methanol/dichloromethane. Evaporation of the appropriate fractions gave ethyl 6-[4-[N-(4-pyridyl)-N-tertiary-butyloxycarbonylamino]phenoxy]hexanoate, 260 mg, as a yellow gum: NMR (CDCl$_3$) δ8.40(2H,dd), 7.16(2H,dd), 7.07(2H,m), 6.90(2H,m), 4.13(2H,q), 3.98(2H,t), 2.34 (2H,t), 1.78(4H,m), 1.57(2H,m), 1.44(9H,s), 1.26(3H;t); m/e 429 (M+H)$^+$.

EXAMPLE 188

6-[4-(4-Pridylamino)phenoxy]hexanoic acid hydrochloride

Following the method of Example 123, but starting from the product of Example 187 and heating at 100° C. for 16 hours instead of 1.5 hours, the title compound was obtained in 80% yield as a freeze-dried solid: NMR (d$_6$DMSO) δ13.63(1H,b), 11.95(1H,b), 10.49(1H,s), 8.21(2H,d), 7.26 (2H,d), 6.98(4H,m), 4.00(2H,t), 2.23(2H,t), 1.70(2H,m), 1.55(2H,m), 1.45(2H,m); m/e 301 (M+H)$^+$; calculated for C$_{17}$H$_{20}$N$_2$O$_2$.HCl. 1.25H$_2$O: C, 56.8; H 6.6; N, 7.8. found: C, 56.8; H, 6.6; N, 7.4%.

EXAMPLE 189

N-[4-[(4,4Pyridyl)piperazin-1-yl]benzoyl]-N-methylglycine, trifluoroacetate

To a solution of ethyl N-[4-[(4-pyridyl)piperazin-1-yl] benzoyl]-N-methylglycinate (78 mg) in methanol (2 ml) as added sodium hydroxide solution (1N, 0.4 ml) and the resultant mixture was stored at room temperature for 1 hour. The pH of the reaction mixture was adjusted to 2 by addition of 2N HCl (aq) (0.45–0.5 ml) and the resultant solution was purified by preparative rp-hplc on a DYNAMAX C-18, 60A [83-201-C] column using an acetonitrile/water mobile phase containing 0.1% trifluoroacetic acid, to give, after lyophilisation, the title compound (46 mg) as a glass: NMR (d$_6$DMSO) δ2.98(3H,s), 3.45(4H,m), 3.86(4H,m), 4.07(2H, s), 6.97(2H,d), 7.23(2H,d), 7.31(2H,m), 8.27(2H,d); mZ 355 (M+H)$^+$; calculated for C$_{19}$H$_{22}$N$_4$O$_3$. 1.0 CF$_3$CO$_2$H. 1.25 H$_2$O: C, 51.4%; H, 5.24%; N, 11.4%; found: C. 51.2%; H, 4.9%; N, 11.2%.

The starting material was prepared as follows:

To a stirred mixture of 4-[(4-pyridyl)piperazin-1-yl]benzoic acid (prepared as in Example 56(i) (311 mg), HOBt.H$_2$O (170 mg) and HBTU (416 mg) in DMF (5 ml) at 0°–5° C. under argon was added diisopropylethylamine (0.75 ml). The ice-bath was removed and the reaction mixture was stirred at room temperature for 15 minutes before solid sarcosine, ethyl ester hydrochloride (154 mg) was added. The reaction mixture was stirred at room temperature under argon overnight then diluted with dichloromethane (30 ml) and water (30 ml). The organic layer was separated and the aqueous layer was re-extracted with dichloromethane (30 ml). The combined organic extracts were washed with water, saturated sodium bicarbonate solution, water, dried (MgSO$_4$) and evaporated. The residue was purified by filtration through a short bed of activated (grade II) alumina by elution with ethyl acetate/methanol, 5:1, to give ethyl N-(4-[(4-pyridyl)piperazin-1-yl[benzoyl]- N-methylglycinate (92 mg) as an amorphous solid: NMR (d$_6$DMSO+CD$_3$CO$_2$D) δ1.18(3H,t), 2.98(3H,s), 3.44(4H,m), 3.79(4H,m), 4.11(4H,m), 6.94 (2H,d), 7.12(2H,d), 7.31(2H,brd), 8.19(2H,d); m/Z 383 (M+H)$^+$.

EXAMPLE 190

N[4-[(4-Pyridyl)piperazin-1-yl]benzoyl]-L-phenylalanine, methyl ester

In a similar manner to Example 189i), 4-[(4-pyridyl) piperazin-1-yl]benzoic acid (311 mg), p-toluene sulphonic acid, monohydrate (418 mg), HOBt.H$_2$O (170 mg), HBTU (416 mg), DMF (5 ml), diisopropylethylamine (1.13 ml) and L-phenylalanine, methyl ester hydrochloride (216 mg) gave, after filtration through a bed of neutral alumina and elution with ethyl acetate/methanol, 6:1, the titled compound as a white crystalline solid (336 mg); m.p. 139°–143.5° C.; NMR (CDCl$_3$) δ32.6(2H,m), 3.50(8H,m), 3.76(3H,s), 5.09(1H,m), 6.46(1H,d), 6.70(2H,m), 6.90(2H,d), 7.13(2H,m), 7.28(3H, m), 7.68(2H,d), 8.31(2H,m); m/z 445 (M+H)$^+$; calculated for C$_{26}$H$_{28}$N$_4$O$_3$. 1.0 H$_2$O: C, 67.5%, H, 6.54%; N, 12.1%; found: C, 67.6%; H, 6.4%; 12.1%.

EXAMPLE 191

N-[4[(4-Pyridyl)piperazin-1-yl]L-phenylalanine

To a solutionof the product of Example 190 (100 mg) in methanol (2.2 ml) was added sodium hydroxide solutiin (1N, 0.44 ml). The resultant mixture was stored at room temperature with occasional swirling of 2.5 hr, then the pH was adjusted to 5 by addition of 2N HCl (aq) (0.22 ml) and 50% aqueous acetic acid (3 drops). The mixture was filtered and evaporated to dryness. The residue was crystallized from hot water containing a trace of methanol to give the title compound as a pale yellow crystalline solid (47 mg); NMR (d$_6$DMSO+CD$_3$CO$_2$D) δ3.05(1H,m), 3.15(1H,m), 3.45(4H,m), 3.77(4H,m), 4.58(1H,m), 6.90(2H,d), 7.12(2H, d), 7.22(5H,m), 7.70(2H,d), 8.19(2H,d); m/Z 431 (M+H)$^+$; calculated for C$_{25}$H$_{26}$N$_4$O$_3$. 0.75 H$_2$O: C, 67.6%; H, 6.24%; N, 12.6%; found: C, 67.6%; H, 6.0%; N, 12.5%.

EXAMPLE 192

(S)-3-[N-[2-Phenenthyl]carboxamido]-3-[4-[4-(4-pyridyl)piperazin-1-yl]]-benzamidopropionic acid To a stirred suspension to benzyl (S)-3-[N-[2-phenethyl] carboxamido]-3-[4-[4-(4-pyridyl)piperazin-1-yl]]]

benzamidopropionate (120 mg) in methanol (3 ml) was added sodium hydroxide solution (1N, 0.5 ml). Within 15 minutes all the solid had dissolved, and the reaction mixture was stirred at room temperature for a further 2 hr. The pH was then adjusted to 5 by addition of 2N HCl (aq) (0.25 ml) and 50% aqueous acetic acid (3 drops). The mixture was filtered and evaporated to dryness. The residue was crystallised from hot water containing a trace of methanol to give the title compound as a pale yellow crystalline solid (66 mg); NMR (d$_6$DMSO+CD$_3$CO$_2$D) δ2.70(4H,m), 3.30(2H,t), 3.56 (4H,m), 3.85(4H,m), 4.73(1H,m), 6.99(2H,d), 7.20(7H,m), 7.80(2H,d), 8.25(2H,d); m/Z 502 (M+H)$^+$; calculated for C$_{28}$H$_{31}$N$_5$O$_4$. 1.25 H$_2$): C, 64.2%; H, 6.44%; N, 13.4%; found: C, 64.2%; H, 6.4%; N, 13.6%.

The starting material was prepared as follows:

i) Boc-L-aspartic acid, 2-phenethylamide, β-benzyl ester (preparation described in Samanen, J. et al (1991), *J. Med. Chem.*, 34, 3114-25) (2 g) was dissolved in a mixture containing dichloromethane (10 ml) and trifluoroacetic acid (10 ml). The resultant pale yellow solution was stored at room temperature for 2 hr after which time the mixture was evaporated to dryness. The oily product was dissolved in dry ether and re-evaporated. This procedure was repeated twice more to give a viscous oily residue containing the trifluoracetic salt of L-aspartic acid, 2-phenethylamide, β-benzyl ester (2.07 g) which was used without further purification.

ii) In a similar manner to Example 189*i*); 4-[[(4-pyridyl) piperazin-1-yl]benzoic acid (311 mg), p-toluene sulphinc acid, monohydrate (627 mg), HOBt.H$_2$O (170 mg), HBTU (416 mg), DMF (15 ml), diisopropylethylamine (1.5 ml) and L-aspartic acid, 2-phenethylamide, β-benzyl ester (440 mg) gave, after purification by flash chromatography on silica, eluting solvent, ethyl acetate/ methanol, 4:1 to 2:1, benzyl (S)-3-(N-[2-phenethyl]-carboxamido)-3-[4[4-(4-pyridyl)piperazin-1-yl]]] benzamidopropionate (268 mg) as a white crytalline solid: NMR (d$_6$DMSO) δ2.70(2H,t), 2.76(1H,m), 2.88(1H,m), 3.25(2H,m), 3.44(4H,m), 3.50(4H,m), 5.08(2H,s), 6.89 (2H,d), 7.02(2H,d), 7.20(5H,m), 7.31(5H,m), 7.78(2H,d), 7.90(1H,t), 8.20(2H,d), 8.36(1H,d); m/Z 592 (M+H)$^+$; calculated for C$_{35}$H$_{37}$N$_5$O$_4$.0.25 H$_2$O: C, 70.5%; H, 6.34%; N, 11.7%; found: C, 70.5%; H, 6.3%; N, 11.7%.

EXAMPLE 193

(R)-3-[N-[2-Phenethyl]carboxamido]-3-[4-[4-(4-pyridyl)piperazin-1-yl]]]-benzamidopropionic acid Following the method of Example 192, but starting from benzyl (R)-3-[N-[2-phenethyl]carobxamido]-3-[4-[4-(4-pyridyl)piperazin-1-yl]]]benzamidopropionate instead of the corresponding (S)-isomer, the titled compound was obtained as a pale yellow crystalline solid in 33% yield: NMR (d$_6$DMSO+CD$_3$CO$_2$D) δ2.71(4H,m), 3.29(2H,t), 3.53 (4H,m), 3.83(4H,m), 4.72(1H,m), 6.99(2H,d), 7.17(7H,m), 7.77(2H,d), 8.24(2H,d); m/Z 502 (M+H)$^+$; calculated for C$_{28}$H$_{31}$N$_5$O$_4$. 1.25 H$_2$O: C, 64.2%; H, 6.44%; N, 13.4%; found: C, 64.2%; H, 6.4%; N, 13.3%.

The starting material was prepared as follows:

i) Boc-D-aspartic acid, 2-phenethylamide, β-benzyl ester (preparation described in Rodriquez, M. et al (1989), *J. Med. Chem.*, 32, 522-8) (1 g) was dissolved in acetonitrile (5 ml) with gently warming, then cooled to room temperature before excess ethereal HCl (5 ml) was added. The reaction mixture was stored at room temperature overnight then evaporated to dryness. The pale yellow oily residue was triturated with dry ether and re-evaporated. This procedure was repeated twice more to give a hygroscopic oil residue containing the hydrochloride salt of D-aspartic acid, 2-phenethylamide, β-benzyl ester (0.55 g) which was used without further purification.

ii) In a similar manner to Example 56, the hydrochloride salt of D-aspartic acid, 2-phenethylamide, β-benzyl ester (363 mg), 4-[(4-pyridyl)piperazin-1-yl]benzoyl chloride (377 mg), diisopropylethylamine (0.87 ml) and DMF (5 ml) gave benzyl (R)-3-[N-[2-phenethyl|carboxamido]-3-[4-[4-4-pyridyl)piperazin-1-yl]]]benzamidopropionate (510 mg) as an off-white, amorphous solid: m/Z 592 (M+H)$^+$.

EXAMPLE 194

(S)-3-[N-(2-Phenethyl)carboxamido]-3-[N-[N-2-[4-(4-pyridyl)piperazin-1-yl]acetyl]glycyl] aminopropionic acid, trifluoroacetate In a similar manner to Example 189, benzyl (S)-3-[N-(2-phenethyl)carbxoamido]-3-[N-[N-2-[4-(4-pyridyl) piperazin-1-yl]acetyl]glycyl]aminopropionate (240 mg), sodium hydroxide solution (1N, 1.4 ml) and methanol (4 ml) gave, after 6 hr, followed by acidification to pH 4, preparative rp-hplc and lyophilisation, the title compound (224 mg) as a colourless glass: NMR (d$_6$DMSO+CD$_3$CO$_2$D) δ2.58 (2H,m), 2.74(2H,t), 3.17(4H,m), 3.31(2H,t), 3.70(2H,m), 3.91(6H,m), 4.62(1H,m), 7.21(7H,m), 8.25(2H;d); m/Z 497 (M+H)$^+$; calculated for C$_{25}$H$_{32}$N$_6$O$_5$. 2.0 CF$_3$CO$_2$H. 1.0 H$_2$O: C, 46.9%; H, 4.89%; N, 11.3%; found: C, 4.67%; H, 4.8%; N, 11.1%.

The starting material was prepared as follows:

i) In a similar manner to Example 192i), N-(N'-Boc-glycyl)-L-aspartic acid, 2-phenethylamide, β-benzyl ester (preparation described in Samanen, J. et al (1991), *J. Med. Chem.*, 34, 3114–25) (370 mg), dichloromethane (2ml) and trifluoroacetic acid (2 ml) gave a hygroscopic oil containing the trifluoroacetate salt of N-glycyl-L-aspartic acid, 2-phenethylamide, β-benzyl ester (340 mg), which was used without further purification.

ii) In a similar manner to Example 189i), 1-(4-pyridyl)-4-carboxymethylpiperazine dihydrochloride (220 mg), HBTU (284 mg), HOBt.H$_2$O (115 mg), DMF (3 ml), diisopropylethylamine (0.53 ml) and the trifluoroacetate salt of N-glycyl-L-aspartic acid, 2-phenethylamide, β-benzyl ester (340 mg) gave, after purification by flash chromatography on silica, eluting solvent, dichloromethane/methanol, 9:1 to 4:1, benzyl (S)-3-(N-[2-phenethyl]carboxamido)-3-[N-[N-2-[4-(4-pyridyl) piperazine-1-yl]acetyl]glycyl]-aminopropionate (249 mg) as a colourless foam: NMR (d$_6$DMSO+CD$_3$CO$_2$D)δ 2.63 (4H,m), 2.69(2H,t), 2.72(2H,m), 3.06(2H,s), 3.25(2H,m), 3.64(4H,m), 3.78(2H,q), 4.62 (1H,m), 5.05(2H,s), 7.06 (2H,d), 7.10–7.35(10H,m), 8.15(2H,d); m/Z 587 (M+H$^+$.

EXAMPLE 195

3-[4-[4-(4-Pyridyl)piperazin-1-yl]butyryl] aminopropionic acid, trifluoroacetate In a similar manner to Example 189, methyl 3-[4-[4-(4-piperazin-1-yl]-butyryl]aminopropionate (163 mg), and sodium hydroxide solution (1N, 1.5 ml) gave, after preparative rp-hplc and lyophilisation, a glassy solid which was crystallised from hot acetonitrile/ether to give the title compound, trifluoroacetate salt (165 mg) as a colourless cystalline solid: m.p. 129°–131° C.; NMR (d$_6$DMSO+ CD$_3$CO$_2$D) δ 1.89(2H,m), 2.19(2H,t), 2.37(2H,t, 3.08(2H, m), 3.25(2H,t), 3.32(4H,m), 3.91(4H,m), 7.26(2H,d), 8.32

(2H,d); m/Z 321 (M+H)⁺; calculated for C₁₆H₂₄N₄O₃. 1.9 CF₃CO₂H: C, 44.3%; H, 4.86%; N, 10.4%; found: C, 44.5%; H, 4.9%; N, 10.3%.

The starting material was prepared as follows:

i) To a stirred suspension of 1-(4-pyridyl)piperazine (5 g) in dry DMF (30 ml) under argon at 0°–5° C. was added, in portions, a solid dispersion of sodium hydride (60%) in mineral oil (1.23 g). On completion of the addition, the ice-bath was removed and the reaction was stirred vigorously at room temperature. After 45 min, a solution of ethyl 4-bromobutyrate (5.85 g) in dry DMF (5 ml) was added and the reaction mixture was stirred at room temperature for 2 hr then diluted carefully with water (50 ml) and poured into dichloromethane (50 ml). The organic layer was separated and the aqueous layer was re-extracted with dichloromethane (50 ml). The combined organic extracts were washed with water, then extracted with 1N HCl(aq) (40 ml). The acidic extract was washed with dichloromethane (40 ml) and the aqueous layer was basified by addition of sodium hydroxide solution (1N, 40 ml) and saturated sodium bicarbonate solution (10 ml). This mixture was then extracted with dichloromethane (50 ml) and the organic extract was washed with water, dried (MgSo₄) and evaporated. The resultant pale yellow oil was dissolved in ether (50 ml) and to this solution was added excess ethereal HCl. An amorphous solid precipitated immediately, which was triturated, collected and washed with dry ether to give ethyl 4-[(4-pyridyl) piperazin-1-yl]-butyrate, dihydrochloride salt (5.09 g) as a white hydrosopic solid: NMR (d₆DMSO+CD₃CO₂D) δ 1.13(3H,t), 1.95(2H,m), 2.38(2H,t), 3.10(2H,m, 3.35(4H, brm), 3.97(4H,brm), 4.02(2H,q), 7.19(2H,d), 8.25(2H,d); m/Z 278 (M+H)⁺.

A mixture of the product of step i) (5 g) and conc. HCl (50 ml) was heated at 100° C. for 45 min. The resultant solution was evaporated to dryness and the residue dissolved again in conc. HCl and heated to 100° C. for a further 45 min. The reaction mixture was evaporated to dryness, and the residue was twice triturated with toluene, and evaporated to dryness, collected and washed with ether. The crude product was crystallised from hot methanol/ether to give 4-[(4-pyridyl)piperazine-1-yl] butyric acid, dihydrochloride as an off-white crystalline solid (3.45 g): m.p. 280°–300° C. (dec); NMR (d₆DMSO) δ 2.00(2H,m), 2.36(2H,t), 3.12(2H,m), 3.00–3.70(4H, vbrm), 3.50–4.50(4H,vbrm), 7.30(2H,d), 8.35(2H,d), 12.2(1H,vbr); m/Z 250 (M+H)⁺; calculated for C₁₃H₁₉N₃O₂.2.0 HCl. 0.5 H₂O: C, 47.1%; H, 6.69%; N, 12.7%; found: C, 47.5%; H, 6.7%; N, 12.5% iii) In a similar manner to Example 189i), the product of step ii) (403 mg), HBTU (474 mg), HOBt.H₂O (190 mg), DMF (5 ml), diisopropylethylamine (1.31 ml) and methyl 3-aminopropionate, hydrochloride (175 mg) gave, after purification by flash chromatography on silica, eluting solvent dichloromethane/methanol, 4:1 to 3:1, methyl 3-[4-[4-(4-pyridyl)-piperazine-1-yl]butyryl] aminopropionate (168 mg) as an amorphous solid: NMR (d₆DMSO+CD₃CO₂D) δ 1.74(2H,m), 2.14(2H,t), 2.42 (2H,t), 2.50(2H,t), 2.62(4H,m), 3.33(2H,t), 3.65(7H,m), 7.12(2H,d), 8.22(2H,d); m/Z 335 (M+H)⁺.

EXAMPLE 196

5-[(4-Pyridyl)piperazin-1-yl]pentanoic acid, dihydrochloride salt

Following the method of Example 195ii), but staring from ethyl 5-[(4-pyridyl)piperazine-1-yl]pentanoate, dihydrochloride salt instead of ethyl 4-[(4-pyridyl)piperazin-1-yl] butyrate, dihydrochloride salt, the title compound was isolated after recrystallisation from wet ethanol, as an off-white crystalline solid in 59% overall yield: m.p. 294°–297° C. (dec); NMR (d₆DMSO+CD₃CO₂D) δ 1.62(2H,m, 1.80(2H, m), 2.32(2H,t), 3.18(2H,m), 3.41(4H,m), 4.05(4H,m) 7.29 (2H,d, 8.34(2H,d; m/Z 264 (M+H)⁺; calculated for C₁₄H₂₁N₃O₂. 2.0 HCl: C, 50.0%; H, 6.89%; N, 12.5%; found: C, 50.5% H, 7.2%; N, 12.2%.

The starting material was prepared as follows:

i) Following the method of Example 195i), but starting from ethyl 5-bromovalerate instead of ethyl 4-bromobutyrate, ethyl 5-[(4-pyridyl-piperazin-1-yl]pentanoate, dihydrochloride salt was isolated as a white hygroscopic solid in 43% overall yield: NMR (d₆DMSO+CD₃CO₂D) δ 1.21 (3H,t), 1.62(2H,m), 1.77(2H,m), 2.38(2H,t), 3.16(2H,m), 3.42(4H,m), 4.05(4H,m), 4.08(2H,q), 7.29(2H,d), 8.34 (2H,d); m/Z 292 (M+H)⁺.

EXAMPLE 197

Methyl 3-[5-[4-(4-pyridyl)piperazine-1-yl]petanoyl] aminopropionate

In a similar manner to Example 189i), the product of Example 196 (840 mg), HBTU (950 mg), HOBt.H₂O (380 mg), DMF (10 ml), diisopropylethylamine (2.6 ml) and methyl 3-aminopropionate, hydrochloride (280 mg) gave, after purification by flash chromatography on neutral alumina, eluting solvent ethyl acetate/methanol, 50:1 to 4:1, the title compound (303 mg) as a white crystalline solid: m.p. 118°–122° C.; NMR (d₆DMSO) δ 145(4H,m), 2.05 (2H,t), 2.27(2H,t, 2.42(6H,m), 3.26(6H,m), 3.58(3H,s), 6.78 (2H,m), 7.83(1H,brt), 8.12(2H,m); m/Z 349 (M+H)⁺; calculated for C₁₈H₂₈N₄O₃: C, 62.0%; H, 8.1%; N, 16.1%; found: C, 62.2%; H, 8.4%; N, 16.0%.

EXAMPLE 198

3-[5-[4-(4-Pyridyl)piperazine-1-yl]pentanoyl] aminopropionic acid

In a similar manner to Example 189, the product of Example 197 (160 mg), methanol (5 ml) and sodium hdyroxide solution (1N, 1.4 ml) gave, after preparative rp-hplc and lyophilisation, a glassy solid which was crystallised from hot acetonitrile/ether to give the title compound, trifluoroacetate salt (160 mg) as a colourless cystalline solid: m.p. 176°–180° C.; NMR (D₆DMSO+CD₃CO₂D) δ 1.64 (4H,m), 2.18(2H,t), 2.45(2H,t), 3.12(2H,t),3.30(2H,t), 3.37 (4H,m), 3.97(4H,m), 7.26(2H,d), 8.33(2H,d); m/Z 335 (M+H)⁺; calculated for C₁₇H₂₆N₄O₃. 2.0 CF₃CO₂H: C, 44.8%; H, 5.02%; N, 9.96%; found: C, 44.6%; H, 5.0%; N, 9.8%.

EXAMPLE 199

4-Oxo-4-[4-[4-(4-pyridyl)piperazine-1-yl]phenyl] aminobutyric acid

To a solution of 1-(4-aminophenyl)-4-(4-pyridyl) piperazine (100 mg) in DMF (8ml) was added succinic anhydride (79 mg). The reaction mixture was stirred at room temperature for 2.5 hr and a precipitate was collected, washed with DMF and ethanol, then dried to give the title compound (106 mg) as a beige-coloured solid: m.p. 263°–264° C.; NMR (d₆DMSO+CF₃CO₂H) δ 2.68(4H,m), 3.80(4H,m, 4.19(4H,m), 7.20(2H,d), 7.56(2H,d), 7.82(2H, d), 8.21(2H,d), 9.62(1H,s); m/Z 355 (M+H)⁺; calculated for

117

$C_{19}H_{22}N_4O_3$. 0.4 $H_2O$: C, 63.1%; H, 6.36%; N, 15.5%; found: C, 63.1%; H, 6.4%; N, 15.7%.

The starting material was prepared as follows:

i) To an intimate mixture of 4-[(4-pyridyl)piperazin-1-yl] benzoic acid (Example 56i)) (500 mg) and hydroxylamine hydrochloride (13.5 mg) was added polyphosphoric acid (16 g). The resultant mixture was heated to 160° C. and maintained at that temperature with stirring for 30 min. The mixture was then allowed to cool to approximately 100° C. before crushed ice, followed by 15% potassium hydroxide solution to give a pH 11 of were added. The suspension was allowed to cool to room temperature and the precipitate was collected, washed with water and air-dried to give 1-(4-aminophenyl)-4-(4-pyridyl) piperazine (159 mg) as a light brown solid: m.p. 204°–208° C.; NMR ($d_6$DMSO) δ 3.00(4H,m), 3.41(4H, m), 4.65(2H,brs), 6.51(2H,d), 6.73(2H,m), 6.85(2H,d), 8.18(2H,d); m/Z 255 M+H) $^+$.

EXAMPLE 200

4-[4-[4-(4-Pyridyl)piperazine-1-yl]phenoxy]butyric acid, hydrochloride salt

A mixture of the product from Example 51 (1.5 g) and methanol (80 ml) was heated to reflux with stirring, and solid pyridine hydrochloride (0.5 g) was added. Heating was stopped and ethyl acetate (10 ml) was added. The reaction mixture was evaporated until a slight turbidity was observed. On further cooling, a precipitate formed which was collected, washed with ethyl acetate and dried to give the title compound (1.33 g) as a beige solid: m.p. >240° C. (dec); NMR ($d_6$DMSO) δ 1.90(2H,m), 2.36(2H,t), 3.17(4H, m), 3.83(4H,m), 3.91(2H,t), 6.89(4H,q), 7.26(2H,d), 8.25 (2H,d), 1.21(1H,br), 13.75(1H,br); m/Z 342 (M+H)$^+$; calculated for $C_{19}H_{23}N_3O_3$. 1.0 HCl: C, 60.4%; H, 6.4%; N, 11.1%; found: C, 60.0%; H, 6.4%, N, 10.8%.

EXAMPLE 201

N-2-Methoxyethyl-4-[4-[4-(4-pyridyl)piperazine-1-yl]phenoxy]butyramide, trifluoroacetate A solution of methoxyethylamine (0.9 ml) in dry dichloromethane (5 ml) was added dropwise to a stirred solution of trimethylaluminium, 2M in toluene (5 ml) at 5°–10° C. under argon. On completion of the addition, the ice-bath was removed and the reaction mixture was stirred at room temperature for 1 hr before a solution of the product of Example 50 (0.62 g) in dichloromethane (5 ml) was added dropwise. The reaction mixture was heated to reflux under argon and stirred at reflux for 2 hr. The reaction mixture was then cooled to room temperature and diluted with dichloromethane (20 ml). A solution of methanol/ dichloromethane, 1:1 (3 ml) was then added dropwise with stirring. The reaction mixture was further diluted with dichloromethane (10 ml), methanol, (3 ml) and water (5 ml). The organic layer was separated, dried ($Na_2SO_4$) and evaporated to dryness. The residue was purified by preparative rp-hplc on a DYNAMAX C-18, 60A [83-201-C] column using an acetonitrile/water mobile phase containing 0.1% trifluoroacetic acid, to give, after lyophilisation, the title compound (56 mg) as an off-white solid: NMR ($d_6$DMSO) δ 1.89(2H,m), 2.22(2H,t), 3.18(6H,m), 3.23(3H,s), 3.32(2H, t), 3.85(6H,m), 6.90(4H,q), 7.28(2H,d), 7.88(1H,brt), 8.25 (2H,d); m/Z 399 (M+H)$^+$; calculated for $C_{22}H_{30}N_4O_3$. 1.7 $CF_3CO_2H$: C; 51.5%; H, 5.4%; N, 9.5%; found: C, 51.4%; H, 5.6%; N, 9.3%.

118

EXAMPLE 202

4-[2-[4-(4-Pyridyl)piperazine-2-one-1-yl]acetyl] phenoxyacetic acid monohydrochloride A solution of methyl 4-[2-(piperazin-2-one-1-yl)acetyl] phenoxyacetate (0.347 g), 4-chloropyridine hydrochloride (0.19 g) and triethylamine (0.178 g) in water (8 ml) and dioxan (1 ml) was heated on a steam bath for 2 hours and then evaporated to dryness. The residue was triturated with water (2 ml) and filtered. The solid thus obtained was recrystallised from water to give the title compound (0.187 g). m.p. 275°–277° C.; NMR ($d_6$DMSO) δ 8.33(2H, d), 8.0(2H,d), 7.21(2H,d), 7.1(2H,d), 4.97(2H,s), 3.94(2H,m), 3.59(2H,m); m/e 370(M+H$^+$; calculated for $C_{19}H_{20}N_3O_5Cl$.0.75 $H_2O$: C, 54.4; H, 5.0; N, 10.0. Found: C, 54.5H, 5.3; N, 9.5%.

The starting material was prepared as follows:

i) To a vigorously stirred mixture of piperazinone (3.23 g), potassium carbonate (4.46 g) in water (15 ml) and tert-butanol (15 ml) at room temperature, was added portionwise over 5 minutes, di tert-butyl dicarbonate (7.75 g). The mixture was stirred for 2 hours. Ethyl acetate (20 ml) was added to extract the solid thus formed and the organic layer separated, filtered through phase separating paper and evaporated. The solid residue recrystallised from ethyl acetate to give 4-tert-butoxycarbonylpiperazin-2-one (5.31 g), m.p. 157°–159° C.; NMR ($d_6$DMSO) δ 8.0(1H,br), 3.81(2H,s), 3.45(2H,t), 3.17(2H,m), 1.4(9H, s); m/e 207 (M+H)$^+$.

ii) To a stirred suspension of the product of step i) (0.5 g) in dry DMF (3 ml) under an argon atmosphere, was added sodium hydride (60% dispersion in mineral oil, 0.1 g). After 1 hour at room temperature, methyl 4-bromoacetylphenoxyacetate (0.72 g) was added and the solution stirred for 1½ hours. The mixture resulting was partitioned between water and ethyl acetate. The organic layer was separated, washed with water and filtered through phase separating phase. Evaporation of the solvent gave an oil which was purified by flash column chromatography, the product being eluted with 1/1 v:v ethyl acetate/hexane to give methyl 4-([2-(4-tert-butoxycarbonyl)piperazin-2-one-1-yl]acetyl) phenoxyacetate as a solid (0.32 g), m.p. 81°–82° C.; NMR ($CDCl_3$) δ 7.97(2H,m), 6.98(2H,m), 4.83(2H,s), 4.71(2H, s), 4.18(2H,s), 3.81(3H,s), 3.72(2H,t), 3.42(2H,t), 1.47 (9H,s).

iii) A solution of the product from step ii) (2.2 g) in TFA (10 ml) was kept at room temperature for 1 hour and then evaporated to dryness. The residue was partitioned between ethyl acetate and aqueous sodium carbonate. The organic layer was filtered through phase separating paper and solvent evaporated. The residue was triturated with ethyl acetate to give a solid, m.p. 128°–132° C. NMR ($d_6$DMSO) δ 7.95(2H, d), 7.06(2H,d), 4.9(2H,s), 3.7(3H, s), 3.3(2H,m), 2.9(2H,m).

EXAMPLE 203

RS 3-Methyl-4-[4-[4-(4-pyridyl)piperazin-1-yl] phenoxy]butyric acid trifluoroacetate To a stirred suspension of 4-[4-(4-pyridyl)piperazin-1-yl] phenol (1.02 g) in dry DMF (10 ml) was added solution hydride (60% dispersion in mineral oil, 0.16 g) and the mixture stirred for 1 hour at room temperature. To the resulting solution was added ethyl-4-bromo-3-methylbutyrate and the mixture stirred for 16 hours. Solvent was evaporated and the residue partitioned between water and dichloromethane. Insoluble material was removed by centrifugation. The organic layer was filtered through phase separating paper (Whatman IPS) and the residue was purified by flash chromatography on silica gel by elution with methanol/dichloromethane/concentrated ammonia (50/950/5) to give ethyl 3-methyl-4-[4-[4-(4-pyridyl)piperazin-1-yl]phenoxy]butyrate (0.27 g) which was hydrolysed in methanol (3 ml) and aqueous sodium hydroxide (1N, 2 ml) for 2 hours at room temperature. The solution was evaporated and the residue purified by reverse phase h.p.l.c (water/acetonitrile/0.1% TFA gradient) to give a glass which crystallised on trituration with ether to give the title compound (0.08 g): m.p. 169°–171° C.; NMR ($d_6$DMSO) δ 13.45(1H, br), 12.07 (1H.br), 8.27(2H,d), 7.28(2H,d), 6.9(4H,m), 3.80 (6H,m), 3.16(4H,t), 2.45(1H,m), 2.37(1H,m), 2.12(1H,m), 1.0(3H,d); m/e 356(M+H)$^+$; calculated for $C_{22}H_{25}N_3O_4F_3 \cdot 0.5\ H_2O$: C, 55.2; H, 5.6; N, 8.9 Found: C, 55.3; H, 5.6; N, 8.7%.

EXAMPLE 204

RS-4-[4-[4-(4-Pyridyl)piperazin-1-yl]phenoxy]-3-vinylbutyric acid, sodium salt

A solution of RS methyl 4-[4-[4-(4-pyridyl)piperazin-1-yl]phenoxy]-3-vinylbutyrate (0.29 g) in 1N sodium hydroxide solution (2.3 ml) and methanol (5 ml) was kept at room temperature for 4 hours. The solution was evaporated and water (2 ml) added to the solid residue. The solid thus obtained was filtered and washed with acetone and ether to give the title compound (0.042 g): m.p. 293°–295° C.; NMR ($d_6$DMSO) δ 8.18(2H,d), 6.9(6H,m), 5.88(1H,m), 4.96(2H, m), 4.0(1H,m), 3.77(1H,t), 3.41(2H,m), 3.10(2H,m), 2.84 (1H,m), 1.98(2H,d), m/e 470(M+H)$^+$; calculated for $C_{21}H_{24}N_3O_3Na \cdot H_2O$: C, 61.9; H, 6.4; N, 10.3. Found: C, 62.1; H, 6.4; N, 10.5%.

The starting material was prepared as follows:
i) A solution of RS 3-vinylbutyrolactone (3.5 g) and sodium acetate (2.56 g) in methanol (30 ml) was kept for 20 hours. Solvent was evaporated and the residue was partitioned between water and ether. The aqueous layer was extracted twice more with ether and the extracts combined, filtered through phase separating paper and evaporated. The residue was purified by filtration chromatography on silica gel (Merck 7736) starting with ⅑ ethyl acetate/hexane and progressing to ⅙ ethyl acetate/hexane as eluent to give methyl 4-hydroxy-3-vinylbutyrate as an oil; NMR (CDCl$_3$) δ 5.73(1H,m), 5.15(2H,m), 3.68(3H,s), 3.60(2H,t), 2.76(1H,m), 2.48 (2H,m), 1.69(1H,t);; m/e 145(M+H)$^+$.
ii) To stirred suspension of 4-[4-[4-(4-pyridyl)piperazin-1-yl]phenol (1.98 g) in dichloromethane (30 ml) at 15° C. was added triphenylphosphine (2.04 g) followed by dropwise addition of diethyl azodicaboxylate (1.35 g). The mixture was stirred until complete solution was obtained. Methyl-4-hydroxy-3-vinylbutyrate (1.2 g) was added drowise and the mixture stirred for 4 hours. The solid which had precipitated during the reaction was the starting phenol and was filtered off. The filtrate was evaporated and the residue treated with ethyl acetate (20 ml) and filtered. The filtrate was extracted with 2N hydrochloric acid (2×10 ml) and the aqueous layer separated and basified with 0.89 S.G. ammoniium hydroxide. The precipitate was extracted twice into ethyl acetate and the combined extracts filtered through phase separating paper and evaporated. The residue was purified by flash chromatography on silica gel, eluting with methanol/dichloromethane/0.89 S.G. ammonium hydroxide v:v:v 7.5/92.5/0.75 to give RS methyl 4-[4-[4-(4-pyridyl)piperazin-1-yl]phenoxy]-3-vinylbutyrate (0.29 g); NMR (CDCl$_3$) δ 8.3(2H,d), 6.88(4H,m), 6.70(2H,d), 5.85(1H, m), 5.20(2H,m), 3.90(2H,m), 3.67(3H,s), 3.48(2H,m), 3.18(2H,m), 3.06(1H,m), 2.68(1H,m), 2.47(1H,m), 1.80 (1H,br); m/e 382 (M+H)$^+$.

EXAMPLE 205

Ethyl 4-[2-allyl-4-[4-(4-pyridyl)piperazin-1-yl]phenoxy]butyrate

In a similar manner to Example 50 but starting from 2-allyl-4-[4-(4-pyridyl)piperazin-1-yl]phenol, the title compound was prepared in 50% yield as a solid, m.p. 53°–55° C. NMR (CDCl$_3$) δ 8.3(2H,d), 6.83(1H,m), 6.79(2H,d), 6.71(2H,d,d), 6.0(1H,m), 5.1(2H,m), 4.15(2H,q), 3.98(2H, t), 3.49(4H,m), 3.39(2H,d), 3.19(4H,m), 2.53(2H,t), 2.11 (2H,q), 1.76(3H,t), m/e 410(M+H)$^+$; calculated for $C_{24}H_{31}N_3O_3 \cdot 0.5\ H_2O$: C, 68.9; H, 7.7; N, 10.0. Found: C, 68.8; H, 7.7; N, 9.9%.

The starting material was prepared as follows:
i) Sodium hydride (60% dispersion in mineral oil, 0.4 g) was added to a stirred suspension of 4-[4-(4-piperazin-1-yl]phenol (2.55 g) in DMF (25 ml) and the mixture stirred for 20 minutes at room temperature. Allyl chloride (0.756 g) was added dropwise and stirring continued for 20 hours. Ice-water (75 ml) was added and the mixture extracted three times with ethyl acetate. The combined extracts were washed with water and brine, dried (MgSO$_4$) and evaporated. The residue was triturated with hexane and filtered to give 4-[4-(4-pyridyl)piperazin-1-yl]phenol allyl ether (2.5 g) as a solid; NMR ($d_6$DMSO) δ 8.18(2H, dd), 6.8–7.0(6H,m), 5.92–6.13(1H,m), 5.2–5.45(2H,m), 4.5(2H,m), 3.45(4H,m), 3.11(4H,m).
ii) The product from step i) (5 g) was heated under argon in gently refluxing diphenyl ether (15 g) for 2½ hours. The mixture was cooled to room temperature and ether (70 ml) was added. The solid material was filtered and purified by flash chromatography on silica gel, eluting with methanol/dichloromethane (¼ v/v) to give 2-allyl-4-(4-pyridyl)piperazin-1-yl]phenol (0.88 g) as a solid, m.p. 180°–182° C.; NMR ($d_6$DMSO) δ 8.88(1H,s), 8.19(2H,dd), 6.87(2H, dd), 6.7(3H,m), 5.88–6.03(1H,m), 3.44(4H,t), 3.28(2H, d), 3.05(4H,t); m/e 296 (M+H)$^+$.

EXAMPLE 206

4-[2-Allyl-4-[4-pyridyl)piperazin-1-yl]phenoxy] butyric acid

In a similar manner to Example 51, but starting from the product of Example 205, the title compound was prepared as solid in 61% yield; m.p. 209°–210° C. (dec); NMR ($d_6$DMSO) δ 8.19(2H,d), 6.84(5H,m), 5.82–6.08(1H,m), 4.92–5.12(2H,m), 3.91(2H,t), 3.44(4H,t), 3.3(2H,d), 3.1(4H, t), 2.4(2H,t), 1.93(2H,t); m/e 382 (M+H)$^+$; calculated for $C_{22}H_{27}N_3O_3$: C, 69.3; H, 7.13; N, 11.0. Found: C, 69.2; H, 7.3; N, 11.2%.

EXAMPLE 207

Ethyl 4-[2-n-propyl-4-[4-(4-pyridyl)piperazin-1-yl]phenoxy]butyrate

In a similar manner to Example 50, but starting from 2-n-propyl-4-[4-(4-pyridyl)piperazin-1-yl]phenol, the title compound was prepared in 24% yield as a solid, m.p.

65°–67° C.; NMR (CDCl$_3$) δ 8.29(1H,d), 6.8(1H,d), 6.73 (2H,d), 6.7(2H,d), 4.13(2H,q), 3.94(2H,t), 3.46(4H,t), 3.18 (4H,t), 2.52(4H,m), 2.09(2H,m), 1.54(2H,m), 1.24(3H,t), 0.94(3H,t); m/e 412(M+H)$^+$.

The starting material was prepared as follows:

The product from Example 205ii) (0.74 g) in ethanol (25 ml) and 1N hydrochloric acid (2.5 ml) was hydrogenated at room temperature and atmospheric pressure over 10% palladium charcoal (0.15 g) until uptake of hydrogen was complete. Catalyst was removed by filtration through diatomaceous earth and the filtrate evaporated. The residue was trituratee with a mixture of ethyl acetate (25 ml) and saturated sodium bicarbonate solution (25 ml) and the insoluble solid was filtered and washed with water and ethyl acetate. The aqueous layer of the filtrate was extracted twice with dichloromethane and the combined organic extracts evaporated. The residue was combined with the ethyl acetate-insoluble material and treated with boiling ethanol (40 ml), unsoluble material being removed by filtration. Evaporation of the filtrate gave 2-n-propyl-4-[4-(4-pyridyl) piperazin-1-yl]phenol (0.7 g) as a solid NMR (d$_6$DMSO) δ 8.84–8.68 (1H,m), 8.18(2H,d), 6.82 (2H,m), 6.7(3H,m), 4.1(1H,m), 3.42(4H,t), 3.17(3H,s), 3.05(4H,t), 2.48 (DMSO), 1.55(2H,m), 0.89(3H,t).

EXAMPLE 208

4-[2-n-Propyl4-[4-(4-pyridyl)piperazin-1-yl] phenoxy]butyric acid

In a similar manner to Example 51, but starting from the product of Example 207 was prepared the title compound in 64% yield; m.p. 207°–209° C. (from isopropanol); NMR (d$_6$DMSO) δ 8.18(2H,d), 6.7–6.92(5H,m), 3.91(2H,t), 3.45 (4H,t), 3.10 (4H,t), 2.5(DMSO), 2.4(2H,t), 1.91(2H,?), 1.54 (2H,m), 0.9(3H,t),+isopropanol (0.69 mole %) at 3.79 and 1.04; m/e 384(M+H)$^+$. Calculated for C$_{22}$H$_{29}$N$_3$O$_3$· 0.7C$_3$H$_7$O: C, 68.0; H, 8.2; N, 9.9. Found C, 68.1; H, 8.2; N, 9.9%.

EXAMPLE 209

Ethyl 4-[2-methyl-4-[4-(4-pyridyl)piperazin-1-yl] phenoxy]butyrate

In a similar manner to Example 50, but starting from 2-methyl-4-[4-(4-pyridyl)piperazin-1-yl]phenol dihydrochloride was prepared the title compound in 29% yield as a gum; NMR (CDCl$_3$) δ 8.3(2H,m), 6.45–6.35(5H,m), 4.14 (2H,q), 3.87(2H,t), 3.14(4H,m), 2.53(2H,t), 2.21(3H,s), 2.11 (2H,m), 1.24(3H,t); m/e 384(M+H)$^+$.

The starting material was prepared as follows:

i) Carbonyl dimidazole (5 g) was added portionwise to a stirred suspension of N-benzyliminodiacetic acid (3.14 g) in dry THF (50 ml) at room temperature under argon. After 5 minutes, the mixture was heated at gentle reflux for 15 minutes and (4-amino-2-methyl)phenylbenzylether (3.0 g) added and the mixture stirred at reflux for 17 hours. Solvent was evaporated and the residue was stirred with ethyl acetate (100 ml) and water (150 ml) for 1½ hours. The solid was filtered, washed with water and dried to give 4-[4-benzyl-2,6-diketopiperazin-1-yl]-2-methylphenylbenzylether (4.7 g); m.p. 118°–126° C. (dec); NMR (CDCl$_3$) δ 7.1–7.32(10H, m), 6.78(3H,s), 4.93(2H,s), 3.56(2H,s), 3.4(4H,s), 2.12(3H,s); m/e 373 (M+H)$^+$.

ii) To a solution of the product of step i) (2.9 g) in dry THF (50 ml) was added lithium aluminium hydride (0.6 g) and the mixture heated at reflux for 1½ hours. The mixture was allowed to cool and more (0.3 g) lithium aluminium hydride added and reflux continued for a further 1½ hours. The mixture was cooled and water (0.9 ml) added followed by sodium hydroxide solution (1N, 3.6 ml) and the mixture refluxed for 10 minutes. The solid was filtered and washed with THF. The filtrate and washings were evaporated and the residue purified by flash chromatography on silica gel, eluting with 5% ethyl acetate in dichloromethane increasing to 25% ethyl acetate. Thus was obtained [2-methyl-4-{4-(benzyl)piperazin-1-yl}] phenylbenzyl ether as a solid (1 g); m.p. 118°–120° C.; NMR (CDCl$_3$) δ 7.2–7.5(10H,m), 6.82(1H,d), 6.80(1H, d), 6.7(1H,m), 5.01(2H,s), 3.1(4H,m), 2.53(3H,s); m/e 373(M+H)$^+$.

iii) A suspension of the product of step ii) (1 g) in 1,2-dichloroethane (25 ml) was cooled in ice-water and treated with 1-chloroethylchloroformate (0.77 g). The mixture was allows to warm to room temperature, stirred for 30 minutes and heated at reflux for 30 minutes. Methanol (20 ml) was added and the mixture refluxed again for 30 minutes and evaporated. The residue was triturated with ether and filtered. The solid was washed with ether and dried to give [2-methyl-[4-piperazin-1-yl] ]phenylbenzylether hydrochloride (0.95 g); m.p. 195°–198° C.; NMR (d$_6$DMSO) δ 9.44(2H,bs), 7.3–7.5 (6H,m), 6.98(2H,m), 5.08(?,s), 4.98(4H,bs), 3.38(4H,d), 2.2(3H,s); m/e 281 (M+H)$^+$.

iv) A mixture of the product of step iii) (0.95 g), 4-chloropyridine hydrochloride (0.46 g) and triethylamine (0.615 g) in water (10 ml) was heated at 100° C. for 3 hours. More 4-chloropyridine (0.34 g) and triethylamine (0.3 ml) was added and reflux continued for a further 3 hours. The solution was cooled and extracted with dichloromethane (2×15 ml). The organic layer was evaporated and the residue was purified by flash chromatography on silica gel, eluting with 5% methanol in dichloromethane, containing 0.4% concentrated ammonia, to give [2-methyl-4-[4-(4-pyridyl)piperazin-1-yl]]phenylbenzyl ether (0.26 g); as a solid; NMR (d$_6$DMSO) δ 8.19(2H,d), 7.25–7.5(5H,m), 6.88(4H,m), 6.74(1H,m), 5.03(2H,s), 3.44(4H,bt), 3.1(4H,bt), 2.18 (3H,s); m/e 360 (M+H)$^+$.

v) A solution of the product of step iv) (0.52 g) in ethanol (20 ml) containing 2N hydrochloric acid (2 ml) was stirred with 10% palladium/carbon (0.16 g) under an atmosphere of hydrogen until hydrogen uptake was complete. The mixture was filtered and the filtrate evaporated. The residue was triturated with hot ethyl acetate and filtered to give, as a solid, 2-methyl-4-[4-(4-pyridyl)piperazin-1-yl] phenol dihydrochloride (0.55 g); NMR (d$_6$DMSO) δ 8.25(2H,d), 7.24(2H,d), 7.12(2H,bd), 6.8(1H,d), 4.02 3.46(4H,m), (4H,m), 2.1(3H,s); m/e 270(M+H)$^+$.

EXAMPLE 210

4-[2-Methyl-4-[4-(4-pyridyl)piperazin-1-yl] phenoxy]-butyric acid

In a similar manner to Example 51, but starting from the product of Example 209, the title compound was obtained in 80% yield as a solid, m.p. 261°–262° C.; NMR (d$_6$DMSO) δ 8.18(2H,d), 6.7–6.9(2H,m), 3.9(2H,t), 3.43(4H,bt), 3.1 (4H,bt), 2.39(2H,t), 2.13(3H,s), 1.72(2H,m; m/e 356 (M+H)$^+$. Calculated for C$_{20}$H$_{25}$N$_3$O$_3$: C, 67.6, H, 7.1; N, 11.8. Found: C, 67.4; H, 6.9; N, 12.2%.

EXAMPLE 211

RS Methyl 2-t-butoxycarbonylamino-4-[4-[4-(4-pyridyl)piperazine-1-yl]phenoxy]butyrate In a similar manner to Example 50, but starting from RS methyl 4-bromo-2-t-butoxycarbonylaminobutyrate, the title compound was prepared in 65% yield as an oil; NMR (CDCl$_3$) δ 8.31(2H,d), 6.9(4H,m), 6.71(2H,m), 5.3(1H,br), 4.5(1H,bd), 4.01(2H,t), 3.77(3H,s), 3.5(4H,m), 3.21(4H,m), 2.3(2H,m), 1.46(9H,s); also signals at 6.03, 2.97 and 2.9 (DMF) and 1.8(H$_2$O); m/e 471 (M+H)$^+$. Calculated for C$_{25}$H$_{34}$N$_4$O$_5$. 0.5DMF. 0.5H$_2$O: C, 61.7; H, 7.5; N, 12.2. Found: C, 61.8; H, 7.2; N, 11.9%.

The starting material was prepared as follows:

i) A solution of RS-methyl-N-butoxycarbonyl homoserinate (1.7 g) and carbon tetrabromide (3.6 g) in dichloromethane (20 ml) was stirred at 5° C. Triphenylphosphine (3.77 g) was added portionwise over 5 minutes. After 2 hours at room temperature the dark solution was evaporated and the residue triturated with ether/hexane (1/1, 30 ml) until a solid was obtained. The solid was filtered and the filtrate evaporated. The residue was purified by flash chromatography, the product being eluted with 25% ethyl acetate/hexane to give RS methyl 4-bromo-2-butyloxycarbonylaminobutyrate (0.41 g) as an oil; NMR (CDCl$_3$) δ 5.16(1H,br), 4.45(1H,m), 3.8(3H,s), 3.45(2H,t), 2.52–2.11(2H,m), 1.48(9H,s); m/e 296 (M+H)$^+$.

EXAMPLE 212

RS 2-t-Butoxycarbonylamino-4-[4-[4-(4-pyridyl) piperazin-1-yl]phenoxy]butyric acid In a similar manner to Example 51, but starting from the compound of Example 211, there was obtained in 58% yield, the title compound as a solid; m.p. 198°–207° C.; NMR (d$_6$DMSO) δ 8.2(2H,d), 6.91(6H,m), 4.06(1H,m), 3.92(2H, t), 3.48(4H,t), 3.12(4H,t), 2.2–1.84(2H,m), 1.37(9H,s); m/e 457(M+H)$^+$. Calculated for C$_{24}$H$_{32}$N$_4$O$_5$.H$_2$O: C, 60.7; H, 7.2; N, 11.8. Found: C, 60.7; H, 7.2; N, 11.7%.

EXAMPLE 213

RS Methyl 2-amino-4-[4-[4-(4-pyridyl)piperazin-1-yl]phenoxy]butyrate

The compound of Example 211 (0.96 g) in TFA (10 ml) was kept at room temperature for 2 hours. The solution was evaporated and the residue dissolved in water (15 ml) and the solution basified with sodium carbonate. The mixture was extracted three times with dichloromethane. Evaporation of the combined extracts gave the title compound (0.56 g); m.p. 125°–127° C.; NMR (d$_6$DMSO) δ 8.2(2H,d), 6.92 (6H,m), 4.0(2H,m), 3.64(3H,s), 3.46(4H,t), 3.15(4H,t), 2.04 (2H,m), 1.84(1H,m); m/e 371(M+H)$^+$. Calculated for C$_{20}$H$_{26}$N$_4$O$_3$. 0.75 H$_2$O: C, 62.5; H, 7.17; N, 14.6. Found: C, 62.8; H, 6.8; N, 14.3%.

EXAMPLE 214

4-[2-[4-(4-Pyridyl)piperazin-2-one-1-yl]acetyl] phenoxyacetic acid, sodium salt

The title compound of Example 61 (0.25 g) in methanol (5 ml) was treated with aqueous sodium hydroxide (1N, 0.65 ml) and the mixture kept at room temperature for 6 hours. The solid thus formed was filtered and washed with methanol to give the title compound (0.18 g); m.p. 317°–318° C.; NMR (d$_6$DMSO) δ 8.2(2H,d), 7.89(2H,d), 6.91(2H,d), 6.83 (2H,d), 4.89(2H,s), 4.21(2H,s), 4.01(2H,s), 3.68(2H,m), 3.51(2H,m); m/e 392(M+H)$^+$; calculated for C$_{19}$H$_{18}$N$_3$O$_5$Na. 0.25H$_2$O: C, 57.6; H, 4.6; N, 10. Found: C, 57.2; H, 4.6; N, 10.4%.

EXAMPLE 215

Ethyl 4-[2-[4-(4-pyridyl)piperazin-2-one-1-yl] acetyl]phenoxyacetate

A crude sample of the product of Example 62 (3.4 g) was treated with a solution, at 0° C., made by adding thionyl chloride (2.25 g) dropwise to ethanol (45 ml) with stirring at below 0° C. The mixture was stirred at room temperature for 2 hours, heated at gentle reflux for 2½ hours, and evaporated. The residue was treated with water and adjusted to pH6 with aqueous sodium bicarbonate solution. The gum which precipitated was separated and the aqueous solution was adjusted to pH8 and extracted with dichloromethane (2×50 ml). The combined extracts were washed with brine, dried and evaporated. The residue was purified by chromatography using a 10 g. Mega Bond Elut silica gel column, eluting with 5% methanol/dichloromethane/0.5% triethylamine to give the title product as a solid (0.2 g); m.p. 163°–165° C.; NMR (CDCl$_3$) δ 8.34(2H,m), 6.98(2H,m)(, 6.63(2H,m), 4.89(2H,s), 4.7(2H,s), 4.29(2H,q), 4.1(2H,s), 3.7(2H,m), 3.6(2H,m), 1.31(3H,t); m/e 398(M+H)$^+$; calculated for C$_{21}$H$_{23}$N$_3$O$_5$: C, 63.5; M, 5.83; N, 10.6. Found: C, 61.5; H, 5.9; N, 10.5%.

EXAMPLE 216

Ethyl N 4-[2-(4-(4-pyridyl)piperazin-2-one-1-yl) acetyl]phenoxyacetylglycinate

The compound of Example 62 (0.37 g) was stirred in DMF (10 ml) with hydroxybenzotriazole (0.17 g) and the mixture cooled in ice-water. 1-(3-Dimethylaminopropyl)-3-ethylcarbodiimide hydrochloride (0.14 g) was added, followed by triethylamine (0.14 ml) and the mixture stirred for 30 minutes. Glycine ethyl ester hydrochloride (0.15 g) was now added, followed by triethylamine (0.28 ml). After ten minutes stirring in the cold, the mixture was allowed to warm to room temperature, stirred for two days and evaporated. Water (10 ml) was added to the residue and sodium bicarbonate added to pH 6–7. The mixture was evaporated and the residue purified by chromatography on a Mega Bond Elut silica gel column (10 g), eluting with 2%–20% methanol/dichloromethane. The product was recrystallised from ethanol to give the title compound as a solid (36 mg); m.p. 209°–211° C.; NMR (d$_6$DMSO) δ 8.55(1H,t), 8.2(2H, brd), 7.99(2H,m), 7.12(2H,m), 6.86(2H,d), 4.92(2H,s), 4.11 (2H,q), 4.02(2H,s), 3.9(2H,d), 3.2(2H,m), 3.52(2H,m), 1.2 (3H,t); m/e 455(M+H); calculated for C$_{23}$H$_{26}$N$_4$O$_6$: C, 60.8; H, 5.77; N, 12.3. Found: C, 60.6; H, 5.7; N, 12.5%.

EXAMPLE 217

Ethyl 4-[2-nitro-4-[4-(4-pyridyl)piperazin-1-yl] phenoxy]butyrate

Sulphur acid (98%, 2.5 ml) was added slowly to the compound of Example 50 (1 g) with stirring at room temperature. The solution was cooled to below 5° C. and a mixture of nitric acid (0.18 ml) and sulphuric acid (0.18 ml) was added dropwise. The solution was stirred at below 10° C. for 1½ hours, poured onto ice and basified with ammonia solution to pH10. The mixture was extracted with ethyl acetate (2×50 ml) and the extract washed with water, dried (MgSO$_4$) and evaporated. The residue was purified by flash chromatography on silica gel, the product being eluted with 5%–10% methanol/dichloromethane to give the title product as an oil (0.18 g); NMR (CDCl$_3$) δ 8.32(2H,d), 7.41(1H,d), 7.14(1H,m), 7.04(1H,d), 6.77(2H,m), 4.17–4.14(4H,m), 3.51–3.28 (8H,m), 2.57(2H,t), 2.14(2H,m), 1.28(3H,t), plus H$_2$O (1.87); m/e 415(M+H)$^+$; calculated for C$_{21}$H$_{26}$N$_4$O$_5$.0.25H$_2$O: C, 60.1; H,6.3; N, 13.1. Found: C, 60.2; H, 6.3; N 13.2%.

EXAMPLE 218

RS Methyl 2-n-butanesulphonylamino-4-[4-[4-(4-pyridyl)piperazin-1-yl]phenoxy]butyrate n-Butanesulphonychloride (0.233 g) was added to a stirred solution of the compound of Example 213 (0.5 g) and triethylamine (0.15 g) in dichloromethane (15 ml) at room temperature. The solution was kept for 2 days and subjected to flash column chromatography on silica gel. The product was kept for 2 days and subjected to flash column chromatography on silica gel. The product was eluted with methanol/dichloromethane/0.88SG ammonia (7/93/0.7) v:v:v to give, after trituration with ether, the title compound in 58% yield as a solid; m.p. 124°–125° C.; NMR (CDCl$_3$) δ 8.3(2H,d), 6.88(4H,q), 6.72(2H,m), 5.18(1H,brd), 4.16 (1H,brq), 4.08(2H,t), 3.8(3H,s), 3.47(4H,m(, 3.18(4H,m), 2.98(2H,m), 2.28(2H,m), 1.73(2H,m), 1.45–1.27(2H,m), 0.9 (3H,t); m/e 491 (M+H)$^+$; calculated for C$_{24}$H$_{34}$N$_4$O$_5$S: C, 58.8; H, 7.0; N, 11.4. Found: C, 58.4; H, 7.0; N, 11.1%.

EXAMPLE 219

RS 2-n-Butanesulphonylamino-4-[4-[4-(4-pyridyl) piperazin-1-yl]phenoxy]butyric acid In a similar manner to Example 51, but starting from the compound of Example 218, was prepared the titled compound in 58% yield as a solid; m.p. 251°–252° C.; NMR (d$_6$DMSO) δ 8.18(2H,d), 7.3(1H,vbr), 6.9(6H,m), 3.97(2H, t), 3.9(1H,m), 3.45(4H,t), 3.11(4H,t), 2.9(2H,t), 2.12(1H,m), 1.92(1H,m), 1.58(2H,m), 0.81(3H,t); m/e 477(M+H)$^+$; calculated for C$_{23}$H$_{32}$N$_4$O$_5$S. 0.5 H$_2$O: C, 56.9; H, 6.8; N, 11.5. Found: C.57.0; H, 6.8; N, 11.3%.

EXAMPLE 220

RS 3-Benzyl-4-[4-[4-(4-pyridyl)piperazin-1-yl] phenoxy]-butyric acid

In a similar manner to Example 51,but starting from RS ethyl 3-benzyl-4-[4-(4-pyridyl)piperazin-1-yl] phenoxybutyrate, was prepared the title compound in 65% yield as a solid; m.p. 205°–206° C.; NMR (d$_6$DMSO) δ 8.2(2H,d), 7.22(5H,m), 6.9(6H,m), 3.8(2H,d), 3.45(4H,m), 3.15(4H,m), 2.72(2H,m), 2.5–2.18(Me$_2$SO+3H,m); m/e 432 (M+H)$^+$; calculated for C$_{26}$H$_{29}$N$_3$O$_3$.0.25H$_2$O: C, 71.6; H, 6.8; N, 9.7. Found: C, 71.9; H, 6.8; N, 9.5%.

The starting material was prepared as follows:

i) A solution of RS 3-benzylbutyrolactone (1.14 g) in ethanol (20 ml) was stirred at 5° C. and gassed for 4 hours with a slow stream of hydrogen bromide. The solution was kept at 5° C. for 20 hours and water (70 ml) added followed by sodium carbonate to neutralise the acid. The mixture was extracted with ethyl acetate and the organic layer filtered through phase separating paper and evaporated to give ethyl 4-benzyl-3-bromobutyrate as an oil; NMR (CDCl$_3$) δ 7.24(5H,m), 4.13(2H,q); 3.45(2H,m), 2.62(2H,d), 2.44(3H,m), 1.25(3H,t); m/e 285(M+H)$^+$.

ii) In a similar manner to Example 50 ,but starting from the product of step i) was prepared RS ethyl 3-benzyl-4-[4-[4-(4-pyridyl)piperazin-1-yl]phenoxy]butyrate in 40% yield as an oil; NMR (CDCl$_3$) δ 8.34(2H,d), 7.29(5H,m), 6.9(4H,m), 6.72(2H,m), 5.13(2H,q), 3.85(2H,m), 3.5(4H, m), 3.3(4H,m), 2.9–2.38(5H,m), 1.26(3H,t); m/e 460(M+H)$^+$.

EXAMPLE 221

RS 3-Phenyl-4-[4-[4-(4-pyridyl)piperazin-1-yl] phenoxy]-butyric acid

In a similar manner to Example 51, but starting from RS methyl 3-phenyl-4-[4-[4-(4-pyridyl)piperazin-1-yl] phenoxy]butyrate, was prepared the title compound in 39% yield as a solid; m.p. 120°–125° C.; NMR (d$_6$DMSO) δ 8.18(2H,d), 7.32(5H,m), 7.25(2H,d), 6.87(6H,m), 4.04(2H, q), 3.45(5H,m), 3.11(4H,t), 2.71(2H,m); m/e 418(M+H)$^+$; calculated for C$_{25}$H$_{27}$N$_3$O$_3$. 0.25H$_2$O: C, 7.1; H, 6.5; N,9.9. Found: C, 7.2; H, 6.5; N,9.8%.

The starting material was prepared as follows:

i) In a similar manner to Example 204ii), but starting from RS ethyl 4-hydroxy-3-phenylbutyrate was made RS methyl-3-phenyl-4-[4-[4-(4-pyridyl)piperazin-1-yl] phenoxy]butyrate in 10% yield as an oil; NMR (d$_6$DMSO+CD$_3$COOD) δ 8.23(2H,d), 7.3(5H,m), 7.17 (2H,d), 6.95(2H,d), 6.83(2H,d), 4.06(2H,m), 3.77(4H,t), 3.55(3H,s), 3.51(1H,m), 3.17(4H, t), 2.83(2H,m); m/e 432(M+H)$^+$.

EXAMPLE 222

N-[1-[2-[4-(4-Pyridyl)piperazin-1-yl]acetyl] piperidin-4-ylmethyl]-4-methylphenylsulphonamide A solution of N-(1-bromoacetylpiperidin-4-ylmethyl)-4-methylphenylsulphonamide (1.0 g), 1-(4-pyridyl)piperazine (600 mg) and triethylamine (0.5 ml) in acetonitrile (20 ml) was stirred for 1 hr and then left to stand overnight. The solvent was evaporated in vacuo and the residue purified by chromatography on silica, eluting with 5% v/v methanol/dichloromethane. Evaporation of the eluant fractions gave a colourless solid (280 mg). The title compound was obtained as colourless prisms (150 mg), m.p. 156°–158° C. (from ethyl acetate); NMR (d$_6$DMSO) δ 0.8–1.2(2H,m); 1.5–1.8 (3H,m); 2.35(3H,s); 2.4(6H,m); 2.6(2H,t); 2.8–3.0(1H,t); 3.2(1H,d); 3.2–3.5(4H,m); 4.0(1H,d); 4.3(1H,d); 6.8(2H,d); 7.4(2H,d), 7.55(1H,t); 7.7(2H,d); 8.2; (2H,d); m/e 472 (M+H)$^+$; calculated for C$_{24}$H$_{33}$N$_5$O$_3$S: C,61.1; H,7.1;N, 14.8; found: C,60.9; N,7.1; N,14.5%.

The starting material was prepared as follows:

i) Sodium hydride (300 mg of a 60% suspension) was added to a stirred solution of 4-methylphenylsulphonamide and the mixture stirred at room temperature until effervescence had ceased. N-benzyloxycarbonylpiperidine-4-methanol mesylate (1.09 g) was added and the mixture heated at 100° C. for 7 hours. After cooling to room temperature it was diluted with water (200 ml) and extracted with ether (4×40 ml); the extracts were combined, washed with water (2×) and brine, dried (MgSO$_4$) and evaporated to yield N-(1-benzyloxycarbonylpiperidin-4-ylmethyl)-4-methylphenylsulphonamide; NMR (d$_6$DMSO) δ 0.81–1.1 (2H,m); 1.5–1.7(3H,m); 2.35(3H,s); 2.6(2H,t); 2.7–2.9 (2H,m); 4.0(2H,d); 5.0(2H,s); 7.2–7.5(7H,m); 7.55(1H,t); 7.7(2H,d); m/e 403 (M+H)$^+$.

ii) To a solution of the product of step i) (1.2 g) in absolute ethanol (30 ml) was added 10% palladium-on-charcoal catalyst (200 mg) and the mixture stirred in an atmosphere of hydrogen until all the starting material had reacted (Tlc). After removal of the catalyst by filtration, the solvent was evaporated in vacuo and the residue dried under high vacuum to yield the free amine as a colourless gum (800 mg). This was dissolved in dichloromethane, the solution stirred with ice-cooling and treated sequentially with triethylamine (0.45 ml) and bromoacetyl bromide (0.3 ml). The mixture was stirred for 1 hr and then washed with water (25 ml) and brine (25 ml), dried (PS paper) and evaporated in vacuo to yield crude N-(1-bromoacetylpiperidin-4-ylmethyl)-4-methylphenylsulphonamide as a colourless gum (1.0 g) which was used without further purification or characterisation.

EXAMPLE 223

N-[2-[1-[2-[4-(4-pyridyl)piperazin-1-yl]acetyl] piperidin-4-ylethyl]-4-methylphenylsulphonamide, dihydrochloride In a similar manner to Example 222, but starting from N-[2-(1-bromoacetyl-piperidin-4-ylethyl]-4- methylphenylsulphonamide, the title compound was obtained as a dihydrochloride salt (160 mg colourless prisms) containing ⅓ mole ethanol of crystallisation, m.p. 258°–260° C. (from ethanol); NMR (d$_6$DMSO+CD$_3$COOD) δ 0.8–1.2 (2H,m); 1.5–1.8(3H,m); 2.4(3H,s); 2.6(2H,m); 2.8(2H,t), 3.0(1H,t), 3.4–3.7(5H,m); 3.9–4.2(4H,m); 4.3–4.5(3H,m); 7.25(2H,d), 7.4(2H,d); 7.7(2H,d); m/e 486 (M+H)$^+$; calculated for C$_{25}$H$_{35}$N$_5$O$_3$S.2HCl.0.33 EtOH: C.53.7; H.6.9; N.12.1; found: C.53.5; H.7.0;N.12.3%.

The starting material was prepared as follows:

i) 4-Piperidine ethanol was reacted with benzyloxycarbonyl chloride in triethylamine to yield (after chromatography) 1-benzyloxycarbonylpiperidin-4-ylethanol as a colourless oil. (2.0 g); NMR (d$_6$DMSO) δ 0.9–1.2(2H,m); 1.2–1.4 (2H,q); 1.5–1.8(3H,m); 2.6–2.9(2H,t); 3.45(2H,q); 4.0 (2H,d); 4.35(1H,t); 5.1(2H,s); 7.35(5H,m); m/e 264 (M+H)$^+$.

ii) A solution of methanesulphonyl chloride (0.85 ml) in dichloromethane (20 ml) was added dropwise to a stirred, ice-cooled solution of triethylamine (1.55 ml) and the product of step i) (2.64 g) in dichloromethane (50 ml). After stirring for 3 hours the reaction mixture was washed with water (3×) and brine, dried (PS paper) and evaporated in vacuo to yield N-benzyloxycarbonylpiperidin-4-ylethanol mesylate as a colourless paste (3.4 g) NMR (d$_6$DMSO) δ 0.9–1.2(2H,m); 1.5–1.8(5H,m); 2.6–2.9(2H, m); 4.0(2H,d); 4.25(2H,t); 4.4(3H,s); 5.1(2H,s); 7.35(5H, m); m/e 342 (M+H)$^+$.

iii) Following a method similar to that described in Example 222i), but starting from the product of step ii) there was obtained N-(1-benzyloxycarbonylpiperidin-4-ylethanol)-4-methylphenylsulphonamide as a colourless gum (900 mg) after chromatography on alumina. NMR (d$_6$DMSO) δ 0.8–1.0 (2H,m); 1.3 (2H,q); 1.4–1.6 (3H,m); 2.4(3H,s); 2.6–2.8(4H,m); 4.0(2H,d); 5.1(2H,s); 7.2–7.4(7H,m); 7.5 (1H,t); 7.7(2H,d); m/e 417 (M+H)$^+$.

iv) In a similar manner to Example 222ii) but starting from the product of step iii) there was obtained N-(1-bromoacetylpiperidin-4-ylmethyl)-4-methylphenylsulphonamide as a pale yellow gum (800 mg). NMR (CDCl$_3$) δ 1.0–1.4(3H,m); 1.45(2H,q); 1.5–1.8(3H,m); 2.45(3H,s); 2.5–2.7(1H,m); 3.0(2H,m); 3.8(2H,m); 4.4–4.7(2H,m); 7.3(2H,d); 7.75(2H,d); m/e 403/405 (M+H)$^+$.

EXAMPLE 224

4-[4-[3-(4-dimethylaminopyrid-3-yl)propyloxy] phenoxy]butyric acid

To a solution of ethyl 4-[4-[3-(4-dimethylaminopyrid-3-yl)propyloxy]phenoxy]butyrate (160 mg) in methanol (10 ml) was added sodium hydroxide solution (2.0 ml of 1.0M) and the solution left until all starting ester had disappeared (Tlc). The reaction mixture was neutralised with hydrochloric acid (2.0 ml) of 1.0M) and evaporated in vacuo. A small amount (5 ml) of water was added and the resulting solution extracted with dichloromethane (3×15 ml). The organic extracts were combined, dried (PS paper) and evaporated to yield the title compound as colourless prisms, (90 mg) m.p. 106°–108° C. (from ethyl acetate); NMR (d$_6$DMSO) δ 1.8–2.1(2H,q;2H,q); 2.4(2H,t); 2.8(2H,t;6H,s); 3.9(2H,t;2H, t); 6.8(5H,m); 8.2(2H,d); m/e 359 (M+H)$^+$; calculated for C$_{20}$H$_{26}$N$_2$O$_4$: C.67.0;H.7.3;N, 7.8; found: C,67.1;H,7.6;N, 7.7%.

The starting material was prepared as follows:

i) A solution of 4-benzyloxyphenol (4.2 g) in dimethyl formamide (50 ml) was treated with sodium hydride (840 mg) of a 60% dispersion), and the mixture stirred until evolution of gas ceased. There was then added ethyl 3-bromobutyrate (2.9 ml), and the solution stirred overnight. It was then poured into water (300 ml) and the mixture extracted with ether (3×50 ml). The combined extracts were washed with water (3×) and brine, dried (MgSO$_4$) and evaporated to give a crude product as a brown oil (6 g). This was purified by chromatography on silica, eluting with hexane containing increasing amounts of ethyl acetate to give ethyl 3-(4-benzyloxyphenoxy) butyrate as a colourless crystalline solid (4.5 g) NMR (d$_6$DMSO) δ 1.25(3H,t); 1.8–2.0(2H,m); 2.45(2H,t); 3.9 (2H,t); 4.1(2H,q); 5.0(2H,s); 6.8–7.0(4H,m); 7.4(5H,m); m/e 314 (M+H)$^+$.

ii) To a solution of the product of step i) (4.5 g) in absolute ethanol (200 ml) was added 10% palladium-on-charcoal catalyst (1.2 g) and the resulting suspension hydrogenated at ambient temperature and pressure until uptake of hydrogen ceased. The catalyst was removed by filtration through celite and the filtrate was concentrated in vacuo to give ethyl 3-(4-hydroxyphenoxy)butyrate as a low-melting crystalline solid (3.0 g) NMR (d$_6$DMSO) δ 1.25 (3H,t); 1.8–2.0(2H,m); 2.5(2H,t); 3.9(2H,t); 4.1(2H,q); 6.7(4H,m); 8.8)1H.brs); m/e 224 (M)$^+$.

iii) A solution of 4-dimethylaminopyridine-3-aldehyde prepared according to J. Het. Chem. 25 p81 (1988).(1.5 g) and ethyl triphenylphosphoranylidene acetate (3.85 g) in acetonitrile (25 ml) was refluxed for seven hours. The solvent was removed in vacuo and the residue dissolved in dilute hydrochloric acid (30 ml of 1M); the solution was washed with ethyl acetate (2×20 ml) and then basified with solid sodium hydrogen carbonate. The resulting solution was extracted with dichloromethane (3×20ml) and the combined extracts washed with brine, dried (PS paper) and evaporated to yield the crude product as a brown oil (2.0 g). This was purified by chromatography on silica, eluting with ethyl acetate, to give ethyl 2-(4-dimethylamino-3-pyridyl)propenoate as a pale yellow oil (1.5 g). NMR (d$_6$DMSO) δ 1.25(3H,t); 2.85(6H,s); 4.2 (2H,q); 6.5(1H,d); 6.9(1H,d); 7.5(1H,d); 8.25(1H,d); 8.5 (1H,s); m/e 221(M+H)$^+$.

iv) To a solution of the product of step iii) (3.6 g) in absolute ethanol (100 ml) was added 5% palladium/charcoal catalyst, and the mixture hydrogenated at ambient temperature and pressure until the theoretical volume of hydrogen had been consumed. The catalyst was removed by filtration through celite and the filtrate evaporated to yield ethyl 2-(4-dimethylamino-3-pyridyl)propanoate as a pale yellow oil (3,1 g) NMR (d$_6$DMSO) δ 1.15(3H,t); 2.65(2H,t); 2.8(6H,s); 2.9(2H,t); 4.05(2H,q); 6.8(2H,d); 8.2(2H,d); m/e 223 (M+H)$^+$.

v) To a stirred solution of the product of step iv) (2.6 g) in tetrahydrofuran (100 ml) was added lithium aluminium hydride (1.2 g) and the resulting suspension stirred for 4 hours at ambient temperature. Excess reducing agent was destroyed by the sequential addition of ethyl acetate, water, and conc. HCl. The mixture was then basified and extracted sequentially with ethyl acetate and dichloromethane. The organic extracts were combined, dried (PS paper and MgSO$_4$) and evaporated to yield 4-dimethylamino-3-(3-hydroxypropyl)pyridine as a pale yellow oil (2.2 g), essentially pure by Tlc; NMR (d$_6$DMSO) δ 1.6–1.8(2H,m); 2.65(2H,t); 2.8(6H,s); 3.5 (2H,t); 4.5(1H,brs); 6.7(2H,d); 8.2(2H,d); m/e 181 (M+H)$^+$.

vi) A solution of the product of step v) (600 mg), the product of step (ii) (750 ml) and triphenylphosphine (920 mg) in tetrahydrofuran (20 ml) was stirred at ambient temperature for 0.5 hr. To this was added diethylazodicarboxylate (0.61 ml) and the resulting solution stirred for 1 hr. The solvent was evaporated and the residue purified by chromatography on silica eluting with 2% v/v ethanol/ dichloromethane. Evaporation of the eluant fractions gave ethyl 4-[4-[3-(4-dimethylaminopyrid-3-yl)propyloxy] phenoy]butyrate as an orange oil (450 mg); NMR ($d_6$DMSO+$CD_3$COOD) δ 1.1(3H,t); 1.8–2.0(2H,q;2H,q); 2.35(2H,t); 2.85(2H,t); 3.1(6H,s); 3.8(2H,t;2H,t); 4.0(2H, q); 6.7(4H,s); 6.9(1H,d); 8.0(2H,d); m/e 387 $(M+H)^+$.

EXAMPLE 225

2-S-(Benzyloxycarbonylamino-3-[4-[3-[4-dimethylamino-pyrid-3-yl]propoxy]phenyl]propionic acid In a similar manner to Example 224 but starting from methyl 2-S-(benzyloxy-carbonylamino)-3-[4-[3-[4-dimethylaminopyrid-3-yl]propoxyphenyl]propionate the crude title compound was prepared as a colourless foam (200 mg). This was dissolved in distilled water (25 ml) containing dilute hydrochloric acid (1.0 ml of 1M), the solution washed with ether (2×10 ml), filtered and lyophilised to give the title compound as a colourless solid (180 mg); NMR ($d_6$DMSO+$CD_3$COOD) δ 2.05(2H,m); 2.7–3.2 (5H,m); 3.2(6H,s); 4.0(2H,t); 4.3(1H,q); 5.0(2H,s); 6.8(2H, d); 7.0(1H,d); 7.2(2H,d); 7.3(5 H,m); 8.1(2H,d; m/e 478 (M+H)+; calculated for $C_{27}H_{31}N_3O_5$.HCl.0.75 $H_2O$: C.61.5;H.6.4;N,8.0;$H_2O$ 2.5; found: C,61.6; H,6.6;N,7.8; $H_2O$ 2.1%.

The starting material was prepared in a similar manner to Example 224 vi), but starting from methyl 2-S-benzyloxycarbonylamino-3-(4-hydroxyphenyl)propionate, yielding a colourless gum (1.0 g); NMR ($d_6$DMSO+ $CD_3$COOD) δ 2.05(2H,m); 2.7–3.2(4H,m); 3.2(6H,s); 3.7 (3H,s); 4.0(2H,t); 4.3(1H,q); 5.0(2H,s); 6.8(2H,d); 7.0(1H, d); 7.2(2H,d); 7.3(5H,m); 8.1(2H,d); m/e 492 $(M+H)^+$.

EXAMPLE 226

Ethyl 3-[4-(4-pyridyl)piperazin-1-yl] phenoxybutyrate

In a similar manner to that described in Example 50, but starting from 3-[4-(4-pyridyl)piperazin-1-yl]phenol, the title compound was prepared as colourless prisms, 560 mg m.p. 160°–162° C. (from ethanol); NMR ($d_6$DMSO) δ 1.2(3H,t); 185–2.05(2H,q); 2.45(2H,t); 3.4(4H,m); 3.85(4H,m); 4.0 (2H,t); 4.1(2H,q); 6.45(1H,m); 6.65(2H,m); 7.15(1H,t); 7.25 (2H,d); 8.2(2H,t); m/e 370 (M+H)$^{30}$ ; calculated for $C_{21}H_{27}N_3O_3$.2HCl. 0.6 $H_2O$: C.55.7; H,6.7; N,9.3; $H_2O$,2.8; found: C,56.0; H,6.8;N,9.2; $H_2O$,3.0%.

The starting material was prepared as follows:
i) 3-[4-(3-pyridyl)piperazin-1-yl)]anisole was prepared in a manner similar to that described in Example 50, but starting from 3-(1-piperazinyl)anisole, giving yellow prisms (from carbon tetrachloride), 4.8 g. NMR ($d_6$ DMSO) δ 3.25(4H,m); 3.45(4H,m); 3.75(3H,s); 6.4(1H, m); 6.5(1H,m); 6.55(1H,m); 6.85(2H,d); 7.15(1H,t); 8.2 (2H,d); m/e 270 $(M+H)^+$.
ii) 3-[4-(4-pyridly)piperazin-1-yl]phenol was prepared in a similar manner to that described in Example 50, but starting from 3-[4-(4-pyridyl)piperazin-1yl]anisole to give the phenol as a pale brown solid, (3.5 g) NMR ($d_6$DMSO) δ 3.3(4H,m); 3.6(4H,m); 6.35(1H,m); 6.5(2H, m); 7.0(2H,d); 7.15(1H,t); 8.3(2H,d); 9.0–9.5(1H,brs); m/e 256 $(M+H)^+$.

EXAMPLE 227

3-[4-(4-Pyridyl)piperazin-1-yl]phenoxybutyric acid

In a manner similar to that described in Example 51, but starting from the product of Example 226, the title compound (180 mg) was obtained as pale yellow prisms, m.p. 196°–198° C. (from water); NMR ($d_6$DMSO) δ 1.8–2.0(2H, q); 2.4(2H,t); 3.25(4H,m); 3.45(4H,m); 4.0(2H,t); 6.4(1H, m); 6.5(2H,m); 6.85(2H,m); 7.15(1H,t); 8.2(2H,d); m/e 342 $(M+H)^+$; calculated for $C_{19}H_{23}N_3O_3$. 0.2 $H_2O$: C.6.61; H,6.8; N,12.2; $H_2O$,1.0; found: C.65.8; H,6.7; N,12.1; $H_2O$, 0.8%.

EXAMPLE 228

Ethyl 3-[4-(4-pyridyl)piperazin-1-yl] phenoxypentanoate

Following the method of Example 226, title compound (340 mg) was obtained as a colourless prisms. m.p. 62°–64°C. (from ethanol); NMR ($d_6$DMSO) δ 1.2(3H,t); 1.6–1.8(4H,m); 2.35(2H,t); 3.25(4H,m); 3.45(4H,m); 3.95 (2H,t); 4.05(2H,q); 6.4(1H,m); 6.5(1H,m); 6.55(1H,m; 6.85 (2H,m); 7.15(1H,t); 8.2(2H,d); m/e 384 $(M+H)^+$; calculated for $C_{22}H_{29}N_3O_3$: C.68.9, H,7.6; N.11.0; found: C.68.7; H.7.8;N.11.0%.

EXAMPLE 229

3-[4-(4-Pyridyl)piperazin-1-yl]phenoxypentanoic acid

Following the method of Example 227, the title compound (150 mg) was obtained as a pale yellow prisms, m.p. 235°–237° C. (from water); NMR ($d_6$DMSO) δ 1.55–1.85 (4H,m); 2.3 (2H,t); 3.35(4H,m); 3.75(4H,m); 4.0(2H,t); 6.4 (1H,m); 6.5(1H,m); 6.55(1H,m); 7.15(3H,m); 8.2(2H,d); m/e 356 $(M+H)^+$; calculated for $C_{20}H_{25}N_3O_3$:C.67.6; H,7.1;N,11.8; found: C,67; H,7.2; N,11.8%.

EXAMPLE 230

Trans-methyl-4-[4-[4-(4-pyridyl)piperazin-1-yl] phenoxy]cyclohexyl carboxylate

To a mixture of 4-((4-pyridyl)piperazin-1-yl)phenol (860 mg), methyl 4-hydroxycyclohexane carboxylate (533 mg) and triphenylphosphine (884 mg) in dry THF (50 ml), cooled to 5° C., was added dropwise diethyl azodicarboxylate (0.53 ml). The resulting mixture was stirred at room temperature for 18 hours. The mixture was concentrated and purified by flash column chromatography on silica, eluting with methanol/dichloromethane (5.95 v/v) to give the title compound (178 mg)as a solid; NMR ($CDCl_3$) δ 1.4–1.65 (4H,m), 2.05–2.1(2H,m), 2.15–2.2(2H,m), 2.3–2.4(1H,m), 3.15–3.2(4H,m), 3.45–3.5(4H,m), 3.7(3H,s), 4.05–4.15(1H, m), 6.7(2H,d), 6.85–6.95(4H,dd), 8.3(2H,d); m/e 396 $(M+H)^+$; calculated for $C_{23}H_{29}N_3O_3$.0.5$H_2O$: c.68.3; H,7.4; N,10.4. Found: C.68.3; N,7.4; N,10.5%.

EXAMPLE 231

Trans-4-[4-[4-(4-pyridyl)piperazin-1-yl]phenoxy] cyclohexane carboxylic acid

In a similar manner to Example 57 was prepared the title compound in 98% yield as a solid; NMR ($d_6$DMSO+ $CF_3$COOD) δ 1.35–1.65(4H,m), 1.95–2.15(4H,m), 2.2–2.35 (1H,m), 3.6–3.75(4H,m), 4.05–4.2(4H,m), 4.25–4.4(1H,m), 7.05(2H,d); 7.35(2H,d). 7.45(2H,d). 8.35(2H,d); m/e 380 (M-H)⁺; calculated for $C_{22}H_{27}N_3O_3.0.5H_2O$: C,67.7; H,7.2; N,10.8. Found: C,67.6;H,7.1; N,10.7%.

EXAMPLE 232

Methyl 6-[4-[4-(4-pyridyl)piperazin-1-yl]phenoxy] pyridine-3-carbxylate

To a suspension of 4-((4-pyridyl)piperazin-1-yl)phenol (1.13 g) in DMF (10 ml) was added a 60% dispersion of sodium hydride in oil (195 mg) and the resulting mixture was stirred for 20 minutes. A solution of methyl 6-chloronicotinate (758 mg) in DMF (2 ml was added and the mixture was heated at 60° C. for 2 hours. The mixture was partitioned between ethyl acetate(100 ml) and water(20 ml). The organic layer was dried (MgSO₄) and evaporated to give an oil which was purified by flash column chromatography on silica. eluting with methanol/dichloromethane (5:95 v/v) to give the title compound as a solid (815 mg): mp 143°–144° C.; NMR (d₆DMSO) δ 3.2–3.35(4H,m), 3.45–3.55(4H,m), 3.85(3H,s), 6.9(2H,dd), 7.05–7.1(4H,m), 8.15–8.3(3H,m), 8.7(2H,d); m/e 391 (M+H)⁺; calculated for $C_{22}H_{22}N_4O_3.0.25H_2O$: C,66.9; H,5.7; N,14.2. Found: C,66.9; H,5.7; N,14.1%.

EXAMPLE 233

6-[4-[4-(4-Pyridyl)piperazin-1yl]phenoxy]pyridine-3-carboxylic acid

In a similar manner to Example 57, but using the product of Example 232, was prepared the title compound in 95% yield as a solid: mp 335°–340° C. (dec); NMR (d₆DMSO+ CF₃COOD) δ 3.4–3.5(4H,m). 3.9–4.0(4H,m). 7.05(1H,d). 7.2(4H,s). 7.3(2H,d). 8.25–8.35(3H,m), 8.7(1H,d); m/e 376 (M+H)⁺; calculated for $C_{21}H_{20}N_4O_3.0.25H_2O$: C,66.2; H,5.4; N,–14.7. Found; C,66.1;H,5.4; N,14.9%.

EXAMPLE 234

4-[(4-Pyridyl)piperazin-1-yl]benzoylisonipecotic acid

In a similar manner to Example 57, but starting from ethyl 4-[(4-pyridyl)piperazin-1-yl]benzoylisonipecotate, the title compound was prepared in 26% yield as a solid; NMR (d₆DMSO+CF₃COOD) δ1.4–1.65(2H,m), 1.8–1.95(2H,m). 2.95–3.15(3H,m), 3.4–3.55(4H,m), 3.8–3.9(4H,m), 3.9–4.1 (2H,m). 6.95(2H,d), 7.2(2H,d). 7.3(2H,d), 8.25(2H,d); m/e 395 (M+H)⁺ calculated for $C_{22}H_{26}N_4O_3.1.6CF_3CO_2H$: C,52.5; H, 4.8; N, 9.7. Found: C, 52.4; H, 5.1; N, 9.8%.

The starting material was prepared as follows:
i) In a similar manner to Example 56 but using ethyl isonipecotate, ethyl 4-[(4-pyridylpiperazin-1-yl] benzoylisoipecotate was prepared in 32% yield as a solid; NMR (d₆DMSO) δ 1.2(3H,t), 1.4–1.6(2H,m), 1.8–1.9 (2H,m), 2.55–2.7(1H,m), 2.95–3.1(2H,m), 3.2–3.5(10H, m), 4.1(2H,q), 6.85(2H,d), 7.0(2H,d), 7.3(2H,d), 8.2(2H, d); m/e 423 (M+H)⁺; calculated for $C_{24}H_{30}N_4O_3.1.6H_2O$: C,63.9; H 7.4; N, 12.4. Found: C, 64.1; H, 7.4; N, 11.9%.

EXAMPLE 235

4-[(4-Pyridyl)piperazin-1-yl]benzoylnipecotic acid

In a similar manner to Example 57, but starting from ethyl 4-[(4-pyridyl)piperazin-1-yl]benzoylnipecotate was prepared the title compound in 35% yield as a solid; NMR (d₆DMSO) δ 1.4–1.75(3H,m). 1.9–2.1(1H,m). 2.3–2.5(1H, m), 2.85–3.15(2H,m), 3.4–3.5(4H,m), 3.8–3.9(4H,m), 4.0–4.3(2H,bm), 6.95(2H,d), 7.25(2H,d), 7.3(2H,d), 8.25 (2H,d); m/e 395 (M+H)⁺; calculated for $C_{22}H_{26}N_4O_3.1.6CF_3COOH$: C, 52.5; H, 4.8; N, 9.7. Found: C, 52.4; H, 4.5; N, 9.3%.

The starting material was prepared as follows:
i) In a similar manner to Example 56 but using ethyl nipecotate, was prepared ethyl 4-[(4-pyridyl)piperazin-1-yl]benzoylnipecotate in 35% yield as a solid; NMR (d₆DMSO) δ 1.5(3H,t), 1.35–1.75(3H,m). 1.9–2.05(1H, m), -2.05(1H,m), 2.3–2.5(1H,m), 2.3–2.5(1H,m), 3.0–3.3 (4H,m), 3.0–3.3(4H,m), 3.4–3.5(4H,m), 4.05(2H,q), 6.85 (2H,d), 6.95(2H,d), 7.25(2H,d), 8.15(2H,d); m/e 423 (M+H)⁺; calculated for $C_{24}H_{30}N_4O_3.0.5H_2O$: C, 66.8; H, 7.2; N, 13.0. Found C, 66.4; H, 7.3; N, 13.1%.

EXAMPLE 236

3-[4-[4-(4-Pyridyl)piperazin-1-yl]]-N-benzylbenzamidopropionic acid

In a similar manner to Example 57, but starting from methyl 3-[4-[4-(4-pyridyl)-piperazin-1-yl]]-N-benzylbenzamido propionate was prepared the title compound in 72% yield as a solid; NMR (d₆DMSO) δ2.5–2.6 (2H,m), 3.4–3.55(6H,m), 3.75–3.85(4H,m), 4.65(2H,s), 6.95(2H,d), 7.15(2H,d), 7.2–7.45(7H,m), 8.25(2H,d); m/e 445 (M+H)⁺; calculated for $C_{26}H_{28}N_4O_3.0.5H_2O$: C, 68.8; H, 6.3; N, 12.3. Found: C, 69.2; H, 5.8; N, 12.4%.

The starting material was prepared as follows:
In similar manner to Example 56, but using N-benzyl β-alanine methyl ester, was prepared methyl 3-[4-[(4-pyridyl)piperazin-1yl]]-N-benzylbenzamido propionate in 34% yield as a solid; NMR (CDCl₃) δ2.0–2.1(2H,m), 2.6–2.7(2H,t), 3.35–3.4(4H,m), 3.45–3.55(4H,m), 3.65 (3H,s), 4.65(2H,s), 6.7(2H,d), 6.85(2H,d), 7.2–7.45(7H, m), 8.2–8.35(2H,m); m/e 459 (M+H)⁺.

EXAMPLE 237

3-[4-[4-(Pyridyl)piperazin-1-yl]phenoxy] cyclohexane carboxylic acid

In a similar manner to Example 57, but starting from methyl 3-[4-[4-(4-pyridyl)-piperazin-1-yl]phenoxy] cyclohexylcarboxylate, was prepared the title compound in 60% yield as a solid; NMR (d₆DMSO) δ 1.2–1.5(4H,m), 1.5–1.9(2H,m), 2.0–2.1(1H,m), 2.25–2.3(2H,m), 2.35–2.45 (1H,m), 3.2–3.25(4H,m), 3.3–3.35(4H,m), 6.85–7.0(4H,m), 7.2(2H,d), 8.2(2H,d); m/e 396 (M+H)⁺; calculated for $C_{22}H_{27}N_3O_3.0.5H_2O$: C,67.6; H, 7.2; N, 10.7 Found: C, 67.9; H, 7.2; N, 10.9%.

The starting material was prepared as follows:
i) In a similar manner to Example 230, but using methyl 3-hydroxy cyclohexane carboxylate, was prepared methyl 3-[4-[4-(4-pyridyl)piperazin-1yl]phenoxy]cyclohexyl carboxylate in 8% yield as solid; NMR (d₆DMSO) δ 1.25–1.6(4H,m), 185–2.0(2H,m), 2.05–2.2(1H,m), 2.3–2.45(2H,m), 3.15–3.25(4H,m), 4H,m), 3.45-3.55(4H, m), 3.65(3H,s), 4.05–4.15(1H,m), 6.7(2H,d), 6.8–7.0(4H, m), 8.3(2H,d); m/e 396 (M+H)⁺.

EXAMPLE 238

4-[4-[4-(Pyridyl)piperazin-1 -yl]phenoxy] piperidineacetic acid

In a similar manner to Example 18, but starting from tert-butyl 4-[4-[4-(pyridyl)-piperazin-1-yl]

phenoxypiperidinyl acetate, was prepared the title compound in 77% yield as a solid; NMR (d$_6$DMSO) δ 1.85–2.2 (4H,m), 3.15–3.25(4H,m), 3.25–3.45(4H,m), 3.8–3.9(4H, m), 4.15(2H,s), 4.55(1H,m), 6.95(4H,s), 7.25(2H,d), 8.25 (2H,d); m/e 397 (M+H)$^+$; calculated for C$_{22}$H$_{28}$N$_4$O$_3$.2.CF$_3$COOH.2.H$_2$O: C, 47.3; H, 5.1; N, 8.45. Found: C, 47.3; H, 4.8; N, 8%.

The starting material was prepared as follows:

i) In a similar manner to Example 230, but using tert-butyl 4-hydroxypiperidinyl acetate, was prepared tert-butyl 4-[4-[4-(pyridyl)piperazin-1-yl]phenoxypiperidinyl acetate in 35% yield as a solid; NMR (d$_6$DMSO+ CD$_3$COOD) δ 1.4(9H,s), 1.6–1.75(2H,m), 1.8–2.0(2H, m), 2.4–2.65(2H,m), 2.8–2.9(2H,m), 3.15–3.25(4H,m), 3.25(2H,s), 3.75–3.8(4H,m), 4.2–4.3(1H,m), 6.85–7.0 (4H,m), 7.15(2H,d), 8.2(2(2H,d); m/e 453 (M+H)$^+$; calculated for C$_{26}$H$_{36}$N$_4$O$_3$.0.5H$_2$O: C,67.7; H, 8.0; N, 12.1. Found: C, 67.9; H, 8.3; N, 12.1%.

EXAMPLE 239

3-[4-4-(4-Pyridyl)piperazin-1-yl]phenoxy] poperidineacetic acid

In a similar manner to Example 18, but starting from tert-butyl 3-[4-[4-(pyridyl)-piperazin-1yl]phenoxy] piperidinyl acetate was prepared the title compound in 75% yield as a solid; NMR (d$_6$DMSO) δ 1.7–2.3(4H,m), 3.2–3.4 (4H,m), 3.9–4.05(4H,m), 4.1(2H,s), 4.1–4.45(4H,m), 4.75–4.85(1H,m), 7.0(2H,d), 7.25–7.4(4H,m), 8.3(2H,d); m/e 397 (M+H)$^+$ The starting material was prepared as follows:

i) In a similar manner to Example 230, but using tert-butyl 3-hydroxypiperidinyl acetate, was prepared tert-butyl 3-[4-[4-(pyridyl)piperazin-1-yl]phenoxy]piperidinyl acetate in 17% yield as an oil; NMR (d$_6$DMSO) δ 1.4(9H,d), 1.6–1.8(2H,m), 1.85–2.0(1H,m), 2.2–2.3(1H, m), 2.5–2.7 (2H,m), 2.95–3.05(2H,m), 3.05–3.15(4H,m), 3.4–3.5(4H,m), 3.65–3.9(2H,m), 4.1–4.25(1H,m), 6.8–6.95(6H,m), 8.2(2H,d); m/e 453 (M+H) $^+$.

EXAMPLE 240

[2-Propyl-4- [2-[4-(4-pyridyl)piperazin-2-one-1-yl] acetyl]]phenoxyacetic acid

Using the method of Example 202 but starting from methyl 2-"propyl-phenoxyacetate, was prepared the title compound: NMR (d$_6$DMSO) δ 0.9(3H,t), 1.55–1.7(2H,m), 2.65(2H,t), 3.45–3.55(2H,m), 365–3.75(2H,m), 4.05(2H,s), 4.9(2H,s), 6.85(2H,d), 6.9(1H,d), 7.75 –7.85(2H,m), 8.2 (2H,d); m/e 412 (M+H)$^+$; calculated for C$_{22}$H$_{25}$N$_3$O$_5$.0.25H$_2$O: C, 63.5; H, 6.1; N, 10.1. Found: C, 63.5; H, 6.2; N, 9.9%.

The starting material was prepared as follows:

i) In a similar manner to Example 3i), but starting from 2-allyl phenol, was prepared methyl 2-allyl-phenoxyacetate as an oil in 97% yield; NMR (d$_6$DMSO) δ 3.45(2H,d), 3.7(3H,s), 4.8(2H,s), 5.0–5.1(2H,m), 5.9–6.1(1H,m), 6.85–6.95(2H,m), 7.1–7.2(2H,m); m/e 207 (M+H)$^+$.

ii) The product of step i) (5.86 g) was dissolved in methanol (100 ml) and a catalytic amount of 10% palladium on carbon was added. The mixture was hydrogenated at atmospheric pressure for 18 hours. The mixture was filtered and concentrated to an oil which was purified by flash column chromatography, eluting with ethyl acetate/ hexane (10:90 v/v) to give methyl 2-"propyl- phenoxyacetate (4.82 g) as an oil; NMR (d$_6$DMSO) δ 1.4(3H,t), 1.5–1.7(2H,m), 2.6(2H,t), 3.7(3H,s), 4.8(2H,s), 6.8–6.95(2H,m), 7.1–7.2(2H,m); m/e 208 (M)$^+$.

EXAMPLE 241

[2-Methyl-4-[2-[4-(4-pyridyl)piperazin-2-one-1-yl] acetyl]]phenoxyacetic acid

In a similar manner to Example 202, but starting from methyl 2-methylphenoxyacetate, was prepared the title compound as a solid; NMR (d$_6$DMSO+CD$_3$COOD) δ 2.3(3H,s), 3.6–3.7(2H,m), 4.35(2H,s), 4.8(2H,s), 4.95(2H,s), 6.95(1H, d), 7.15(2H,d), 7.8–7.9(2H,d); m/e 384 (M+H)$^+$; calculated for C$_{20}$H$_{21}$N$_3$O$_5$.1H$_2$O: C, 59.8; H, 5.8; N, 10.0. Found: C, 59.3; H, 5.8: N, 10.1%.

EXAMPLE 242

Ethyl 4-[4-[4-(4-pyridyl)piperazin-2-one-1yl] phenoxy]butyrate

In a similar manner to that described in Example 50, but starting from 4-[4-(4-pyridyl)piperazin-2-one-1-yl] phenol, the title compound was prepared as a colourless solid (100 mg); NMR (d$_6$DMSO) δ1.2(3H,t); 1.9–2.05(2H,q); 2.45 (2H,t); 3.85(2H,m); 3.95(2H,m+2H,t); 4.05(2H,q); 4.4(2H, s); 6.9(2H,d); 7.15(2H,d); 7.25(2H,d); 8.25(2H,d); m/e 384 (M+H)$^+$.

The starting material was prepared as follows:

i) To a stirred suspension of 4-(4-pyridly)piperazin-2-one (880 mg) in dimethyl formamide (20 ml) was added potassium hydride (1.0 ml of a 20% dispersion) and the mixture stirred for 0.5 hr, after which time was added copper (I) iodide (1.0 g). After 0.25 hr there was added 4-benzyloxybromobenzene (1.2 g) and the mixture stirred at 140° C. in an argon atmosphere for 2 hr. The reaction mixture was diluted with water and brine and extracted with dichloromethane (3×40 ml); the combined extracts were washed with water and brine, dried (PS paper) and evaporated to give crude product as a pasty solid (2.0 g). This was purified by flash chromatography on silica, eluting with dichloromethane/methanol/conc. ammonia (97.5:0.5 v/v) to give 4-benzyloxy [4-(4-pyridyl) piperazin-2-one-1-yl]benzene as a colourless solid (1.1 g) NMR δ (d$_6$DMSO) 3.7–3.9(4H,m); 4.1(2H,s); 5.1(2H,s); 6.85(2H,d); 7.05(2H,d); 7.25(2H,d); 7.3–7.6(5H,m); 8.2 (2H,d); m/e 360 (M+H)$^+$.

ii) To a solution of the product of step i) (1.1 g) in a mixture of methanol (500 ml) and tetrahydrofuran (100 ml) was added 30% palladium-on-charcoal catalyst (300 mg) and the mixture stirred in an atmosphere of hydrogen at ambient temperature and pressure until all the starting material had been consumed. After removal of the catalyst by filtration, the solvent was evaporated in vacuo to give 4-[4-(4-pyridyl)piperazin-2-one-1-yl] phenol as a colourless solid, essentially one spot by tlc, which was used without further purification or characterisation.

EXAMPLE 243

4-[4-[4-(4-Pyridyl)piperazin-2-one-1-yl]phenoxy] butyric acid

In a manner similar to that described in Example 51, but starting from the product of Example 242, the title compound was prepared as a colourless soil (94 mg); NMR (d$_6$DMSO) δ 1.8–2.0(2H,q); 2.35(2H,t); 3.7–4.0(4H,m+2H, t); 4.3(2H,s); 6.85(2H,d); 7.05(2H,d; 7.2(2H,d); 8.15(2H,d); m/e 356 (M+H)$^+$.

EXAMPLE 244

4-[2-Nitro-4-[4-(4-pyridyl)piperazin-1-yl]phenoxy] butyric acid

In a similar manner to Example 51, but starting from the compound of Example 217, the title compound was obtained in 68% yield as a solid; m.p. 219°–220° C.; NMR ($d_6$DMSO) δ 8.2(2H,d), 7.4(1H,d), 7.27(2H,m), 6.98(2H,d), 4.08(2H,t), 3.23(4H,brt), 2.36(2H,t), 1.69(2H,m); m/e 387 (M+H)$^+$. Calculated for $C_{19}H_{22}N_4O_5$. $H_2O$: C, 56.4; H, 5.98; N, 13.9. Found: C, 56.7; H, 5.7; N, 13.9%.

EXAMPLE 245

(S)-3-[1-[1-(4-Pyridyl)piperidin-4-yl]hexahydro-2oxodiazepin-4-carboxamido]propionic acid, trifluoroacetate In a similar manner to Example 189, methyl (S)-3-[1-[1-(4-pyridyl)piperidin-4-yl]-hexahydro-2-oxodiazepin-4-carboxamido]propionate (72 mg), methanol (5 ml) and sodium hydroxide solution (1N, 0.36 ml) gave, after preparative rp-hplc and lyophilisation, the title compound (81 mg) a an off-white glassy solid: NMR ($d_6$DMSO) δ 1.70 (8H,m), 2.40(2H,t), 3.20(6H,m), 3.65(1H,m), 4.12(1H,m), 4.29(2H,m), 5.58(1H,d), 7.20(2H,d, 8.00(1H,t), 8.19(2H,d), 13.25(1H,brs); m/Z 390 (M+H)$^+$; calculated for $C_{19}H_{27}N_5O_4$. 1.5 $CF_3CO_2H$. 1.0 $H_2O$: C, 45.7%; H, 5.3%; N, 12.1%; found: C, 45.8%; H, 5.2%; N, 12.0%.

The starting material was prepared as follows:

A mixture of 1,4-dioxa-8-azaspiro[4.5]decane (51.2 ml), 4-chloropyridine hydrochloride (20 g) and potassium carbonate (18.4 g) in isoamyl alcohol (400 ml) was gently refluxed for 18 hr. The reation mixture was cooled and filtered. The filtrate was evaporated to give a waxy solid which was triturated with hexane to give 8-(4-pyridyl)-1,4-dioxa-8-azaspiro]4,5]decane (24.16 g) as a colourless solid; NMR ($d_6$DMSO) δ 1.65–1.70(4H,m), 3.45–3.55 (4H,m), 3.9(4H,s), 6.90(2H,m), 8.15(2H,m); m/Z 221 (M+H)$^+$ ii) A solution of 8-(4-pyridyl)-1,4-dioxa-8-azaspiro[4.5] decane (10 g) in 2N sulphuric acid (140 ml) and tetrahydrofuran (70 ml) was stirred for 72 hr. The reaction was quenched with water (700 ml) and extracted with dichloromethane (400 ml). The organic extracts were dried (MgSO$_4$) and evaporated to give a yellow solid which was purified by flash chromatography on silica, eluting with methanol/dichloromethane (10:90 v/v) to give 1-(4-pyridyl)-4-oxopiperidine as a solid (3.97 g); m.p. 101°–104° C.; NMR ($d_6$DMSO) δ 2.45(4H,t), 3.75(4H,t), 6.85(2H,m), 8.20(2H,m); m/e 177 (M+H)$^+$.

To a stirred solution of $N^\alpha$-Z-L-ornithine, tert-butyl ester (preparation described in Milewska, M. J. et al (1990), Synthesis, 233-4) (1.56 g) and 1-(4-pyridyl)-4-oxopiperidine (0.94 g) in methanol (50 ml) at room temperature was added sodium cyanoborohydride (0.30 g), acetic acid was added dropwise with stirring until the pH of the reaction mixture was 5. The reaction mixture was stirred for 2 hr at room temperature then evaporated to near dryness. The residue was partitioned between saturated aqueous sodium carbonate solution (50 ml) and ethyl acetate (100 ml). The organic layer was separated, washed with brine, dried (MgSO$_4$) and evaporated. The residue was purified by flash chromatography on silica, eluting with methanol/dichloromethane/concentrated ammonia, 10:90:0.1 to 10:90:0.2, to give tert. butyl (S)-2-(benzyloxycarbonyl)amino-5-[1-(4-pyridyl)piperidin-4yl]aminopentanoate (1.35 g) as a yellow gum: NMR ($d_6$DMSO) δ 1.22(9H,s), 1.70(6H,m), 1.97(2H,m), 2.85 (4H,m), 3.22(1H,m), 3.75(1H,m), 4.06(2H,m), 4.90(2H, d), 6.93(2H,d), 7.20(5H,m), 8.06(2H,d); m/Z 483 (M+H)$^+$.

iv) To a solution of the product of step iii) (1.34 g) and acetic acid (0.48 ml) in methanol under argon was added 10% Pd on C (100 mg). The mixture was covered with a blanket of hydrogen and stirred at room temperature for 4 hr. The catalyst was then removed by filtration through a pad of kieselguhr and the pH of the filtrate was adjusted to 4 by addition of acetic acid. To this mixture, under argon, was then added a further quantity of 10% Pd on C (100 mg), it was covered again with hydrogen and stirred at room temperature for 3 days. The catalyst was filtered off through a pad of kieselguhr and the filtrate was evaporated to dryness. Toluene (100 ml) was then added to the residue and the solvents were again removed in vacuo to give tert. butyl (S)-2-amino-5-[1-(4-pyridly)piperidin-4-yl]-aminopentanoate, triacetate salt (1.68 g) as a yellow gum: NMR ($d_6$DMSO+$CD_3CO_2D$) δ 1.49(9H,s), 1.70 (6H,m), 2.23(2H,m), 3.03(2H,m), 3.25(2H,m), 3.50(1H, m), 3.96(1H,m), 4.30(2H,m), 7.18(2H,d), 8.20(2H,d) m/Z 349 (M+H)$^+$.

v) To a mixture of the product of step iv) (1.65 g) triethylamine (1.2 ml) and tetrahydrofuran (15 ml) was added with stirring carbonyl diimidazole (0.5 g). The resultant reaction mixture was stirred at room temperature for 20 hr then at reflux for 4 hr. The solvents were then removed in vacuo and the residue was dissolved in dichloromethane, washed with water and brine, dried (MgSO$_4$) and evaporated to dryness. The residue was purified by flash chromatography on silica, by elution with methanol/ dichloromethane (15% v/v to 25% v/v) to give a yellow gum, which, on trituration with ether gave tert. butyl (S)-1-[1-(4-pyridly)piperidin-4-yl]hexahydro-2-oxodiazepin-4-carboxylate (257 mg) as a white solid: NMR ($d_6$DMSO+$CD_3CO_2D$) δ 1.37(9H,s), 1.70(8H,m), 3.10(4H,m), 3.78(1H,m), 4.11(1H,m), 4.21(2H,m), 7.06 (2H,d), 8.08(2H,d); m/Z 375 (M+H)$^+$.

vi) A solution of the product of step v) (219 mg) in trifluoroacetic acid (5 ml) was stirred at room temperature for 90 min then evaporated to dryness. The residue was triturated with ether and the resultant solid was collected to give (S)-1-[1-(4-pyridyl)piperidin-4yl]-hexahydro-2-oxodiazepin-4-carboxylic acid, trifluoroacetate salt (124 mg) as a cream-coloured solid: NMR ($d_6$DMSO) δ 1.70 (8H,m), 3.05(2H,m), 3.20(2H,m), 3.81(1H,m), 4.12(1H, m), 4.30(2H,m), 5.59(1H,d), 7.20(2H,d), 8.18(2H,d), 13.35(1H,brs) m/Z 319 (M+H)$^+$.

vii) In a similar manner to Example 189i), the product of step vi), (210 mg), HBTU (203 mg), HOBt.$H_2O$ (82 mg), DMF (5 ml), diisoproylethylamine (0.47 ml) and methyl 3-aminopropionate, hydrochloride (75 mg) gave, after purification by flash chromatography on alumina, eluting solvent dichloromethane/methanol, 20:1, methyl (S)-3-[1-[1-(4-pyridyl)piperidin- 4-yl]hexahydro-2-oxodiazepin-4-carboxamido]propionate (78 mg) as a yellow gum: NMR ($d_6$DMSO) δ 1.70(8H,m), 2.45(2H,m), 2.88(2H,m), 3.06(2H,m), 3.32(2H,m), 3.63(4H,m), 4.02 (3H,m), 5.52(1H,d), 6.81(2H,d), 8.03(1H,t), 8.12(2H,d); m/Z 404 (M+H)$^+$.

EXAMPLE 246

(−)-(3R)-3-Methyl-4-{4-[4-(4-pyridyl)piperazin-1-yl]phenoxy}butyric acid hydrochloride Sodium hydride (60% dispersion in mineral oil, 2.44 g) was added to a stirred suspension of 4-[4-(4-pyridyl)

piperazin-1-yl]phenol (15.5 g) in dry DMF (120 ml) and the mixture stirred for 45 min. tert-Butyl (3R)-3-methyl-4-(p-toluenesulphonyloxy)butyrate (20 g) was added and the mixture stirred for 20 hours. The mixture was evaporated and the residue partitioned between dichloromethane and water. The organic layer was washed with water, filtered through phase separating paper (Whatman IPS) and evaporated. The residue was triturated under diethyl ether. The solid so obtained was recrystallised from ethyl acetate to give tert-butyl (−)-(3-methyl-4-{4-[4-(4-pyridyl)piperazin-1-yl]phenoxy}butyrate (10.6 g); m.p. 112°–113° C.; [alpha]$_D$=−5.5° (conc.=1 g/100 ml of methanol; 20° C.); NMR (CDCl$_3$) δ 8.3(2H,d), 6.89(4H,m), 6.7(2H,m), 3.79(2H,d), 3.46(4H,m), 3.28(4H,m), 2.31–2.53(2H,m), 2.08–2.21(1H, m), 1.44(9H,s), 1.07(3H,d).

A mixture of tert-butyl (−)-(3R)-3-methyl-4-{4-[4-(4-pyridyl)piperazin-1-yl]phenoxy}butyrate (10.53 g) and 1N aqueous hydrochloric acid (250 ml) was stirred for 44 hours. 1N aqueous sodium hydroxide solution (250 ml) was added and the mixture cooled to 5° C. The mixture was filtered and the filtrate evaporated. Water (150 ml) was added and the resultant precipitate isolated and washed in turn with water, acetone and diethyl ether. The material so obtained was stirred with 1N aqueous hydrochloric acid (25 ml) for 16 hours. The mixture was cooled to 5° C. and filtered. The solid so obtained was washed in turn with water, acetone and diethyl ether and dried to give (−)-(3R)-3-methyl-4-{4-[4-(4-pyridyl)piperazin-1-yl]phenoxy}butyric acid hydrochloride (7.9 g); m.p. 203°–205° C.; [alpha]$_D$=−6.2° (conc.=1 g/100 ml of methanol; 20° C.); NMR (d$_6$DMSO) δ 13.8(1H, br), 12.1(1H,br), 8.27(2H,d), 7.28(2H,d), 6.9(4H,m), 3.8 (6H,m), 3.18(4H,t), 2.45(1H,m), 2.23(1H,m), 2.12(1H,m), 1.0(3H,d); m/e 356(M+H)$^+$; Calculated for C$_{20}$H$_{25}$N$_3$O$_3$.HCl.H$_2$O: C, 58.5; H, 6.8; N, 10.2; Found: C, 58.3; H, 6.9; N, 10.2%;

The chiral starting material was prepared as follows:

i) Sodium bis(trimethylsilyl)amide (1M in THF, 170 ml) was added dropwise to a solution of (4S)-4-isopropyl-3-propionyloxazolidin-2-one (*J. Am. Chem. Soc.*, 1981, 103, 2127; 28.4 g) in dry THF (500 ml) which had been cooled to −70° C. and placed under an atmosphere of argon. The rate of addition was adjusted such that the temperature of the reaction mixture did not rise above −67° C. The resultant solution was stirred at −70° C. for 30 min. tert-Butyl bromoacetate (42.3 g) was added dropwise and the solution stirred at −70° C. for 3 hours. The solution was then allowed to warm to room temperature. The solvent was evaporated and the residue partitioned between diethyl ether and water. The organic phase was separated, filtered through phase separating paper (Whatman IPD) and evaporated. The residue was triturated under hexane at −40° C. to give a solid (21.6 g). A second crop of solid (4.4 g) was obtained by evaporation of the hexane solution and purification of the residue by filtration chromatography on silica gel starting with hexane and progressing to 1/10 ethyl acetate/hexane. The two batches of solid were combined and recrystallised from hexane to give (4S)-3-[(2R)-3-tert-butoxycarbonyl-2-methylpropionyl]-4-isopropyloxazolidin-2-one (22.5 g); m.p. 64°–65° C.; NMR (CDCl$_3$) δ 4.41(1H,m), 4.21(2H, m), 4.12(1H,m), 2.79(1H,m), 2.28–2.4(2H,m), 1.41(9H,s) 1.16(3H,d), 0.9(6H,m).

ii) Hydrogen peroxide (30%, 44 ml) and lithium hydroxide monohydrate (6.38 g) were added in turn to a stirred mixture of (4S)-3-[(2R)-3-tert-butoxycarbonyl-2-methylpropionyl]-4-isopropyloxazolidin-2-one (22.5 g), water (280 ml) and THF (800 ml) which had been cooled to 5° C. The resultant mixture was stirred at 5° C. for 3 hours. A saturated aqueous sodium metabisulphite solution was added to destroy the excess hydrogen peroxide and the solvent evaporated. The residue was extracted with dichloromethane. The aqueous solution was acidified by the addition of an aqueous citric acid solution and extracted with dichloromethane. The extracts were combined, washed with water and filtered through phase separating paper. The filtrate was evaporated to give 1-tert-butyl (3R)-3-methyl-succinate as an oil (12.9 g); NMR (CDCl$_3$) δ 2.9(1H,m), 2.64(1H,m), 2.37(1H,m), 1.4(9H.s), 1.23(3H,d).

iii) Borane-dimethyl sulphide complex (10M, 10.3 ml) was added over 15 min to a stirred mixture of 1-tert-butyl (3R)-3-methylsuccinate (12.9 g) and THF (200 ml) which had been cooled to −10° C. and placed under an atmosphere of argon. The mixture was stirred at −10° C. for 30 min. The mixture was allowed to warm to room temperature and stirred for 1 hour. The mixture was recooled to 5° C. and methanol (50 ml) was added portionwise. The mixture was allowed to warm to room temperature and stirred for 30 min. The mixture was evaporated and the residue partitioned between dichloromethane (100 ml) and water (100 ml). The organic phase was filtered through phase separating paper and evaporated to give tert-butyl (3R)-4-hydroxy-3-methylbutyrate as an oil (11 g); NMR (CDCl$_3$) δ 3.55(2H,m), 2.1–2.4(3H,m), 1.46 (9H,s), 0.98(3H,d).

iv) p-Toluenesulphonyl chloride (13.2 g) was added portionwise to a stirred mixture of tert-butyl (3R)-4-hydroxy-3-methylbutyrate (11 g), triethylamine (21 ml) and dichloromethane (120 ml) and the mixture stirred for 20 hours. The mixture was washed in turn with water and dilute aqueous sodium carbonate solution. The organic solution was filtered through phase separating paper and evaporated to give tert-butyl (3R)-3-methyl-4-(p-toluenesulphonyloxy)butyrate as an oil (20 g); NMR (CDCl$_3$) δ 7.6(2H,d), 7.33(2H,d), 3.92(2H,d), 2.45(3H,s), 2.18–2.47(2H,m), 2.0–2.15(1H,m), 1.42(9H,s), 0.95(3H, d).

EXAMPLE 247

Illustrative pharmaceutical dosage forms suitable for presenting the compounds of the invention for therapeutic or prophylactic use include the following, which may be obtained by conventional procedures well known in the art.

| a) Tablet I | mg/tablet |
| --- | --- |
| Active ingredient | 1.0 |
| Lactose Ph. Eur. | 93.25 |
| Croscarmellose sodium | 4.0 |
| Maize starch paste (5% w/v aqueous paste) | 0.75 |
| Magnesium stearate | 1.0 |

| b) Tablet II | mg/tablet |
| --- | --- |
| Active ingredient | 50 |
| Lactose | 223.75 |
| Croscarmellose sodium | 6.0 |
| Maize starch | 15.0 |
| Polyvinylpyrrolidone (5% w/v aqueous paste) | 2.25 |
| Magnesium stearate | 3.0 |

| c) Tablet III | mg/tablet |
| --- | --- |
| Active ingredient | 100 |

|  |  |
|---|---|
| Lactose | 182.75 |
| Croscarmellose sodium | 12.0 |
| Maize starch paste (5% w/v aqueous paste) | 2.25 |
| Magnesium stearate | 3.0 |

| (d) Capsule | mg/capsule |
|---|---|
| Active ingredient | 10 |
| Lactose Ph. Eur. | 488.5 |
| Magnesium stearate | 1.5 |

| (e) Injection | mg/ml |
|---|---|
| Active ingredient (acid addition salt) | 1.0 |
| Sodium chloride | 9.0 |
| Purified water to 1.0 ml | |

EXAMPLE 248

The following is a description of a study of the effects of the (−)-(3R) compound of Example 246 and the corresponding (3RS)-racemic mixture of Example 203 in the rat. Four groups of ten Alderley Park Wistar rats (each group comprising 5 male and 5 female rats) were dose orally with the (3RS)-racemic mixture of Example 203 at daily doses of 0, 25, 100 or 500 mg/kg. Dosing was continued for a total of seven days. The animals were killed and examined. Adverse effects were noted in the livers of six of the group of ten rats dosed at 500 mg/kg/day.

Four groups of ten Alderley Park Wistar rats (each group comprising 5 male and 5 female rats) were dosed orally with the (−)-(3R) compound of Example 246 at daily doses of 0, 50, 250 and 1000 mg/kg. The highest dose was not tolerated. After four or five days, four of the animals from this group were killed. The remaining six animals were dosed at 500 mg/kg/day for the remainder of the study. Dosing was continued for a total of fourteen days. The animals were killed and examined. No adverse effects were noted in the livers of the group of rats dosed at 250 mg/kg/day. The six animals dosed at 1000 mg/kg/day for three or four days and then at 500 mg/kg/day for ten or eleven days also showed no adverse effect on the liver.

Based on such observations, it is seen that the (−)-(3R) compound of Example 246 causes no significant adverse effect on the rat liver at 500 mg/kg/day.

By implication, the (−)-(3R) compound of Example 246 is less toxic than the (3RS)-racemic mixture of Example 203.

I claim:

1. The optically active compound tert-butyl (3R)-3-methyl-4-hydroxybutyrate, or a derivative thereof reactive in the formation of an ether linkage by nucleophilic substitution with a phenolic compound, substantially free of the (3S) stereoisomer.

2. A compound according to claim 1, wherein the reactive derivative is tert-butyl (3R)-3-methyl-4-(p-toluenesulphonyloxy)butyrate.

* * * * *